(12) United States Patent
Worthington et al.

(10) Patent No.: US 9,096,525 B2
(45) Date of Patent: *Aug. 4, 2015

(54) IMINIPYRIDINE DERIVATIVES AND THEIR USES AS MICROBIOCIDES

(71) Applicant: Syngenta Crop Protection, LLC, Greensboro, NC (US)

(72) Inventors: Paul Anthony Worthington, Maidenhead (GB); Daniel Stierli, Stein (CH); Fredrik Cederbaum, Stein (CH); Kurt Nebel, Hochwald (CH); Antoine Daina, Romont (CH)

(73) Assignee: Syngenta Crop Protection, LLC, Greensboro, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/971,439

(22) Filed: Aug. 20, 2013

(65) Prior Publication Data

US 2013/0338105 A1   Dec. 19, 2013

Related U.S. Application Data

(63) Continuation of application No. 12/528,198, filed as application No. PCT/EP2008/001315 on Feb. 8, 2008, now Pat. No. 8,513,286.

(30) Foreign Application Priority Data

Feb. 22, 2007   (EP) .................................. 07003637

(51) Int. Cl.
| | |
|---|---|
| *C07D 213/85* | (2006.01) |
| *C07D 401/02* | (2006.01) |
| *A01N 43/40* | (2006.01) |
| *C07D 213/74* | (2006.01) |
| *C07D 213/16* | (2006.01) |
| *C07D 401/04* | (2006.01) |
| *C07D 401/10* | (2006.01) |
| *C07D 401/12* | (2006.01) |
| *C07D 401/14* | (2006.01) |
| *C07D 407/04* | (2006.01) |
| *C07D 407/10* | (2006.01) |
| *C07D 409/10* | (2006.01) |
| *C07D 417/10* | (2006.01) |
| *A01N 43/42* | (2006.01) |
| *A01N 43/50* | (2006.01) |
| *A01N 43/54* | (2006.01) |
| *A01N 43/653* | (2006.01) |
| *A01N 43/713* | (2006.01) |
| *A01N 43/72* | (2006.01) |
| *A01N 43/84* | (2006.01) |
| *A01N 55/00* | (2006.01) |
| *C07D 413/12* | (2006.01) |
| *C07F 7/08* | (2006.01) |

(52) U.S. Cl.
CPC ............. *C07D 213/74* (2013.01); *A01N 43/40* (2013.01); *A01N 43/42* (2013.01); *A01N 43/50* (2013.01); *A01N 43/54* (2013.01); *A01N 43/653* (2013.01); *A01N 43/713* (2013.01); *A01N 43/72* (2013.01); *A01N 43/84* (2013.01); *A01N 55/00* (2013.01); *C07D 213/16* (2013.01); *C07D 213/85* (2013.01); *C07D 401/04* (2013.01); *C07D 401/10* (2013.01); *C07D 401/12* (2013.01); *C07D 401/14* (2013.01); *C07D 407/04* (2013.01); *C07D 407/10* (2013.01); *C07D 409/10* (2013.01); *C07D 413/12* (2013.01); *C07D 417/10* (2013.01); *C07F 7/0812* (2013.01)

(58) Field of Classification Search
None
See application file for complete search history.

(56) References Cited

U.S. PATENT DOCUMENTS 8,513,286 B2 *   8/2013   Worthington et al. ........ 514/332

FOREIGN PATENT DOCUMENTS

| | | |
|---|---|---|
| EP | 0314429 | 5/1989 |
| EP | 0314429 A2 | 5/1989 |
| EP | 0376279 | 7/1990 |
| EP | 0376279 A2 | 7/1990 |
| EP | 0407346 A2 | 1/1991 |
| EP | 0407346 | 9/1991 |
| EP | 1291343 | 3/2003 |
| EP | 1291343 A1 | 3/2003 |
| WO | 0046203 | 8/2000 |
| WO | 0046203 A2 | 8/2000 |
| WO | 0187845 | 11/2001 |
| WO | 0187845 A2 | 11/2001 |
| WO | 2004063191 | 7/2004 |

(Continued)

OTHER PUBLICATIONS

Beaudin et al, Organic Process Research & Development, 2003, vol. 7, pp. 873-878.

(Continued)

*Primary Examiner* — Zinna Northington Davis
(74) *Attorney, Agent, or Firm* — R. Kody Jones

(57) ABSTRACT

Compounds of the formula I

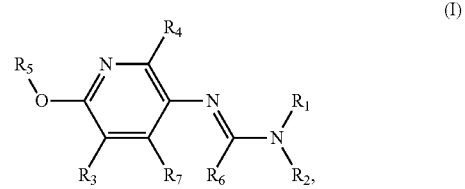

in which the substituents are as defined in claim 1 are suitable for use as microbiocides.

14 Claims, No Drawings

(56) References Cited

FOREIGN PATENT DOCUMENTS

| WO | 2004063191 | A1 | 7/2004 |
|----|------------|----|--------|
| WO | 2005051381 |    | 6/2005 |
| WO | 2005051381 | A1 | 6/2005 |
| WO | 2005068444 |    | 7/2005 |
| WO | 2005068444 | A2 | 7/2005 |
| WO | 2006078621 |    | 7/2006 |
| WO | 2006078621 | A2 | 7/2006 |
| WO | 2006108059 |    | 10/2006 |
| WO | 2006108059 | A1 | 10/2006 |

OTHER PUBLICATIONS

Fahrenholtz K E et al—A Novel Isothiocyanate Dimer—J Org Chem 1980, 45 (p. 4219-4223).

Takemoto et al—Novel Potassium Channel Openers : Synthesis and Pharmacological Evaluation of New N-(Substituted-3-pyridyl)-N'-alkylthioureas and Related Compounds—J Med Chem 1994, 37 (p. 18-25).

Beaudin J et al—Synthesis and Purification of 6-Ethoxy-4-oxo-1,4-dihydro- [1,]naphthyridine-3-carboxylic Acid Benzylamide—Organic Process R&D 2003, 7 (p. 873-878).

Pascual et al—N-(Pyrid-3-yl)thioureas and Derivatives as Acaricides. I. Synthesis and Biological Properties—Plant Protection Division, Ciba-Geigy AG—Pestic Sci 1994 (p. 253-263).

Takahashi et al—partial translation—Yakugakuzassi 1945 vol. 65, No. 2, p. 14.

Solov'eva et al—Investigation of the Z E Isomerism of N-(S-Pyrimidyl)- and N-(S-Pyridyl) Acetamidines—Chemistry of Heterocyclic Compounds 1975, vol. 11, No. 8 (p. 985-990).

* cited by examiner

IMINIPYRIDINE DERIVATIVES AND THEIR USES AS MICROBIOCIDES

This application is a continuation of U.S. Ser. No. 12/528,198, filed Aug. 21, 2009 now U.S. Pat. No. 8,513,286, which is a 371 of International Application No. PCT/EP2008/001315, filed Feb. 20, 2008, which claims priority from EP 07003637.1 filed Feb. 22, 2007; the contents of all above-named applications are incorporated herein by reference.

The present invention relates to novel microbiocidally active, in particular fungicidally active, pyridylamidine compounds. It further relates to intermediates used in the preparation of these compounds, to compositions which comprise these compounds and to their use in agriculture or horticulture for controlling or preventing infestation of plants by phytopathogenic microorganisms, preferably fungi.

Certain phenylamidine derivatives have been proposed in the literature as microbicidally active ingredients in pesticides. For example, WO 00/46184 and WO 03/093224 disclose phenylamidines which are useful as fungicides. However, the biological properties of these known compounds are not entirely satisfactory for controlling or preventing infestation of plants by phytopathogenic microorganisms, which is why there is a need to provide other compounds which have microbicidal properties. There have now been found novel pyridylamidines having microbiocidal activity.

The present invention accordingly relates to compounds of formula I

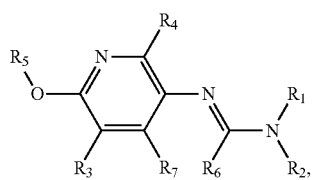

(I)

wherein aa) $R_1$ and $R_2$, independently from each other, are hydrogen, cyano, formyl, nitro, $C_1$-$C_7$alkyl, $C_2$-$C_6$alkenyl, $C_2$-$C_6$alkynyl, $C_2$-$C_7$alkylcarbonyl, $C_3$-$C_7$alkenylcarbonyl, $C_4$-$C_9$cycloalkylcarbonyl, $C_1$-$C_6$alkoxy-$C_1$-$C_6$alkyl, $C_1$-$C_6$alkylthio-$C_1$-$C_6$alkyl, $C_2$-$C_7$alkylcarbonyl-$C_1$-$C_6$alkyl, $C_3$-$C_6$alkenyloxy-$C_1$-$C_6$alkyl, $C_3$-$C_6$alkynyloxy-$C_1$-$C_6$alkyl, benzyloxy-$C_1$-$C_6$alkyl, $C_3$-$C_9$cycloalkyl-$C_1$-$C_6$alkyl, $C_2$-$C_7$alkyloxycarbonyl, $C_4$-$C_7$alkenyloxycarbonyl, $C_4$-$C_7$alkynyloxycarbonyl, $C_4$-$C_8$cycloalkyloxycarbonyl, $C_1$-$C_6$alkylsulfonyl, $C_1$-$C_6$haloalkylsulfonyl, $C_1$-$C_6$alkylsulfinyl or $C_1$-$C_6$haloalkylsulfinyl; or ab) $R_1$ and $R_2$, independently from each other, are —Si($R_{51}$)($R_{52}$)($R_{53}$), wherein $R_{51}$, $R_{52}$, $R_{53}$, independently of each other, are halogen, cyano, $C_1$-$C_6$alkyl, $C_2$-$C_6$alkenyl, $C_3$-$C_8$cycloalkyl, $C_5$-$C_8$cycloalkenyl, $C_2$-$C_6$alkynyl, $C_1$-$C_6$alkoxy, benzyl or phenyl; or ac) $R_1$ and $R_2$, independently from each other, are —Si($OR_{54}$)($OR_{55}$)($OR_{56}$), wherein $R_{54}$, $R_{55}$, $R_{56}$, independently of each other, are $C_1$-$C_6$alkyl, $C_3$-$C_6$alkenyl, $C_3$-$C_8$cycloalkyl, $C_3$-$C_6$alkynyl, benzyl or phenyl; or ad) $R_1$ and $R_2$, independently from each other, are phenylsulfonyl, phenylsufinyl, phenylcarbonyl, phenoxycarbonyl, benzyl, benzylcarbonyl or benzyloxycarbonyl; or ae) $R_1$ and $R_2$, independently from each other, are phenylsulfonyl, phenylsufinyl, phenylcarbonyl, phenoxycarbonyl, benzyl, benzylcarbonyl, benzyloxycarbonyl mono- to polysubstituted ae1) by substituents independently selected from the group consisting of hydroxy, mercapto, halogen, cyano, azido, nitro, —$SF_5$, amino, $C_1$-$C_6$alkyl, $C_1$-$C_6$haloalkyl, $C_3$-$C_8$cycloalkyl, $C_3$-$C_8$halocycloalkyl, $C_2$-$C_6$alkenyl, $C_2$-$C_6$haloalkenyl, $C_2$-$C_6$alkynyl, $C_2$-$C_6$haloalkynyl, $C_1$-$C_6$alkoxy, $C_1$-$C_6$haloalkoxy, $C_1$-$C_6$alkoxy$C_1$-$C_6$alkyl, $C_1$-$C_6$alkylthio$C_1$-$C_6$alkyl, $C_3$-$C_6$alkenyloxy, $C_3$-$C_6$haloalkenyloxy, $C_3$-$C_6$alkynyloxy, $C_1$-$C_6$alkylthio, $C_1$-$C_6$haloalkylthio, $C_1$-$C_6$alkylsulfinyl, $C_1$-$C_6$haloalkylsulfinyl, $C_1$-$C_6$alkylsulfonyl, $C_1$-$C_6$haloalkylsulfonyl, benzyloxy, phenoxy, benzyl and phenyl, where benzyloxy, phenoxy, benzyl and phenyl for their part may be mono- to polysubstituted on the phenyl ring by substituents independently selected from the group consisting of halogen, cyano, hydroxy, $C_1$-$C_6$alkyl, $C_1$-$C_6$haloalkyl and $C_1$-$C_6$alkoxy; or ae2) by substituents independently selected from the group consisting of carboxy, —C(=O)—Cl, —C(=O)—F, $C_2$-$C_7$alkoxycarbonyl, $C_2$-$C_7$alkylthiocarbonyl, $C_2$-$C_7$haloalkoxycarbonyl, $C_3$-$C_7$alkenyloxycarbonyl, $C_3$-$C_7$haloalkenyloxycarbonyl, $C_3$-$C_7$alkynyloxycarbonyl, benzyloxycarbonyl and phenoxycarbonyl, where benzyloxycarbonyl and phenoxycarbonyl for their part may be mono- to polysubstituted on the phenyl ring by substituents independently selected form the group consisting of halogen, cyano, hydroxy, $C_1$-$C_6$alkyl, $C_1$-$C_6$haloalkyl and $C_1$-$C_6$alkoxy; or ae3) by substituents independently selected from the group consisting of formyl, $C_2$-$C_7$alkylcarbonyl, $C_2$-$C_7$haloalkylcarbonyl, $C_3$-$C_7$alkenylcarbonyl, phenylcarbonyl and benzylcarbonyl, where phenylcarbonyl and benzylcarbonyl for their part may be mono-to polysubstituted on the phenyl ring by substituents independently selected form the group consisting of halogen, cyano, hydroxy, $C_1$-$C_6$alkyl, $C_1$-$C_6$haloalkyl and $C_1$-$C_6$alkoxy; or ae4) by substituents independently selected from the group consisting of aminosulfonyl, $C_1$-$C_6$alkylaminosulfonyl, N,N-di($C_1$-$C_6$alkyl)aminosulfonyl, —C(=O)$NR_{57}R_{58}$, —C(=S)$NR_{57}R_{58}$ and —$NR_{57}R_{58}$, wherein $R_{57}$ and $R_{58}$, independently of each other, are hydrogen, $C_1$-$C_6$alkyl, $C_1$-$C_6$haloalkyl, $C_3$-$C_6$alkenyl, $C_3$-$C_6$haloalkenyl, $C_3$-$C_6$alkynyl, $C_3$-$C_8$cycloalkyl, $C_3$-$C_8$halocycloalkyl, phenyl or benzyl, where phenyl, benzyl for their part may be mono- to polysubstituted on the phenyl ring by substituents independently selected form the group consisting of halogen, cyano, hydroxy, $C_1$-$C_6$alkyl, $C_1$-$C_6$haloalkyl and $C_1$-$C_6$alkoxy, or $R_{57}$ and $R_{58}$ together with their interconnecting nitrogen atom are aziridino, azetidino, pyrazolino, pyrazolidino, pyrrolino, pyrrolidino, imidazolino, imidazolidino, triazolino, tetrazolino, piperazino, piperidino, morpholino, thiomorpholino, each of which, in turn, may be mono- or polysubstituted by substituents selected from the group consisting of methyl, halogen, cyano and nitro; and substituents at nitrogen atoms in the ring systems being other than halogen; or af) either $R_1$ or $R_2$ is af1) hydroxy, amino, $C_1$-$C_6$alkoxy, $C_3$-$C_6$alkenyloxy, $C_3$-$C_8$cycloalkyloxy, $C_3$-$C_6$alkynyloxy or benzyloxy; or af2) $C_1$-$C_6$alkoxy, $C_3$-$C_6$alkenyloxy, $C_3$-$C_8$cycloalkyloxy, $C_3$-$C_6$alkynyloxy, benzyloxy mono- to polysubstituted by substituents independently selected from the group consisting of halogen, cyano, hydroxy, $C_1$-$C_6$alkyl, $C_1$-$C_6$haloalkyl, $C_1$-$C_6$alkoxy and $C_1$-$C_6$haloalkoxy; or ag) $R_1$ and $R_2$, independently from each other, are $C_1$-$C_7$alkyl, $C_2$-$C_6$alkenyl, $C_2$-$C_6$alkynyl, $C_2$-$C_7$alkylcarbonyl, $C_3$-$C_7$alkenylcarbonyl, $C_4$-$C_9$cycloalkylcarbonyl, $C_1$-$C_6$alkoxy-$C_1$-$C_6$alkyl, $C_1$-$C_6$alkylthio-$C_1$-$C_6$alkyl, $C_3$-$C_6$alkenyloxy-$C_1$-$C_6$alkyl, $C_2$-$C_6$alkylcarbonyl-$C_1$-$C_6$alkyl, $C_3$-$C_6$alkynyloxy-$C_1$-$C_6$alkyl, benzyloxy-$C_1$-$C_6$alkyl, $C_3$-$C_8$cycloalkyl-$C_1$-$C_6$alkyl, $C_2$-$C_7$alkyloxycarbonyl, $C_4$-$C_7$alkenyloxycarbonyl, $C_4$-$C_7$alkynyloxycarbonyl or $C_4$-$C_9$cycloalkyloxycarbonyl, mono- to polysubstituted by substituents independently selected from the group consisting of halogen, cyano, nitro, hydroxy, mercapto, azido, $C_1$-$C_6$alkyl, $C_1$-$C_6$haloalkyl, $C_1$-$C_6$alkoxy, $C_1$-$C_6$haloalkoxy, $C_1$-$C_6$alkylthio, $C_1$-$C_6$alkylsulfinyl, $C_1$-$C_6$alkylsulfonyl, $C_2$-$C_7$alkoxycarbonyl, formyl, $C_2$-$C_7$alkylcarbonyl, —Si($R_{51}$)($R_{52}$)($R_{53}$) and —Si($OR_{54}$)($OR_{55}$)($OR_{56}$); or ah) $R_1$ and $R_2$, independently from each other, are the group A-;
wherein A is a three- to ten-membered monocyclic or fused bicyclic ring system which can be aromatic, partially saturated or fully saturated and can contain 1 to 4 hetero atoms selected from the group consisting of nitrogen, oxygen and sulfur, it not being possible for each ring system to contain more than 2 oxygen atoms and more than 2 sulfur atoms, and it being possible for the three- to ten-membered ring system itself to be mono- or polysubstituted A1) by substituents independently selected from the group consisting of halogen, cyano, nitro, hydroxy, mercapto, nitro, azido, formyl, carboxy, —C(=O)—Cl, =O, =S, —C(=O)—F, $C_1$-$C_6$alkyl, $C_2$-$C_6$alkenyl, $C_2$-$C_6$alkynyl, $C_3$-$C_8$cycloalkyl, $C_5$-$C_8$cycloalkenyl, $C_5$-$C_8$cycloalkynyl, $C_1$-$C_6$haloalkyl, $C_2$-$C_6$haloalkenyl, $C_2$-$C_6$haloalkynyl, $C_3$-$C_8$halocycloalkyl, $C_5$-$C_8$halocycloalkenyl, $C_5$-$C_8$halocycloalkynyl, $C_1$-$C_6$alkoxy, $C_1$-$C_6$haloalkoxy, $C_3$-$C_6$alkenyloxy, $C_3$-$C_6$haloalkenyloxy, $C_3$-$C_6$alkynyloxy, $C_3$-$C_8$cycloalkyloxy, $C_3$-$C_8$halocycloalkyloxy, $C_3$-$C_8$cycloalkenyloxy, $C_3$-$C_8$halocycloalkenyloxy, benzyloxy and phenoxy, where benzyloxy and phenoxy, in turn, may be mono- to polysubstituted by substituents independently selected from the group consisting of halogen, cyano, nitro, hydroxy, mercapto, azido, amino, —SF$_5$, $C_1$-$C_6$alkyl, $C_1$-$C_6$haloalkyl, $C_1$-$C_6$alkoxy, $C_1$-$C_6$haloalkoxy, $C_1$-$C_6$alkoxy$C_1$-$C_6$alkyl, $C_1$-$C_6$alkylthio, $C_1$-$C_6$alkylsulfinyl and $C_1$-$C_6$alkylsulfonyl; or A2) by substituents independently selected from the group consisting of HC(=NOR$_{59}$)—, ($C_1$-$C_6$alkyl)C(=NOR$_{59}$)—, ($C_1$-$C_6$haloalkyl)C(=NOR$_{59}$)—, ($C_1$-$C_6$alkyl)C(=NOR$_{59}$)$C_1$-$C_6$alkyl- and ($C_1$-$C_6$haloalkyl)C(=NOR$_{59}$)$C_1$-$C_6$alkyl-, wherein $R_{59}$ is hydrogen, $C_1$-$C_6$alkyl, $C_1$-$C_6$haloalkyl, $C_3$-$C_6$alkenyl, $C_3$-$C_6$haloalkenyl, $C_3$-$C_6$alkynyl, $C_3$-$C_8$cycloalkyl, $C_3$-$C_8$halocycloalkyl, benzyl and phenyl, and benzyl and phenyl mono- to polysubstituted by halogen, cyano, hydroxy, $C_1$-$C_6$alkyl, $C_1$-$C_6$haloalkyl or $C_1$-$C_6$alkoxy; or A3) by substituents independently selected from the group consisting of $C_1$-$C_6$alkylthio, $C_1$-$C_6$haloalkylthio, $C_1$-$C_6$alkylsulfinyl, $C_1$-$C_6$alkylsulfonyl, ($R_{14}$)S(=O)(=NR$_{13}$)— and ($R_{14}$)($R_{15}$)S(=O)=N—, wherein $R_{13}$ is hydrogen, $C_1$-$C_6$alkyl, $C_1$-$C_6$haloalkyl, $C_3$-$C_6$alkenyl, $C_3$-$C_6$haloalkenyl, $C_3$-$C_6$alkynyl, $C_3$-$C_8$cycloalkyl, $C_3$-$C_8$halocycloalkyl, phenyl or benzyl, or is phenyl or benzyl mono- to polysubstituted by halogen, cyano, hydroxy, $C_1$-$C_6$alkyl, $C_1$-$C_6$haloalkyl or $C_1$-$C_6$alkoxy, and $R_{14}$ and $R_{15}$, independently of each other, are $C_1$-$C_6$alkyl, $C_3$-$C_8$cycloalkyl, $C_1$-$C_6$haloalkyl, $C_3$-$C_8$halocycloalkyl, $C_2$-$C_6$alkenyl, $C_2$-$C_6$haloalkenyl, $C_2$-$C_6$alkynyl, benzyl or phenyl, or benzyl or phenyl independently of each other, substituted by substituents selected from the group consisting of halogen, cyano, hydroxy, $C_1$-$C_6$alkyl, $C_1$-$C_6$haloalkyl and $C_1$-$C_6$alkoxy; or A4) by substituents independently selected from the group consisting of —NR$_{57}$R$_{58}$, —C(=O)NR$_{57}$R$_{58}$ and —C(=S)NR$_{57}$R$_{58}$; or A5) by substituents independently selected from the group consisting of formyl, $C_2$-$C_7$alkylcarbonyl, $C_2$-$C_7$haloalkylcarbonyl, $C_3$-$C_7$alkenylcarbonyl, $C_3$-$C_7$haloalkenylcarbonyl, $C_4$-$C_9$cycloalkylcarbonyl, $C_4$-$C_9$halocycloalkylcarbonyl, $C_2$-$C_7$alkoxycarbonyl, $C_2$-$C_7$haloalkoxycarbonyl, $C_3$-$C_7$alkenyloxycarbonyl, $C_3$-$C_7$alkynyloxycarbonyl, $C_4$-$C_9$cycloalkoxycarbonyl, $C_2$-$C_7$alkylthiocarbonyl and benzyloxycarbonyl, and benzyloxycarbonyl mono- to polysubstituted by substituents independently selected from the group consisting of halogen, cyano, hydroxy, $C_1$-$C_6$alkyl, $C_1$-$C_6$haloalkyl and $C_1$-$C_6$alkoxy; or A6) by substituents independently selected from the group consisting of —Si($R_{51}$)($R_{52}$)($R_{53}$) and —Si($OR_{54}$)($OR_{55}$)($OR_{56}$); or A7) by substituents independently selected from the group consisting of aminosulfinyl, ($C_1$-$C_6$alkyl)aminosulfonyl, N,N-di($C_1$-$C_6$alkyl)aminosulfonyl, di($C_1$-$C_6$alkyl)amino, ($C_1$-$C_6$alkyl)amino, phenyl, phenoxy, benzyl and benzyloxy, where phenyl, phenoxy, benzyl and benzyloxy for their part may be mono- to polysubstituted on the phenyl ring by substituents independently selected form the group consisting of halogen, cyano, hydroxy, amino, nitro, azido, mercapto, formyl, —SF$_5$, $C_1$-$C_6$alkyl, $C_1$-$C_6$haloalkyl, $C_2$-$C_6$alkenyl, $C_2$-$C_6$haloalkenyl, $C_2$-$C_6$alkynyl, $C_1$-$C_6$alkoxy, $C_1$-$C_6$haloalkoxy, $C_1$-$C_6$alkylthio, $C_1$-$C_6$haloalkylthio, $C_3$-$C_6$alkenylthio, $C_3$-$C_6$haloalkenylthio, $C_3$-$C_6$alkynylthio, $C_1$-$C_3$alkoxy-$C_1$-$C_3$alkylthio, $C_2$-$C_6$alkylcarbonyl-$C_1$-$C_3$alkylthio, $C_2$-$C_6$alkoxycarbonyl-$C_1$-$C_3$6alkylthio, cyano-$C_1$-$C_6$alkylthio, $C_1$-$C_6$alkylsulfinyl, $C_1$-$C_6$haloalkylsulfinyl, $C_1$-$C_6$alkylsulfonyl, $C_1$-$C_6$haloalkylsulfonyl, aminosulfonyl, ($C_1$-$C_6$alkyl)aminosulfonyl, N,N-di($C_1$-$C_6$alkyl)aminosulfonyl, di($C_1$-$C_6$alkyl)amino and ($C_1$-$C_6$alkyl)amino; or ai) $R_1$ and $R_2$, independently from each other, are —C(=O)NR$_{57}$R$_{58}$; or aj) $R_1$ and $R_2$ together form a $C_2$-$C_6$alkylene bridge which may be mono- to polysubstituted by halogen, cyano, $C_1$-$C_6$alkyl or $C_1$-$C_6$haloalkyl groups; or ak) $R_1$ and $R_2$ together with their interconnecting nitrogen atom are pyrazolino, pyrazolidino, pyrrolino, imidazolino, imidazolidino, triazolino, tetrazolino, piperazino, morpholino, thiomorpholino, each of which, independently of each other, may be mono- to polysubstituted by methyl groups, halogen, cyano and nitro; or al) the fragment

can be

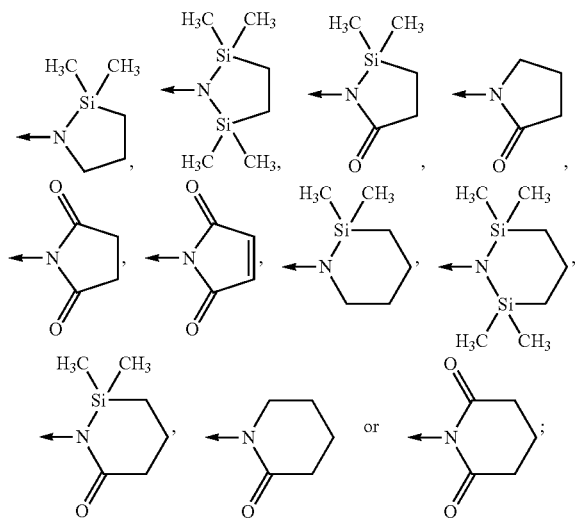

wherein each of the meanings of said fragment can be mono- to polysubstituted by substituents independently selected from the group consisting of halogen, cyano, $C_1$-$C_6$alkyl, $C_1$-$C_6$haloalkyl and $C_1$-$C_6$alkoxy;

ba) $R_3$, $R_4$ and $R_7$, independently from each other, are ba1) hydrogen, halogen, cyano, nitro, mercapto, hydroxy, azido, —$SF_5$, —$NR_{64}R_{65}$, wherein $R_{64}$ and $R_{65}$, independently of each other, are hydrogen, $C_1$-$C_6$alkyl, $C_1$-$C_6$haloalkyl, $C_3$-$C_6$alkenyl, $C_3$-$C_6$haloalkenyl, $C_3$-$C_6$alkynyl, $C_3$-$C_8$cycloalkyl, $C_3$-$C_8$halocycloalkyl, phenyl or benzyl, where phenyl, benzyl for their part may be mono- to polysubstituted on the phenyl ring by substituents independently selected form the group consisting of halogen, cyano, hydroxy, $C_1$-$C_6$alkyl, $C_1$-$C_6$haloalkyl and $C_1$-$C_6$alkoxy, or $R_{64}$ and $R_{65}$ together with their interconnecting nitrogen atom are aziridino, azetidino, pyrazolino, pyrazolidino, pyrrolino, pyrrolidino, imidazolino, imidazolidino, triazolino, tetrazolino, piperazino, piperidino, morpholino, thiomorpholino, each of which, in turn, may be mono- or polysubstituted by substituents selected from the group consisting of methyl, halogen, cyano and nitro; and substituents at nitrogen atoms in the ring systems being other than halogen; or $R_3$, $R_4$ and $R_7$, independently from each other, are —C(=S)$NH_2$, —N=C=O, —N=C=S, amino, $(R_{51})(R_{52})(R_{53})Si$—, $(R_{51})(R_{52})(R_{53})Si$—($C_1$-$C_6$alkyl)-, $(R_{51})(R_{52})(R_{53})Si$—($C_2$-$C_6$alkinyl)-, $(OR_{54})(OR_{55})(OR_{56})Si$— or $(OR_{214})(OR_{215})(OR_{216})Si$— ($C_1$-$C_6$alkyl)-; wherein $R_{214}$, $R_{215}$ and $R_{216}$ independently of each other, are halogen, cyano, $C_1$-$C_6$alkyl, $C_2$-$C_6$alkenyl, $C_3$-$C_8$cycloalkyl, $C_5$-$C_8$cycloalkenyl, $C_2$-$C_6$alkynyl, benzyl or phenyl; or $R_3$, $R_4$ and $R_7$, independently from each other, are ba2) $C_1$-$C_6$alkylthio, $C_1$-$C_6$alkylsulfinyl, $C_1$-$C_6$alkylsulfonyl, $C_1$-$C_6$haloalkylthio, $C_1$-$C_6$haloalkylsulfinyl, $C_1$-$C_6$haloalkylsulfonyl, aminosulfinyl, aminosulfonyl, $C_1$-$C_6$alkoxy, $C_1$-$C_6$haloalkoxy, $C_3$-$C_6$alkenyloxy, $C_3$-$C_6$haloalkenyloxy, $C_3$-$C_6$alkinyloxy, ($C_1$-$C_6$alkyl)aminosulfonyl, di($C_1$-$C_6$alkyl)aminosulfonyl, $C_1$-$C_6$alkoxy, $C_2$-$C_6$alkenyloxy, $C_2$-$C_6$alkynyloxy, $C_1$-$C_6$alkyl-S(=O)($R_{14}$)=N—, ($R_{14}$)S(=O)(=N—$R_{13}$)—, ($R_{14}$)($R_{15}$)S(=O)=N—, —S—$C_3$-$C_6$-alkenyl, —S—$C_3$-$C_6$-alkynyl, —S—$C_3$-$C_8$-cycloalkyl, S-benzyl, or —S—$C_3$-$C_6$-alkenyl, —S—$C_3$-$C_6$-alkynyl, —S—$C_3$-$C_8$-cycloalkyl or S-benzyl; all of which can be mono- to polysubstituted by substituents selected from the group consisting of halogen, cyano, $C_1$-$C_6$-alkyl, $C_1$-$C_6$-haloalkyl, $C_1$-$C_6$-alkoxy; or $R_3$, $R_4$ and $R_7$, independently from each other, are ba3) $C_1$-$C_6$alkyl, $C_2$-$C_6$alkenyl or $C_2$-$C_6$alkynyl, or $C_1$-$C_6$alkyl, $C_2$-$C_6$alkenyl or $C_2$-$C_6$alkynyl mono- to polysubstituted by substituents independently selected from the group consisting of halogen, hydroxy, mercapto, cyano, nitro, $C_1$-$C_6$alkyl, $C_1$-$C_6$haloalkyl, $C_1$-$C_6$alkoxy, $C_1$-$C_6$hydroxyalkyl, tri(alkyl)silyl, $C_1$-$C_6$haloalkoxy, $C_1$-$C_6$alkylthio, $C_1$-$C_6$haloalkylthio, $C_1$-$C_6$alkylsulfinyl, $C_1$-$C_6$haloalkylsulfinyl, $C_1$-$C_6$alkylsulfonyl and $C_1$-$C_6$haloalkylsulfonyl; or $R_3$, $R_4$ and $R_7$, independently from each other, are ba4) formyl, $C_2$-$C_7$alkoxycarbonyl, $C_2$-$C_7$haloalkoxycarbonyl, $C_3$-$C_7$alkenyloxycarbonyl, $C_3$-$C_7$haloalkenyloxycarbonyl, $C_2$-$C_7$alkylcarbonyl, carboxy, —C(=O)—Cl, —C(=O)—F, $C_2$-$C_7$haloalkylcarbonyl, $C_3$-$C_7$alkenylcarbonyl or $C_3$-$C_7$haloalkenylcarbonyl; or $R_3$, $R_4$ and $R_7$, independently from each other, are ba5) phenyl, phenoxy, benzyl or benzyloxy, or phenoxy, benzyl or benzyloxy mono- to polysubstituted by substituents independently selected from the group consisting of halogen, cyano, nitro, hydroxy, mercapto, azido, amino, —$SF_5$, $C_1$-$C_6$alkyl, $C_1$-$C_6$haloalkyl, $C_1$-$C_6$alkoxy, $C_1$-$C_6$haloalkoxy, $C_1$-$C_6$alkylthio, $C_1$-$C_6$alkylsulfinyl and $C_1$-$C_6$alkylsulfonyl; or bb) $R_3$, $R_4$ and $R_7$, independently of each other, are the groups A—, A-O— or A-($C_1$-$C_6$alkyl)-, wherein the group A is as defined above under ah);

ca) $R_5$ is hydrogen, $C_1$-$C_{13}$alkyl, $C_2$-$C_{12}$alkenyl, $C_2$-$C_{12}$alkynyl, $C_1$-$C_{12}$alkylsulfonyl, $C_2$-$C_{12}$alkenylsulfonyl, phenylsulfonyl or benzylsulfonyl, or is $C_1$-$C_{12}$alkyl, $C_2$-$C_{12}$alkenyl, $C_2$-$C_{12}$alkynyl, $C_1$-$C_{12}$alkylsulfonyl, $C_2$-$C_{12}$alkenylsulfonyl, phenylsulfonyl or benzylsulfonyl mono-to polysubstituted by substituents independently selected from the group consisting of halogen, cyano, nitro, hydroxy, mercapto, azido, formyl, $C_2$-$C_7$alkylcarbonyl, $C_2$-$C_7$haloalkylcarbonyl, $C_1$-$C_6$alkyl, $C_1$-$C_6$haloalkyl, $C_1$-$C_6$alkoxy, $C_1$-$C_6$haloalkoxy, $C_1$-$C_6$alkylthio, $C_1$-$C_6$alkylsulfinyl and $C_1$-$C_6$alkylsulfonyl; or cb1) $R_5$ is formyl, $C_2$-$C_{12}$alkylcarbonyl, $C_3$-$C_{12}$alkenylcarbonyl, $C_3$-$C_{12}$alkynylcarbonyl, $C_4$-$C_{12}$cycloalkylcarbonyl, benzylcarbonyl, phenylcarbonyl, $C_2$-$C_{12}$alkoxycarbonyl, $C_4$-$C_{12}$alkenyloxycarbonyl, $C_4$-$C_{12}$alkynyloxycarbonyl, $C_4$-$C_{12}$cycloalkoxycarbonyl, benzyloxycarbonyl or phenoxycarbonyl, or is cb2) $C_2$-$C_{12}$alkylcarbonyl, $C_3$-$C_{12}$alkenylcarbonyl, $C_3$-$C_{12}$alkynylcarbonyl, $C_4$-$C_{12}$cycloalkylcarbonyl, benzylcarbonyl, phenylcarbonyl, $C_2$-$C_{12}$alkoxycarbonyl, $C_4$-$C_{12}$alkenyloxycarbonyl, $C_4$-$C_{12}$alkynyloxycarbonyl, $C_4$-$C_{12}$cycloalkoxycarbonyl, benzyloxycarbonyl or phenoxycarbonyl mono- to polysubstituted by substituents independently selected from the group consisting of halogen, cyano, $C_1$-$C_6$alkyl, $C_1$-$C_6$haloalkyl and $C_1$-$C_6$alkoxy; or cc) $R_5$ is $(R_{51})(R_{52})(R_{53})Si$—, $(R_{51})(R_{52})(R_{53})Si$—($C_1$-$C_{12}$alkyl)-, $(R_{51})(R_{52})(R_{53})Si$—($C_3$-$C_8$cycloalkyl)-, $(R_{54}O)(R_{55}O)(R_{56}O)Si$—, $(R_{54}O)(R_{55}O)(R_{56}O)Si$—($C_1$-$C_{12}$alkyl)- or $(R_{54}O)(R_{55}O)(R_{56}O)Si$—($C_3$-$C_8$cycloalkyl)-; or cd) $R_5$ is $C_1$-$C_6$alkyl-B—$C_1$-$C_{12}$alkyl-, $C_2$-$C_6$alkenyl-B—$C_1$-$C_{12}$alkyl-, $C_2$-$C_6$alkynyl-B—$C_1$-$C_{12}$alkyl-, $C_3$-$C_8$cycloalkyl-B—$C_1$-$C_{12}$alkyl-, benzyl-B—$C_1$-$C_{12}$alkyl-, phenyl-B—$C_1$-$C_{12}$alkyl-, $C_1$-$C_6$alkyl-B—$C_2$-$C_{12}$alkenyl-, $C_2$-$C_6$alkenyl-B—$C_2$-$C_{12}$alkenyl-, $C_2$-$C_6$alkynyl-B—$C_2$-$C_{12}$alkenyl-, $C_3$-$C_8$Cycloalkyl-B—$C_2$-$C_{12}$alkenyl-, benzyl-B—$C_2$-$C_{12}$alkenyl-, phenyl-B—$C_2$-$C_{12}$alkenyl-, $C_1$-$C_6$alkyl-B—$C_2$-$C_{12}$alkynyl-, $C_2$-$C_6$alkenyl-B—$C_2$-$C_{12}$alkynyl-, $C_2$-$C_6$alkynyl-B—$C_2$-$C_{12}$alkynyl-, $C_3$-$C_8$cycloalkyl-B—$C_2$-$C_{12}$alkynyl-, benzyl-B—$C_2$-$C_{12}$alkynyl-, phenyl-B—$C_2$-$C_{12}$alkynyl-, $C_1$-$C_6$alkyl-B—$C_3$-$C_8$cycloalkyl-, $C_2$-$C_6$alkenyl-B—$C_3$-$C_8$cycloalkyl-, $C_2$-$C_6$alkynyl-B—$C_3$-$C_8$cycloalkyl-, $C_3$-$C_8$cycloalkyl-B—$C_3$-$C_8$cycloalkyl-, benzyl-B—$C_3$-$C_{12}$cycloalkyl- or phenyl-B—$C_3$-$C_{12}$cycloalkyl-, wherein the group B is —C(=O)—, —C(=S)—, —C(=NOR$_{59}$)—, —C(R$_{60}$)=NO—, —ON=C(R$_{60}$)—, —O—C(=O)—, —C(=O)—O—, —O—, —S—, —S(=O)—, —S(=O)$_2$—, —S(=O)(=NR$_{13}$)—, —S(=O)(R$_{14}$)=N—, —N=S(=O)(R$_{14}$)—, —N(R$_{62}$)—C=O)—, —C=O)—N(R$_{62}$)—, —N(R$_{62}$)—SO$_2$— or —SO$_2$—N(R$_{62}$)—;

cd1) wherein R$_{60}$ is hydrogen, $C_1$-$C_6$alkyl, $C_3$-$C_8$cycloalkyl, $C_1$-$C_6$haloalkyl, $C_3$-$C_8$halocycloalkyl, $C_2$-$C_6$alkenyl, $C_2$-$C_6$haloalkenyl, $C_2$-$C_6$alkynyl, benzyl or phenyl, or benzyl or phenyl mono- to polysubstituted by substituents independently selected form the group consisting of halogen, cyano, hydroxy, $C_1$-$C_6$alkyl, $C_1$-$C_6$haloalkyl and $C_1$-$C_6$alkoxy, and cd2) R$_{62}$ is hydrogen, $C_1$-$C_6$alkyl, $C_3$-$C_8$cycloalkyl, $C_1$-$C_6$haloalkyl, $C_3$-$C_8$halocycloalkyl, $C_3$-$C_6$alkenyl, $C_3$-$C_6$alkynyl, benzyl or phenyl, or benzyl or phenyl mono- to polysubstituted by substituents independently selected form the group consisting of halogen, cyano, hydroxy, $C_1$-$C_6$alkyl, $C_1$-$C_6$haloalkyl and $C_1$-$C_6$alkoxy; or ce) R$_5$ is $C_1$-$C_6$alkyl-B—$C_1$-$C_{12}$alkyl-, $C_2$-$C_6$alkenyl-B—$C_1$-$C_{12}$alkyl-, $C_2$-$C_6$alkynyl-B—$C_1$-$C_{12}$alkyl-, $C_3$-$C_8$cycloalkyl-B—$C_1$-$C_{12}$alkyl-, benzyl-B—$C_1$-$C_{12}$alkyl-, phenyl-B—$C_1$-$C_{12}$alkyl-, $C_1$-$C_6$alkyl-B—$C_2$-$C_{12}$alkenyl-, $C_2$-$C_6$alkenyl-B—$C_2$-$C_{12}$alkenyl-, $C_2$-$C_6$alkynyl-B—$C_2$-$C_{12}$alkenyl-, $C_3$-$C_8$cycloalkyl-B—$C_2$-$C_{12}$alkenyl-, benzyl-B—$C_2$-$C_{12}$alkenyl-, phenyl-B—$C_2$-$C_{12}$alkenyl-, $C_1$-$C_6$alkyl-B—$C_2$-$C_{12}$alkynyl-, $C_2$-$C_6$alkenyl-B—$C_2$-$C_{12}$alkynyl-, $C_2$-$C_6$alkynyl-B—$C_2$-$C_{12}$alkynyl-, $C_3$-$C_8$cycloalkyl-B—$C_2$-$C_{12}$alkynyl-, benzyl-B—$C_2$-$C_{12}$alkynyl-, phenyl-B—$C_2$-$C_{12}$alkynyl-, $C_1$-$C_6$alkyl-B—$C_3$-$C_8$cycloalkyl-, $C_2$-$C_6$alkenyl-B—$C_3$-$C_8$cycloalkyl-, $C_2$-$C_6$alkynyl-B—$C_3$-$C_8$cycloalkyl-, $C_3$-$C_8$cycloalkyl-B—$C_3$-$C_8$cycloalkyl-, benzyl-B—$C_3$-$C_{12}$cycloalkyl-, phenyl-B—$C_3$-$C_{12}$cycloalkyl-, all of which, in turn, are substituted by substituents independently selected from the group consisting of halogen, cyano, hydroxy, mercapto, $C_1$-$C_6$haloalkyl, $C_1$-$C_6$alkoxy, formyl, $C_2$-$C_6$alkylcarbonyl, $C_1$-$C_6$alkylthio, $C_1$-$C_6$alkylsulfinyl and $C_1$-$C_6$alkylsulfonyl; or cf) R$_5$ is A-, A-($C_1$-$C_6$alkyl)-, A-O—($C_1$-$C_6$alkyl)-, A-($C_2$-$C_6$alkenyl)-, A-O—($C_2$-$C_6$alkenyl)-, A-($C_2$-$C_6$-alkynyl)-, A-O—($C_2$-$C_6$alkynyl)-, A-($C_3$-$C_8$cycloalkyl)- or A-O—($C_3$-$C_8$cycloalkyl)-; wherein the group A is as defined above under ah); or cg) R$_5$ signifies the group —N=C(R$_8$)R$_9$;

cg1) wherein R$_8$ and R$_9$, independently from each other, are hydrogen, halogen, cyano, $C_1$-$C_{12}$alkyl, $C_2$-$C_{12}$alkenyl, $C_2$-$C_{12}$alkinyl, $C_1$-$C_{12}$alkoxy, formyl, $C_2$-$C_{12}$alkylcarbonyl, $C_3$-$C_{12}$alkenylcarbonyl, carboxy, $C_2$-$C_{12}$alkoxycarbonyl or $C_4$-$C_{12}$alkenyloxycarbonyl, or $C_1$-$C_{12}$alkyl, $C_2$-$C_{12}$alkenyl, $C_2$-$C_{12}$alkinyl, $C_1$-$C_{12}$alkoxy, $C_2$-$C_{12}$alkylcarbonyl, $C_3$-$C_{12}$alkenylcarbonyl, $C_2$-$C_{12}$alkoxycarbonyl or $C_4$-$C_{12}$alkenyloxycarbonyl mono- to polysubstituted by substituents independently selected from the group consisting of halogen, cyano, nitro, hydroxy, mercapto, $C_1$-$C_6$alkyl, $C_1$-$C_6$haloalkyl, $C_1$-$C_6$alkoxy, $C_1$-$C_6$haloalkoxy, $C_1$-$C_6$alkylthio, $C_1$-$C_6$alkylsulfinyl and $C_1$-$C_6$alkylsulfonyl; or cg2) R$_8$ and R$_9$ together form a $C_2$-$C_8$alkylene bridge which may optionally be mono- to polysubstituted by substituents independently selected from the group consisting of halogen, cyano, $C_1$-$C_6$alkyl and $C_1$-$C_6$haloalkyl; or cg3) R$_8$ and R$_9$, independently from each other, are the groups A-, A-O— or A-($C_1$-$C_6$alkyl)-; wherein the group A is as defined above under ah);

d) R$_6$ is hydrogen, halogen, cyano, formyl, $C_1$-$C_6$alkyl, $C_1$-$C_6$haloalkyl, —SH, —S—$C_1$-$C_6$alkyl, —S—$C_1$-$C_6$haloalkyl, —S—$C_1$-$C_6$haloalkyl, $C_2$-$C_6$alkenyl, $C_2$-$C_6$haloalkenyl or $C_2$-$C_6$alkinyl; and agronomically acceptable salts/metallic complexes/metalloidic complexes/isomers/structural isomers/stereo-isomers/diastereoisomers/enantiomers/tautomers/N-oxides of those compounds.

Substituents at a nitrogen atom are always different from halogen. A hydroxy, mercapto or amino substituent is not to be placed on an α-carbon relativ to a heteroatom of a core fragment.

The alkyl groups occurring in the definitions of the substituents can be straight-chain or branched and are, for example, methyl, ethyl, n-propyl, isopropyl, n-butyl, sec-butyl, isobutyl, tert-butyl, pentyl, hexyl, heptyl and octyl and their branched isomers. Alkoxy, alkenyl and alkynyl radicals are derived from the alkyl radicals mentioned. The alkenyl and alkynyl groups can be mono- or polyunsaturated.

The cycloalkyl groups occurring in the definitions of the substituents are, for example, cyclopropyl, cyclobutyl, cyclopentyl or cyclohexyl.

Halogen is generally fluorine, chlorine, bromine or iodine, preferably fluorine, bromine or chlorine. This also applies, correspondingly, to halogen in combination with other meanings, such as haloalkyl or haloalkoxy.

Haloalkyl groups preferably have a chain length of from 1 to 4 carbon atoms. Halonalkyl is, for example, fluoromethyl, difluoromethyl, trifluoromethyl, chloromethyl, dichloromethyl, trichloromethyl, 2,2,2-trifluoroethyl, 2-fluoroethyl, 2-chloroethyl, pentafluoroethyl, 1,1-difluoro-2,2,2-trichloroethyl, 2,2,3,3-tetrafluoroethyl and 2,2,2-trichloroethyl; preferably trichloromethyl, difluorochloromethyl, difluoromethyl, trifluoromethyl and dichlorofluoromethyl.

Suitable haloalkenyl groups are alkenyl groups which are mono- di- or trisubstituted by halogen, halogen being fluorine, chlorine, bromine and iodine and in particular fluorine and chlorine, for example 2,2-difluoro-1-methylvinyl, 3-fluoropropenyl, 3-chloropropenyl, 3-bromopropenyl, 2,3,3-trifluoropropenyl, 2,3,3-trichloropropenyl and 4,4,4-trifluorobut-2-en-1-yl.

Suitable haloalkynyl groups are, for example, alkynyl groups which are mono- or polysubstituted by halogen, halogen being bromine, iodine and in particular fluorine and chlorine, for example 3-fluoropropynyl, 3-chloropropynyl, 3-bromopropynyl, 3,3,3-trifluoro-propynyl and 4,4,4-trifluorobut-2-yn-1-yl.

Alkoxy is, for example, methoxy, ethoxy, propoxy, i-propoxy, n-butoxy, isobutoxy, sec-butoxy and tert-butoxy; preferably methoxy and ethoxy. Halogenalkoxy is, for example, fluoromethoxy, difluoromethoxy, trifluoromethoxy, 2,2,2-trifluoroethoxy, 1,1,2,2-tetrafluoroethoxy, 2-fluoroethoxy, 2-chloroethoxy, 2,2-difluoroethoxy and 2,2,2-trichloroethoxy; preferably difluoromethoxy, 2-chloroethoxy and trifluoromethoxy.

Alkoxycarbonyl is, for example, methoxycarbonyl, ethoxycarbonyl, propoxycarbonyl, isopropoxycarbonyl, n-butoxycarbonyl, isobutoxycarbonyl, sec-butoxycarbonyl or tert-butoxycarbonyl; preferably methoxycarbonyl or ethoxycarbonyl. Haloalkoxy groups preferably have a chain length of from 1 to 6 carbon atoms. Haloalkoxy is, for example, fluoromethoxy, difluoromethoxy, trifluoromethoxy, 2,2,2-trifluoroethoxy, 1,1,2,2-tetrafluoroethoxy, 2-fluoroethoxy, 2-chloroethoxy, 2,2-difluoroethoxy and 2,2,2-trichloroethoxy; preferably difluoromethoxy, 2-chloroethoxy and trifluoromethoxy. Alkylthio groups preferably have a chain length of from 1 to 6 carbon atoms.

Alkoxyalkyl is, for example, methoxymethyl, methoxyethyl, ethoxymethyl, ethoxyethyl, n-propoxymethyl, n-propoxyethyl, isopropoxymethyl or isopropoxyethyl.

Alkylthio is, for example, methylthio, ethylthio, propylthio, isopropylthio, n-butylthio, isobutyl-thio, sec-butylthio or tert-butylthio, preferably methylthio and ethylthio. Alkylsulfinyl is, for example, methylsulfinyl, ethylsulfinyl, propylsulfinyl, isopropylsulfinyl, n-butylsulfinyl, isobutylsulfinyl, sec-butylsulfinyl, tert-butylsulfinyl; preferably methylsulfinyl and ethylsulfinyl. Alkylsulfonyl is, for example, methylsulfonyl, ethylsulfonyl, propylsulfonyl, isopropylsulfonyl, n-butylsulfonyl, isobutylsulfonyl, sec-butylsulfonyl or tert-butylsulfonyl; preferably methylsulfonyl or ethylsulfonyl.

$C_2$-$C_6$alkylcarbonyl is, for example, methylcarbonyl, ethylcarbonyl, propylcarbonyl, isopropylcarbonyl, n-butylcarbonyl, isobutylcarbonyl, sec-butylcarbonyl, tert-butylcarbonyl or n-pentylcarbonyl and their branched isomers, preferably methylcarbonyl and ethylcarbonyl. Haloalkylcarbonyl radicals are derived from the alkyl radicals mentioned.

In the context of the present invention "mono- to polysubstituted" in the definition of the substituents, means typically, depending on the chemical structure of the substituents, monosubstituted to seven-times substituted, preferably monosubstituted to five-times substituted, more preferably mono-, double- or triple-substituted.

According to the present invention, a three- to ten-membered monocyclic or fused bicyclic ring system which may be aromatic, partially saturated or fully saturated is, depending of the number of ring members, for example, selected from the group consisting of

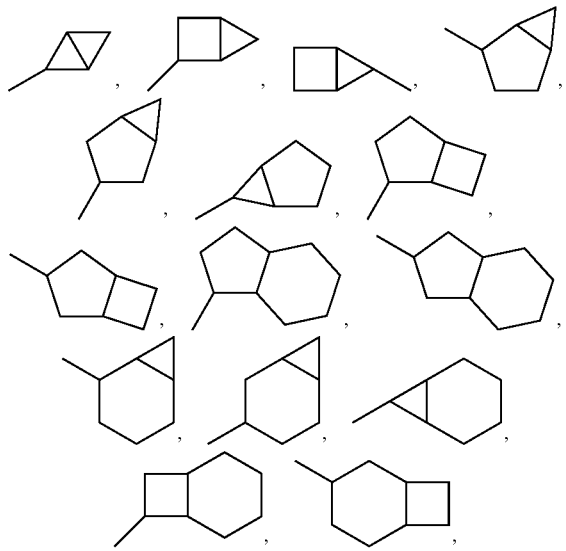

cyclopropyl, cyclobutyl, cyclopentyl, cyclohexyl, where said cycloalkylgroups for their part may be preferably unsubstituted or substituted by $C_1$-$C_6$alkyl or halogen, or is phenyl, benzyl, naphthyl or the following heterocyclic groups: pyrrolyl; pyridyl; pyrazolyl; pyrimidyl; pyrazinyl; imidazolyl; thiadiazolyl; quinazolinyl; furyl; oxadiazolyl; indolizinyl; pyranyl; isobenzofuranyl; thienyl; naphthyridinyl; (1-methyl-1H-pyrazol-3-yl)-; (1-ethyl-1H-pyrazol-3-yl)-; (1-propyl-1H-pyrazol-3-yl)-; (1H-pyrazol-3-yl)-; (1,5-dimethyl-1H-pyrazol-3-yl)-; (4-chloro-1-methyl-1H-pyrazol-3-yl)-; (1H-pyrazol-1-yl)-; (3-methyl-1H-pyrazol-1-yl)-; (3,5-dimethyl-1H-pyrazol-1-yl)-; (3-isoxazolyl)-; (5-methyl-3-isoxazolyl)-; (3-methyl-5-isoxazolyl)-; (5-isoxazolyl)-; (1H-pyrrol-2-yl)-; (1-methyl-1H-pyrrol-2-yl)-; (1H-pyrrol-1-yl)-; (1-methyl-1H-pyrrol-3-yl)-; (2-furanyl)-; (5-methyl-2-furanyl)-; (3-furanyl)-; (5-methyl-2-thienyl)-; (2-thienyl)-; (3-thienyl)-; (1-methyl-1H-imidazol-2-yl)-; (1H-imidazol-2-yl)-; (1-methyl-1H-imidazol-4-yl)-; (1-methyl-1H-imidazol-5-yl)-; (4-methyl-2-oxazolyl)-; (5-methyl-2-oxazolyl)-; (2-oxazolyl)-; (2-methyl-5-oxazolyl)-; (2-methyl-4-oxazolyl)-; (4-methyl-2-thiazolyl)-; (5-methyl-2-thiazolyl)-; (2-thiazolyl)-; (2-methyl-5-thiazolyl)-; (2-methyl-4-thiazolyl)-; (3-methyl-4-isothiazolyl)-; (3-methyl-5-isothiazolyl)-; (5-methyl-3-isothiazolyl)-; (1-methyl-1H-1,2,3-triazol-4-yl)-; (2-methyl-2H-1,2,3-triazol-4-yl)-; (4-methyl-2H-1,2,3-triazol-2-yl)-; (1-methyl-1H-1,2,4-triazol-3-yl)-; (1,5-dimethyl-1H-1,2,4-triazol-3-yl)-; (3-methyl-1H-1,2,4-triazol-1-yl)-; (5-methyl-1H-1,2,4-triazol-1-yl)-; (4,5-dimethyl-4H-1,2,4-triazol-3-yl)-; (4-methyl-4H-1,2,4-triazol-3-yl)-; (4H-1,2,4-triazol-4-yl)-; (5-methyl-1,2,3-oxadiazol-4-yl)-; (1,2,3-oxadiazol-4-yl)-; (3-methyl-1,2,4-oxadiazol-5-yl)-; (5-methyl-1,2,4-oxadiazol-3-yl)-; (4-methyl-3-furazanyl)-; (3-furazanyl)-; (5-methyl-1,2,4-oxadiazol-2-yl)-; (5-methyl-1,2,3-thiadiazol-4-yl)-; (1,2,3-thiadiazol-4-yl)-; (3-methyl-1,2,4-thiadiazol-5-yl)-; (5-methyl-1,2,4-thiadiazol-3-yl)-; (4-methyl-1,2,5-thiadiazol-3-yl)-; (5-methyl-1,3,4-thiadiazol-2-yl)-; (1-methyl-1H-tetrazol-5-yl)-; (1H-tetrazol-5-yl)-; (5-methyl-1H-tetrazol-1-yl)-; (2-methyl-2H-tetrazol-5-yl)-; (2-ethyl-2H-tetrazol-5-yl)-; (5-methyl-2H-tetrazol-2-yl)-; (2H-tetrazol-2-yl)-; (2-pyridyl)-; (6-methyl-2-pyridyl)-; (4-pyridyl)-; (3-pyridyl)-; (6-methyl-3-pyridazinyl)-; (5-methyl-3-pyridazinyl)-; (3-pyridazinyl)-; (4,6-dimethyl-2-pyrimidinyl)-; (4-methyl-2-pyrimidinyl)-; (2-pyrimidinyl)-; (2-methyl-4-pyrimidinyl)-; (2-chloro-4-pyrimidinyl)-; (2,6-dimethyl-4-pyrimidinyl)-; (4-pyrimidinyl)-; (2-methyl-5-pyrimidinyl)-; (6-methyl-2-pyrazinyl)-; (2-pyrazinyl)-; (4,6-dimethyl-1,3,5-triazin-2-yl)-; (4,6-dichloro-1,3,5-triazin-2-yl)-; (1,3,5-triazin-2-yl)-; (4-methyl-1,3,5-triazin-2-yl)-; (3-methyl-1,2,4-triazin-5-yl)-; (3-methyl-1,2,4-triazin-6-yl)-;

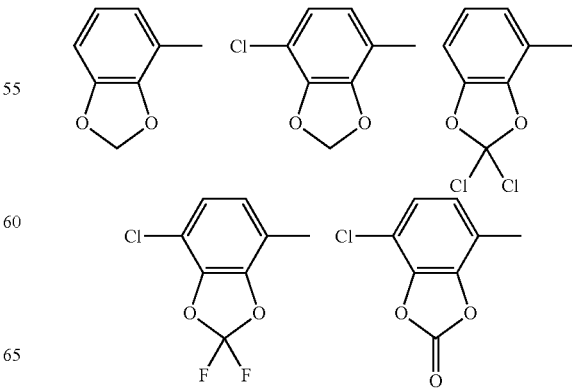

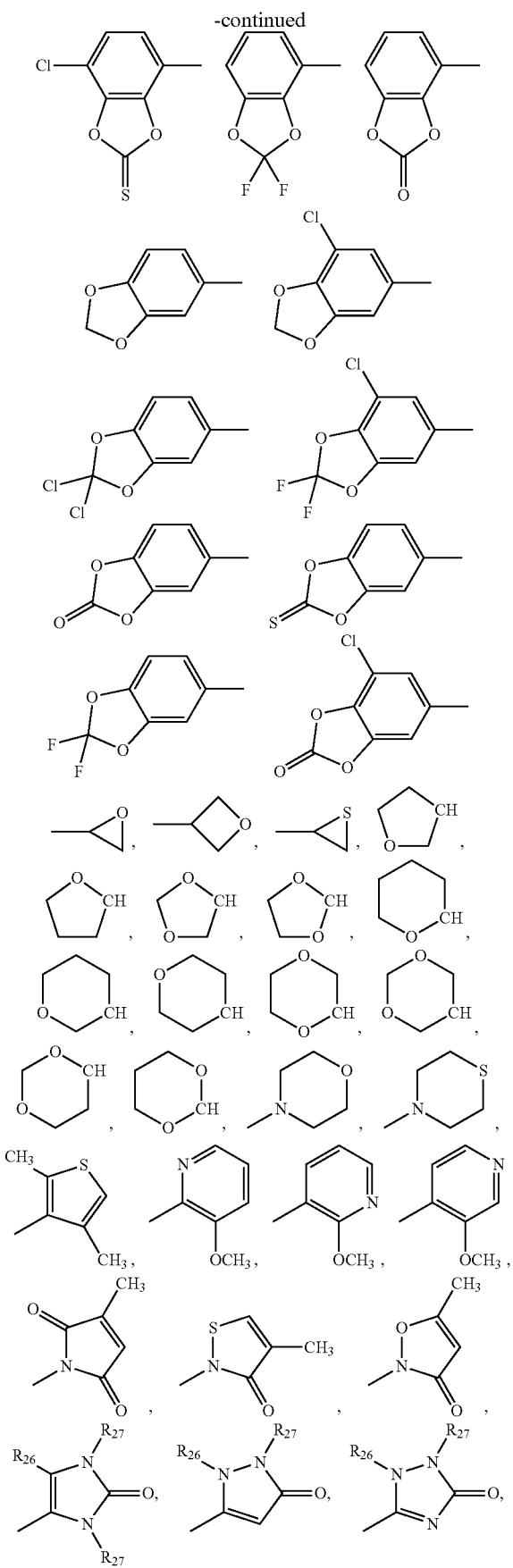
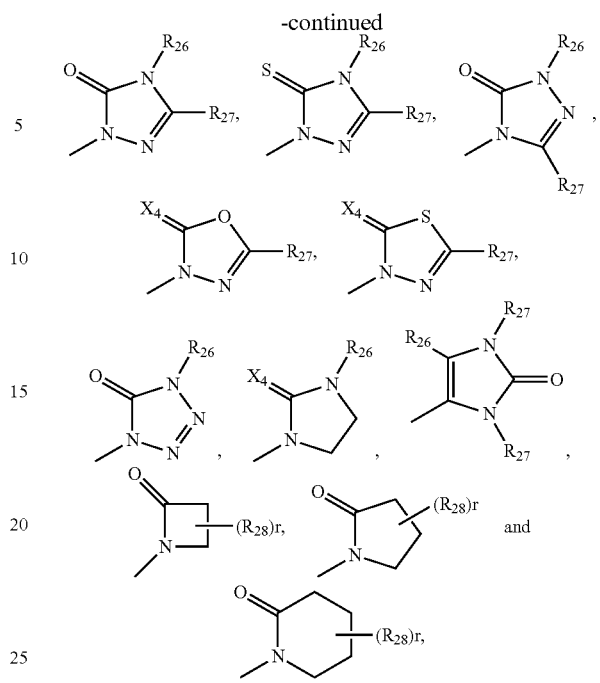

wherein each $R_{26}$ is methyl, each $R_{27}$ and each $R_{28}$ are independently hydrogen, $C_1$-$C_3$alkyl, $C_1$-$C_3$alkoxy, $C_1$-$C_3$alkylthio or trifluoromethyl, $X_4$ is oxygen or sulfur and r=1, 2, 3 or 4.

Where no free valency is indicated in those definitions, for example as in

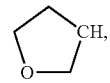

the linkage site is located at the carbon atom labelled "CH" or in a case such as, for example,

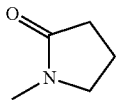

at the bonding site indicated at the bottom left.

Preferred compounds are those, wherein
ba) $R_3$, $R_4$ and $R_7$, independently from each other, are
ba1) hydrogen, halogen, cyano, nitro, mercapto, hydroxy, azido, —$SF_5$, —N=C=O, —N=C=S, amino, $(R_{51})(R_{52})(R_{53})$Si—, $(R_{51})(R_{52})(R_{53})$Si—$(C_1$-$C_6$alkyl)-, $(R_{51})(R_{52})(R_{53})$Si— $(C_2$-$C_6$alkinyl)-, $(OR_{54})(OR_{55})(OR_{56})$Si— or $(OR_{214})(OR_{215})(OR_{216})$Si—$(C_1$-$C_6$alkyl)- wherein $R_{214}$, $R_{215}$ and $R_{216}$ independently of each other, are halogen, cyano, $C_1$-$C_6$alkyl, $C_2$-$C_6$alkenyl, $C_3$-$C_8$cycloalkyl, $C_5$-$C_8$cycloalkenyl, $C_2$-$C_6$alkynyl, benzyl or phenyl; or $R_3$, $R_4$ and $R_7$, independently from each other, are
ba2) $C_1$-$C_6$alkylthio, $C_1$-$C_6$alkylsulfinyl, $C_1$-$C_6$alkylsulfonyl, $C_1$-$C_6$haloalkylthio, $C_1$-$C_6$haloalkylsulfinyl, $C_1$-$C_6$haloalkylsulfonyl, aminosulfinyl, $(C_1$-$C_6$alkyl)aminosulfonyl, di$(C_1$-$C_6$alkyl)aminosulfonyl, $C_1$-$C_6$alkyl-S(=O)$(R_{14})$=N—, $(R_{14})$S(=O)

(=N—$R_{13}$)— or ($R_{14}$)($R_{15}$)S(=O)=N—; or $R_3$, $R_4$ and $R_7$, independently from each other, are ba3) $C_1$-$C_6$alkyl, $C_2$-$C_6$alkenyl or $C_2$-$C_6$alkynyl, or $C_1$-$C_6$alkyl, $C_2$-$C_6$alkenyl or $C_2$-$C_6$alkynyl mono- to polysubstituted by substituents independently selected from the group consisting of halogen, hydroxy, mercapto, cyano, nitro, $C_1$-$C_6$alkyl, $C_1$-$C_6$haloalkyl, $C_1$-$C_6$alkoxy, $C_1$-$C_6$hydroxyalkyl, tri(alkyl)silyl, $C_1$-$C_6$haloalkoxy, $C_1$-$C_6$alkylthio, $C_1$-$C_6$haloalkylthio, $C_1$-$C_6$alkylsulfinyl, $C_1$-$C_6$haloalkylsulfinyl, $C_1$-$C_6$alkylsulfonyl and $C_1$-$C_6$haloalkylsulfonyl; or $R_3$, $R_4$ and $R_7$, independently from each other, are ba4) formyl, $C_2$-$C_7$alkoxycarbonyl, $C_2$-$C_7$haloalkoxycarbonyl, $C_3$-$C_7$alkenyloxycarbonyl, $C_3$-$C_7$haloalkenyloxycarbonyl, $C_2$-$C_7$alkylcarbonyl, carboxy, —C(=O)—Cl, —C(=O)—F, $C_2$-$C_7$haloalkylcarbonyl, $C_3$-$C_7$alkenylcarbonyl or $C_3$-$C_7$haloalkenylcarbonyl; or $R_3$, $R_4$ and $R_7$, independently from each other, are ba5) phenyl, phenoxy, benzyl or benzyloxy, or phenoxy, benzyl or benzyloxy mono- to polysubstituted by substituents independently selected from the group consisting of halogen, cyano, nitro, hydroxy, mercapto, azido, amino, —$SF_5$, $C_1$-$C_6$alkyl, $C_1$-$C_6$haloalkyl, $C_1$-$C_6$alkoxy, $C_1$-$C_6$haloalkoxy, $C_1$-$C_6$alkylthio, $C_1$-$C_6$alkylsulfinyl and $C_1$-$C_6$alkylsulfonyl; or bb) $R_3$, $R_4$ and $R_7$, independently of each other, are the groups A-, A-O— or A-($C_1$-$C_6$alkyl)-, wherein the group A is as defined above under ah);

d) $R_6$ is hydrogen, halogen, cyano, formyl, $C_1$-$C_6$alkyl, $C_1$-$C_6$haloalkyl, $C_2$-$C_6$alkenyl, $C_2$-$C_6$haloalkenyl or $C_2$-$C_6$alkinyl. and agronomically acceptable salts/metallic complexes/metalloidic complexes/isomers/structural isomers/stereoisomers/diastereoisomers/enantio-mers/tautomers/N-oxides of those compounds.

In a preferred group of compounds, $R_1$ and $R_2$, independently of each other, are hydrogen, cyano, $C_1$-$C_6$alkyl, $C_3$-$C_6$cycloalkyl, $C_2$-$C_6$alkenyl, $C_2$-$C_6$alkynyl, benzyl or $C_2$-$C_7$alkylcarbonyl, each of which may be mono- to polysubstituted by substituents independently selected from the group consisting of halogen, $C_1$-$C_6$alkyl, $C_1$-$C_6$haloalkyl, $C_1$-$C_6$alkylthio and $C_1$-$C_6$alkoxy; or and $R_2$ together form a $C_2$-$C_6$alkylene bridge which may be mono- to polysubstituted by methyl groups; or $R_1$ and $R_2$ together with their interconnecting nitrogen atom are pyrazolino, pyrazolidino, pyrrolino, imidazolino, imidazolidino, triazolino, tetrazolino, piperazino, morpholino, thiomorpholino, each of which, independently of each other, may be mono- to polysubstituted by methyl groups; or $R_1$ is hydrogen, cyano, $C_1$-$C_6$alkyl, $C_3$-$C_6$cycloalkyl, $C_2$-$C_6$alkenyl, $C_2$-$C_6$alkynyl, benzyl or $C_2$-$C_7$alkylcarbonyl, each of which may be mono- to polysubstituted by substituents independently selected from the group consisting of halogen, $C_1$-$C_6$alkyl, $C_1$-$C_6$haloalkyl, $C_1$-$C_6$alkylthio and $C_1$-$C_6$alkoxy and $R_2$ is hydroxy, amino, $C_1$-$C_6$alkoxy, $C_3$-$C_6$alkenyloxy, $C_3$-$C_8$cycloalkyloxy or $C_3$-$C_6$alkynyloxy; or $R_2$ is hydrogen, cyano, $C_1$-$C_6$alkyl, $C_3$-$C_6$cycloalkyl, $C_2$-$C_6$alkenyl, $C_2$-$C_6$alkynyl, benzyl or $C_2$-$C_7$alkylcarbonyl, each of which may be mono- to polysubstituted by substituents independently selected from the group consisting of halogen, $C_1$-$C_6$alkyl, $C_1$-$C_6$haloalkyl, $C_1$-$C_6$alkylthio and $C_1$-$C_6$alkoxy and $R_1$ is hydroxy, amino, $C_1$-$C_6$alkoxy, $C_3$-$C_6$alkenyloxy, $C_3$-$C_8$cycloalkyloxy or $C_3$-$C_6$alkynyloxy.

Further compounds of formula I are preferred, wherein $R_6$ is hydrogen, fluoro, chloro, bromo, cyano, $C_1$-$C_6$alkyl, $C_1$-$C_6$haloalkyl or CHO;

$R_7$ is hydrogen, $C_1$-$C_6$-alkyl, $C_1$-$C_6$-haloalkyl, halogen or cyano;

$R_4$ is hydrogen, $C_1$-$C_6$-alkyl, $C_1$-$C_6$-haloalkyl, $C_3$-$C_7$cycloalkyl, halogen, cyano, hydroxy, $C_1$-$C_6$alkoxy, amino, azido, mercapto, $C_1$-$C_6$alkylthio, $C_1$-$C_6$alkylsulfinyl, $C_1$-$C_6$alkylsulfonyl, CHO, $C_2$-$C_7$alkylcarbonyl, aziridino, azetidino, pyrazolino, pyrazolidino, pyrrolino, pyrrolidino, imidazolino, imidazolidino, triazolino, tetrazolino, piperazino, piperidino, morpholino, thiomorpholino; or aziridino, azetidino, pyrazolino, pyrazolidino, pyrrolino, pyrrolidino, imidazolino, imidazolidino, triazolino, tetrazolino, piperazino, piperidino, morpholino, thiomorpholino, each of which, in turn, is mono- or polysubstituted by substituents selected from the group consisting of methyl, halogen; or $R_4$ is phenyl, or phenyl which is mono- to polysubstituted by substituents independently selected from the group consisting of halogen, cyano, hydroxy, $C_1$-$C_6$alkyl, $C_1$-$C_6$haloalkyl and $C_1$-$C_6$alkoxy;

$R_3$ is hydrogen, $C_1$-$C_6$-alkyl, $C_2$-$C_6$alkenyl, $C_2$-$C_6$alkynyl, $C_3$-$C_7$cycloalkyl, halogen, cyano, azido, nitro, —N=C=O, —N=C=S, —C(=O)$NH_2$, —C(=S)NH2, —C(=O)NH($CH_3$), —C(=S)NH($CH_3$), —C(=O)N($CH_3$)$_2$, —$SO_2NH_2$, —$SO_2$NH($CH_3$), —$SO_2$N($CH_3$)$_2$, —C(=S)N($CH_3$)$_2$, —COOH, tri($C_1$-$C_4$alkyl)silyl, tri-($C_1$-$C_4$alkoxy)silyl, hydroxy, $C_1$-$C_6$alkoxy, amino, azido, mercapto, $C_1$-$C_6$alkylamino, $C_2$-$C_{12}$dialkylamino, $C_3$-$C_6$alkenylamino, $C_6$-$C_{12}$dialkenylamino, $C_1$-$C_6$alkyl$C_3$-$C_6$alkenylamino, $C_1$-$C_6$alkylthio, $C_1$-$C_6$alkylsulfinyl, $C_1$-$C_6$alkylsulfonyl, $C_1$-$C_6$haloalkylthio, $C_1$-$C_6$haloalkylsulfinyl, $C_1$-$C_6$haloalkylsulfonyl, CHO, $C_2$-$C_7$alkylcarbonyl, $C_2$-$C_6$alkoxycarbonyl, $C_3$-$C_6$alkenyloxycarbonyl, $C_3$-$C_6$alkynyloxycarbonyl, phenyl, aziridino, azetidino, pyrazolino, pyrazolidino, pyrrolino, pyrrolidino, imidazolino, imidazolidino, triazolino, tetrazolino, piperazino, piperidino, morpholino or thiomorpholino; or $R_3$ is aziridino, azetidino, pyrazolino, pyrazolidino, pyrrolino, pyrrolidino, imidazolino, imidazolidino, triazolino, tetrazolino, piperazino, piperidino, morpholino, thiomorpholino mono- or polysubstituted by substituents independently selected from the group consisting of methyl, halogen and phenyl, or by phenyl mono- to polysubstituted by substituents independently selected from the group consisting of halogen, cyano, hydroxy, $C_1$-$C_6$alkyl, $C_1$-$C_6$haloalkyl and $C_1$-$C_6$alkoxy; or $R_3$ is $C_1$-$C_6$-alkyl, $C_2$-$C_6$alkenyl, $C_2$-$C_6$alkynyl, $C_3$-$C_7$cycloalkyl, $C_1$-$C_6$alkoxy, $C_2$-$C_7$alkylcarbonyl, $C_2$-$C_6$alkoxycarbonyl, $C_3$-$C_6$alkenyloxycarbonyl, $C_3$-$C_6$alkynyloxycarbonyl or phenyl, or is phenyl mono- to polysubstituted by substituents independently selected from the group consisting of halogen, cyano, nitro, $C_1$-$C_6$alkyl, $C_1$-$C_6$haloalkyl, hydroxy, $C_1$-$C_6$alkoxy, $C_1$-$C_6$haloakoxy and phenyl, which phenyl in turn may be mono- to polysubstituted by substituents independently selected from the group consisting of halogen, cyano, hydroxy, $C_1$-$C_6$alkyl, $C_1$-$C_6$haloalkyl and $C_1$-$C_6$alkoxy;

$R_5$ is phenyl, phenyl-$C_1$-$C_{12}$alkyl, phenyl-$C_3$-$C_{12}$cyclolkyl, phenyl-$C_3$-$C_{12}$alkenyl, or phenyl, phenyl-$C_1$-$C_{12}$alkyl, phenyl-$C_3$-$C_{12}$cyclolkyl, phenyl-$C_3$-$C_{12}$alkenyl mono- to polysubstituted by substituents independently selected from the group consisting of halogen, cyano, nitro, amino, azido, hydroxy, mercapto, trialkylsilyl, trialkoxysilyl, CHO, COOH, $C_1$-$C_6$alkyl, $C_1$-$C_6$haloalkyl, $C_1$-$C_6$hydroxyalkyl, $C_3$-$C_8$cycloalkyl, $C_3$-$C_8$halocycloalkyl, $C_2$-$C_6$alkenyl, $C_2$-$C_6$haloalkenyl, $C_2$-$C_6$alkynyl, $C_2$-$C_6$haloalkynyl, $C_1$-$C_6$alkoxy, $C_1$-$C_6$haloalkoxy, $C_3$-$C_6$alkenyloxy, $C_3$-$C_6$haloalkenyloxy, $C_3$-$C_6$alkynyloxy, $C_3$-$C_6$cycloalkoxy, $C_3$-$C_6$halocycloalkoxy, $C_1$-$C_6$alkylthio, $C_1$-$C_6$alkylsulfinyl, $C_1$-$C_6$alkylsulfonyl, $C_1$-$C_6$haloalkylthio, $C_1$-$C_6$haloalkylsulfinyl, $C_1$-$C_6$haloalkylsulfonyl, —C(=O)NH$_2$, —C(=S)NH2, —C(=O)NH(CH$_3$), —C(=S)NH(CH$_3$), —C(=O)N(CH$_3$)$_2$, —SO$_2$NH$_2$, —SO$_2$NH(CH$_3$), —SO$_2$N(CH$_3$)$_2$ and —C(=S)N(CH$_3$)$_2$.

Special emphasis should also be given to compounds of formula I wherein $R_5$ is hydrogen, $(R_{51})(R_{52})(R_{53})$Si—($C_1$-$C_{12}$alkyl)-, tri$C_1$-$C_6$alkylsilyl, phenyl-di$C_1$-$C_6$alkylysilyl, $C_1$-$C_{12}$alkyl, $C_3$-$C_{12}$alkenyl, $C_3$-$C_{12}$alkynyl, $C_3$-$C_{12}$cycloalkyl, $C_3$-$C_{12}$cycloalkyl-$C_1$-$C_{12}$alkyl, $C_5$-$C_{12}$cycloalkenyl, $C_1$-$C_{12}$alkoxy-$C_1$-$C_{12}$alkyl, $C_1$-$C_{12}$alkenyloxy-$C_1$-$C_{12}$alkyl, $C_1$-$C_{12}$alkynyloxy-$C_1$-$C_{12}$alkyl, $C_1$-$C_{12}$alkylthio-$C_1$-$C_{12}$alkyl, $C_1$-$C_{12}$alkylsulfenyl-$C_1$-$C_{12}$alkyl, $C_1$-$C_{12}$alkylsulfonyl-$C_0$-$C_{12}$alkyl, $C_2$-$C_{12}$alkylcarbonyl-$C_0$-$C_{12}$alkyl, $C_3$-$C_{12}$alkenylcarbonyl-$C_0$-$C_{12}$alkyl, $C_2$-$C_{12}$alkoxylcarbonyl-$C_0$-$C_{12}$alkyl, $C_3$-$C_{12}$alkenyloxycarbonyl-$C_0$-$C_{12}$alkyl or $C_3$-$C_{12}$alkynyloxycarbonyl-$C_0$-$C_{12}$alkyl, or $R_5$ is $C_1$-$C_{12}$alkyl, $C_3$-$C_{12}$alkenyl, $C_3$-$C_{12}$alkynyl, $C_3$-$C_{12}$cycloalkyl, $C_3$-$C_{12}$cycloalkyl-$C_1$-$C_{12}$alkyl, $C_5$-$C_{12}$cycloalkenyl, $C_1$-$C_{12}$alkoxy-$C_1$-$C_{12}$alkyl, $C_1$-$C_{12}$alkenyloxy-$C_1$-$C_{12}$alkyl, $C_1$-$C_{12}$alkynyloxy-$C_1$-$C_{12}$alkyl, $C_1$-$C_{12}$alkylthio-$C_1$-$C_{12}$alkyl, $C_1$-$C_{12}$alkylsulfenyl-$C_1$-$C_{12}$alkyl, $C_1$-$C_{12}$alkylsulfonyl-$C_0$-$C_{12}$alkyl, $C_2$-$C_{12}$alkylcarbonyl-$C_0$-$C_{12}$alkyl, $C_3$-$C_{12}$alkenylcarbonyl-$C_0$-$C_{12}$alkyl, $C_2$-$C_{12}$alkoxylcarbonyl-$C_0$-$C_{12}$alkyl, $C_3$-$C_{12}$alkenyloxycarbonyl-$C_0$-$C_{12}$alkyl, $C_3$-$C_{12}$alkynyloxycarbonyl-$C_0$-$C_{12}$alkyl mono- to polysubstituted by substituents independently selected from the group consisting of halogen, cyano, nitro, amino, hydroxy, mercapto, CHO, COOH, $C_1$-$C_6$-trialkylsilyl, tri$C_1$-$C_6$alkoxysilyl, $C_1$-$C_6$alkyl, $C_1$-$C_6$haloalkyl, $C_3$-$C_8$cycloalkyl, $C_3$-$C_8$halocycloalkyl, $C_1$-$C_6$alkenyl, $C_1$-$C_6$haloalkenyl, $C_1$-$C_6$alkoxy, $C_1$-$C_6$haloalkoxy, $C_2$-$C_7$alkylcarbonyl, $C_2$-$C_7$alkoxycarbonyl, $C_2$-$C_7$alkenyloxycarbonyl, $C_2$-$C_7$alkynyloxycarbonyl, $C_1$-$C_6$alkylthio, $C_1$-$C_6$alkylsulfinyl, $C_1$-$C_6$alkylsulfonyl, —C(=O)NH$_2$, —C(=S)NH$_2$, —C(=O)NH(CH$_3$), —C(=S)NH(CH$_3$), —C(=O)N(CH$_3$)$_2$ and —C(=S)N(CH$_3$)$_2$. and $R_{51}$, $R_{52}$, and $R_{53}$ are as defined above.

A further preferred subgroup is represented by the compounds of formula I wherein $R_1$ and $R_2$, independently of each other, are $C_1$-$C_6$alkyl, $C_2$-$C_6$alkinyl, hydrogen or pyridine; or $R_1$ and $R_2$ together with their interconnecting nitrogen atom are pyrrolino;

$R_3$ is hydrogen, $C_1$-$C_6$haloalkyl, $C_1$-$C_6$alkyl, halogen, cyano, nitro, $C_1$-$C_4$alkoxy, phenyl, phenyl substituted by halogen, $(R_{51})(R_{52})(R_{53})$Si—($C_2$-$C_6$alkinyl)-, wherein $R_{51}$, $R_{52}$ and $R_{53}$ is as defined above; especially hydrogen, $C_1$-$C_6$alkyl, halogen, cyano, nitro, $C_1$-$C_4$alkoxy, phenyl, phenyl substituted by halogen, $(R_{51})(R_{52})(R_{53})$Si—($C_2$-$C_6$alkinyl)-, wherein $R_{51}$, $R_{52}$ and $R_{53}$ is as defined above;

$R_4$ is hydrogen, halogen, phenyl, imidazolyl, amino, $C_1$-$C_6$alkoxy or $C_1$-$C_6$alkyl;

$R_5$ is $C_1$-$C_{12}$alkyl or the group A, wherein

A is a three- to ten-membered monocyclic or fused bicyclic ring system which can be aromatic, partially saturated or fully saturated and can contain 1 to 4 hetero atoms selected from the group consisting of nitrogen, oxygen and sulfur, it not being possible for each ring system to contain more than 2 oxygen atoms and more than 2 sulfur atoms, and it being possible for the three- to ten-membered ring system itself to be mono- or polysubstituted by substituents independently selected from the group consisting of halogen, $C_1$-$C_6$alkyl, $C_1$-$C_6$haloalkyl, $C_1$-$C_6$alkoxy and $C_1$-$C_6$alkylthio;

$R_6$ is hydrogen; and $R_7$ is hydrogen or $C_1$-$C_6$alkyl.

In further preferred compounds of formula I, $R_6$ is —SH, —S—$C_1$-$C_6$alkyl or —S—$C_1$-$C_6$haloalkyl.

In an outstanding group of compounds of formula I $R_1$ and $R_2$, independently of each other, are $C_3$-$C_7$cycloalkyl, $C_1$-$C_6$alkyl, $C_2$-$C_6$alkinyl, hydrogen or pyridine;

or $R_1$ and $R_2$ together with their interconnecting nitrogen atom are pyrrolino;

especially $R_1$ and $R_2$, independently of each other, are $C_1$-$C_6$alkyl, $C_2$-$C_6$alkinyl, hydrogen or pyridine;

or $R_1$ and $R_2$ together with their interconnecting nitrogen atom are pyrrolino;

$R_3$ is hydrogen, $C_1$-$C_6$alkyl, $C_1$-$C_6$alkoxy, $C_1$-$C_6$haloalkyl, halogen, cyano, phenyl, phenyl substituted by halogen, $(R_{51})(R_{52})(R_{53})$Si—($C_2$-$C_6$alkinyl)-, wherein $R_{51}$, $R_{52}$ and $R_{53}$ is as defined above;

especially hydrogen, $C_1$-$C_6$alkyl, halogen, cyano, phenyl, phenyl substituted by halogen, $(R_{51})(R_{52})(R_{53})$Si—($C_2$-$C_6$alkinyl)-, wherein $R_{51}$, $R_{52}$ and $R_{53}$ is as defined above;

$R_4$ is hydrogen, halogen, $C_1$-$C_6$alkoxy or $C_1$-$C_6$alkyl;

especially hydrogen or $C_1$-$C_6$alkyl;

$R_5$ is $C_1$-$C_6$alkyl, phenyl or pyridyl or $C_1$-$C_6$alkyl, phenyl or pyridyl mono- or disubstituted by halogen, $C_1$-$C_6$alkyl, $C_1$-$C_6$haloalkyl, $C_1$-$C_6$alkoxy, $C_1$-$C_6$alkylthio, especially $C_1$-$C_6$alkyl, phenyl or pyridyl or phenyl or pyridyl mono- or disubstituted by halogen, $C_1$-$C_6$alkyl, $C_1$-$C_6$haloalkyl, $C_1$-$C_6$alkoxy, $C_1$-$C_6$alkylthio, $R_6$ is hydrogen; and $R_7$ is hydrogen or $C_1$-$C_6$alkyl. Further preferred embodiments of the present invention are the embodiments E1 to E151, which are defined as compounds of formula I which are represented by one formula selected from the group consisting of the formulae T1 to T151 as described below, wherein in formulae T1 to T151 the meanings of the substituents $R_1$, $R_2$, $R_5$ and $R_6$ have the preferred meanings as mentioned above.

For example, embodiment E1 is represented by the compounds of formula T1

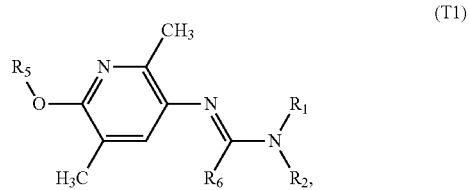

(T1)

wherein $R_1$ and $R_2$, independently of each other, are hydrogen, cyano, $C_1$-$C_6$alkyl, $C_3$-$C_6$cycloalkyl, $C_2$-$C_6$alkenyl, $C_2$-$C_6$alkynyl, benzyl or $C_2$-$C_7$alkylcarbonyl, each of which may be mono- to polysubstituted by substituents independently selected from the group consisting of halogen, $C_1$-$C_6$alkyl, $C_1$-$C_6$haloalkyl, $C_1$-$C_6$alkylthio and $C_1$-$C_6$alkoxy; or $R_1$ and $R_2$ together form a $C_2$-$C_6$alkylene bridge which may be mono- to polysubstituted by methyl groups; or $R_1$ and $R_2$ together with their interconnecting nitrogen atom are pyrazolino, pyrazolidino, pyrrolino, imidazolino, imidazolidino, triazolino, tetrazolino, piperazino, morpholino, thiomorpholino, each of which, independently of each other, may be mono- to polysubstituted by methyl groups; or $R_1$ is hydrogen, cyano, $C_1$-$C_6$alkyl, $C_3$-$C_6$cycloalkyl, $C_2$-$C_6$alkenyl, $C_2$-$C_6$alkynyl, benzyl or $C_2$-$C_7$alkylcarbonyl, each of which may be mono- to polysubstituted by substituents independently selected from the group consisting of halogen, $C_1$-$C_6$alkyl, $C_1$-$C_6$haloalkyl, $C_1$-$C_6$alkylthio and $C_1$-$C_6$alkoxy and $R_2$ is hydroxy, amino, $C_1$-$C_6$alkoxy, $C_3$-$C_6$alkenyloxy, $C_3$-$C_8$cycloalkyloxy or $C_3$-$C_6$alkynyloxy; or $R_2$ is hydrogen, cyano, $C_1$-$C_6$alkyl, $C_3$-$C_6$cycloalkyl, $C_2$-$C_6$alkenyl, $C_2$-$C_6$alkynyl, benzyl or $C_2$-$C_7$alkylcarbonyl, each of which may be mono- to polysubstituted by substituents independently selected from the group consisting of halogen, $C_1$-$C_6$alkyl, $C_1$-$C_6$haloalkyl, $C_1$-$C_6$alkylthio and $C_1$-$C_6$alkoxy and $R_1$ is hydroxy, amino, $C_1$-$C_6$alkoxy, $C_3$-$C_6$alkenyloxy, $C_3$-$C_8$cycloalkyloxy or $C_3$-$C_6$alkynyloxy;

$R_6$ is hydrogen, fluoro, chloro, bromo, cyano, $C_1$-$C_6$alkyl, $C_1$-$C_6$haloalkyl or CHO; and $R_5$ is phenyl, phenyl-$C_1$-$C_{12}$alkyl, phenyl-$C_3$-$C_{12}$cyclolkyl, phenyl-$C_3$-$C_{12}$alkenyl, or phenyl, phenyl-$C_1$-$C_{12}$alkyl, phenyl-$C_3$-$C_{12}$cyclolkyl, phenyl-$C_3$-$C_{12}$alkenyl mono- to polysubstituted by substituents independently selected from the group consisting of halogen, cyano, nitro, amino, azido, hydroxy, mercapto, trialkylsilyl, trialkoxysilyl, CHO, COOH, $C_1$-$C_6$alkyl, $C_1$-$C_6$haloalkyl, $C_1$-$C_6$hydroxyalkyl, $C_3$-$C_8$cycloalkyl, $C_3$-$C_8$halocycloalkyl, $C_2$-$C_6$alkenyl, $C_2$-$C_6$haloalkenyl, $C_2$-$C_6$alkynyl, $C_2$-$C_6$haloalkynyl, $C_1$-$C_6$alkoxy, $C_1$-$C_6$haloalkoxy, $C_3$-$C_6$alkenyloxy, $C_3$-$C_6$haloalkenyloxy, $C_3$-$C_6$alkynyloxy, $C_3$-$C_6$cycloalkoxy, $C_3$-$C_6$halocycloalkoxy, $C_1$-$C_6$alkylthio, $C_1$-$C_6$alkylsulfinyl, $C_1$-$C_6$alkylsulfonyl, $C_1$-$C_6$haloalkylthio, $C_1$-$C_6$haloalkylsulfinyl, $C_1$-$C_6$haloalkylsulfonyl, —C(=O)NH2, —C(=S)NH2, —C(=O)NH(CH_3), —C(=S)NH(CH_3), —C(=O)N(CH_3)_2, —SO_2NH_2, —SO_2NH(CH_3), —SO_2N(CH_3)_2 and —C(=S)N(CH_3)_2.

Special emphasis should also be given to compounds of embodiment E1 wherein $R_5$ is hydrogen, tri$C_1$-$C_6$alkylsilyl, phenyl-di$C_1$-$C_6$alkylsilyl, $C_1$-$C_{12}$alkyl, $C_3$-$C_{12}$alkenyl, $C_3$-$C_{12}$alkynyl, $C_3$-$C_{12}$cycloalkyl, $C_3$-$C_{12}$cycloalkyl-$C_1$-$C_{12}$alkyl, $C_6$-$C_{12}$cycloalkenyl, $C_1$-$C_{12}$alkoxy-$C_1$-$C_{12}$alkyl, $C_1$-$C_{12}$alkenyloxy-$C_1$-$C_{12}$alkyl, $C_1$-$C_{12}$alkynyloxy-$C_1$-$C_{12}$alkyl, $C_1$-$C_{12}$alkylthio-$C_1$-$C_{12}$alkyl, $C_1$-$C_{12}$alkylsulfenyl-$C_1$-$C_{12}$alkyl, $C_1$-$C_{12}$alkylsulfonyl-$C_0$-$C_{12}$alkyl, $C_2$-$C_{12}$alkylcarbonyl-$C_0$-$C_{12}$alkyl, $C_3$-$C_{12}$alkenylcarbonyl-$C_0$-$C_{12}$alkyl, $C_2$-$C_{12}$alkoxylcarbonyl-$C_0$-$C_{12}$alkyl, $C_3$-$C_{12}$alkenyloxycarbonyl-$C_0$-$C_{12}$alkyl, $C_3$-$C_{12}$alkynyloxycarbonyl-$C_0$-$C_{12}$alkyl or $C_3$-$C_{12}$alkynyloxycarbonyl-$C_0$-$C_{12}$alkyl, or $R_5$ is $C_1$-$C_{12}$alkyl, $C_3$-$C_{12}$alkenyl, $C_3$-$C_{12}$alkynyl, $C_3$-$C_{12}$cycloalkyl, $C_3$-$C_{12}$cycloalkyl-$C_1$-$C_{12}$alkyl, $C_6$-$C_{12}$cycloalkenyl, $C_1$-$C_{12}$alkoxy-$C_1$-$C_{12}$alkyl, $C_1$-$C_{12}$alkenyloxy-$C_1$-$C_{12}$alkyl, $C_1$-$C_{12}$alkynyloxy-$C_1$-$C_{12}$alkyl, $C_1$-$C_{12}$alkylthio-$C_1$-$C_{12}$alkyl, $C_1$-$C_{12}$alkylsulfenyl-$C_1$-$C_{12}$alkyl, $C_1$-$C_{12}$alkylsulfonyl-$C_0$-$C_{12}$alkyl, $C_2$-$C_{12}$alkylcarbonyl-$C_0$-$C_{12}$alkyl, $C_3$-$C_{12}$alkenylcarbonyl-$C_0$-$C_{12}$alkyl, $C_2$-$C_{12}$alkoxylcarbonyl-$C_0$-$C_{12}$alkyl, $C_3$-$C_{12}$alkenyloxycarbonyl-$C_0$-$C_{12}$alkyl, $C_3$-$C_{12}$alkynyloxycarbonyl-$C_0$-$C_{12}$alkyl mono- to polysubstituted by substituents independently selected from the group consisting of halogen, cyano, nitro, amino, hydroxy, mercapto, CHO, COOH, $C_1$-$C_6$-trialkylsilyl, tri$C_1$-$C_6$alkoxysilyl, $C_1$-$C_6$alkyl, $C_1$-$C_6$haloalkyl, $C_3$-$C_8$cycloalkyl, $C_3$-$C_8$halocycloalkyl, $C_1$-$C_6$alkenyl, $C_1$-$C_6$haloalkenyl, $C_1$-$C_6$alkoxy, $C_1$-$C_6$haloalkoxy, $C_2$-$C_7$alkylcarbonyl, $C_2$-$C_7$alkoxycarbonyl, $C_2$-$C_7$alkenyloxycarbonyl, $C_2$-$C_7$alkynyloxycarbonyl, $C_1$-$C_6$alkylthio, $C_1$-$C_6$alkylsulfinyl, $C_1$-$C_6$alkylsulfonyl, —C(=O)NH_2, —C(=S)NH_2, —C(=O)NH(CH_3), —C(=S)NH(CH_3), —C(=O)N(CH_3)_2 and —C(=S)N(CH_3)_2.

In further preferred group of compounds of embodiment E1, $R_6$ is —SH, —S—$C_1$-$C_6$alkyl or —S—$C_1$-$C_6$haloalkyl.

In an outstanding group of compounds of embodiment E1, $R_1$ and $R_2$, independently of each other, are $C_1$-$C_6$alkyl, $C_2$-$C_6$alkinyl, hydrogen or pyridine;

or $R_1$ and $R_2$ together with their interconnecting nitrogen atom are pyrrolino;

$R_5$ is $C_1$-$C_6$alkyl, phenyl or pyridyl or phenyl or pyridyl mono- or disubstituted by substituents selected from the group consisting of halogen, $C_1$-$C_6$alkyl, $C_1$-$C_6$haloalkyl, $C_1$-$C_6$alkoxy and $C_1$-$C_6$alkylthio; and $R_6$ is hydrogen. The substituents $R_1$, $R_2$, $R_5$ and $R_6$ of the embodiments E2 to E151 are defined accordingly.

Compounds of formula I as well as intermediates and reagents used can be prepared by methods known to a skilled chemist in a variety of ways, or they are commercially available.

Compounds of formula I can be prepared by a number of known methods from amino compounds of formula II. Such methods include the following:

a) Scheme 1 below: An amide of formula $(R_6)C(=O)$—N$(R_1)(R_2)$, or a formamide of formula HC(=O)—N$(R_1)(R_2)$, is treated with reagents like POCl_3, PCl_3, SOCl_2, COCl_2, Ph—SO_2Cl, Me_2N—SO_2Cl, $(CF_3CO)_2O$ and then with an amino compound of formula II.

b) Scheme 1 below: Reacting the amino derivative of formula II, wherein $R_3$, $R_4$, $R_5$ and $R_7$ is as defined under formula I above, with a compound of formula $R_6$—$C(OR)_2$—$N(R_1)(R_2)$, wherein $R_1$, $R_2$ and $R_6$ is as defined under formula I above, or with a compound of formula $R_6$—C(OR)(NR_1R_2)_2$, wherein R is preferably an alkyl or phenyl group and $R_1$, $R_2$ and $R_6$ is as defined under formula I above, or, for the former reagent, the two R together form an alkylidene fragment. Such transformations are described in the literature, e.g. in: Bashkirskii Khimicheskii Zhurnal (2000), 7 (2), 5-9; Indian Journal of Chemistry, Section B: Organic Chemistry Including Medicinal Chemistry (1981), 20B(12), 1075-7; ARKIVOC (Gainesville, Fla., United States) (2004), (10), 20-38.

Scheme 1

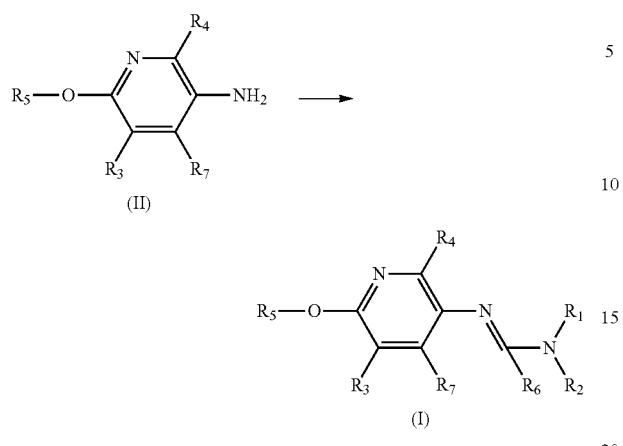

c) Scheme 2 below: An amino derivative of formula II can be converted into an amide and this, in turn, into the final compound of formula I by a two step sequence: 1) activation (using e.g. $PCl_5$ or $Ph_3PO$ together with $(CF_3SO_2)_2O$, followed 2) by the reaction with a amine of formula $HN(R_1)(R_2)$, wherein $R_1$ and $R_2$ is as defined under formula I above. Such methods are describe in the literature, e.g. in Journal of Organic Chemistry (1989), 54 (5), 1144-9; Zhurnal Organicheskoi Khimii (1989), 25 (2), 357-67.

Scheme 2

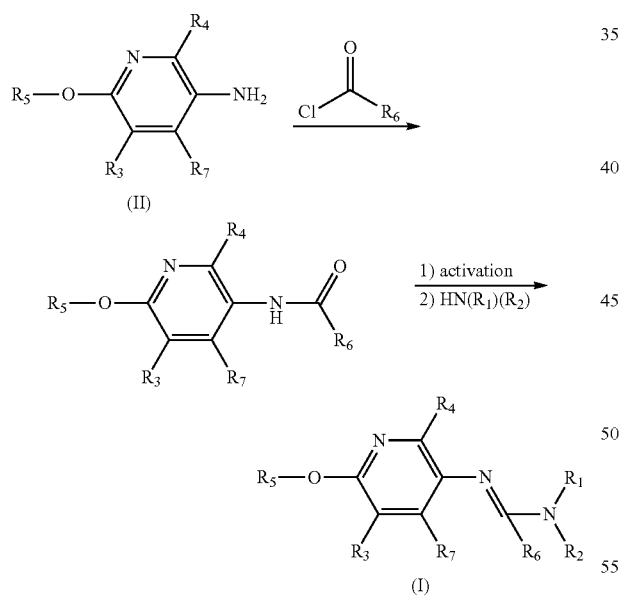

d) Scheme 3 below: An amino derivative of formula II can first be transformed into the corresponding isocyanate. This one, in turn, is then reacted with a formamide of general formula $HC(=O)-N(R_1)(R_2)$, wherein $R_1$ and $R_2$ is as defined under formula I above, to obtain a formamidine of formula I. Such methods are to be found in the literature, e.g. in Journal of Pharmaceutical Sciences (1964), 53 (12), 1539-40; Journal für Praktische Chemie (Leipzig) (1961), 13, 265-71.

Scheme 3

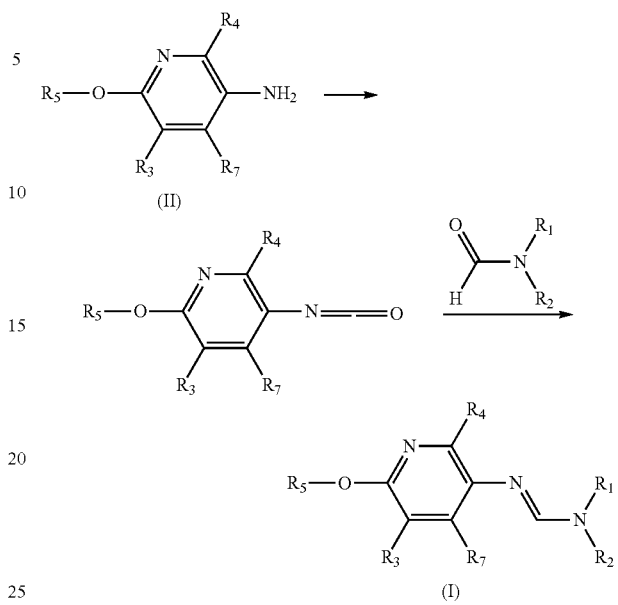

e) Scheme 4 below: Compounds of general formulas ($I_{e2}$) and ($I_{e1}$) are subsets of compounds described by general formula (I). Compounds of general formula ($I_{e2}$) can be obtained by reacting a compound of general formula ($I_{e1}$) with an amine of formula $HN(R_{1e})(R_{2e})$ under appropriate conditions. Fragments of the formula $-N(R_{1e1})(R_{2e1})$ are a subset of fragments of the formula $-N(R_1)(R_2)$, and compounds of the formula $HN(R_{1e2})(R_{2e2})$ form a subset of compounds of formula $HNR_1R_2$. Such procedures can be found in the literature, e.g. in Tetrahedron Letters (1989), 30 (1), 47-50; Khimicheskii Zhurnal (2000), 7 (2), 5-9.

Scheme 4

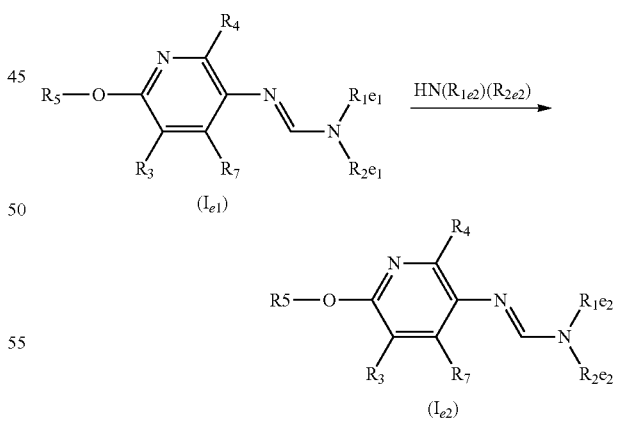

f) Scheme 5 below: Compounds of general formula $I_{f1}$ being a subset of compounds of formula I, may be prepared by acylating or alkylating compounds of formula $I_{f1}$. Such protocols are to be found in the literature, e.g. in Chemical & Pharmaceutical Bulletin (1983), 31 (10), 3534-43; Zhurnal Organicheskoi Khimii (1989), 25 (2), 357-67; Tetrahedron (2000), 56 (39), 7811-7816; Journal of the Chemical Society, Transactions (1923), 123, 3359-75.

Scheme 5

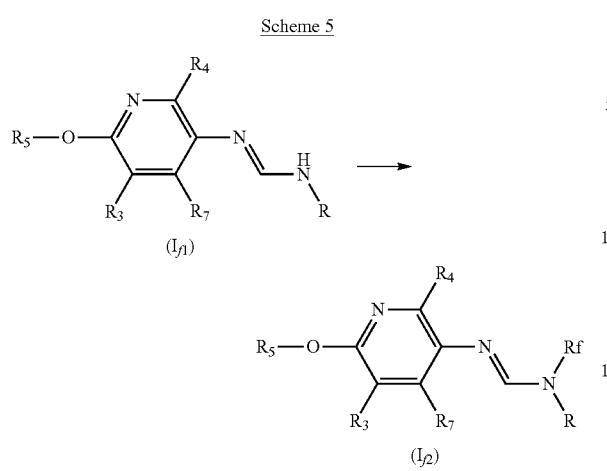

Substituents of formulas R and R$_f$ are subsets of substituents of formula R$_1$ (or R$_2$).

Compounds of formula II may be prepared from the corresponding nitro derivatives of formula III by a variety of reduction procedures.

g) Scheme 6 below: The reduction methods include transformation of the nitro compound of formula III, wherein R$_3$, R$_4$, R$_5$ and R$_7$ is as defined under formula I above, in the presence of a catalyst, e.g. Pd-, Ni- or Pt-based catalysts, and molecular hydrogen, in a suitable solvent at ambient temperature or at elevated temperatures, at normal or at a higher pressure, or the reduction may be carried out by one of several metal reduction methods, e.g. using metals such as Fe, Sn, Zn or reagents such as SnCl$_2$ in an acidic and/or protic medium.

Scheme 6

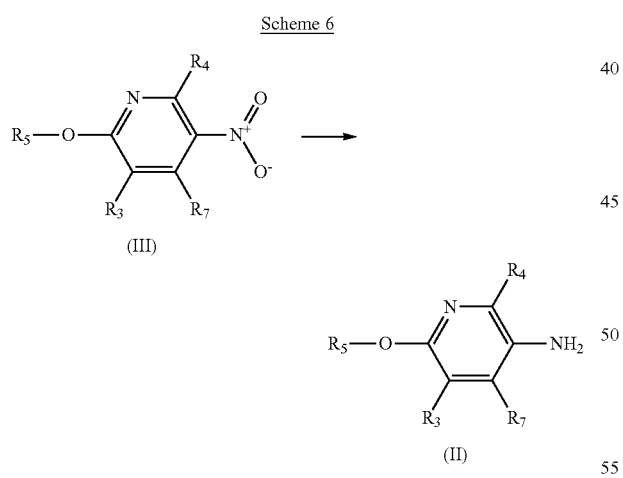

Nitro compounds of formula III may be prepared in a number of ways. These include the following:

h) Scheme 7 below: Compounds of formula III can be obtained from compounds of1 formula IV, wherein R$_3$, R$_4$ and R$_7$ are as defined under formula I above, having a leaving group R$_{100}$, where R$_{100}$ is SH—, nitro, halogen, imidazolyl, triazolyl, C$_1$-C$_6$alkylthio, C$_1$-C$_6$alkylsulfenyl or C$_1$-C$_6$alkysulfonyl, preferably halogen, C$_1$-C$_6$alkylthio, C$_1$-C$_6$alkylsulfenyl, C$_1$-C$_6$alkylsulfonyl, in particular F, Cl, Br, I, MeS—, MeSO— or MeSO$_2$—; or R$_{100}$ is imidazolyl, triazolyl, PhSO$_2$—, CF$_3$SO$_2$—O—, p-MeC$_6$H$_4$SO$_2$O—, O$_2$N—) by reaction with R$_5$—OH, wherein R$_5$ is as defined under formula I above, in the presence of a base. This conversion may be effected by using a preformed salt of R$_5$OH.

Scheme 7:

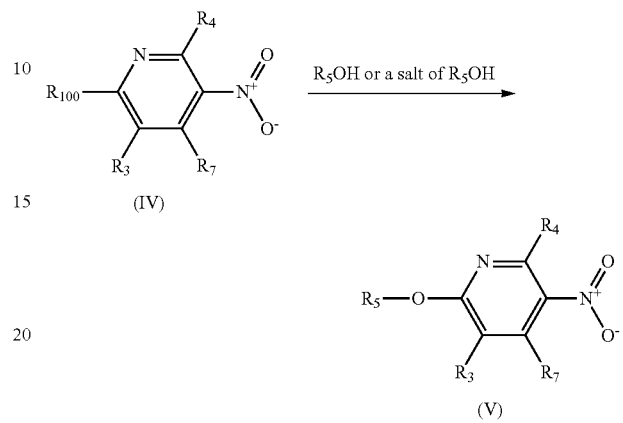

i) Scheme 8 below: Compounds of formula III, may be obtained by reacting a precursor of formula IV$_i$ either with an electrophilic precursor R$_{5i}$—X, R$_{5i}$ being a being a suitable subset of R$_5$ and X being a leaving group such as a halogen or MeSO$_2$O or p-MeC$_6$H$_4$SO$_2$O, the reaction conducted preferentially in the presence of a base. Or, alternatively, compound IV, can be reacted with an alcohol of formula R$_5$, —OH under Mitsunobu conditions, using e.g. Ph$_3$P, EtO-C—N═N—CO-OEt in solvents such as dioxane, THF or toluene. Such methods are described in the literature, e.g. in Journal of Medicinal Chemistry (2006), 49 (15), 4455-4458; Tetrahedron Letters (2006), 47 (28), 4897-4901.

Scheme 8

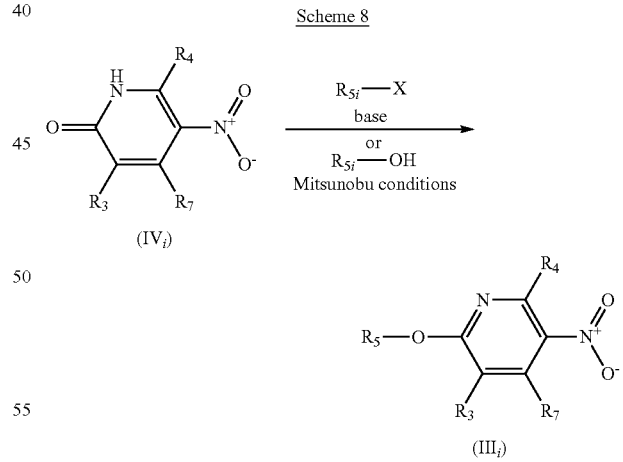

j) Scheme 9 below: Nitro compounds of formula III$_j$, being a subset of compounds of formula III, can also be obtained by using a suitable precursor V$_j$ with a group Y, e.g. a halogen or a group CF$_3$SO$_2$O, that can be used to introduce R$_{3j}$, R$_{3j}$ being a subset of R$_3$. For such transformations a large number of methods are firmly established and described in the literature (e.g. Suzuki, Suzuki-Miyaura, Negishi, Stille coupling reactions, or Heck and Sonogashira reactions).

Scheme 9

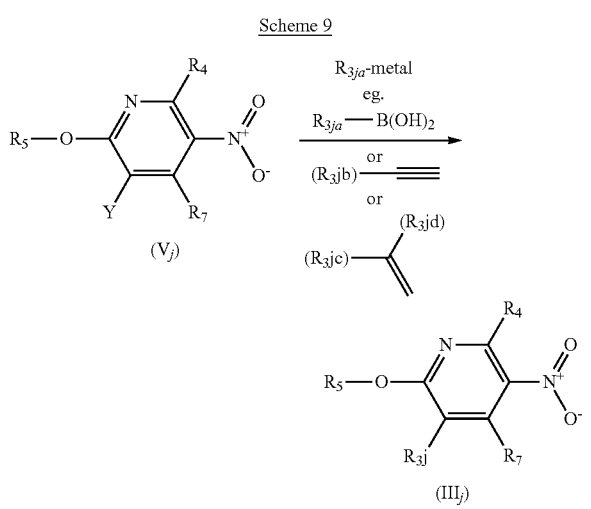

$R_{3ja}$, $R_{3jb}$, $R_{3jc}$, and $R_{3jd}$ are such that the resulting fragment $R_{3j}$ is within the definition of fragments of substituent $R_3$.

k) Scheme 10 below: Compounds of formula III$_k$, being a subset of compounds described by formula III, may be obtained as described in scheme 10 by using well-established methods. This includes e.g. Suzuki-Miyaura and Stille coupling reactions using the electrophilic species $(R_{3k1})$—X, X being a leaving group, in particular Cl, Br or I. Within the definition given in scheme 10, $R_{3k1}$ is part of the many molecular scaffolds that are commonly used for the reactions possible here. $(R_{3k1})$—X includes aryl-, hetaryl- or vinyl-based halides. The method described here includes also reactions with a precursor $(R_{5k2})$—H, forming a nucleophilic species under appropriate conditions to be attached to the pyridine core fragment of $(V_k)$. Among the latter cases are e.g. amination reactions or reactions with a precursor carbonyl compound (displaying CH acidity ∏ to the carbonyl). In both cases, there are many catalytic systems described in the literature to effect transformation.

Scheme 10

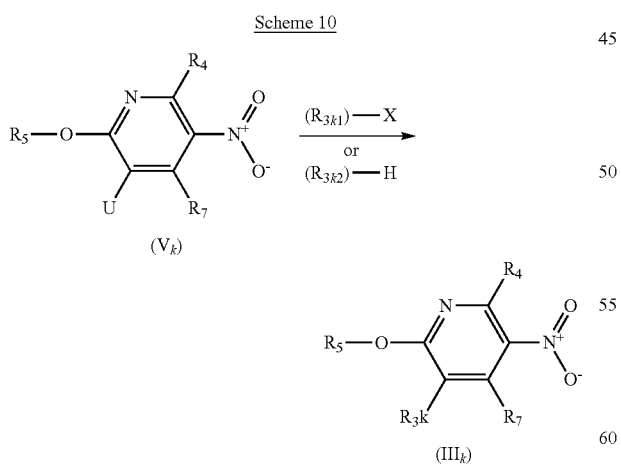

U being a metal-based fragment (eg. B(OH)$_2$ or SnBu$_3$) $R_{3ka}$, $R_{3k}$ both being such that fragments of formula $R_{3k}$ are within the definition of fragments of formula $R_3$.

l) Scheme 11 below: Compounds of formula III$_L$, being a subset of compounds of formula III, may be obtained by the reaction of electrophilic compounds of formula $(R_{3La})$—X (X being a leaving group, such as a halogen or MeSO$_2$O) with the anion generated from compounds of formula V$_L$ with a base under suitable conditions, as is well-described in the literature.

Scheme 11

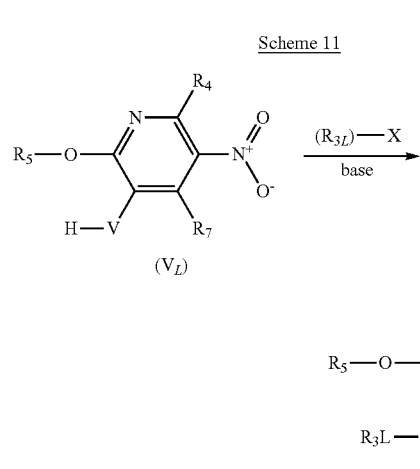

H—V being a fragment that can give a anionic fragment V— upon reaction with a base, and H—V and (R$_{3L}$) being such that the fragments of formula R$_{3L}$—V— are a subset of fragments of general formula R$_3$—.

m) Scheme 12 below: Compounds of formula III$_m$, being a subset of compounds of formula III, can also be prepared by transforming a precursor functional group $R_{3m1}$ into the group $R_{3m}$. Fragments of formula $R_{3m}$, being a subset of the fragments defined by the formula $R_3$, and the precursor fragment of formula $R_{3ma}$ being such that the definitions of formula $R_{3m}$ are valid after the transformation has been carried out. By way of example: $(R_{3m1})$— can be HCO— that can be converted into F$_2$CH— using reagents such as DAST or SF$_4$, or $(R_{3m1}$—) can be H$_3$C—H$_2$C—S— that can be transformed into H$_3$C—H$_2$C—S(=O)— and H$_3$C—H$_2$C—S(=O)$_2$— oxidatively using standard methods that are well-described in the literature; or $(R_{3m1}$—) can be —C=S)NH$_2$ that can be transformed into a optionally substituted thiazolyl fragment using standard methods as described in the literature.

Scheme 12

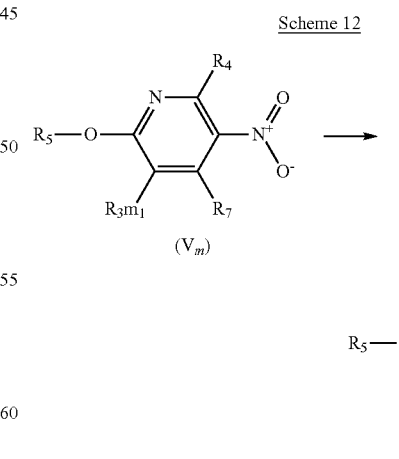

n) The methods introduced above—under j) to m)—dealing with the introduction and transformation of the substituent $R_3$, can also be applied in the cases of the substituents $R_4$ and $R_7$.

o) Scheme 13 below: The methods mentioned above under j) to m) are also applicable, in a proper form, for the elaboration of compounds of formula $III_o$, describing compounds of a subset of compounds of the formula III. In this case, a suitable substituent $R_{5o1}$, is transformed into a substituent $R_{5o}$, substituents $R_{5o}$ being a subset of substituent $R_5$.

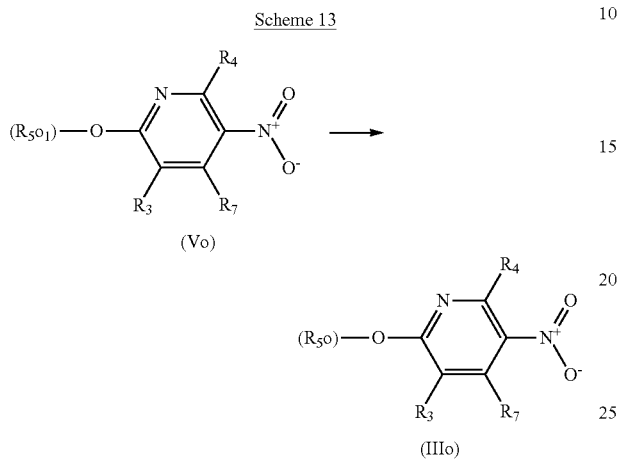

p) Scheme 14 below: The methods as described above under chapters g) to o) are also valid for the cases, where the nitro group is replaced by a hydrogen or by a amino group, or by a suitably protected amino group (such as are e.g. —NH—C(=O)—CH$_3$, —NH—C(=O)-tert-butyl, —NH-benzoyl, —N(C(=O)—CH$_3$)$_2$, -phthaloyl, —N(benzyl)$_2$, —NH—C(=O)—O-tert-butyl), or by some amidine group —N=C(R$_6$)—N(R$_1$)(R$_2$). One skilled in the art knows, however, that this is not a general principle, but applies to cases with compatible functional groups. By way of example, this scenario is shown in scheme 14 for the transformations described in chapter m) above for the case where an amidine group is present instead of the nitro function (formula X). Cf. definitions of $R_{3m1}$ and $R_{3m}$ in chapter m) above and $R_{100}$ is as defined in chapter h) above. The compounds of formula X wherein $R_1$, $R_2$, $R_3$, $R_4$, $R_6$ and $R_7$ are as defined under formula I in claim I and $R_{100}$ is SH—, nitro, halogen, imidazolyl, triazolyl, $C_1$-$C_6$alkylthio, $C_1$-$C_6$alkylsulfenyl or $C_1$-$C_6$alkysulfonyl are novel and therefore represent a further object of the present invention.

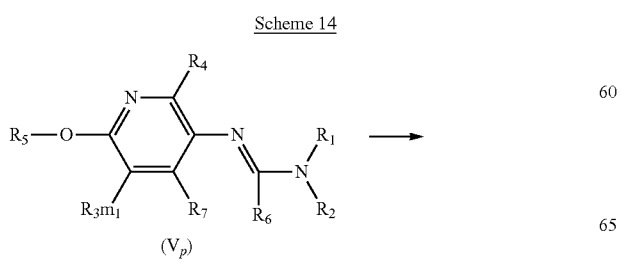

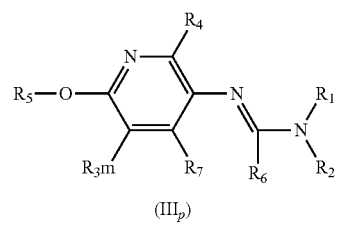

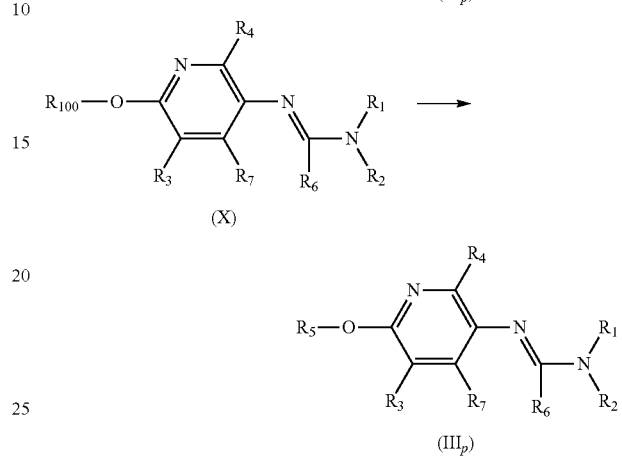

q) Scheme 15 below: Compounds of the formula III can be prepared by direct nitration of a suitable precursor, provided the nitration protocol in question is compatible with the starting material. This nitration can be carried out in a number of well-established ways. E.g. using the mixed acid system of HNO$_3$ and H$_2$SO$_4$. Along these lines, the precursor VI may be dissolved first in H$_2$SO$_4$ and reacted with the mixed acid system, or it may be treated directly with the mixed acid system under a variety of conditions. In addition, the nitration may be carried out in an inert solvent system, using nitrating agents such as BF$_4$NO$_4$. Nitration may also be carried out using HNO$_3$ in an appropriate solvent such as H$_2$O, AcOH, acetic acid anhydride. The same methods may also be applied to a suitable precursor of formula VII to give a compound of formula IV. X is a leaving group as defined in chapter h) above.

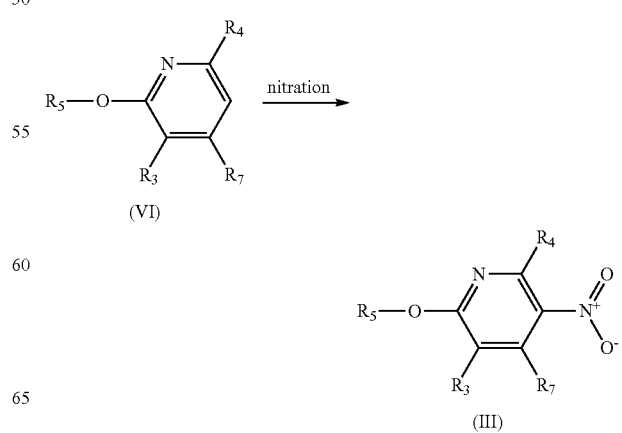

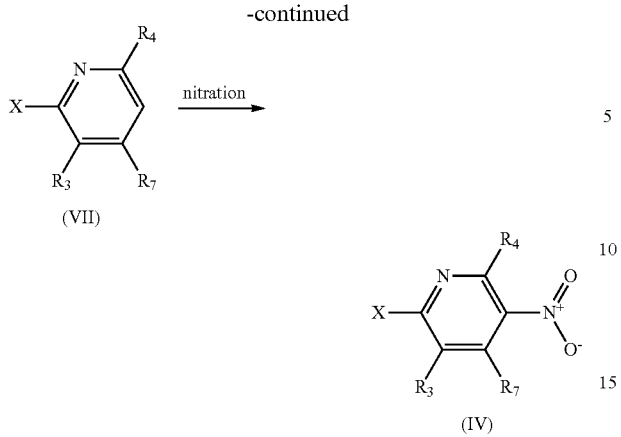

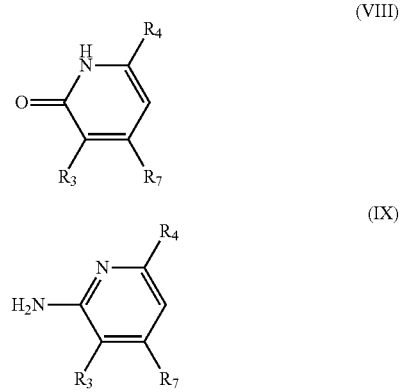

r) Scheme16 below: Compounds of formula VII can be synthesized by a number of well-established methods. In particular by transforming a precursors of formulae VIII or IX. X is a leaving group as defined in chapter h) above.

r1) If a compound of formula VIII is the precursor the methods include the transformation to a compound where X is Cl, with reagents such as $PCl_5$, $POCl_3$, $SOCl_2$ or ClCO—COCl normally under heating in an inert solvent, either without or in the presence of a suitable base. If X is Br, the preferred reagents include $POBr_3$, $PBr_3$ and NBS together with $Ph_3P$. If X is $CF_3SO_2O$, preferred preparative methods use reagents such as $(CF_3SO_2)_2O$ in the presence of a base, e.g. $Et_3N$ or 2,6-lutidine.

r2) If a compound of formula (IX) is the precursor, preferred procedures include the following. If X is equal to Cl or Br, a Sandmeyer-type protocol can be used, i.e. diazotization followed by reaction with cuprous chloride or bromide. Or, X is F, in which case, after diazotization, a diazonium fluoroborate salt is produced that is then converted to the fluoro derivative. The fluoroborate may also be produced with an organic nitrite and $BF_3$-etherate.

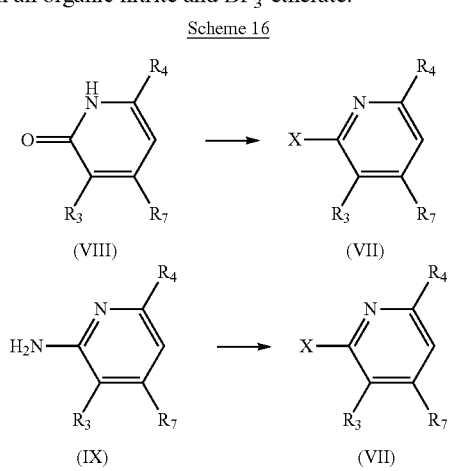

s) Scheme 17 below: A large number of compounds of formulae VIII and IX or of compounds being potential precursors thereof are commercially available. In addition, there are many ways of achieving the syntheses of pyridine building blocks of general formulae VIII and 1×as is amply documented in the literature. By way of example, we mention the following 3 syntheses within the general definition of compounds of formula IX in schemes 18 to 20 below.

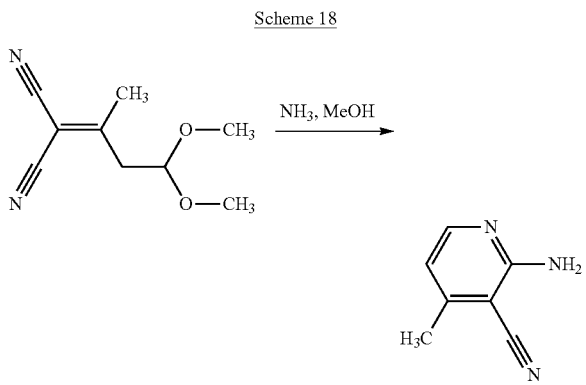

Journal of Organic Chemistry (2005), 70 (4), 1364-1368

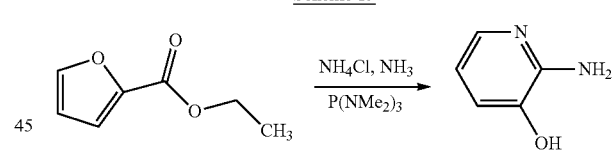

Journal of Heterocyclic Chemistry (1977), 14 (2), 203-5

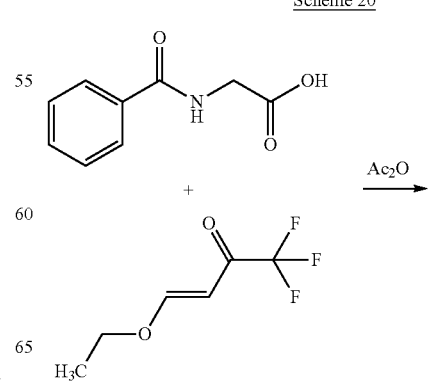

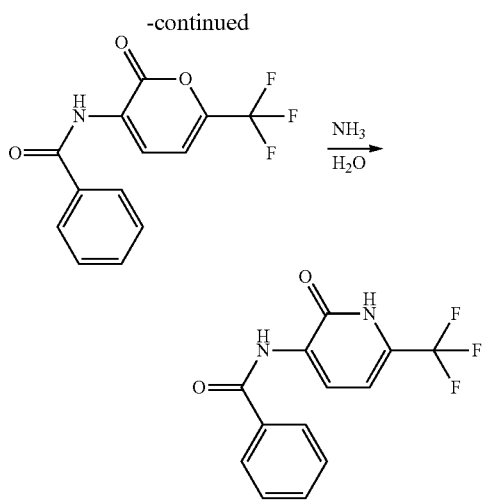

Synthesis (2005), (8), 1269-1278

The reactions leading to compounds of formula I are advantageously carried out in aprotic inert organic solvents. Such solvents are hydrocarbons such as benzene, toluene, xylene or cyclohexane, chlorinated hydrocarbons such as dichloromethane, trichloromethane, tetrachloromethane or chlorobenzene, ethers such as diethyl ether, ethylene glycol dimethyl ether, diethylene glycol dimethyl ether, tetrahydrofuran or dioxane, nitriles such as acetonitrile or propionitrile, amides such as N,N-dimethylformamide, diethylformamide or N-methylpyrrolidinone. The reaction temperatures are advantageously between −20° C. and +120° C. In general, the reactions are slightly exothermic and, as a rule, they can be carried out at room temperature. To shorten the reaction time, or else to start the reaction, the mixture may be heated briefly to the boiling point of the reaction mixture. The reaction times can also be shortened by adding a few drops of base as reaction catalyst. Suitable bases are, in particular, tertiary amines such as trimethylamine, triethylamine, quinuclidine, 1,4-diazabicyclo[2.2.2]octane, 1,5-diazabicyclo[4.3.0]non-5-ene or 1,5-diazabicyclo-[5.4.0]undec-7-ene. However, inorganic bases such as hydrides, e.g. sodium hydride or calcium hydride, hydroxides, e.g. sodium hydroxide or potassium hydroxide, carbonates such as sodium carbonate and potassium carbonate, or hydrogen carbonates such as potassium hydrogen carbonate and sodium hydrogen carbonate may also be used as bases. The bases can be used as such or else with catalytic amounts of a phase-transfer catalyst, for example a crown ether, in particular 18-crown-6, or a tetraalkylammonium salt.

The compounds of formula I can be isolated in the customary manner by concentrating and/or by evaporating the solvent and purified by recrystallization or trituration of the solid residue in solvents in which they are not readily soluble, such as ethers, aromatic hydrocarbons or chlorinated hydrocarbons.

The compounds of formula I and, where appropriate, the tautomers thereof, can be present in the form of one of the isomers which are possible or as a mixture of these, for example in the form of pure isomers, such as antipodes and/or diastereomers, or as isomer mixtures, such as structural isomer, stereo isomer, diastereoisomer and enantiomer mixtures, for example racemates, diastereomer mixtures or racemate mixtures, depending on the number, absolute and relative configuration of asymmetric carbon atoms which occur in the molecule and/or depending on the configuration of non-aromatic double bonds which occur in the molecule; the invention relates to the pure isomers and also to all isomer mixtures which are possible and is to be understood in each case in this sense hereinabove and hereinbelow, even when stereochemical details are not mentioned specifically in each case.

Diastereo-isomeric mixtures or racemate mixtures of compounds I, which can be obtained depending on which starting materials and procedures have been chosen can be separated in a known manner into the pure diasteromers or racemates on the basis of the physicochemical differences of the components, for example by fractional crystallization, distillation and/or chromatography.

Enantiomeric mixtures, such as racemates, which can be obtained in a similar manner can be resolved into the optical antipodes by known methods, for example by recrystallization from an optically active solvent, by chromatography on chiral adsorbents, for example high-performance liquid chromatography (HPLC) on acetyl celulose, with the aid of suitable microorganisms, by cleavage with specific, immobilized enzymes, via the formation of inclusion compounds, for example using chiral crown ethers, where only one enantiomer is complexed, or by conversion into diastereomeric salts, for example by reacting a basic end-product racemate with an optically active acid, such as a carboxylic acid, for example camphor, tartaric or malic acid, or sulfonic acid, for example camphorsulfonic acid, and separating the diastereomer mixture which can be obtained in this manner, for example by fractional crystallization based on their differing solubilities, to give the diastereomers, from which the desired enantiomer can be set free by the action of suitable agents, for example basic agents.

Pure diastereomers or enantiomers can be obtained according to the invention not only by separating suitable isomer mixtures, but also by generally known methods of diastereoselective or enantioselective synthesis, for example by carrying out the process according to the invention with starting materials of a suitable stereochemistry.

It is advantageous to isolate or synthesize in each case the biologically more effective isomer, for example enantiomer or diastereomer, or isomer mixture, for example enantiomer mixture or diastereomer mixture, if the individual components have a different biological activity.

The compounds I and, where appropriate, the tautomers thereof, can, if appropriate, also be obtained in the form of hydrates and/or include other solvents, for example those which may have been used for the crystallization of compounds which are present in solid form.

It has now been found that the compounds of formula I according to the invention have, for practical purposes, a very advantageous spectrum of activities for protecting useful plants against diseases that are caused by phytopathogenic microorganisms, such as fungi, bacteria or viruses.

The invention relates to a method of controlling or preventing infestation of useful plants by phytopathogenic microorganisms, wherein a compound of formula I is applied as active ingredient to the plants, to parts thereof or the locus thereof. The compounds of formula I according to the invention are distinguished by excellent activity at low rates of application, by being well tolerated by plants and by being environmentally safe. They have very useful curative, preventive and systemic properties and are used for protecting numerous useful plants. The compounds of formula I can be used to inhibit or destroy the diseases that occur on plants or parts of plants (fruit, blossoms, leaves, stems, tubers, roots) of different crops of useful plants, while at the same time protecting also those parts of the plants that grow later e.g. from phytopathogenic microorganisms.

It is also possible to use compounds of formula I as dressing agents for the treatment of plant propagation material, in particular of seeds (fruit, tubers, grains) and plant cuttings (e.g. rice), for the protection against fungal infections as well as against phytopathogenic fungi occurring in the soil.

Furthermore the compounds of formula I according to the invention may be used for controlling fungi in related areas, for example in the protection of technical materials, including wood and wood related technical products, in food storage or in hygiene management.

The compounds of formula I are, for example, effective against the phytopathogenic fungi of the following classes: Fungi imperfecti (e.g. *Botrytis, Pyricularia, Helminthosporium, Fusarium, Septoria, Cercospora* and *Alternaria*) and Basidiomycetes (e.g. *Rhizoctonia, Hemileia, Puccinia*). Additionally, they are also effective against the Ascomycetes classes (e.g. *Venturia* and *Erysiphe, Podosphaera, Monilinia, Uncinula*) and of the Oomycetes classes (e.g. *Phytophthora, Pythium, Plasmopara*). Outstanding activity has been observed against powdery mildew (*Erysiphe* spp.). Furthermore, the novel compounds of formula I are effective against phytopathogenic bacteria and viruses (e.g. against *Xanthomonas* spp, *Pseudomonas* spp, *Erwinia amylovora* as well as against the tobacco mosaic virus). Good activity has been observed against Asian soybean rust (*Phakopsora pachyrhizi*).

Within the scope of the invention, useful plants to be protected typically comprise the following species of plants: cereal (wheat, barley, rye, oat, rice, maize, sorghum and related species); beet (sugar beet and fodder beet); pomes, drupes and soft fruit (apples, pears, plums, peaches, almonds, cherries, strawberries, raspberries and blackberries); leguminous plants (beans, lentils, peas, soybeans); oil plants (rape, mustard, poppy, olives, sunflowers, coconut, castor oil plants, cocoa beans, groundnuts); cucumber plants (pumpkins, cucumbers, melons); fibre plants (cotton, flax, hemp, jute); citrus fruit (oranges, lemons, grapefruit, mandarins); vegetables (spinach, lettuce, asparagus, cabbages, carrots, onions, tomatoes, potatoes, paprika); lauraceae (avocado, *cinnamomum*, camphor) or plants such as tobacco, nuts, coffee, eggplants, sugar cane, tea, pepper, vines, hops, bananas and natural rubber plants, as well as ornamentals.

The term "useful plants" is to be understood as including also useful plants that have been rendered tolerant to herbicides like bromoxynil or classes of herbicides (such as, for example, HPPD inhibitors, ALS inhibitors, for example primisulfuron, prosulfuron and trifloxysulfuron, EPSPS (5-enol-pyrovyl-shikimate-3-phosphate-synthase) inhibitors, GS (glutamine synthetase) inhibitors) as a result of conventional methods of breeding or genetic engineering. An example of a crop that has been rendered tolerant to imidazolinones, e.g. imazamox, by conventional methods of breeding (mutagenesis) is Clearfield® summer rape (Canola). Examples of crops that have been rendered tolerant to herbicides or classes of herbicides by genetic engineering methods include glyphosate- and glufosinate-resistant maize varieties commercially available under the trade names RoundupReady® and LibertyLink®.

The term "useful plants" is to be understood as including also useful plants which have been so transformed by the use of recombinant DNA techniques that they are capable of synthesising one or more selectively acting toxins, such as are known, for example, from toxin-producing bacteria, especially those of the genus *Bacillus*.

Transgenic plants containing one or more genes that code for an insecticidal resistance and express one or more toxins are known and some of them are commercially available. Examples of such plants are: YieldGard® (maize variety that expresses a CryIA(b) toxin); YieldGard Rootworm® (maize variety that expresses a CryIIIB(b1) toxin); YieldGard Plus® (maize variety that expresses a CryIA(b) and a CryIIIB(b1) toxin); Starlink® (maize variety that expresses a Cry9 (c) toxin); Herculex I® (maize variety that expresses a CryIF(a2) toxin and the enzyme phosphinothricine N-acetyltransferase (PAT) to achieve tolerance to the herbicide glufosinate ammonium); NuCOTN 33B® (cotton variety that expresses a CryIA(c) toxin); Bollgard I® (cotton variety that expresses a CryIA(c) toxin); Bollgard II® (cotton variety that expresses a CryIA(c) and a CryIIA(b) toxin); VIPCOT® (cotton variety that expresses a VIP toxin); NewLeaf® (potato variety that expresses a CryIIIA toxin); Nature-Gard®, Agrisure® GT Advantage (GA21 glyphosate-tolerant trait), Agrisure® CB Advantage (Bt11 corn borer (CB) trait) and Protecta®.

The term "useful plants" is to be understood as including also useful plants which have been so transformed by the use of recombinant DNA techniques that they are capable of synthesising antipathogenic substances having a selective action, such as, for example, the so-called "pathogenesis-related proteins" (PRPs, see e.g. EP-A-0 392 225). Examples of such antipathogenic substances and transgenic plants capable of synthesising such antipathogenic substances are known, for example, from EP-A-0 392 225, WO 95/33818, and EP-A-0 353 191. The methods of producing such transgenic plants are generally known to the person skilled in the art and are described, for example, in the publications mentioned above.

The term "locus" of a useful plant as used herein is intended to embrace the place on which the useful plants are growing, where the plant propagation materials of the useful plants are sown or where the plant propagation materials of the useful plants will be placed into the soil. An example for such a locus is a field, on which crop plants are growing.

The term "plant propagation material" is understood to denote generative parts of the plant, such as seeds, which can be used for the multiplication of the latter, and vegetative material, such as cuttings or tubers, for example potatoes. There may be mentioned for example seeds (in the strict sense), roots, fruits, tubers, bulbs, rhizomes and parts of plants. Germinated plants and young plants which are to be transplanted after germination or after emergence from the soil, may also be mentioned. These young plants may be protected before transplantation by a total or partial treatment by immersion. Preferably "plant propagation material" is understood to denote seeds.

The compounds of formula I can be used in unmodified form or, preferably, together with carriers and adjuvants conventionally employed in the art of formulation.

Therefore the invention also relates to compositions for controlling and protecting against phytopathogenic microorganisms, comprising a compound of formula I and an inert carrier, and to a method of controlling or preventing infestation of useful plants by phytopathogenic microorganisms, wherein a composition, comprising a compound of formula I as active ingredient and an inert carrier, is applied to the plants, to parts thereof or the locus thereof.

To this end compounds of formula I and inert carriers are conveniently formulated in known manner to emulsifiable concentrates, coatable pastes, directly sprayable or dilutable solutions, dilute emulsions, wettable powders, soluble powders, dusts, granulates, and also encapsulations e.g. in polymeric substances. As with the type of the compositions, the methods of application, such as spraying, atomising, dusting, scattering, coating or pouring, are chosen in accordance with the intended objectives and the prevailing circumstances. The compositions may also contain further adjuvants such as stabilizers, antifoams, viscosity regulators, binders or tackifiers as well as fertilizers, micronutrient donors or other formulations for obtaining special effects.

Suitable carriers and adjuvants can be solid or liquid and are substances useful in formulation technology, e.g. natural or regenerated mineral substances, solvents, dispersants, wetting agents, tackifiers, thickeners, binders or fertilizers. Such carriers are for example described in WO 97/33890.

The compounds of formula I or compositions, comprising a compound of formula I as active ingredient and an inert carrier, can be applied to the locus of the plant or plant to be treated, simultaneously or in succession with further compounds. These further compounds can be e.g. fertilizers or micronutrient donors or other preparations which influence the growth of plants. They can also be selective herbicides as well as insecticides, fungicides, bactericides, nematicides, molluscicides or mixtures of several of these preparations, if desired together with further carriers, surfactants or application promoting adjuvants customarily employed in the art of formulation.

A preferred method of applying a compound of formula I, or a composition, comprising a compound of formula I as active ingredient and an inert carrier, is foliar application. The frequency of application and the rate of application will depend on the risk of infestation by the corresponding pathogen. However, the compounds of formula I can also penetrate the plant through the roots via the soil (systemic action) by drenching the locus of the plant with a liquid formulation, or by applying the compounds in solid form to the soil, e.g. in granular form (soil application). In crops of water rice such granulates can be applied to the flooded rice field. The compounds of formula I may also be applied to seeds (coating) by impregnating the seeds or tubers either with a liquid formulation of the fungicide or coating them with a solid formulation.

A formulation, i.e. a composition comprising the compound of formula I and, if desired, a solid or liquid adjuvant, is prepared in a known manner, typically by intimately mixing and/or grinding the compound with extenders, for example solvents, solid carriers and, optionally, surface-active compounds (surfactants).

The agrochemical formulations will usually contain from 0.1 to 99% by weight, preferably from 0.1 to 95% by weight, of the compound of formula I, 99.9 to 1% by weight, preferably 99.8 to 5% by weight, of a solid or liquid adjuvant, and from 0 to 25% by weight, preferably from 0.1 to 25% by weight, of a surfactant.

Whereas it is preferred to formulate commercial products as concentrates, the end user will normally use dilute formulations.

Advantageous rates of application are normally from 5 g to 2 kg of active ingredient (a.i.) per hectare (ha), preferably from 10 g to 1 kg a.i./ha, most preferably from 20 g to 600 g a.i./ha. When used as seed drenching agent, convenient rates of application are from 10 mg to 1 g of active substance per kg of seeds. The rate of application for the desired action can be determined by experiments. It depends for example on the type of action, the developmental stage of the useful plant, and on the application (location, timing, application method) and can, owing to these parameters, vary within wide limits.

Said methods are particularly effective against the phytopathogenic organisms of the kingdom Fungi, phylum Basidiomycot, class Uredinomycetes, subclass Urediniomycetidae and the order Uredinales (commonly referred to as rusts). Species of rusts having a particularly large impact on agriculture include those of the family Phakopsoraceae, particularly those of the genus *Phakopsora*, for example *Phakopsora pachyrhizi*, which is also referred to as Asian soybean rust, and those of the family Pucciniaceae, particularly those of the genus *Puccinia* such as *Puccinia graminis*, also known as stem rust or black rust, which is a problem disease in cereal crops and *Puccinia recondita*, also known as brown rust.

An embodiment of said method is a method of protecting crops of useful plants against attack by a phytopathogenic organism and/or the treatment of crops of useful plants infested by a phytopathogenic organism, said method comprising simultaneously applying glyphosate, including salts or esters thereof, and at least one compound of formula I, which has activity against the phytopathogenic organism to at least one member selected from the group consisting of the plant, a part of the plant and the locus of the plant.

Surprisingly, it has now been found that the compounds of formula I, or a pharmaceutical salt thereof, described above have also an advantageous spectrum of activity for the treatment and/or prevention of microbial infection in an animal.

"Animal" can be any animal, for example, insect, mammal, reptile, fish, amphibian, preferably mammal, most preferably human. "Treatment" means the use on an animal which has microbial infection in order to reduce or slow or stop the increase or spread of the infection, or to reduce the infection or to cure the infection. "Prevention" means the use on an animal which has no apparent signs of microbial infection in order to prevent any future infection, or to reduce or slow the increase or spread of any future infection.

According to the present invention there is provided the use of a compound of formula I in the manufacture of a medicament for use in the treatment and/or prevention of microbial infection in an animal. There is also provided the use of a compound of formula I as a pharmaceutical agent. There is also provided the use of a compound of formula I as an antimicrobial agent in the treatment of an animal. According to the present invention there is also provided a pharmaceutical composition comprising as an active ingredient a compound of formula I, or a pharmaceutically acceptable salt thereof, and a pharmaceutically acceptable diluent or carrier. This composition can be used for the treatment and/or prevention of antimicrobial infection in an animal. This pharmaceutical composition can be in a form suitable for oral administration, such as tablet, lozenges, hard capsules, aqueous suspensions, oily suspensions, emulsions dispersible powders, dispersible granules, syrups and elixirs. Alternatively this pharmaceutical composition can be in a form suitable for topical application, such as a spray, a cream or lotion. Alternatively this pharmaceutical composition can be in a form suitable for parenteral administration, for example injection. Alternatively this pharmaceutical composition can be in inhalable form, such as an aerosol spray.

The compounds of formula I are effective against various microbial species able to cause a microbial infection in an animal. Examples of such microbial species are those causing Aspergillosis such as *Aspergillus fumigatus, A. flavus, A. terrus, A. nidulans* and *A. niger*; those causing Blastomycosis such as *Blastomyces dermatitidis*; those causing Candidiasis such as *Candida albicans, C. glabrata, C. tropicalis, C. parapsilosis, C. krusei* and *C. lusitaniae*; those causing Coccidioidomycosis such as *Coccidioides immitis*; those causing Cryptococcosis such as *Cryptococcus neoformans*; those causing Histoplasmosis such as *Histoplasma capsulatum* and those causing Zygomycosis such as *Absidia corymbifera, Rhizomucor pusillus* and *Rhizopus arrhizus*. Further examples are *Fusarium* Spp such as *Fusarium oxysporum* and *Fusarium solani* and *Scedosporium* Spp such as *Scedosporium apiospermum* and *Scedosporium prolificans*. Still further examples are *Microsporum* Spp, *Trichophyton* Spp, *Epidermophyton* Spp, *Mucor* Spp, *Sporothorix* Spp, *Phialophora* Spp, *Cladosporium* Spp, *Petriellidium* spp, *Paracoccidioides* Spp and *Histoplasma* Spp.

The following non-limiting Examples illustrate the above-described invention in greater detail without limiting it.

PREPARATION EXAMPLES

Example P1

Preparation of N'-[6-(4-Chloro-3-trifluoromethyl-phenoxy)-5-(4-fluoro-phenyl)-2-methyl-pyridin-3-yl]-N-ethyl-N-methyl-formamidine a) Preparation of 3,5-dibromo-6-methyl-pyridin-2-ol

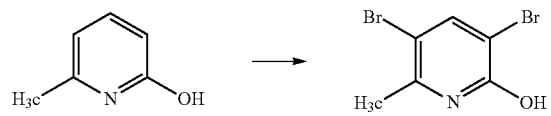

In a 1.5 l five-necked reaction flask equipped with a mechanical stirrer, protected from sunlight with aluminium foil, 30.0 g of 6-methyl-pyridin-2-ol is suspended in 300 ml of dry acetonitrile and stirred at ambient temperature. Under cooling with an ice/water cooling bath, 97.9 g of N-bromo-succinimide (NBS) is added slowly portion-wise over a time interval of 25 minutes. A minor exothemicity is observed (temperature up to 29° C.). As the suspension is difficult to stir, an additional 300 ml of dry acetonitrile is added and stirring continued at ambient temperature for 1.75 hours. Thereafter, the suspension was filtered, the filter cake thoroughly washed with methanol in order to remove the succinimide, and dried to give 64.1 g of the compound as a white solid (m.p. >225° C.).

b) Preparation of 3-bromo-6-methyl-pyridin-2-ol

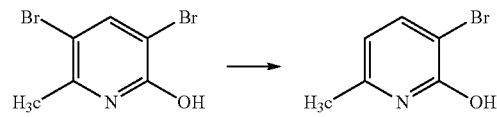

In a 1.5 l five-necked reaction flask (flame-dried), 63.1 g of 3,5-dibromo-6-methyl-pyridin-2-ol is suspended in 300 ml of dry THF and stirred under argon at ambient temperature. The reaction mixture is cooled down to −78 to −80° C. (Et$_2$O/dry ice cooling bath). 295 ml of a 1.6 M solution of n-butyllithium in hexane is added over 2.5 hour, whereby a temperature increase to −74° C. is observed (yellow-orange suspension). Stirring is continued at −78 to −80° C. for 1 hour. Then, 42.6 ml of water is added slowly over 15 minutes. After stirring at −78° C. for 20 minutes, the temperature was allowed to reach ambient temperature overnight. The next day, the mixture is concentrated in vacuo to give a yellow wet solid. After adding 200 ml of an ageous NaCl solution, extraction is done using AcOEt at a pH value of 9 giving 37.2 g (gum) after drying the organic phase over sodium sulfate, filtration and concentration in vacuo and concentrating the water phase in vacuo leads to 70.1 g of a solid. The combined batches thus obtained are purified by flash chromatography [silica gel (column: h=25 cm, Ø=12 cm) with tert-butylmethylether together with 1 volume % of AcOH]. The fractions containing predominantly the compound are combined (29.7 g altogether) and suspended in Et$_2$O at ambient temperature, the mixture stirred, then filtered, the filter cake washed with Et$_2$O to give 14.7 g of the compound as a white solid after drying (m.p.=212-213° C.).

$^1$H NMR (400 MHz, CDCl$_3$): δ 2.35(s, 3H), 5.97(d, 1H), 7.71(d, 1H), 12.35(broad, 1H).

c): Preparation of 3-bromo-6-methyl-5-nitro-pyridin-2-ol

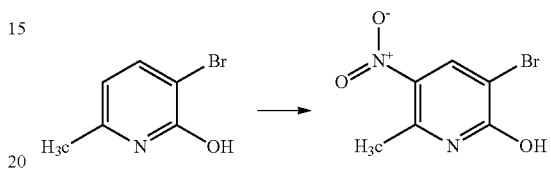

In a 500 ml single-necked round-bottomed flask, 230 ml of a 65% ageous HNO$_3$ solution is added and stirred under cooling (ice/water cooling bath). 7.00 g of 3-bromo-6-methyl-pyridin-2-ol 2 at ambient temperature is introduced portion-wise. Stirring is continued for 3.5 hours at ambient temperature. After pouring the mixture into 200 ml of an ice/water mixture (pH 1), the water phase is extracted with AcOEt. The organic phase is washed twice with water brought to pH 4 by adding ageous NaOH solution (pH meter), then dried over sodium sulfate, filtered and concentrated in vacuo to give 7.52 g of a yellow solid. This crude material is suspended in diethyl ether and stirred for 1 hour at ambient temperature, filtered, washed with the same solvent and dried to give 3.89 g of the compound as a yellow-orange solid (m.p. >220° C.).

$^1$H NMR (400 MHz, CDCl$_3$): δ 2.86(s, 3H), 8.66(s, 1H), 12.75(broad, 1H).

d) Preparation of 3-bromo-2-chloro-6-methyl-5-nitro-pyridine

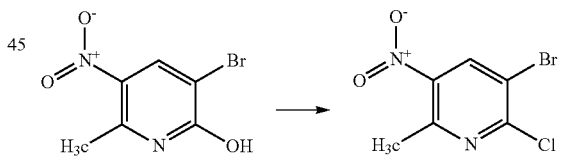

In a 100 ml single-necked round-bottomed flask equipped with a condenser, 4.36 g of the pyridone is introduced into 17 ml of phosphorous oxide chloride (brown suspension). This mixture is then stirred under heating to reflux for 7 h. After cooling the mixture to ambient temperature, it is concentrated in vacuo at 50° C., followed by adding toluene and concentrating in vacuo for three times, to obtain a brown oily gum. This gum is treated with ice followed by an excess of saturated aqueous sodium bicarbonate solution. The extraction is carried out with AcOEt. The organic phase is dried over sodium sulfate, filtered and concentrated in vacuo to get 3.79 g of a brown solid. Purification by flash chromatography over a silica gel cartridge (50 g, 150 ml) of a solid deposition with heptane/ethyl acetate 95:5 (v:v) gives 3.32 g of the compound as a light yellow solid (m.p.=76-78° C.).

$^1$H NMR (400 MHz, CDCl$_3$): δ 2.82(s, 3H), 8.55(s, 1H).

e) Preparation of 3-bromo-2-(4-chloro-3-trifluoromethyl-phenoxy)-6-methyl-5-nitro-pyridine

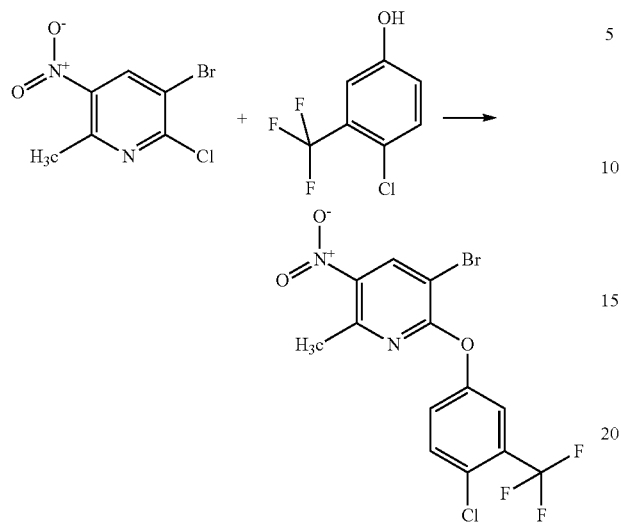

In a 50 mL single-necked round-bottomed flask, 0.13 ml of hexamethyldisilazane and 1.21 g of 4-chloro-3-trifluoromethyl-phenol are dissolved and stirred in 3.0 ml of dry dioxane under Argon atmosphere at ambient temperature. To this mixture, 270 mg of 55% sodium hydride suspension is added carefully (gas evolution) and stirring is continued for 30 minutes. After this, a solution of 1.55 g of 3-bromo-2-chloro-6-methyl-5-nitro-pyridine in 4.0 ml of dry dioxane is added dropwise by syringe and stirring is continued for 22 hours at ambient temperature. The reaction is then quenched by the addition of an excess of a dilute aqueous NaOH solution (pH=12 of water phase) and extraction carried out with cyclohexane. The organic phase is dried over sodium sulfate, filtered and concentrated in vacuo to obtain an orange oil. Purification by flash chromatography over a silica gel cartridge (50 g, 150 ml) using heptane/ethyl acetate 95:5 (v:v) as eluent gave 480 mg of the compound in the form of a wet solid.

$^1$H NMR (400 MHz, CDCl$_3$): δ 2.65(s, 3H), 7.07(dd, 1H), 7.55(d, 1H), 7.58(d, 1H), 8.65(s, 1H).

f) Preparation of 2-(4-chloro-3-trifluoromethyl-phenoxy)-3-(4-fluoro-phenyl)-6-methyl-5-nitro-pyridine

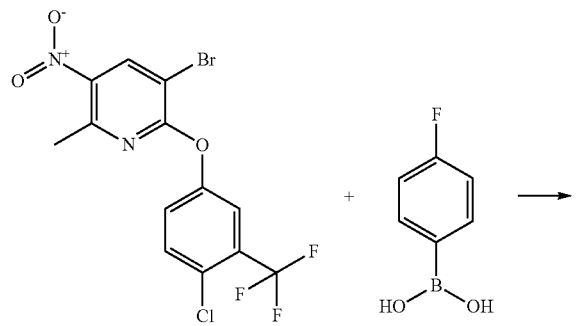

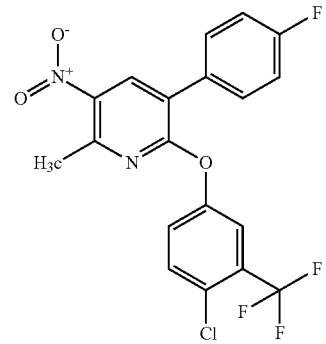

In a 50 mL single-necked round-bottomed flask equipped with a condensor 260 mg of 3-bromo-2-(4-chloro-3-trifluoromethyl-phenoxy)-6-methyl-5-nitro-pyridine and 97 mg the p-fluorophenyl boronic acid are dissolved and stirred in 1.7 ml of dioxane at ambient temperature (yellow solution) under Argon atmosphere. 228 mg K$_3$PO$_4$ dissolved in 0.85 ml of H$_2$O is then added. The mixture is then degassed by stirring under Argon for 15 min. Now, 4.3 mg of tricyclohexylphosphine together with 3.6 mg of bis(benzylideneacetone)palladium are added. Thereafter, the solution is stirred vigorously at 100° C. for 6.5 h. The dark brown suspension is then cooled down to ambient temperature, followed by the addition of 10 ml of saturated aqueous NH$_4$Cl solution. This mixture is extracted with AcOEt. The organic phase is dried over Na$_2$SO$_4$, filtered and concentrated in vacuo to give 340 mg of a dark brown oil. After purification by flash chromatography [silica gel cartridge (20 g, 60 ml) of a solid deposition with heptane/ethyl acetate 95:5 (v:v), then 9:1 (v/v)] 120 mg of the compound is obtained as a yellow oil.

TLC: Plates: Merck DC-Plates, silica gel F$_{254}$, saturated atmosphere in developing tank, UV detection, eluent: heptane/ethyl acetate 2:1 (v:v); R$_f$ of compound=0.50.

g) Preparation of 6-(4-Chloro-3-trifluoromethyl-phenoxy)-5-(4-fluoro-phenyl)-2-methyl-pyridin-3-ylamine

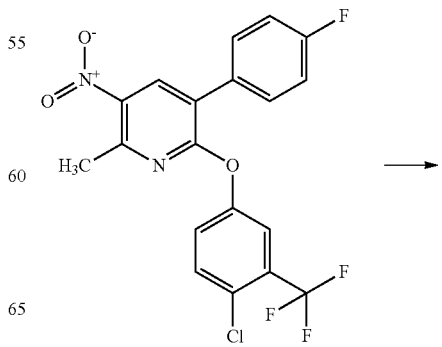

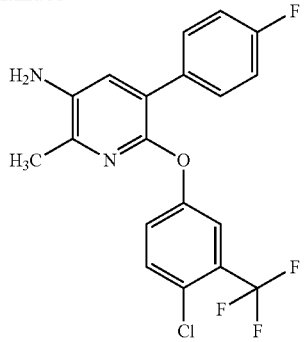

In a 50 mL single-necked round-bottomed flask equipped with a condensor, 120 mg of starting material is stirred in 0.50 ml of methanol (light yellow suspension). Under ice cooling, 0.50 ml of concentrated aqueous HCl is added dropwise by syringe (more precipitation). The ice bath is removed and 270 mg of anhydrous SnCl$_2$ is added slowly (light yellow suspension). Stirring is continued under heating to reflux for 6.5 h (light yellow solution). Then, the resulting mixture is concentrated in vacuo to give a beige wet solid. After adding AcOEt, 5 ml of 4 M aqueous NaOH solution is added. After extraction, the organic phase is dried over Na$_2$SO$_4$, filtered (sintered glass filter) and the solvent removed in vacuo to give 110 mg of the compound in unpurified form (light yellow brown oil). Purification was done by flash chromatography (silica gel cartridge (20 g, 60 mL) of a solid deposition with heptane/ethyl acetate 2:1 (v:v)) to give 60 mg of the compound as a yellow oil. RP HPLC: retention time of compound: 2.10 minutes h) Preparation of N'-[6-(4-chloro-3-trifluoromethyl-phenoxy)-5-(4-fluoro-phenyl)-2-methyl-pyridin-3-yl]-N-ethyl-N-methyl-formamidine

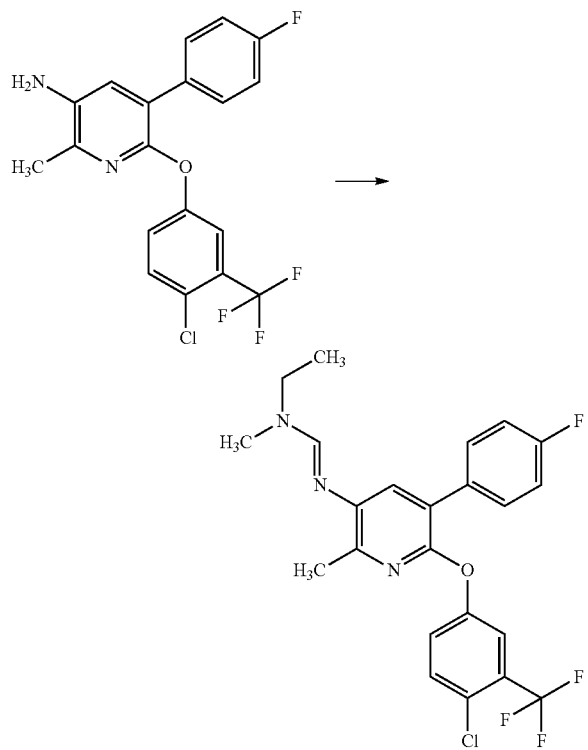

In a 25 ml single-necked round-bottomed flask, 30 mg of ethylmethylformamide is solubilized in 0.5 ml of dry dichloromethane at ambient temperature (colourless solution). Under stirring, 50 mg of phosphorous oxide chloride is added dropwise by syringe. Stirring at ambient temperature is continued for 1.5 hours, whereupon a pink-orange solution is obtained. After this, 60 mg of the starting material dissolved in 1 ml of dry dichloromethane is added dropwise by syringe, giving a yellow solution. Stirring is continued at ambient temperature for 2 hours. The mixture is then poured onto ice/water (pH=2, water phase). 2 M aqueous NaOH is then added to get a pH of about 11 and stirring is continued for 5 minutes. The mixture is then extracted with two 10 ml portions of diethyl ether. The combined organic phases are then dried over sodium sulfate, filtered and the solvent is removed in vacuo to obtain 80 mg of the compound in unpurified form as a yellow oil. RP HPLC: Retention time of compound: 1.55 minutes.

Example P2

Preparation of N'-[5-bromo-6-(4-chloro-3-trifluoromethyl-phenoxy)-2-methyl-pyridin-3-yl]-N-ethyl-N-methyl-formamidine a) Preparation of 5-Bromo-6-(4-chloro-3-trifluoromethyl-phenoxy)-2-methyl-pyridin-3-ylamine

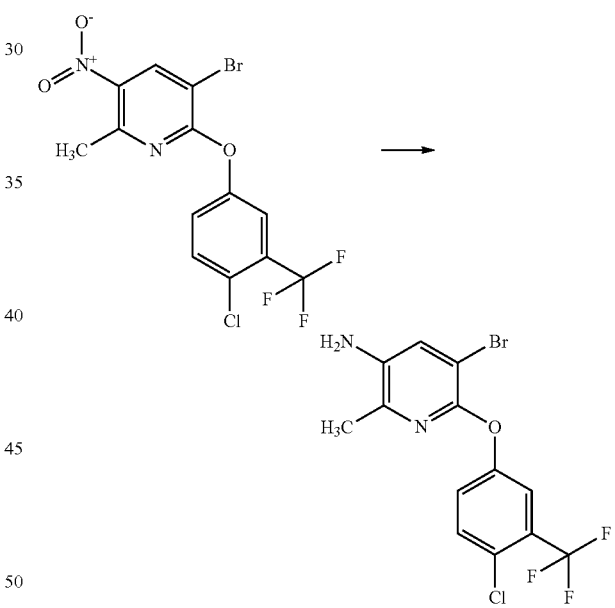

In a 50 ml single-necked round-bottomed flask equipped with a condensor, 140 mg of crude 3-bromo-2-(4-chloro-3-trifluoromethyl-phenoxy)-6-methyl-5-nitro-pyridine is stirred in 0.50 ml of methanol (yellow suspension). Under cooling with an ice/water bath, 0.50 ml of concentrated aqueous HCl is added dropwise by syringe (precipitation). The ice bath is removed and 322 mg of anhydrous SnCl$_2$ is added in portions. Stirring is continued under heating to reflux for 4.5 h (yellow solution). After cooling the mixture to ambient temperature, it is concentrated in vacuo to give a yellow oil. After adding AcOEt, 5 ml of 4 M aqueous NaOH solution is added (pH 12). After extraction, the AcOEt phase is dried over Na$_2$SO$_4$, filtered and the solvent removed in vacuo to give 150 mg of a yellow oil. Purification was done by flash chromatography [silica gel cartridge (20 g, 60 ml) of a solid deposition with heptane/ethyl acetate 2:1 (v:v)] to give 80 mg of the compound in the form of a light yellow solid. RP HPLC: Retention time of compound: 2.04 minutes.

b) Preparation of N'-[5-bromo-6-(4-chloro-3-trifluoromethyl-phenoxy)-2-methyl-pyridin-3-yl]-N-ethyl-N-methyl-formamidine

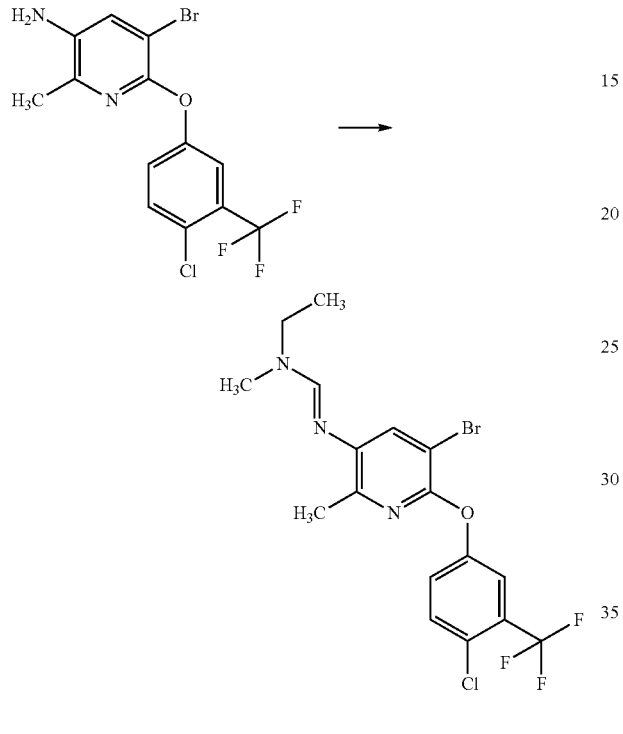

In a 25 ml single-necked round-bottomed flask, 36.5 mg of ethylmethylformamide is solubilized in 0.5 ml of dry dichloromethane at ambient temperature (colourless solution). Under stirring, 0.038 ml of phosphorous oxide chloride is added dropwise by syringe. Stirring at ambient temperature is continued for 1.75 hours, whereupon a pink-orange solution is obtained. To this solution, 80 mg of 5-bromo-6-(4-chloro-3-trifluoromethyl-phenoxy)-2-methyl-pyridin-3-ylamine dissolved in 1.0 ml of dry dichloromethane is added dropwise by syringe, giving a yellow solution. Stirring is continued at an ambient temperature for 45 minutes. The mixture is then poured into ice/water (pH=2, water phase). 2 M aqueous NaOH is then added to get a pH of about 11 and stirring is continued for 10 minutes. The mixture is then extracted with two 10 ml portions of diethyl ether. The combined organic phases are then dried over sodium sulfate, filtered and the solvent is removed in vacuo to obtain 80 mg of the compound as a yellow oil (mixture of E and Z isomer).

$^1$H NMR (400 MHz, CDCl$_3$): δ 1.15-1.35(broad, 3H), 2.34 (s, 3H), 3.03(s, 3H), 3.25-3.60(broad, 2H), 7.16 and 7.19(dd, 1H), 7.35(s, 1H), 7.42(m, 1H), 7.45(m, 1H), 7.30-7.55(broad, 1H).

TLC: Plates: Merck DC-Platrd, silica gel F$_{254}$, saturated atmosphere in developing tank, UV detection, eluent: heptane/ethyl acetate 2:1 (v:v); R$_f$ of compound=0.27.

Example P3

Preparation of N'-[6-(4-chloro-3-trifluoromethyl-phenoxy)-2-methyl-5-trimethylsilanylethynyl-pyridin-3-yl]-N-ethyl-N-methyl-formamidine a) Preparation of 2-(4-chloro-3-trifluoromethyl-phenoxy)-6-methyl-5-nitro-3-trimethylsilanylethynyl-pyridine

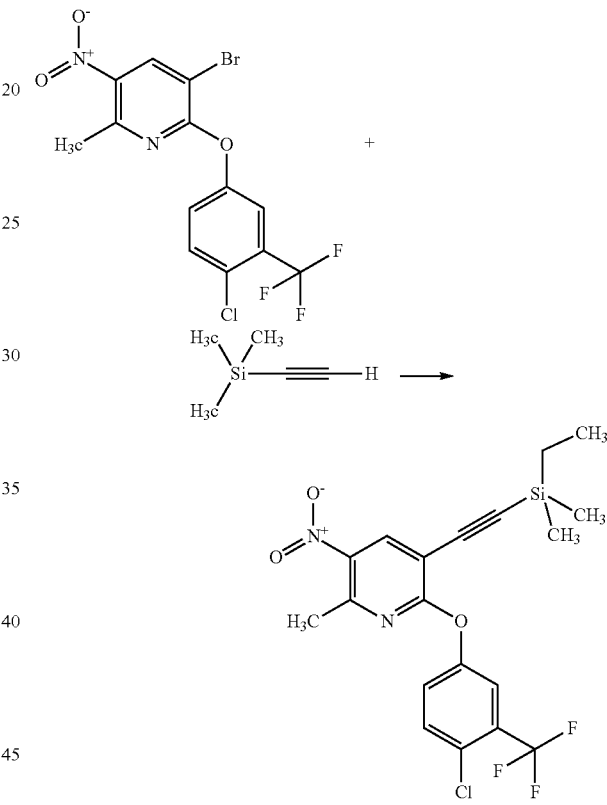

In a 50 ml single-necked round-bottomed flask equipped with a condensor 220 mg of 3-bromo-2-(4-chloro-3-trifluoromethyl-phenoxy)-6-methyl-5-nitro-pyridine is dissolved in 4.0 ml of diisopropylamine and the solution is stirred at ambient temperature under Argon atmosphere. After 20 minutes, 15 mg of cuprous iodide and 56 mg of bis(triphenylphosphin)palladium dichloride are added. This is followed by the dropwise addition of 0.081 ml of ethynyltrimethylsilane. The red solution thus obtained is stirred at 70° C. for 5 h. After cooling the mixture to ambient temperature, it is concentrated in vacuo to obtain 490 mg of a brown solid. Purification of this crude product was carried out by flash chromatography over a silica gel cartridge (20 g; 60 ml) of a solid deposition, with heptane/ethyl acetate 98:2 (v:v) to obtain 40 mg of the compound as a brown oil.

TLC: Plates: Merck DC-Platten, Kieselgel F$_{254}$, saturated atmosphere in developing tank, UV detection, eluent: heptane/ethyl acetate 2:1 (v:v); R$_f$ of compound=0.63.

b) Preparation of 6-(4-chloro-3-trifluoromethyl-phenoxy)-5-ethynyl-2-methyl-pyridin-3-ylamine

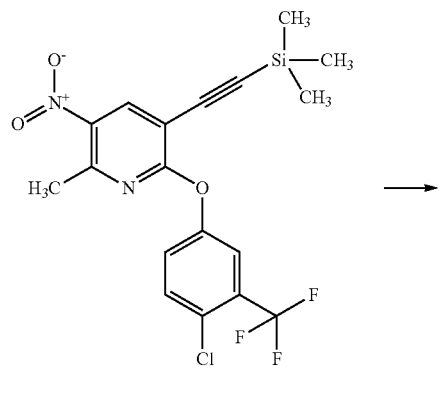

c) Preparation of N'-[6-(4-chloro-3-trifluoromethyl-phenoxy)-2-methyl-5-trimethylsilanylethynyl-pyridin-3-yl]-N-ethyl-N-methyl-formamidine

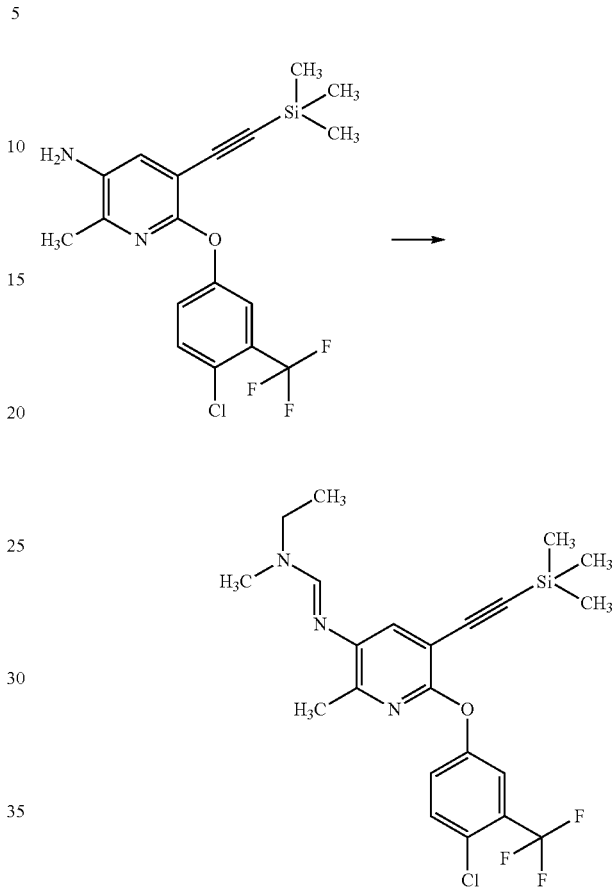

In a 50 ml single-necked round-bottomed flask equipped with a condensor, 35 mg of 2-(4-chloro-3-trifluoromethyl-phenoxy)-6-methyl-5-nitro-3-trimethylsilanylethynyl-pyridine is stirred in 0.50 ml of methanol. Under cooling with an ice/water bath, 0.50 ml of concentrated aqueous HCl is added dropwise by syringe (some precipitation is observed). The ice bath is removed and 77 mg of anhydrous $SnCl_2$ is added in portions. Stirring is continued under heating to reflux for 2 h. After cooling the mixture to ambient temperature, it is concentrated in vacuo to give a brown solid. After adding AcOEt, 5 ml of 4 M aqueous NaOH solution is added (pH 12). Following extraction, the AcOEt phase is dried over $Na_2SO_4$, filtered and the solvent removed in vacuo to give 30 mg a brown oil. Purification was done by flash chromatography [silica gel cartridge (5 g, 20 ml) with heptane/ethyl acetate 3:1 (v:v)] to give 7 mg of a 1. fraction (6-(4-chloro-3-trifluoromethyl-phenoxy)-2-methyl-5-trimethylsilanylethynyl-pyridin-3-ylamine) and 15 mg of a 2. fraction of the compound as a brown solid. RP HPLC: Retention time of compound: 1.87 minutes.

In a 10 ml single-necked round-bottomed flask, 3.1 mg of ethylmethylformamide is solubilized in 0.25 ml of dry dichloromethane at ambient temperature (colourless solution). Under stirring, 0.0032 ml of phosphorous oxide chloride is added dropwise by syringe. Stirring at ambient temperature is continued for 1.0 hour, whereupon a pink-orange solution is obtained. To this solution, 7.0 mg of 6-(4-chloro-3-trifluoromethyl-phenoxy)-2-methyl-5-trimethylsilanylethynyl-pyridin-3-ylamine dissolved in 0.75 ml of dry dichloromethane is added dropwise by syringe, giving a yellow solution. Stirring is continued at room temperature for 2.5 hours. The mixture is then poured into ice/water (pH=2, water phase). 2 M aqueous NaOH is then added to get a pH of about 11 and stirring is continued for 15 minutes. The mixture is then extracted with two 10 ml portions of diethyl ether. The combined organic phases are then dried over sodium sulfate, filtered and the solvent is removed in vacuo to obtain 6.0 mg of the compound as a yellow oil. RP HPLC: retention time of compound: 1.61 minutes.

Example P4

Preparation of N'-[5-bromo-2-methyl-6-(4-methyl-pentyloxy)-pyridin-3-yl]-N-ethyl-N-methyl-formamidine a) Preparation of 3-bromo-6-methyl-2-(4-methyl-pentyloxy)-5-nitro-pyridine

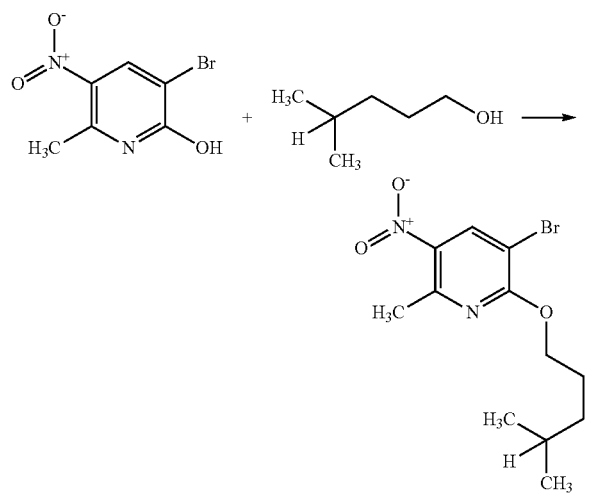

In a 50 ml single-necked round-bottomed flask, 1.00 g of 3-bromo-6-methyl-5-nitro-pyridin-2-ol is dissolved in 4.50 ml of dry dioxane and stirred at ambient temperature under Ar (yellow-orange suspension). 0.593 ml of 4-methyl-1-pentanol together with 2.354 g of triphenylphosphine are added. Then, 0.801 ml of diethyl azodicarboxylate (DEAD) is added dropwise by syringe over 10 min, during this addition a moderate exothermicity is observed. Stirring is continued at ambient temperature for 4.5 hours. The reaction mixture is then quenched by the addition of 10 ml of water (pH=5-6), followed by the extraction with pentane (3×20 mL). The combined organic phases are dried over sodium sulfate, filtered and the solvent removed in vacuo to give 1.87 g of the compound as a yellow-orange oil.

TLC: Plates: Merck DC-Platten, Kieselgel $F_{254}$, saturated atmosphere in developing tank, UV detection, eluent: heptane/ethyl acetate 1:1 NM; $R_f$ of compound=0.72.

b) Preparation of 5-bromo-2-methyl-6-(4-methyl-pentyloxy)-Pyridin-3-ylamine

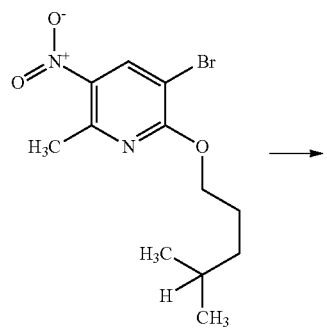

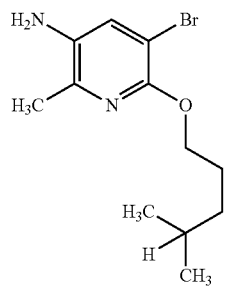

In a 50 ml single-necked round-bottomed flask equipped with a condensor, 1.36 g of crude 3-bromo-6-methyl-2-(4-methyl-pentyloxy)-5-nitro-pyridine is dissolved in 3.15 ml of methanol and the resulting solution stirred. Under cooling using an ice/water bath, 3.15 ml of concentrated aqueous HCl is added dropwise by syringe (precipitation is observed). The ice bath is removed and 2.23 g anhydrous $SnCl_2$ is added in portions. Stirring is continued under heating to reflux for 5.5 h (yellow suspension). After cooling this mixture to ambient temperature, it is concentrated in vacuo to give a yellow solid. After adding dichloromethane, 10 ml of a 4 M aqueous NaOH solution is added (pH 12). After extraction, the organic phase is dried over $Na_2SO_4$, filtered and the solvent removed in vacuo to give 1.62 g of a yellow oil. Purification is done by flash chromatography [silica gel cartridge (50 g, 150 ml) of a solid deposition with heptane/ethyl acetate 4:1 (v:v)] to give 490 mg of the compound in the form of a yellow oil. RP HPLC: Retention time of compound: 2.12 minutes.

c) Preparation of N'-[5-bromo-2-methyl-6-(4-methyl-pentyloxy)-pyridin-3-yl]-N-ethyl-N-methyl-formamidine

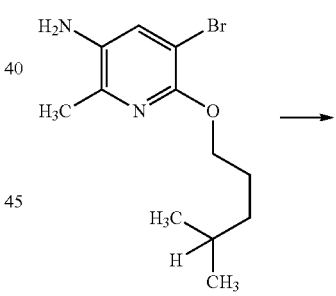

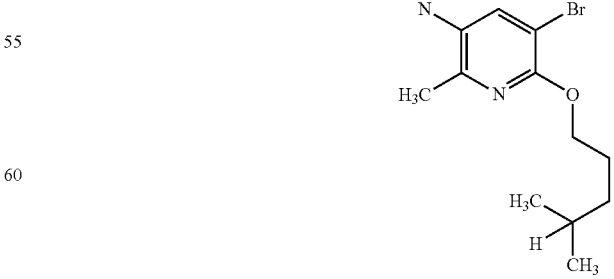

In a 50 ml single-necked round-bottomed flask, 182 mg of ethylmethylformamide is solubilized in 3.0 ml of dry dichloromethane (colourless solution). Under stirring, 0.191 ml of phosphorous oxide chloride is added dropwise by syringe at ambient temperature. Stirring at ambient temperature is continued for 1.75 hours, whereupon a pink-orange solution is formed. 300 mg of 5-bromo-2-methyl-6-(4-methyl-pentyloxy)-pyridin-3-ylamine dissolved in 1.50 ml of dry dichloromethane is then added dropwise by syringe, the solution turning yellow. Stirring is continued at ambient temperature for 5 hours. The solution is then poured into ice/water (pH=2, water phase). 2 M aqueous NaOH is added to a pH of about 11 and the mixture is stirred for 10 minutes. The mixture is then extracted with two 10 ml portions of diethyl ether. The combined ether phases are dried over sodium sulfate, filtered and the solvent is removed in vacuo to obtain 380 mg of the compound as a yellow oil.

$^1$H NMR (400 MHz, CDCl$_3$): δ 0.91(d, 6H), 1.15-1.40(m, m, 5 H), 1.61(m, 1H), 1.78(m, 2H), 2.38(s, 3H), 3.04(broad, 3H), 3.25-3.60(broad, 2H), 4.30(t, 2H), 7.28(s, 1H), 7.30-7.50(broad, 1H). TLC: Plates: Merck DC-Plates, silica gel F$_{254}$, saturated atmosphere in developing tank, UV detection, eluent: heptane/ethyl acetate 1:1 (v:v); R$_f$ of compound=0.48.

Example P5

Preparation of N'-[5-(4-Chloro-phenyl)-2-methyl-6-(4-methyl-pentyloxy)-pyridin-3-yl]-N-ethyl-N-methyl-formamidine

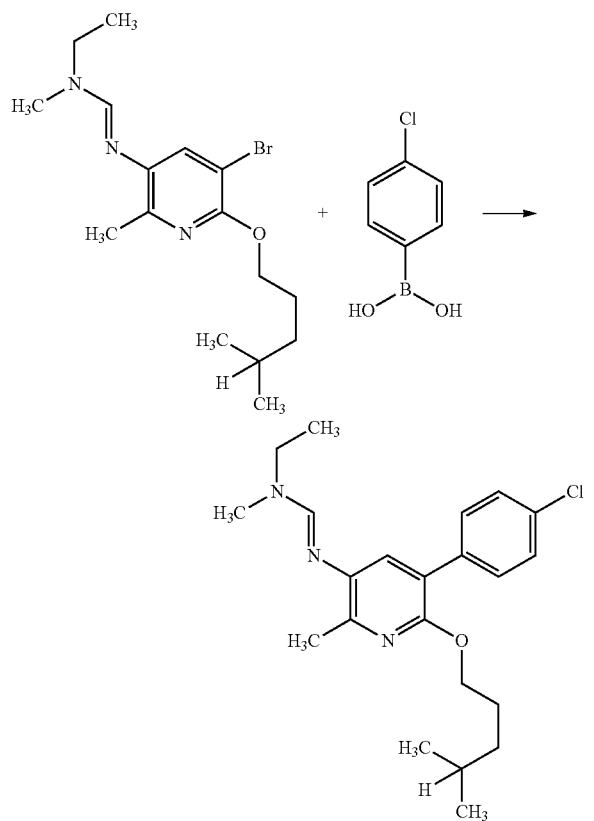

In a 10 ml single-necked round-bottomed flask equipped with a condensor (equipment flame-dried), 160 mg of crude N'-[5-bromo-2-methyl-6-(4-methyl-pentyloxy)-pyridin-3-yl]-N-ethyl-N-methyl-formamidine and 77.2 mg p-chlorophenyl boronic acid are dissolved in 1.20 ml of dioxane. To this solution, 162 mg of K$_3$PO$_4$ in 0.60 ml of water is added at ambient temperature under Argon atmosphere. The resulting biphasic mixture is degassed under Argon atmosphere for 20 minutes, whereupon 3.0 mg of tricyclohexylphosphine and 2.6 mg of bis(benzylideneacetone)palladium are added. The resulting suspension is vigorously stirred at a temperature of 100° C. for 5 hours. After letting the reaction mixture reach ambient temperature, 5.0 ml of a saturated aqueous NH$_4$Cl solution is added. The water phase is extracted with AcOEt. The organic phase is dried over sodium sulfate, filtered and the solvent removed in vacuo to get 220 mg of a yellow oil. Purification by flash chromatography over a silica gel cartridge (20 g; 60 ml) of a solid deposition with heptane/ethyl acetate 9:1, then 4:1, then 3:2 (v:v) gave 80 mg of the compound as a yellow oil.

$^1$H NMR (400 MHz, CDCl$_3$): δ 0.88(d, 6H); 1.20(t, 3H), 1.23(m, 2H), 1.58(m, 1H), 1.72(m, 2H), 2.44(s, 3H), 3.02(s, 3H), 3.15-3.60(broad, 2H), 4.29(t, 2H), 7.06(s, 1H), 7.34(d, 2H), 7.42(broad, 1H), 7.52(d, 2H).

Example P6

Preparation of N-ethyl-N-methyl-N'-[2-methyl-6-(4-methyl-pentyloxy)-pyridin-3-yl]-formamidine

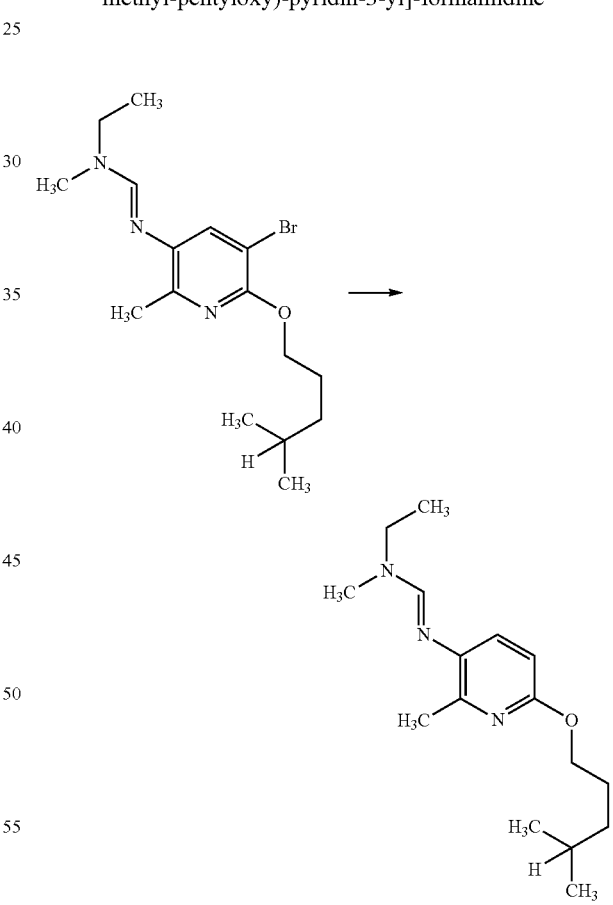

In a 50 ml single-necked round-bottomed flask (flame dried) 150 mg of N'-[5-bromo-2-methyl-6-(4-methyl-pentyloxy)-pyridin-3-yl]-N-ethyl-N-methyl-formamidine is dissolved in 1.0 ml of absolute THF and stirred under Argon atmosphere. The solution is cooled down to −82° C. (dry ice/acetone cooling bath). Under stirring, 0.263 ml of a 1.6 M solution of n-butyllithium in hexane is added dropwise by syringe. Stirring at −82° C. is continued for 45 min. Then, 0.091 ml of trimethylchlorsilane is added dropwise by syringe and stirring continued at −82° C. for 3 hours. After this period of time, the reaction mixture is allowed to warm up to ambient temperature. Afterwards, the reaction is quenched by the addition of 0.020 ml of AcOH, followed by 5.0 ml of water. The water phase is extracted with diethyl ether and the resulting organic phase is dried over sodium sulfate, filtered and the solvent removed in vacuo to give 30 mg of a yellow oil. The aqueous phase is then brought to pH 7 by the addition of 10 ml of a saturated aqueous solution of NaHCO$_3$. This is followed by extraction using diethyl ether, drying of the organic phase, filtration and concentration in vacuo to give 90 mg of a yellow oil. The 2 oily fractions are combined and purified by flash chromatography [silica gel cartridge (20 g, 60 ml) with heptane/ethyl acetate 95:5, then 9:1, then 4:1 (v:v)] to give 30 mg of the compound as a yellow oil.

$^1$H NMR (400 MHz, CDCl$_3$): δ 0.90(d, 6H), 1.20(t, 3H), 1.33(m, 2H), 1.60(m, 1H); 1.76(m, 2H), 2.41(s, 3H), 2.99(s, 3H), 3.20-3.50(broad, 1H), 3.35(broad, 1H), 4.18(t, 2H), 6.46 (d, 1H), 7.01(d, 1H), 7.38(broad, 1H). RP HPLC: Retention time of compound: 1.26 minutes.

Example P7

Preparation of N'-[6-(4-chloro-3-trifluoromethyl-phenoxy)-5-methyl-pyridin-3-yl]-N-ethyl-N-methyl-formamidine a) Preparation of 2-chloro-3-methyl-5-nitro-pyridine

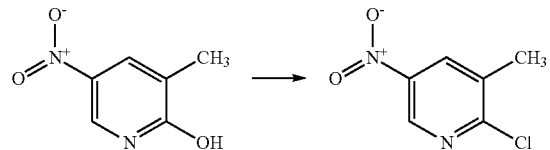

A 350 ml three-necked round-bottomed flask equipped with a magnetic bar, a thermometer, a dropping funnel and a reflux condenser is charged with 3-methyl-5-nitro-pyridin-2-ol (23.1 g), and 1,2-dichloroethane (150 ml). Phosphorous oxide chloride (17 ml) is added dropwise. Into this mixture DMF (11.5 ml) is added dropwise at room temperature. The reaction mixture is heated at 70° C. under stirring for 0.5 hour. After cooling the mixture to ambient temperature, it is concentrated in vacuo at 50° C., to obtain a brown oily gum. Purification of this gum by flash chromatography over silica gel with hexane/ethyl acetate 7:3 (v:v) gives 23.34 g of the compound as a light yellow solid (MP: 40-42° C.).

$^1$H NMR (400 MHz, CDCl$_3$): δ 2.55(s, 3H, CH$_3$), 8.35(d, 1H), 9.11(d, 1H).

b) Preparation of 2-(4-chloro-3-trifluoromethyl-phenoxy)-3-methyl-5-nitro-pyridine

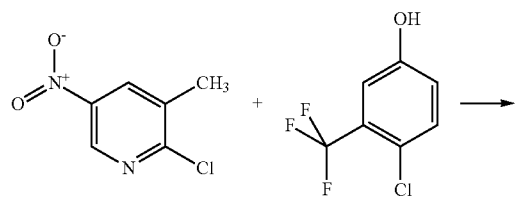

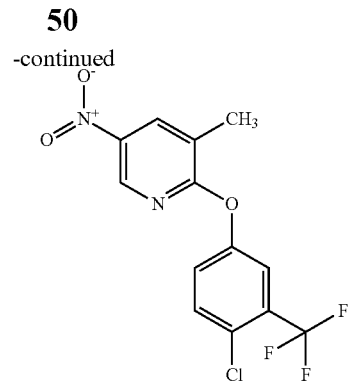

A 250 ml two-necked round-bottomed flask equipped with a magnetic bar, a thermometer and a reflux condenser is charged with DMF (50 ml), 4-chloro-3-trifluoromethyl-phenol (4.6 g), 2-chloro-3-methyl-5-nitro-pyridine (4.0 g) and potassium carbonate (6.4 g). The reaction mixture is heated at 100° C. for 2.5 hours. After cooling the mixture to room temperature it is then poured into water (200 ml). The mixture is then extracted with ethylacetate (2×40 ml). The combined organic layers are dried over sodium sulfate, filtered and the solvent is removed in vacuo to obtain 6.10 g of the compound as yellow solid (MP: 95-97° C.).

$^1$H NMR (400 MHz, CDCl$_3$): δ 2.50(s, 3H, CH$_3$), 7.30 (dxd, 1H), 7.49(d, 1H), 7.55(d, 1H), 8.35(d, 1H), 8.80(d, 1H).

c) Preparation of 6-(4-chloro-3-trifluoromethyl-phenoxy)-5-methyl-pyridin-3-ylamine

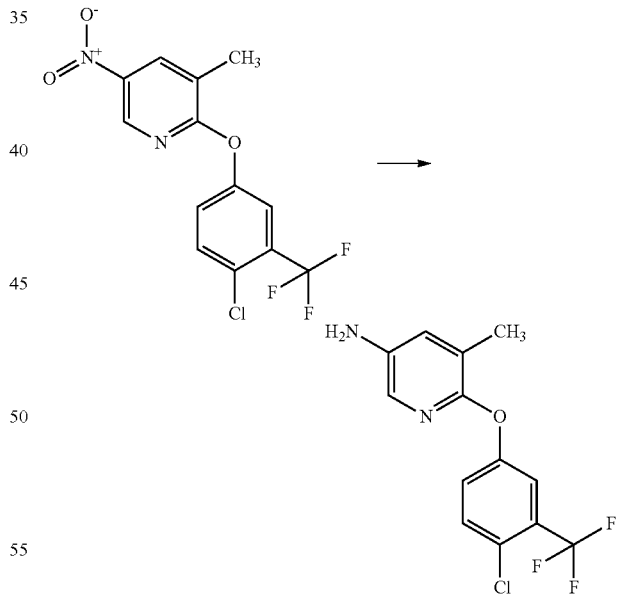

A 250 ml two-necked round-bottomed flask equipped with a KPG-stirrer, a thermometer and a reflux condenser is charged with ethanol (100 ml), water (10 ml), iron (3.11 g) and hydrochloric acid 37% (0.3 ml). The reaction mixture is heated at 50° C. 2-(4-chloro-3-trifluoromethyl-phenoxy)-3-methyl-5-nitro-pyridine (5.81 g) is added portionwise. The mixture was heated at reflux for 2 hours. After cooling the mixture to 50° C. it is filtered through celite. The filtrate is poured into water (200 ml) and extracted with ethylacetate (2×50 ml). The combined organic layers are washed with brine (100 ml), dried over sodium sulfate, filtered and the solvent is removed in vacuo to obtain 4.20 g of the compound as yellow solid (MP: 92-94° C.).

$^1$H NMR (400 MHz, CDCl$_3$): δ 2.25 (s, 3H, CH$_3$), 3.55 (s$_{br}$, 2H, NH$_2$), 6.98 (d, 1H), 7.14 (dxd, 1H), 7.38 (d, 1H), 7.45 (d, 1H), 7.52 (d, 1H).

d) Preparation of N'-[6-(4-chloro-3-trifluoromethyl-phenoxy)-5-methyl-pyridin-3-yl]-N-ethyl-N-methyl-formamidine

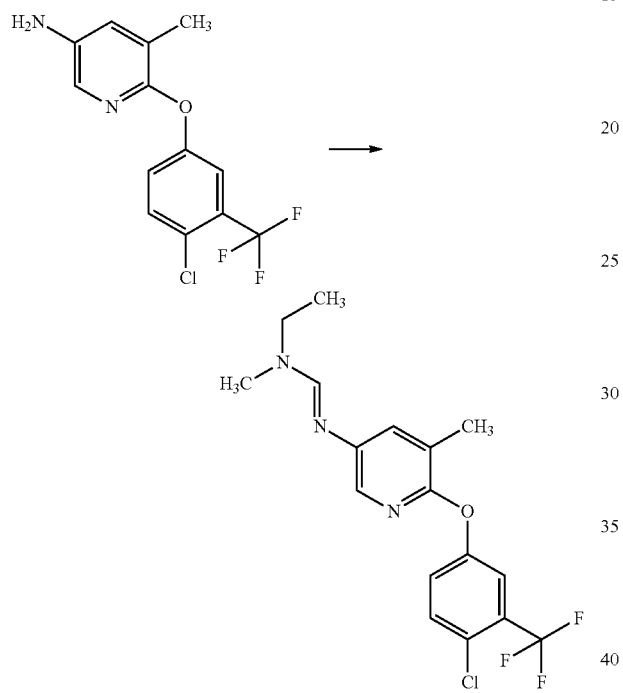

Example P8

Preparation of N'-[6-(4-chloro-3-trifluoromethyl-phenoxy)-5-methyl-pyridin-3-yl]-N-ethyl-N-pyridin-2-yl-formamidine

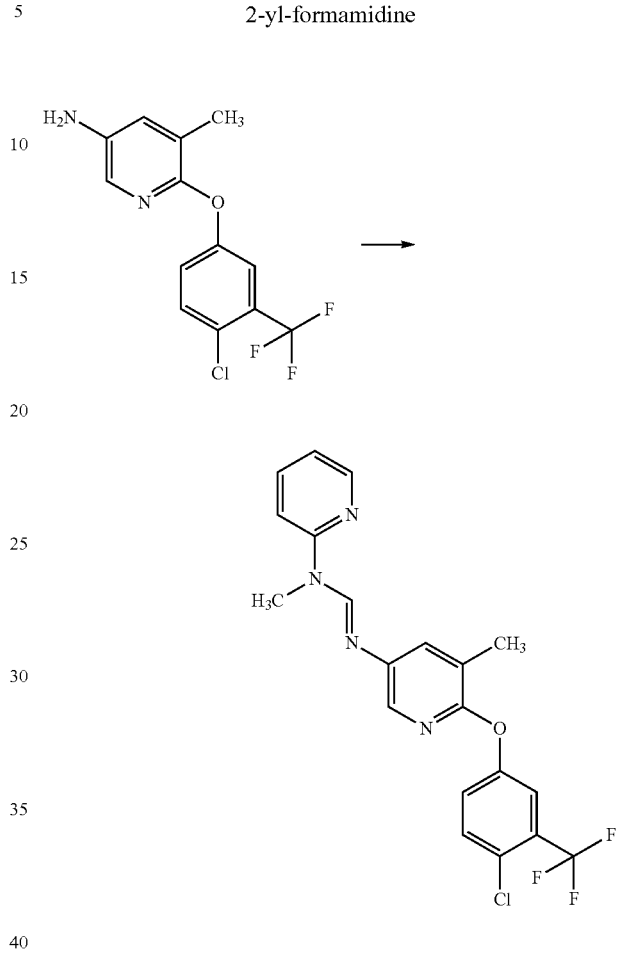

In a 25 ml single-necked round-bottomed flask, ethylmethylformamide (350 mg) is solubilized in dry dichloromethane (4 ml) at ambient temperature (colourless solution). Under stirring phosphorous oxide chloride (0.4 ml) is added dropwise by syringe. Stirring at ambient temperature is continued for 1 hour, whereupon a pink-orange solution is obtained. To this solution, 6-(4-Chloro-3-trifluoromethyl-phenoxy)-5-methyl-pyridin-3-ylamine (0.6 g) dissolved in 1.0 ml of dry dichloromethane is added dropwise by syringe, giving a yellow solution. Stirring is continued at an ambient temperature for 1 hour. The mixture is then poured into ice/water (pH=2, water phase). 2 M aqueous NaOH is then added to get a pH of about 11 and stirring is continued for 10 minutes. The mixture is then extracted with dichloromethane (2×50 ml). The combined organic phases are then dried over sodium sulfate, filtered and the solvent is removed in vacuo. Purification of this gum by flash chromatography over silica gel with hexane/ethyl acetate 1:2 (v:v) gives 0.52 g of the compound as a yellow oil.

$^1$H NMR (400 MHz, CDCl$_3$): δ 1.19-1.24(t, 3, CH$_3$), 2.28 (s, 3H, CH$_3$), 3.00(s, 3H, CH$_3$), 3.28-3.53(m, 2H, CH$_2$), 7.15-7.26(m, 2H), 7.40(d, 1H), 7.46(d, 1H), 7.55(s$_{br}$, 1H), 7.65(d, 1H).

In a 25 ml single-necked round-bottomed flask, N-methyl-N-pyridin-2-yl-formamide (0.5 ml) is solubilized in dry dichloromethane (4 ml) at ambient temperature (colourless solution). Under stirring phosphorous oxide chloride (0.4 ml) is added dropwise by syringe. Stirring at ambient temperature is continued for 1 hour. To this solution, 6-(4-Chloro-3-trifluoromethyl-phenoxy)-5-methyl-pyridin-3-ylamine (0.6 g) dissolved in 1.0 ml of dry dichloromethane is added dropwise by syringe, giving a yellow solution. Stirring is continued at an ambient temperature for 1 hour. The mixture is then poured into ice/water (pH=2, water phase). 2 M aqueous NaOH is then added to get a pH of about 11 and stirring is continued for 10 minutes. The mixture is then extracted with dichloromethane (2×50 ml). The combined organic phases are then dried over sodium sulfate, filtered and the solvent is removed in vacuo. Purification of this gum by flash chromatography over silica gel with hexane/ethyl acetate 1:1 (v:v) gives 0.33 g of the compound as a yellow oil.

$^1$H NMR (400 MHz, CDCl$_3$): δ 2.34(t, 3, CH$_3$), 3.53(s, 3H, CH$_3$), 6.96(d, 1H), 7.00(dxd, 1H), 7.21(dxd, 1H), 7.38(d, 1H), 7.45-7.51(m, 2H), 7.68-7.72(m, 1H), 7.79(d, 1H), 8.33 (dxd, 1H), 9.11(s, 1H).

Example P9

Preparation of [6-(4-chloro-3-trifluoromethyl-phenoxy)-5-methyl-pyridin-3-yl]-(1-pyrrolidin-1-methylidene)-amine

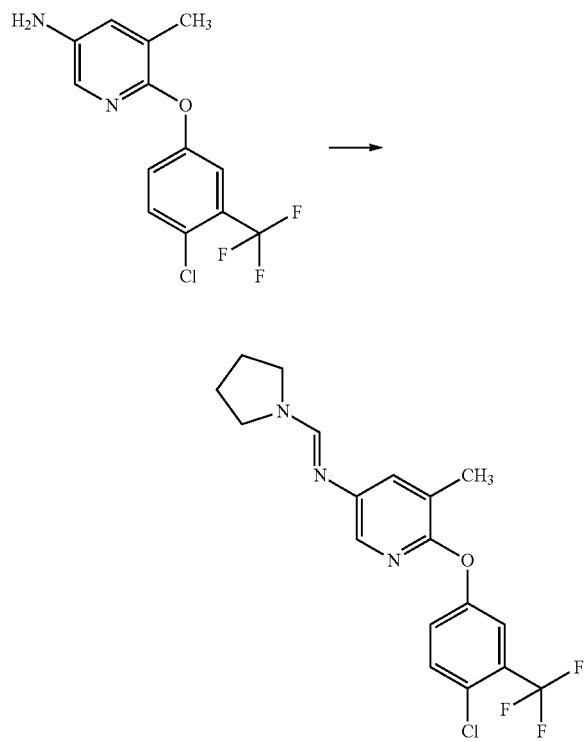

In a 25 ml single-necked round-bottomed flask, pyrrolidine-1-carbaldehyde (0.4 ml) is solubilized in dry dichloromethane (4 ml) at ambient temperature (colourless solution). Under stirring phosphorous oxide chloride (0.4 ml) is added dropwise by syringe. Stirring at ambient temperature is continued for 1 hour. To this solution, 6-(4-Chloro-3-trifluoromethyl-phenoxy)-5-methyl-pyridin-3-ylamine (0.6 g) dissolved in 1.0 ml of dry dichloromethane is added dropwise by syringe, giving a yellow solution. Stirring is continued at an ambient temperature for 1 hour. The mixture is then poured into ice/water (pH=2, water phase). 2 M aqueous NaOH is then added to get a pH of about 11 and stirring is continued for 10 minutes. The mixture is then extracted with dichloromethane (2×50 ml). The combined organic phases are then dried over sodium sulfate, filtered and the solvent is removed in vacuo. Purification of this gum (0.7 g) by flash chromatography over silica gel with ethyl acetate gives 0.59 g of the compound as a yellow oil.

$^1$H NMR (400 MHz, CDCl$_3$): δ 1.95 (m$_{br}$, 4H, 2×CH$_2$), 2.28 (s, 3H, CH$_3$), 3.50-3.55(m, 4H, 2×CH$_2$), 7.17(dxd, 1H), 7.23(d, 1H), 7.39(d, 1H), 7.55(d, 1H), 7.64(d, 1H), 7.75(s, 1H).

Example P10

Preparation of N'-[6-(3-tert-butyl-phenoxy)-5-methyl-pyridin-3-yl]-N-ethyl-N-methyl-formamidine a) Preparation of 2-(3-tert-butyl-phenoxy)-3-methyl-5-nitro-pyridine

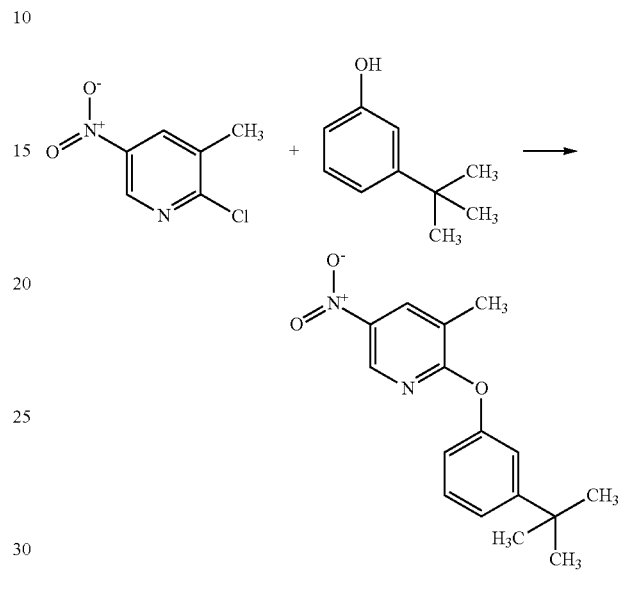

A 50 ml two-necked round-bottomed flask equipped with a magnetic bar, a thermometer and a reflux condenser is charged with DMF (50 ml), 3-tert-butyl-phenol (1.5 g), 2-chloro-3-methyl-5-nitro-pyridine (1.73 g) and potassium carbonate (2.76 g). The reaction mixture is heated at 60° C. for 2 hours. After cooling the mixture to room temperature it is then poured into water (200 ml). The mixture is then extracted with ethylacetate (2×40 ml). The combined organic layers are dried over sodium sulfate, filtered and the solvent is removed in vacuo. Purification of this crude material by flash chromatography over silica gel with hexane/ethyl acetate 4:1 (v:v) gives 2.55 g of the compound as a yellow oil.

$^1$H NMR (400 MHz, CDCl$_3$): δ 1.30(s, 9H, 3×CH$_3$), 2.48 (s, 3H, CH$_3$), 6.95(dxd, 1H), 7.18(m, 1H), 7.30-7.41(m, 2H), 8.30(d, 1H), 8.85(d, 1H).

b) Preparation of 6-(3-tert-butyl-phenoxy)-5-methyl-pyridin-3-ylamine

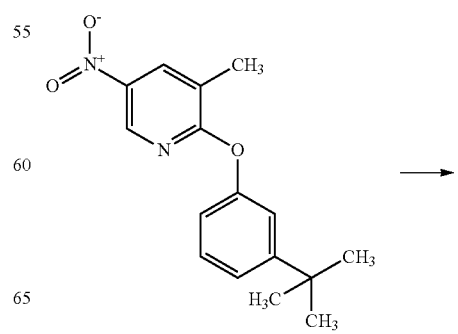

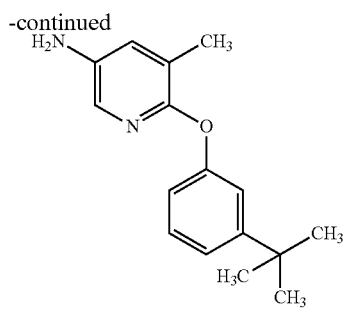

A 100 ml two-necked round-bottomed flask equipped with a KPG-stirrer, a thermometer and a reflux condenser is charged with ethanol (50 ml), water (5 ml), iron (1.43 g) and hydrochloric acid 37% (0.2 ml). The reaction mixture is heated at 50° C. 2-(3-tert-Butyl-phenoxy)-3-methyl-5-nitro-pyridine (2.26 g) was added portionwise. The mixture is heated at reflux for 3 hours. After cooling the mixture to 50° C. it is filtered through celite. The filtrate is poured into water (200 ml) and extracted with ethylacetate (2×50 ml). The combined organic layers are washed with brine (100 ml), dried over sodium sulfate, filtered and the solvent is removed in vacuo. Purification by flash chromatography over silica gel with hexane/ethyl acetate 1:1 (v:v) gives 1.10 g of the compound as a brownish solid (MP: 83-84° C.).

$^1$H NMR (400 MHz, CDCl$_3$): δ 1.32(s, 9H, 3×CH$_3$), 2.25 (s, 3H, CH$_3$), 3.35(s$_{br}$, 2H, NH$_2$), 6.75(dxd, 1H), 6.80(d, 1H), 7.07-7.15(m, 2H), 7.23(d, 1H), 7.55(d, 1H).

c) Preparation of N'-[6-(3-tert-butyl-phenoxy)-5-methyl-pyridin-3-yl]-N-ethyl-N-methyl-formamidine In a 25 ml single-necked round-bottomed flask, ethylmethylformamide (350 mg) is solubilized in dry dichloromethane (4 ml) at ambient temperature (colourless solution). Under stirring phosphorous oxide chloride (0.4 ml) is added dropwise by syringe. Stirring at ambient temperature is continued for 0.5 hour, whereupon a pink-orange solution is obtained. To this solution, 6-(3-tert-butyl-phenoxy)-5-methyl-pyridin-3-ylamine (0.51 g) dissolved in 5.0 ml of dry dichloromethane is added dropwise by syringe, giving a yellow solution. Stirring is continued at an ambient temperature for 2 hours. The mixture is then poured into ice/water (pH=2, water phase). 2 M aqueous NaOH is then added to get a pH of about 11 and stirring is continued for 10 minutes. The mixture is then extracted with dichloromethane (2×50 ml). The combined organic phases are then dried over sodium sulfate, filtered and the solvent is removed in vacuo. Purification of this gum by flash chromatography over silica gel with ethyl acetate gives 0.56 g of the compound as a brown oil.

$^1$H NMR (400 MHz, CDCl$_3$): δ 1.19-1.24(t, 3, CH$_3$), 1.30 (s, 9H, 3×CH$_3$), 2.28(s, 3H, CH$_3$), 3.00(s, 3H, CH$_3$), 3.25-3.35(m$_{br}$, 2H, CH$_2$), 6.80(dxd, 1H), 7.08-7.12(m, 2H), 7.20-7.27(m, 2H), 7.53(s$_{br}$, 1H), 7.67(d, 1H).

Example P11

Preparation of N'-[6-(3,4-Dichloro-phenoxy)-2,4-diisopropyl-pyridin-3-yl]-N,N-dimethyl-formamidine

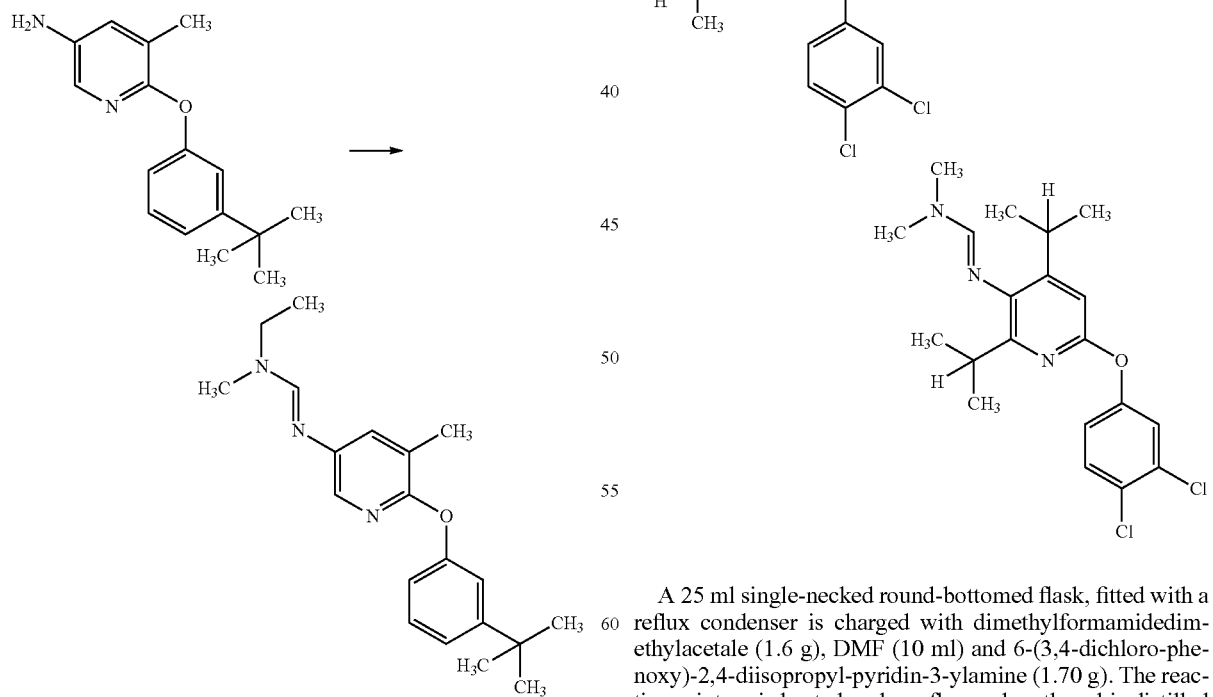

A 25 ml single-necked round-bottomed flask, fitted with a reflux condenser is charged with dimethylformamidediethylacetale (1.6 g), DMF (10 ml) and 6-(3,4-dichloro-phenoxy)-2,4-diisopropyl-pyridin-3-ylamine (1.70 g). The reaction mixture is heated under reflux and methanol is distilled off for 2.5 hours. The mixture is then concentrated in vacuo at 50° C. The crude material is crystallised from hexane/toluene acetate 4:1 (v:v): to obtain 1.41 g of the compound as a white solid (MP: 102-103° C.).

$^1$H NMR (400 MHz, CDCl$_3$): δ 1.11-1.17(2q, 12H, 4×CH$_3$), 3.20(s, 6H, 2×CH$_3$), 3.08-3.20(m, 2H), 6.08(s, 1H), 6.85(dxd, 1H), 7.14(s, 1H), 7.28(d, 1H), 7.37(d, 1H).

Example P12

Preparation of N'-[6-(2,4-Dichloro-phenoxy)-Pyridin-3-yl]-N-ethyl-N-methyl-formamidine

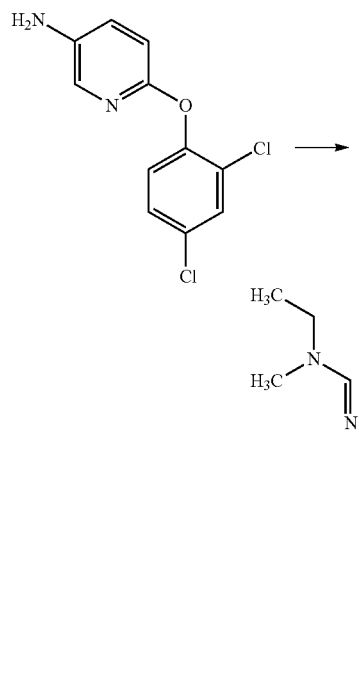

In a 25 ml single-necked round-bottomed flask, ethylmethylformamide (350 mg) is solubilized in dry dichloromethane (4 ml) at ambient temperature (colourless solution). Under stirring phosphorous oxide chloride (0.4 ml) is added dropwise by syringe. Stirring at ambient temperature is continued for 1 hour. To this solution, 6-(2,4-Dichloro-phenoxy)-pyridin-3-ylamine (0.5 g) dissolved in 1.0 ml of dry dichloromethane is added dropwise by syringe, giving a yellow solution. Stirring is continued at an ambient temperature for 1 hour. The mixture is then poured into ice/water (pH=2, water phase). 2 M aqueous NaOH is then added to get a pH of about 11 and stirring is continued for 10 minutes. The mixture is then extracted with dichloromethane (2×50 ml). The combined organic phases are then dried over sodium sulfate, filtered and the solvent is removed in vacuo. Purification by flash chromatography over silica gel with hexane/ethyl acetate 3:4 (v:v) gives 0.31 g of the compound as a yellow oil.

$^1$H NMR (400 MHz, CDCl$_3$): δ 1.18-1.23(t, 3H, CH$_3$), 2.98(s, 3H, CH$_3$), 3.25-3.51(m$_{br}$, 2H, CH$_2$), 6.84-6.89(d, 1H), 7.09(d, 1H), 7.23(dxd, 1H), 7.35(dxd, 1H), 7.45(d, 1H), 7.50(s$_{br}$, 1H), 7.75(d, 1H).

Example P13

Preparation of N'-[6-(4-chloro-3-trifluoromethyl-phenoxy)-4-methyl-pyridin-3-yl]-N-ethyl-N-methyl-formamidine a) Preparation of 2-chloro-4-methyl-5-nitro-pyridine

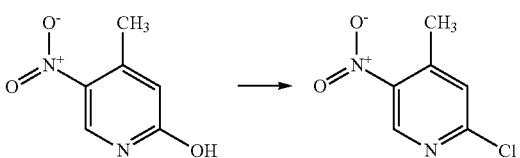

A 100 ml three-necked round-bottomed flask equipped with a magnetic bar, a thermometer, a dropping funnel and a reflux condenser is charged with 4-methyl-5-nitro-pyridin-2-ol (5.0 g), and 1,2-dichloroethane (30 ml). Phosphorous oxide chloride (3.6 ml) is added dropwise. Into this mixture DMF (2.5 ml) is added dropwise at ambient temperature. The reaction mixture is heated at 70° C. under stirring for 0.5 hours. After cooling the mixture to ambient temperature, it is concentrated in vacuo at 50° C., to obtain a brown oily gum. Purification of this gum by flash chromatography over silica gel with hexane/ethyl acetate 7:3 (v:v) gives 4.91 g of the compound as a light yellow solid (MP: 35-38° C.).

$^1$H NMR (400 MHz, CDCl$_3$): δ 2.68(s, 3H, CH$_3$), 7.38(d, 1H), 8.98(d, 1H).

b) Preparation of 2-(4-chloro-3-trifluoromethyl-phenoxy)-4-methyl-5-nitro-pyridine

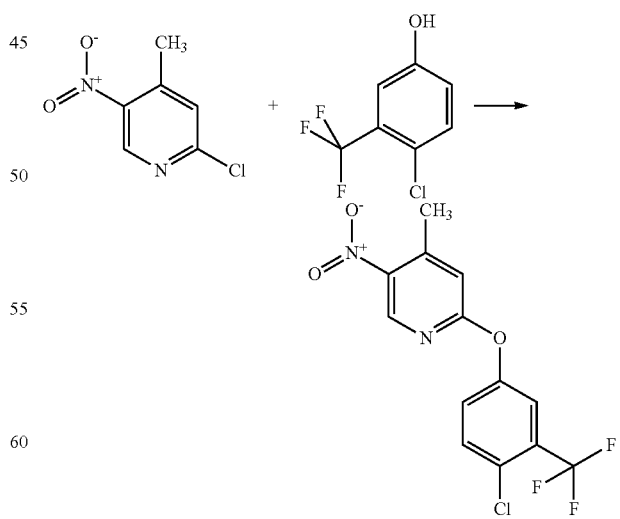

A 250 ml two-necked round-bottomed flask equipped with a magnetic bar, a thermometer and a reflux condenser is charged with DMF (30 ml), 4-chloro-3-trifluoromethyl-phenol (4.5 g), 2-chloro-4-methyl-5-nitro-pyridine (4.0 g) and potassium carbonate (6.4 g). The reaction mixture is stirred at ambient temperature for 1 hour, poured into water (300 ml), acidified with HCl 5 molar (15 ml) and then extracted with ethylacetate (4×50 ml). The combined organic layers are washed with brine (100 ml), dried over sodium sulfate, filtered and the solvent is removed in vacuo. Purification by flash chromatography over silica gel with hexane/ethyl acetate 7:3 (v:v) gives 7.03 g of the compound as a red solid (MP: 75-80° C.).

$^1$H NMR (400 MHz, CDCl$_3$): δ 2.70(s, 3H, CH$_3$), 6.93(s, 1H), 7.28(dxd, 1H), 7.49(d, 1H), 7.56(d, 1H), 8.35(s, 1H).

c) Preparation of 6-(4-chloro-3-trifluoromethyl-phenoxy)-4-methyl-pyridin-3-ylamine

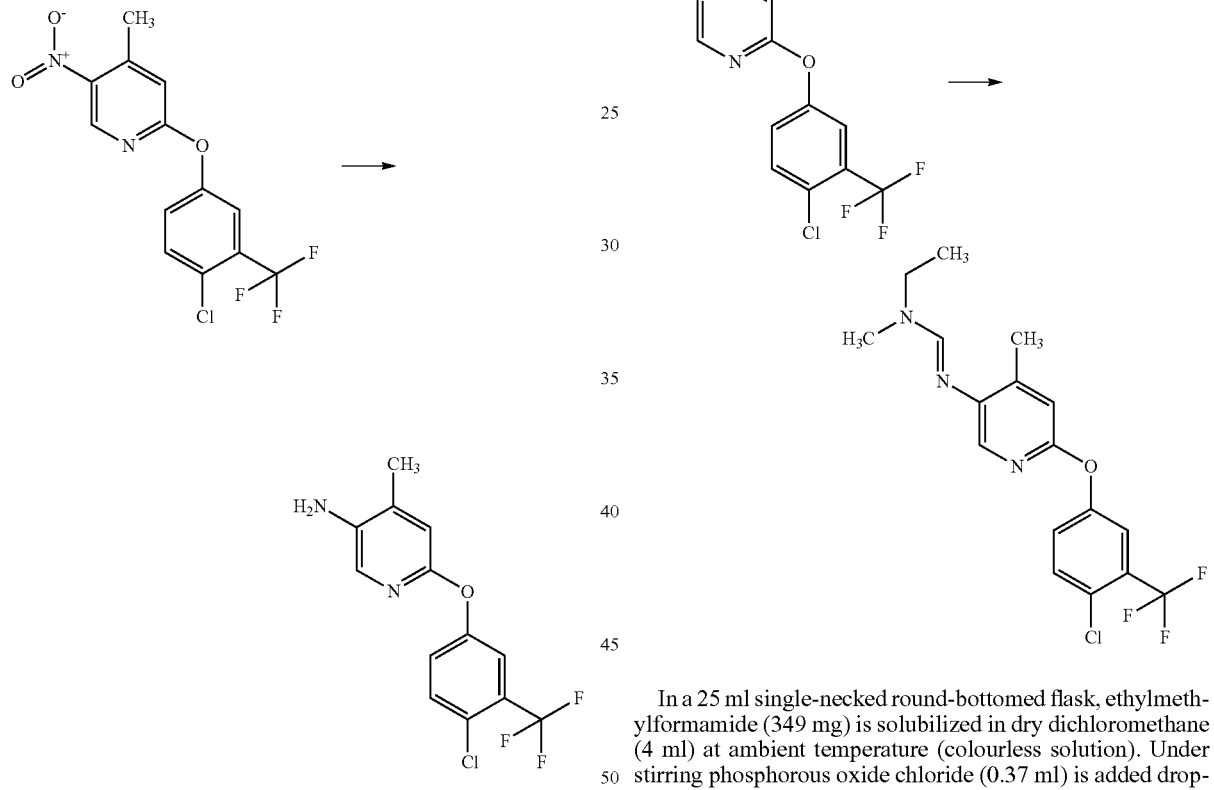

A 100 ml two-necked round-bottomed flask equipped with a KPG-stirrer, a thermometer and a reflux condenser is charged with ethanol (50 ml), water (5 ml), iron (1.29 g) and hydrochloric acid 37% (0.2 ml). The reaction mixture is heated at 50° C. 2-(4-chloro-3-trifluoromethyl-phenoxy)-4-methyl-5-nitro-pyridine (2.4 g) is added portionwise. The mixture is heated at reflux for 1 hour. After cooling the mixture to 50° C. is filtered through celite. The filtrate is poured into water (100 ml) and extracted with ethylacetate (2×50 ml). The combined organic layers are washed with brine (100 ml), dried over sodium sulfate, filtered and the solvent is removed in vacuo. Purification by flash chromatography over silica gel with hexane/ethyl acetate 1:1 (v:v) gives 1.90 g of the compound as a brownish solid (MP: 105-107° C.).

$^1$H NMR (400 MHz, CDCl$_3$): δ 2.23(s, 3H, CH$_3$), 3.50(s$_{br}$, 2H, NH$_2$), 6.75(s, 1H), 7.18(dxd, 1H), 7.40(d, 1H), 7.43(d, 1H), 7.63(d, 1H).

d) Preparation of N'-[6-(4-chloro-3-trifluoromethyl-phenoxy)-4-methyl-pyridin-3-yl]-N-ethyl-N-methyl-formamidine In a 25 ml single-necked round-bottomed flask, ethylmethylformamide (349 mg) is solubilized in dry dichloromethane (4 ml) at ambient temperature (colourless solution). Under stirring phosphorous oxide chloride (0.37 ml) is added dropwise by syringe. Stirring at ambient temperature is continued for 1 hour, whereupon a pink-orange solution is obtained. To this solution, 6-(4-Chloro-3-trifluoromethyl-phenoxy)-4-methyl-pyridin-3-ylamine (605 mg) dissolved in 1.0 ml of dry dichloromethane is added dropwise by syringe, giving a yellow solution. Stirring is continued at an ambient temperature for 1 hour. The mixture is then poured into ice/water (pH=2, water phase). 2 M aqueous NaOH is then added to get a pH of about 11 and stirring is continued for 10 minutes. The mixture is then extracted with dichloromethane (2×50 ml). The combined organic phases are then dried over sodium sulfate, filtered and the solvent is removed in vacuo. Purification of this gum by flash chromatography over silica gel with hexane/ethyl acetate 1:1 (v:v) gives 0.67 g of the compound as a brownish oil.

$^1$H NMR (400 MHz, CDCl$_3$): δ 1.19-1.24(t, 3, CH$_3$), 2.30 (s, 3H, CH$_3$), 3.00(s, 3H, CH$_3$), 3.28-3.53(m, 2H, CH$_2$), 6.78 (s, 1H), 7.19(dxd, 1H), 7.39-7.45(m, 3H), 7.54(s, 1H).

Example P14

Preparation of N'-[6-(4-chloro-3-trifluoromethyl-phenoxy)-4-methyl-pyridin-3-yl]-N-methyl-N-(1-methyl-prop-2-ynyl)-formamidine a) Preparation of N-Methyl-N-(1-methyl-prop-2-ynyl)-formamide

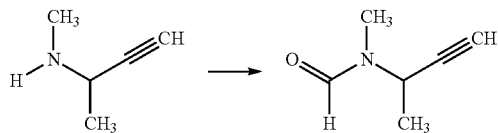

A 350 ml three-necked round-bottomed flask equipped with a magnetic bar, a thermometer, a dean stark water separator and a reflux condenser is charged with methyl-(1-methyl-prop-2-ynyl)-amine (8.31 g) and toluene (100 ml). Formic acid (6.9 g) is added dropwise. The reaction mixture is heated at reflux for 2 hours. After cooling the mixture to ambient temperature, it is concentrated in vacuo at 50° C., to obtain a brown liquid. Purification over silica gel with hexane/ethyl acetate 1:1 (v:v) gives 4.83 g of the compound as a brownish liquid.

$^1$H NMR (400 MHz, CDCl$_3$): δ 1.38+1.49(2d, 3H, CH$_3$), 2.30+2.43(2d, 1H, CH), 2.90+2.98(2s, 3H, CH$_3$), 4.62+5.38 (2m, 1H, CH), 6.78(s, 1H), 7.99+8.16(2s, 1H).

b) Preparation of N'-[6-(4-chloro-3-trifluoromethyl-phenoxy)-4-methyl-pyridin-3-yl]-N-methyl-N-(1-methyl-prop-2-ynyl)-formamidine

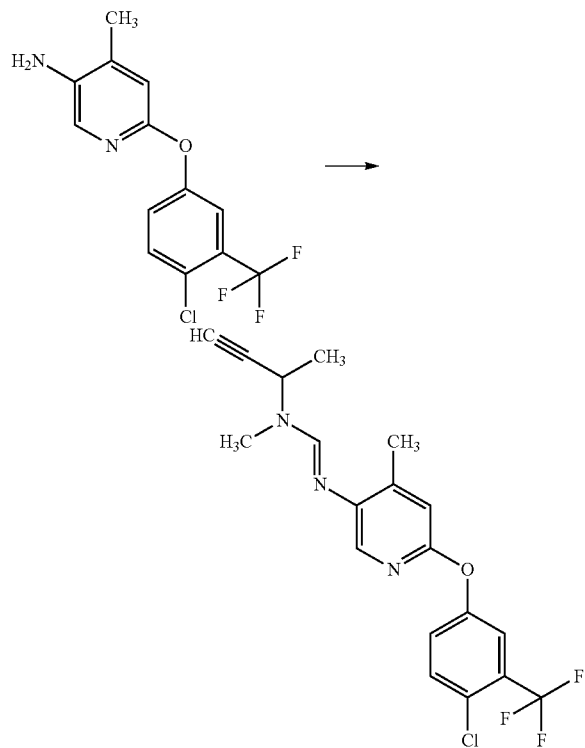

In a 25 ml single-necked round-bottomed flask, N-Methyl-N-(1-methyl-prop-2-ynyl)-formamide (223 mg) is solubilized in dry dichloromethane (4 ml) at ambient temperature (colourless solution). Under stirring a mixture of phosphorous oxide chloride (0.18 ml) in dichloromethane (1 ml) is added dropwise by syringe. Stirring at ambient temperature is continued for 1 hour. To this solution, 6-(4-Chloro-3-trifluoromethyl-phenoxy)-4-methyl-pyridin-3-ylamine (303 mg) dissolved in 10 ml of dry dichloromethane is added dropwise by syringe, giving a yellow solution. Stirring is continued at an ambient temperature for 3 hours. The mixture is then poured into ice/water (pH=2, water phase). 2 M aqueous NaOH is then added to get a pH of about 11 and stirring is continued for 10 minutes. The mixture is then extracted with dichloromethane (2×50 ml). The combined organic phases are then dried over sodium sulfate, filtered and the solvent is removed in vacuo. Purification of this gum by flash chromatography over silica gel with hexane/ethyl acetate 3:2 (v:v) gives 198 mg of the compound as a brownish oil.

$^1$H NMR (400 MHz, CDCl$_3$): δ 1.38+1.48(2d, 3H, CH$_3$), 2.20(s, 3H, CH$_3$), 2.30+2.40(2d, 1H, CH), 2.89+2.98(2s, 3H, CH$_3$), 4.43+5.38(2m, 1H, CH), 6.72(s, 1H), 7.15(dxd, 1H), 7.38(d, 1H), 7.42(d, 1H), 7.62(s, 1H), 7.98+8.15(2s, 1H).

RP HPLC Method

HPLC from Agilent: HP1100 quaternary HPLC pump, HP1100 Variable Wavelength Detector, HP1100 thermostated column compartment and HP1100 solvent degasser. A=water with 0.04% HCOOH, B=Acetonitril/Methanol (4:1, v/v)+0.05% HCOOH Column: Phenomenex Gemini C18, 3 micrometer particle size, 110 Angström, 30×3 mm, Temp: 60° C.

The gradient timetable contains 5 entries which are:

| Time | A % | B % | C % | D % | Flow (ml/min) |
|---|---|---|---|---|---|
| 0.00 | 95.0 | 5.0 | 0.0 | 0.0 | 1.700 |
| 2.00 | 0.0 | 100.0 | 0.0 | 0.0 | 1.700 |
| 2.80 | 0.0 | 100.0 | 0.0 | 0.0 | 1.700 |
| 2.90 | 95.0 | 5.0 | 0.0 | 0.0 | 1.700 |
| 3.10 | 95.0 | 5.0 | 0.0 | 0.0 | 1.700 |

Example P15

Preparation of -2-(4-methyl-pentyloxy)-5-nitro-pyridine

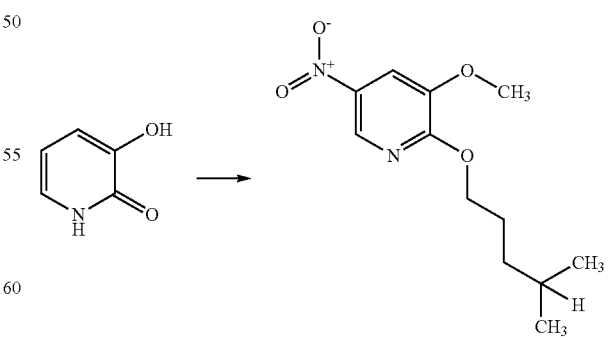

In a 350 ml 5-necked reaction flask (mechanical stirrer, dropping funnel, thermometer), 3-Hydroxy-1H-pyridin-2-one [CA registry number 626-06-2] (35.0 g) is suspended in water (120 ml) at an ambient temperature. Under stirring, sodium hydroxide (13.48 g) is added portionwise over 10 minutes, whereupon an exothemic reaction is observed. The mixture is then immersed in a cooling bath (common salt/crushed ice) to obtain a temperature of 0° C. Afterwards, dimethyl sulfate (41.72 g) is added over 15 minutes while cooling and stirring is continued. Thereafter, the cooling bath is removed and the mixture is stirred overnight at room temperature. The mixture is then extracted with ethyl acetate. The organic phase is dried over sodium sulfate, filtered and the solvent removed in vacuo to give a dark brown viscous material.

This material is taken up in 112 mol of conc. sulfuric acid and transferred into a 350 ml 5-necked reaction flask. After stirring and cooling in an ice/water bath, a freshly prepared solution of mixed acid [freshly prepared from sulfuric acid (31.7 ml) and fumic nitric acid (31.8 ml)] is added dropwise over 1.5 h while keeping the temperature below 15° C. Stirring is continued at a temperature below 10° C. for an additional 45 minutes. Then, the mixture is carefully transferred onto ice and then water is added (to give finally 700 ml of water phase). The resulting precipitate is stirred for 40 minutes, then filtered and the filter cake washed with water to give 19.6 g of an orange solid after drying.

In a 350 ml 5-necked reaction flask equipped with a condensor, a suspension of this intermediate (5.00 g) in dry dioxane (30.0 ml) is stirred at room temperature. First, 1-bromo-4-methylpentane (5.82 g) then silver oxide (13.62 g) is added. The resulting suspension is stirred under heating to refulx for 13.5 h. After cooling to room temperature, ethyl acetate (50 ml) is added and the mixture filtered through a pad of Hyflo and washed with ethyl acetate (50 ml). The organic pahes is washed with water and brine, then, dried over sodium sulfate, filtered and the solvent removed in vacuo to give 4.00 g of an orange oil. This raw product is purified by chromatography over silica gel (eluent: hexanes/ethyl acetate 9:1 (v:v)). This way 1.49 g of the title compound in form of a yellow solid is obtained (MP: 48-49° C.).

$^1$H NMR (400 MHz, CDCl$_3$): δ 0.92(d, 6H), 1.32(m, 2 H), 1.62(m, 1H), 1.86(m, 2H), 3.96(s, 3H), 4.48(t, 2H), 7.76(d, 1H), 7.68(d, 1H).

LC: UV Detection: 220 nm; R$_t$=2.08 min.

TLC: Plates: Merck DC-Plates, silica gel F$_{254}$, saturated atmosphere in developing tank, UV detection, eluent: heptane/ethyl acetate 1:1 (v:v); R$_f$ of title compound=0.63.

Example P16

Preparation of 2-Bromo-5-methoxy-6-(4-methyl-pentyloxy)-pyridin-3-ylamine

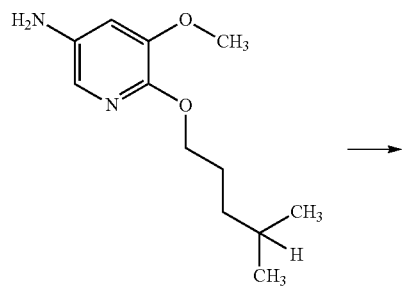

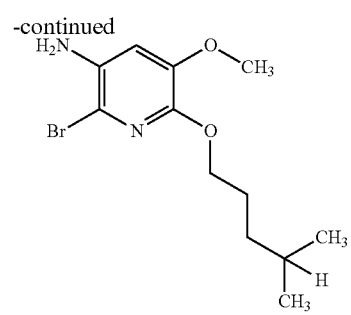

In a 50 ml three-necked round-bottomed flask equipped with a condensor, 5-Methoxy-6-(4-methyl-pentyloxy)-pyridin-3-ylamine (70 mg) is dissolved in dry acetonitril (0.50 ml) and stirred at room temperature. Under stirring, N-bromosuccinimde (55 mg) is added. Stirring is continued for 1.25 h under heating to reflux. After this, a 2 M aqueous solution of sodium hydroxide (20 ml, pH of 10) is added and extraction is done using ether (three times with 20 ml). The organic layer is washed with a 10% aqueous sodium bisulfite solution (20 ml). After drying over sodium sulfate, the organic layer is filtered and the solvent removed in vacuo to give a 40 mg of a brown gum. After chromatography on silica gel (eluent: hexanes/ethyl acetate 2:1 (v:v), 6.3 mg of the title compound are obtained in the form of a red oil.

$^1$H NMR (400 MHz, CDCl$_3$): δ 0.90(d, 6H), 1.29(m, 2 H), 1.60(m, 1H), 1.79(m, 2H), 3.67(s, 3H), 3.81(s, 3H), 4.26(t, 2H), 6.61(s, 1H).

LC: UV Detection: 220 nm; R$_t$=1.94 min.

TLC: Plates: Merck DC-Plates, silica gel F$_{254}$, saturated atmosphere in developing tank, UV detection, eluent: heptane/ethyl acetate 1:2 (v:v); R$_f$ of title compound=0.47.

Example P17

Preparation of 6-(4-Methyl-pentyloxy)-3-nitro-pyridin-2-ylamine

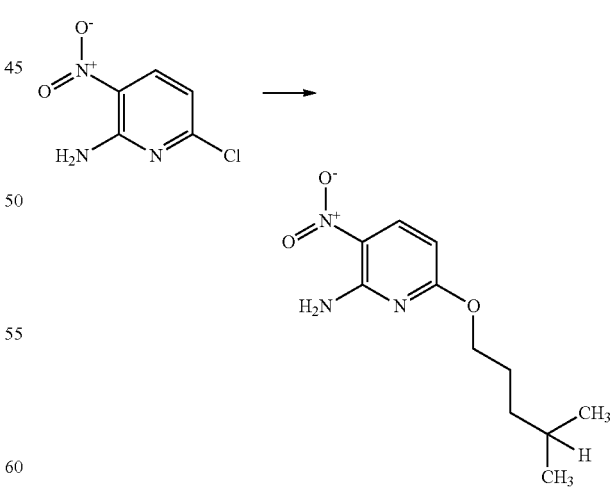

A) In a 100 ml three-necked round-bottomed flask equipped with a condensor and a thermometer, sodium hydride (2.51 g of a 55% suspension in mineral oil) is suspended in dry tetrahydrofuran (15 ml) and hexamethyldisilazane (0.60 ml) is added and the mixture stirred for 20 minutes at room temperature under argon. Under stirring, 4-methyl-1-pentanol (7.23 ml) was added dropwise by syringe over 10 minutes whereupon gas formation and a temperature increase to 31° C. is observed. Stirring is continued for an additional 50 minutes.

B) In a 200 ml five-necked reaction flask equipped with a mechanical stirrer, dropping funnel, condensor and thermometer, 6-chloro-3-nitro-pyridin-2-ylamine (5.00 g, cf. registry number 27048-04-0) is suspended in dry tetrahydrofuran (15 ml) at room temperature under argon. Under stirring, the suspension obtained as described under A), is added in small portions over 15 minutes. Occasional cooling with an ice/water bath is used to keep the temperature under 30° C. To make stirring easier more dry tetrahydrofuran is added (20 ml). Stirring is continued for 3.5 h. Afterwards, quenching is carried out by carefully adding an excess of water (50 ml). Extraction is done then by using ether (60 ml twice). The organic phase is washed with brine, dried over sodium sulfate, filtered. The solvent is then removed in vacuo to give 10.78 g of a yellow-brown oil. Chromatography on silica gel (eluent: hexanes/ethyl acetate 97:3 (v:v)) gives then 6.89 g of the title compound in the form of a yellow solid (MP: 57-58° C.).

$^1$H NMR (400 MHz, CDCl$_3$): δ 0.91(d, 6H), 1.28(m, 2 H), 1.60(m, 1H), 1.75(m, 2H), 4.28(t, 2H), 4.90-8.20(broad, 2H), 6.11(d, 1H), 8.28(d, 1H).

LC: UV Detection: 220 nm; $R_t$=1.97 min.

TLC: Plates: Merck DC-Plates, silica gel $F_{254}$, saturated atmosphere in developing tank, UV detection, eluent: heptane/ethyl acetate 9:1 (v:v); $R_f$ of title compound=0.22.

Example P18

Preparation of 5-Bromo-6-(4-methyl-pentyloxy)-3-nitro-pyridin-2-ylamine

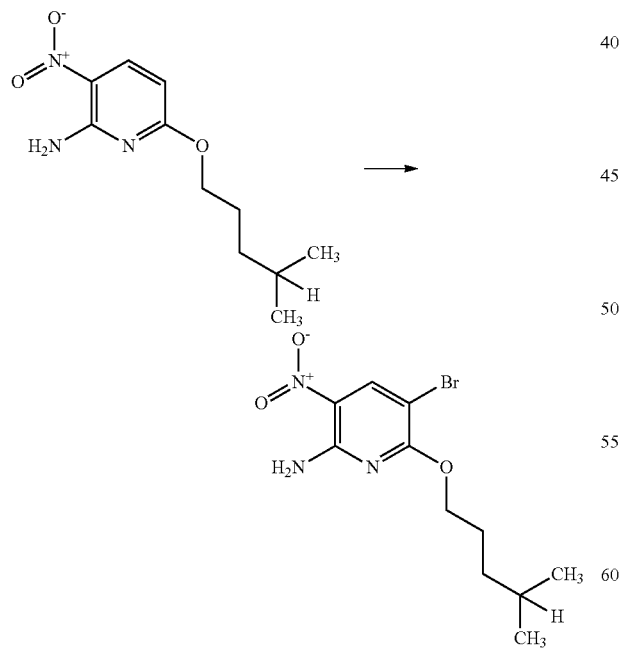

In a 50 ml three-necked round-bottomed flask equipped with a condensor, 6-(4-methyl-pentyloxy)-3-nitro-pyridin-2-ylamine (1.83 g) is dissolved in dry acetonitril (8.00 ml) and stirred at room temperature under argon. Under stirring, N-bromosuccinimide (1.36 g) is added. Stirring is continued for 3.5 h under heating to reflux. After this, water is added (30 ml) and extraction is done using ether (twice with 60 ml each time). The organic layer is washed with a 10% aqueous sodium bisulfite solution (40 ml). After drying over sodium sulfate, the organic layer is filtered and the solvent removed in vacuo to give a 2.41 g of a dark red oil. After chromatography on silica gel (eluent: hexanes/ethyl acetate 94:6 (v:v), 1.87 g of the title compound are obtained in the form of a dark red oil.

$^1$H NMR (400 MHz, CDCl$_3$): δ 0.92(d, 6H), 1.33(m, 2 H), 1.62(m, 1H), 1.81(m, 2H), 4.34(t, 2H), 4.70-8.40(broad, 2H), 8.52(s, 1H).

LC: UV Detection: 220 nm; $R_t$=2.16 min.

TLC: Plates: Merck DC-Plates, silica gel $F_{254}$, saturated atmosphere in developing tank, UV detection, eluent: heptane/ethyl acetate 9:1 (v:v); $R_f$ of title compound=0.20.

Preparation of 5-Chloro-6-(4-methyl-pentyloxy)-3-nitro-pyridin-2-ylamine:

This compound can be obtained in an analogous from 6-(4-methyl-pentyloxy)-3-nitro-pyridin-2-ylamine using N-chloro-succinimide.

$^1$H NMR (400 MHz, CDCl$_3$): δ 0.92(d, 6H), 1.32(m, 2 H), 1.61(m, 1H), 1.81(m, 2H), 4.36(t, 2H), 4.80-8.30(broad, 2H), 8.37(s, 1H).

LC: UV Detection: 220 nm; $R_t$=2.13 min.

TLC: Plates: Merck DC-Plates, silica gel $F_{254}$, saturated atmosphere in developing tank, UV detection, eluent: heptane/ethyl acetate 9:1 (v:v); $R_f$ of title compound=0.18.

MP: 53-54° C.

Example P19

Preparation of 2,5-Dibromo-6-(4-methyl-pentyloxy)-3-nitro-pyridine

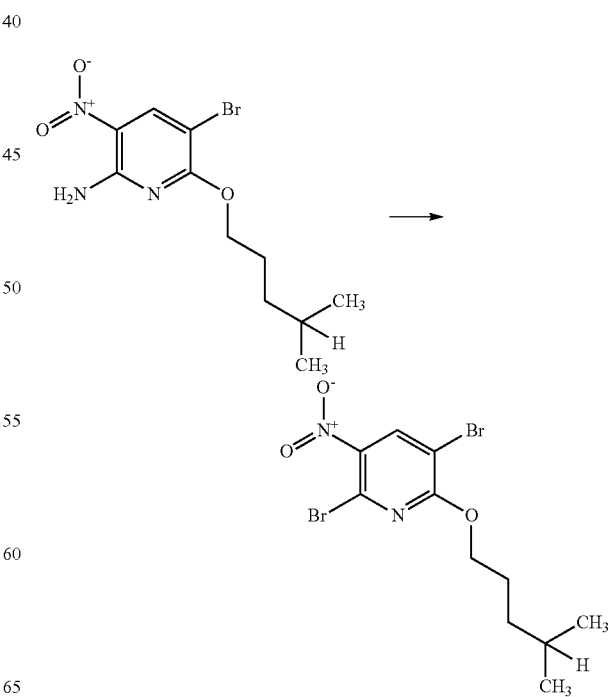

A) In a 25 ml single-necked round-bottomed flask 1.41 ml of a 48% ageous hydrobromic acid solution is added dropwise to dimethylsulfoxide (7.40 ml) under stirring and cooling with an ice/water bath to keep the temperature at about room temperature.

B) In a 50 ml three-necked reaction flask with a condensor, 5-bromo-6-(4-methyl-pentyloxy)-3-nitro-pyridin-2-ylamine (1.00 g) is dissolved in dimethylsulfoxide (3.70 ml). Under stirring, potassium nitrite (1.07 g) and copper(I) bromide (90 mg) are added. Under stirring, the temperature is kept between 35 and 38° C. while the solution obtained under A) is added dropwise over 5 minutes. Stirring is continued for an additional 18 h within the same temperature range whereupon a dark brown suspension is obtained. After cooling to room temperature, the suspension is brought onto a saturated ageous sodium carbonate solution (70 ml, pH is 8). Extraction is carried out using ether (three times with 40 ml). The combined organic phases are dried over sodium sulfate and then filtered over a pad of silica (on top of a sintered glass filter disk). After washing with ether the combined ether phases are concentrated in vacuo to give 790 mg of the title compound in the form of a yellow oil.

$^1$H NMR (400 MHz, CDCl$_3$): δ 0.93(d, 6H), 1.35(m, 2 H), 1.63(m, 1H), 1.84(m, 2H), 4.47(t, 2H), 8.43(s, 1H).

TLC: Plates: Merck DC-Plates, silica gel F$_{254}$, saturated atmosphere in developing tank, UV detection, eluent: heptane/ethyl acetate 9:1 (v:v); R$_f$ of title compound=0.56.

Example P20

Preparation of 3-Bromo-2-(4-methyl-pentyloxy)-5-nitro-6-phenyl-pyridine

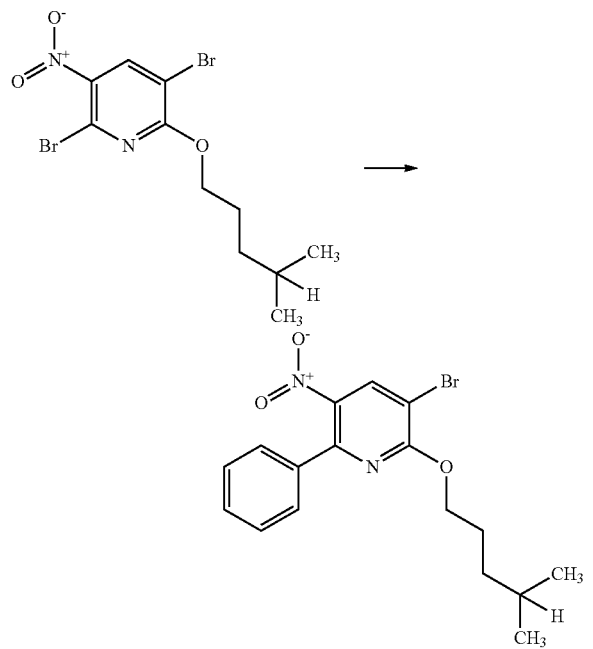

In a 50 ml three-necked round-bottomed flask with a condensor, 2,5-dibromo-6-(4-methyl-pentyloxy)-3-nitro-pyridine (200 mg) is dissolved in a mixture of toluene (6.00 ml) and ethanol (0.75 ml) under argon. Under stirring, potassium carbonate (159 mg) in water (0.95 ml) is added, whereupon a yellow biphasic mixture is obtained. Phenylboronic acid is added (63.8 mg). Stirring at room temperature is continued for 15 minutes while a stream of argon is led over the mixture. After this, tetrakis(triphenylphosphine)-palladium (18.1 mg) is added and the solution stirred under heating to reflux for 3.5 h. The mixture is then stirred at room temperature overnight. Then, a saturated ageous solution of ammonium chloride (25 ml) is added and extraction is carried out with ether (twice with 30 ml). The organic phase is dried over sodium sulfate, filtered and the solvent removed in vacuo to give 220 mg of a yellow oil. After purification on silica gel (eluent: hexanes/ethyl acetate gradient from 100:0 to 98:2) 140 mg of an yellow oil is obtained, containing a mixture of the title compound (43%), along with the two following by-products:

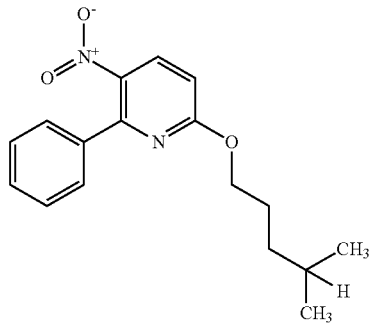

6-(4-Methyl-pentyloxy)-3-nitro-2-phenyl-pyridine
36%

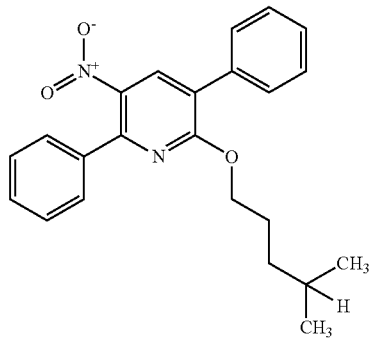

2-(4-Methyl-pentyloxy)-5-nitro-3,6-diphenyl-pyridine
21%

This mixture is ised as such for the following reduction step to obtain the corresponding anilines.

Example P21

Preparation of 5-Bromo-6-(4-methyl-pentyloxy)-2-phenyl-pyridin-3-ylamine

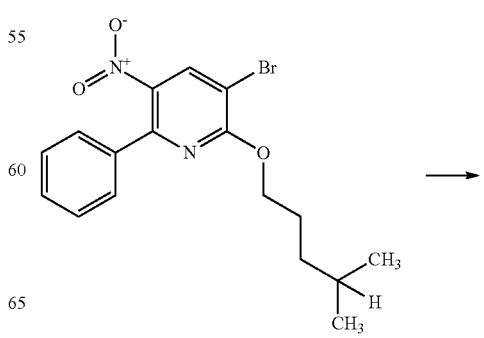

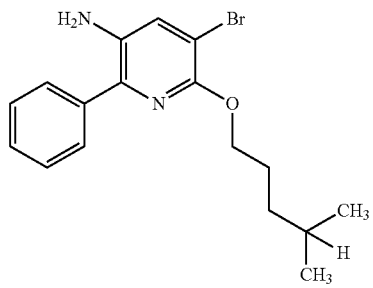

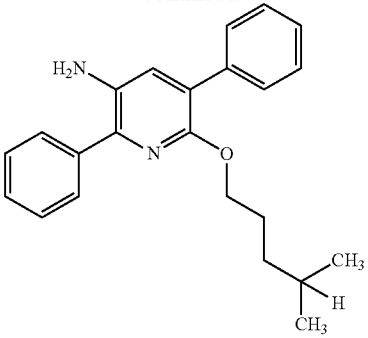

6-(4-Methyl-pentyloxy)-2,5-diphenyl-pyridin-3-ylamine

This mixture is used directly for the following step.

Example P22

Preparation of N-Ethyl-N-methyl-N'-[6-4-methyl-pentyloxyl-2,5-diphenyl-pyridin-3-yl]-formamidine

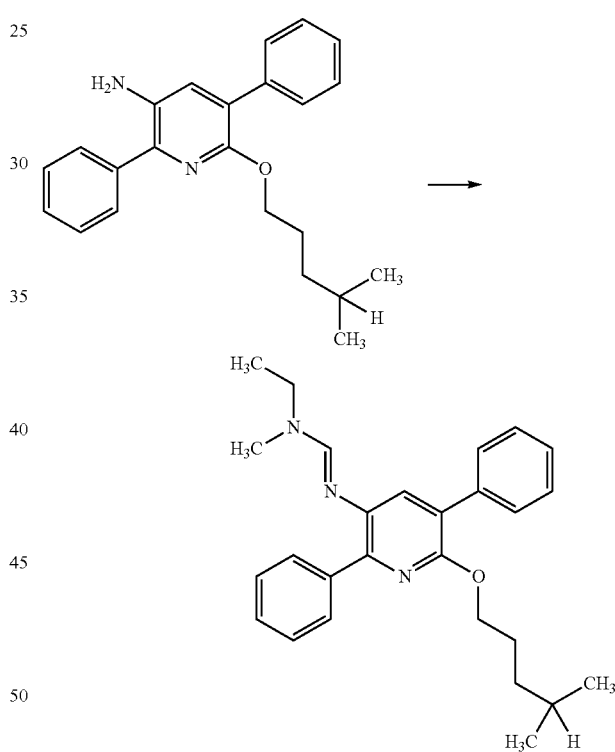

In a 25 ml three-necked reaction flask with a condensor, the mixture obtained above (140 mg) (containing 3-bromo-2-(4-methyl-pentyloxy)-5-nitro-6-phenyl-pyridine (43%), 6-(4-methyl-pentyloxy)-3-nitro-2-phenyl-pyridine (35%), and 2-(4-methyl-pentyloxy)-5-nitro-3,6-diphenyl-pyridine (21%)) was solubilized in methanol (0.50 ml). Under stirring and cooling with an ice/water bath, 37% ageous hydrochloric acid (0.15 ml) is added dropwise. After removing the cooling bath, tin powder (88 mg) is added. The resulting suspension is then stirred under heating to reflux for 3.25 h. Then, the mixture is allowed to reach room temperature and the methanol is removed in vacuo. To the resulting orange gum, 2 molar ageous sodium hydroxide solution is added (10 ml). Extraction is carried out using ethyl acetate (twice with 20 ml). The organic layer is dried over sodium sulfate, filtered and the solvent is removed in vacuo to give 130 mg of a yellow gum. The raw material is purified by chromatography on silica gel (eluent: hexanes/ethyl acetat 97:3 (v:v)). 50 mg of the title compound is obtained in the form of a yellow oil.

$^1$H NMR (400 MHz, CDCl$_3$): δ 0.91(d, 6H), 1.33(m, 2 H), 1.61(m, 1H), 1.79(m, 2H), 3.56(s, 3H), 4.31(t, 2H), 7.33(s, 1H), 7.37(tt, 1H), 7.46(td, 2H), 7.71(dt, 2H).

LC: UV Detection: 220 nm; R$_t$=2.30 min.

TLC: Plates: Merck DC-Plates, silica gel F$_{254}$, saturated atmosphere in developing tank, UV detection, eluent: heptane/ethyl acetate 3:1 (v:v); R$_f$ of title compound=0.35.

Along with this, a mixture of the two following compounds in the form of a yellow oil (53 mg) is isolated as well.

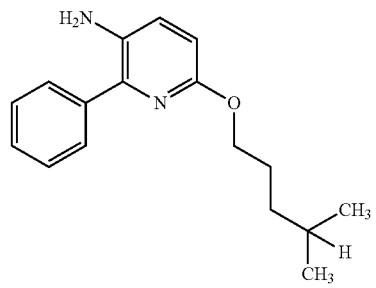

6-(4-Methyl-pentyloxy)-2-phenyl-pyridin-3-ylamine

In a 8 ml Supelco vessel (closed by a septum), ethylmethylformamide (13.7 mg) is solubilized in dry dichloromethane (3.00 ml) at ambient temperature (colourless solution). Under stirring phosphorous oxide chloride (0.37 ml) is added dropwise by syringe. Stirring at ambient temperature is continued for 1.5 hour, whereupon a light-orange solution is obtained. To this solution, 36.2 mg of the mixture of the two by-products obtained above [consisting of 6-(4-methyl-pentyloxy)-2,5-diphenyl-pyridin-3-ylamine and 6-(4-methyl-pentyloxy)-2-phenyl-pyridin-3-ylamine] as a solution in dry dichloromethane (2.00 ml) is added dropwise by syringe, giving a light-brown solution. Stirring is continued at an ambient temperature for 3.5 hours. The mixture is then poured into ice/water. 2 M aqueous NaOH (10 ml) is then added to get a pH of about 12 and stirring is continued for 10 minutes. The mixture is then extracted with dichloromethane (2×20 ml). The combined organic phases are then dried over sodium sulfate, filtered and the solvent is removed in vacuo. Purification of the yellow gum by flash chromatography over silica gel with hexane/ethyl acetate 4:1 (v:v) gives 17.1 mg of the title compound as a yellow oil (66%).

$^1$H NMR (400 MHz, CDCl$_3$): δ 0.90(d, 6H), 1.15(t, 3H), 1.33(m, 2 H), 1.59(m, 1H), 1.79(m, 2H), 2.98(s, 3H), 3.10-3.70(broad, 2H), 4.41(t, 2H), 7.33(m, 8H), 7.67(dd, 2H), 8.18(dd, 2H).

LC: UV Detection: 220 nm; R$_t$=1.61 min.

TLC: Plates: Merck DC-Plates, silica gel F$_{254}$, saturated atmosphere in developing tank, UV detection, eluent: heptane/ethyl acetate 3:1 (v:v); R$_f$ of title compound=0.18.

Example P23

Preparation of 2-Bromo-5-chloro-6-(4-methyl-pentyloxy)-3-nitro-pyridine

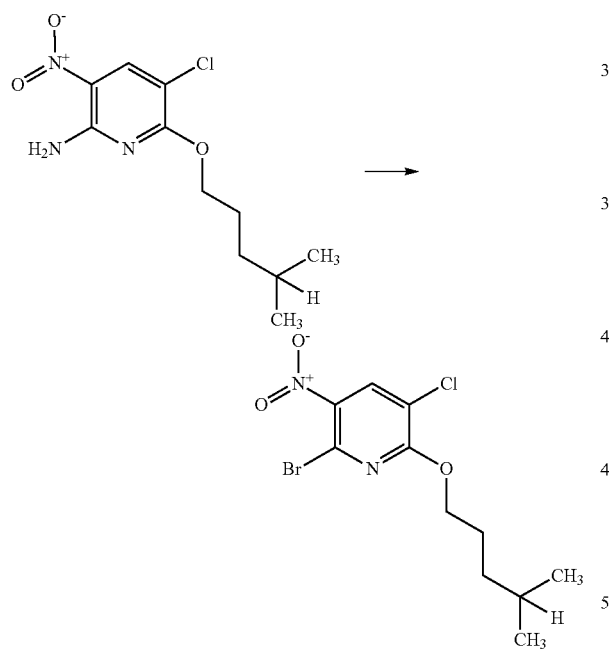

A) In a 25 ml single-necked round-bottomed flask 1.40 ml of a 48% ageous hydrobromic acid solution is added dropwise to dimethylsulfoxide (7.30 ml) under stirring and cooling with an ice/water bath to keep the temperature at about room temperature.

B) In a 50 ml three-necked reaction flask with a condensor, 5-chloro-6-(4-methyl-pentyloxy)-3-nitro-pyridin-2-ylamine (850 mg) is dissolved in dimethylsulfoxide (3.70 ml) at room temperature. Under stirring, potassium nitrite (1.06 g) and copper(I) bromide (89 mg) are added. Under stirring, the temperature is kept between 35 and 38° C. while the solution obtained under A) is added dropwise over 6 minutes. Stirring is continued for an additional 20 h within the same temperature range whereupon a dark brown solution is obtained. After cooling to room temperature, the suspension is brought onto a saturated ageous sodium carbonate solution (50 ml, pH is 9). Extraction is carried out using ether (three times with 50 ml). The combined organic phases are dried over sodium sulfate and then filtered over a pad of silica (on top of a sintered glass filter disk). After washing with ether the combined ether phases are concentrated in vacuo to give 810 mg of the title compound in the form of a yellow oil. After purification by chromatography on silica gel (eluent: hexanes/ethyl acetate 95:5 (v:v)) 870 mg of the title compound are obtained in the form of yellow oil.

$^1$H NMR (400 MHz, CDCl$_3$): δ 0.93(d, 6H), 1.35(m, 2 H), 1.63(m, 1H), 1.85(m, 2H), 4.48(t, 2H), 8.28(s, 1H).

TLC: Plates: Merck DC-Plates, silica gel F$_{254}$, saturated atmosphere in developing tank, UV detection, eluent: heptane/ethyl acetate 9:1 (v:v); R$_f$ of title compound=0.55.

Example P24

Preparation of 5-Methoxy-6-(4-methyl-pentyloxy)-pyridin-3-ylamine

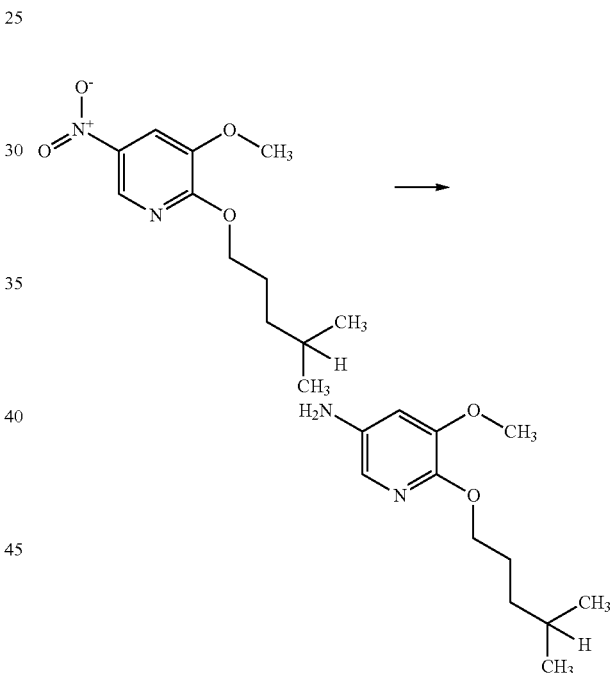

In a 25 ml three-necked reaction flask with a condensor, 3-Methoxy-2-(4-methyl-pentyloxy)-5-nitro-pyridine is solubilized in methanol (2.00 ml). Under stirring and cooling with an ice/water bath, 37% ageous hydrochloric acid (0.82 ml) is added. After removing the cooling bath, tin powder (470 mg) is added. The resulting suspension is then stirred under heating to reflux for 3.5 h. Then, the mixture is allowed to reach room temperature and the methanol is removed in vacuo. To the resulting yellow gum, 2 molar ageous sodium hydroxide solution is added (25 ml). Extraction is carried out using ethyl acetate (twice with 30 ml). The organic layer is dried over sodium sulfate, filtered and the solvent is removed in vacuo to give 350 mg of a brown oil. The raw material is purified by chromatography on silica gel (eluent: hexanes/ethyl acetat 2:1 (v:v)). 170 mg of the title compound (38.5%) is obtained in the form of a red oil.

$^1$H NMR (400 MHz, CDCl$_3$): δ 0.90(d, 6H), 1.30(m, 2 H), 1.59(m, 1H), 1.81(m, 2H), 3.36(s, 2H), 3.82(s, 3H), 4.27(t, 2H), 6.56(d, 1H), 7.21(d, 1H).

LC: UV Detection: 220 nm; R$_t$=1.47 min.

TLC: Plates: Merck DC-Plates, silica gel F$_{254}$, saturated atmosphere in developing tank, UV detection, eluent: heptane/ethyl acetate 1:1 (v:v); R$_f$ of title compound=0.15.

Along with this, 70 mg of a mixture of two by-products in the form of a brown oil was obtained as well. This mixture could be separated by a second chromatography on silica gel (eluent: toluene/acetone 97:3 (v:v)) to give the following compounds:

Compound A

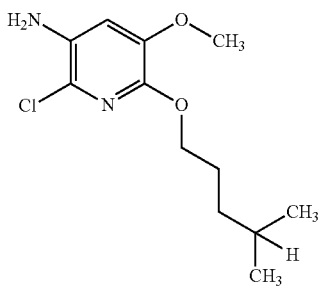

2-Chloro-5-methoxy-6-(4-methyl-pentyloxy)-pyridin-3-ylamine
35 mg (86%, along with some 14% of compound B)

Compound B

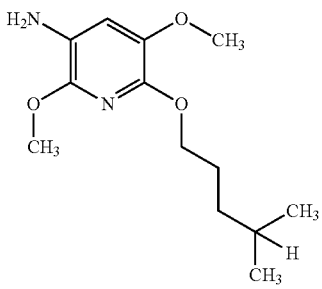

2,5-Dimethoxy-6-(4-methyl-pentyloxy)-pyridin-3-ylamine
55% (92%, along with some 8% of compound A)

Example P25

Preparation of 2-(4-Methyl-pentyloxy)-5-nitro-3,6-bis-trifluoromethyl-pyridine

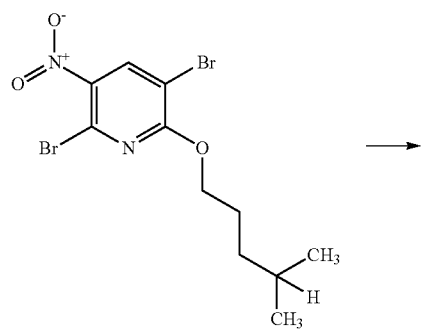

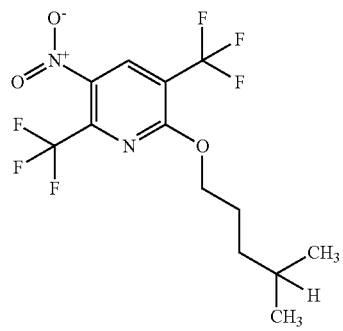

In a 10 ml single-necked round-bottomed flask equipped with a condensor, 2,5-dibromo-6-(4-methyl-pentyloxy)-3-nitro-pyridine (150 mg) is dissolved in dry dichloromethane (1.00 ml). To the reulting yellow solution, methyl-2,2-difluoro-2-(fluorosulfonyl)-acetate (377 mg), copper(i)-iodide (90 mg) and hexamethylphosphoramide (HMPA) (350 mg) are added. The resulting suspension is stirred under heating to reflux for 6 hours. The progress of the transformation is followed by $^{19}$F-NMR (CDCl$_3$). Stirring is continued overnight at an ambient temperature. Saturated ammonium chloride solution is then added (30 ml) and the mixture extracted with ether (2×20 ml). The combined organic phases are then dried over sodium sulfate, filtered and the solvent is removed in vacuo. Purification of the yellow oil obtained (120 mg) by flash chromatography over silica gel with hexane/ethyl acetate 98:2 (v:v) gives 100 mg of the title compound as a yellow oil.

$^1$H NMR (400 MHz, CDCl$_3$): δ 0.92(d, 6H), 1.34(m, 2H), 1.63(m, 1H), 1.85(m, 2H), 4.59(t, 2H), 8.49(s, 1H).

TLC: Plates: Merck DC-Plates, silica gel F$_{254}$, saturated atmosphere in developing tank, UV detection, eluent: heptane; R$_f$ of title compound=0.11.

Example P26

Preparation of 5-Chloro-6-(4-methyl-pentyloxy)-3-nitro-pyridine-2-carbonitrile

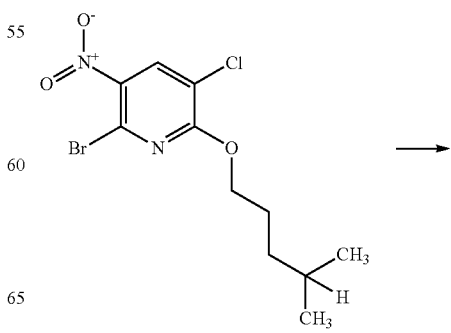

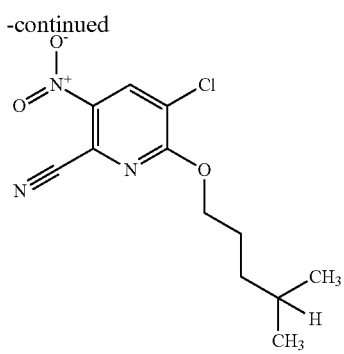

In a 10 ml single-necked round-bottomed flask equipped with an efficient condensor, 2-bromo-5-chloro-6-(4-methyl-pentyloxy)-3-nitro-pyridine (200 mg) is dissolved in dry acetonitrile (3.00 ml). To the reulting yellow solution, copper (I) cyanide (109 mg) is added. The resulting suspension is stirred under heating to reflux for 6 hours whereupon a brown solution is obtained. The progress of the transformation is followed by GC-MS. The mixture is allowed to reaxch ambient temperature. Saturated ammonium chloride solution (20 ml) along with some ice is then added and the mixture extracted with ether (2×20 ml). The combined organic phases are then dried over sodium sulfate, filtered and the solvent is removed in vacuo to give 150 mg of the title compound in the form of a yellow oil (89%).

$^1$H NMR (400 MHz, CDCl$_3$): δ 0.93(d, 6H), 1.36(m, 2H), 1.63(m, 1H), 1.87(m, 2H), 4.54(t, 2H), 8.53(s, 1H).

TLC: Plates: Merck DC-Plates, silica gel F$_{254}$, saturated atmosphere in developing tank, UV detection, eluent: heptane/ethyl acetate 9:1 NM; R$_f$ of title compound=0.28.

Example P27

Preparation of 3-Chloro-2-(4-methyl-pentyloxy)-5-nitro-6-trifluoromethyl-pyridine

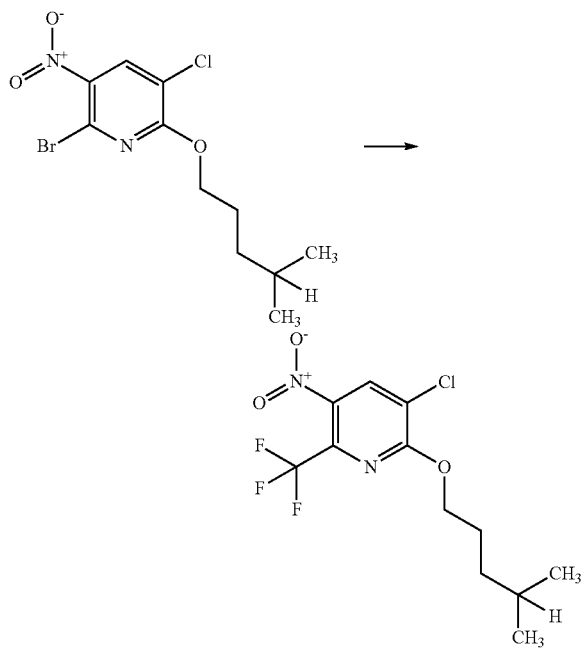

In a 10 ml single-necked round-bottomed flask equipped with an efficient condensor, 2-bromo-5-chloro-6-(4-methyl-pentyloxy)-3-nitro-pyridine (150 mg) is dissolved in dry dimethylformamide (1.20 ml). To the reulting yellow solution, methyl-2,2-difluoro-2-(fluorosulfonyl)-acetate (256 mg), copper(i)-iodide (102 mg) and hexamethylphosphoramide (HMPA) (400 mg) are added. The resulting suspension is stirred and heating to 100° C. for 2 hours. The progress of the transformation is followed by GC-MS. The reaction mixture is allowed to reach room temperature. Saturated ammonium chloride solution is then added (30 ml, pH about 3) and the mixture extracted with ether (2×30 ml). The combined organic phases are then dried over sodium sulfate, filtered through a pad of silica gel and the solvent is removed in vacuo. Purification of the yellow oil obtained (120 mg) by flash chromatography over silica gel with hexane/ethyl acetate 98:2 (v:v) gives 120 mg of the title compound as a yellow oil (83%).

$^1$H NMR (400 MHz, CDCl$_3$): δ 0.93(d, 6H), 1.35(m, 2H), 1.62(m, 1H), 1.86(m, 2H), 4.52(t, 2H), 8.26(s, 1H).

TLC: Plates: Merck DC-Plates, silica gel F$_{254}$, saturated atmosphere in developing tank, UV detection, eluent: heptane; R$_f$ of title compound=0.11.

Example P28

Preparation of 6-Chloro-2-methoxy-3-nitro-pyridine

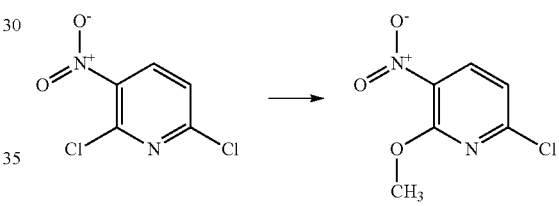

A) In a 50 ml three-necked round-bottomed flask equipped with an condensor and a thermometer, sodium hydride (2.26 g of a 0.55% dispersion in mineral oil) is suspended in dry dioxane (10 ml) under argon. Then, hexamethyldisilazane (0.81 ml)) is added. Under stirring, dry methanol (2.10 ml) is added dropwise by syringe (foaming, gas escapes). The temperature is kept below 34° C. by cooling using an ice/water bath. After the addition, stirring is continued at an ambient temperature for 50 minutes. To make the following tranfer of the suspension easier more dioxane is added (10 ml).

B) In a 200 ml five-necked reaction flask equipped with an condensor, mechanical stirrer, dropping funnel and thermometer, 2,6-dichloro-3-nitro-pyridine [CA registry number 136901-10-5] (10.0 g) dissolved in dry dioxane (40 ml) is stirred under argon. The suspension freshly prepared as described under A), is added slowly over 12 minutes (again foaming and gas formation). An ice/water bath is used to keep the temperature below 32° C. Stirring at an ambient temperature is continued for 2 hours. Progress of reaction is monitored by thin layer chromatography (cf. below).

Water is then added (50 ml, pH about 8-9) and the mixture extracted with ether (2×50 ml). The combined organic phases are then dried over sodium sulfate, filtered and the solvent is removed in vacuo to give 10.45 g of a light yellow solid. Purification of the yellow oil obtained (120 mg) by flash chromatography over silica gel with hexane/ethyl acetate 97:3 (v:v) gives 8.00 g of the title compound as a light yellow solid (MP: 73-74° C., yield: 82%).

$^1$H NMR (400 MHz, CDCl$_3$): δ 4.14 (s, 3H), 7.05 (d, 1H), 8.28 (d, 1H).

TLC: Plates: Merck DC-Plates, silica gel F$_{254}$, saturated atmosphere in developing tank, UV detection, eluent: hexanes/ethyl acetate 9:1 (v:v); R$_f$ of title compound=0.33, R$_f$ of starting material=0.21.

Only minor amounts of the isomer of the title compound and of the bis-methoxy-pyridine are found.

Example P29

Preparation of 2-Methoxy-6-(4-methyl-pentyloxy)-3-nitro-pyridine

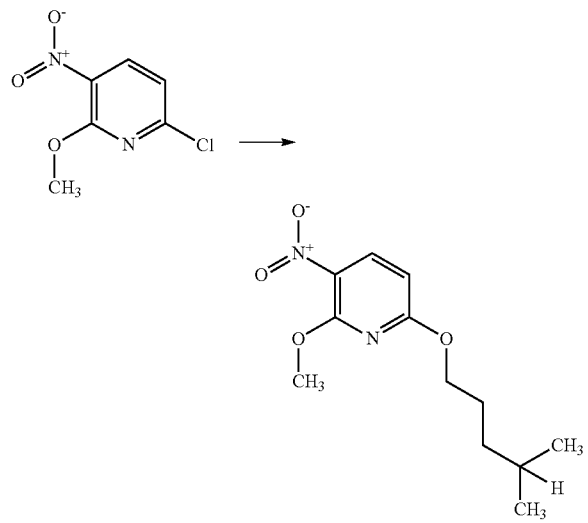

A) In a 100 ml five-necked reaction flask equipped with an condensor, mechanical stirrer, dropping funnel and a thermometer, sodium hydride (1.16 g of a 0.55% dispersion in mineral oil) is suspended in dry dioxane (20 ml) under argon. Then, hexamethyldisilazane (0.44 ml) is added and stirring continued for 15 minutes. Under stirring, 4-methyl-1-pentanol (3.33 ml) is added dropwise by syringe over 5 minutes (foaming, gas escapes, slightly exothermic). The temperature doesn't go beyond 25° C. Stirring is continued for 60 minutes at an ambient temperature whereupon a light yellow suspension is obtained.

B) Afterwards, 6-chloro-2-methoxy-3-nitro-pyridine dissolved in dry dioxane (10 ml) is added over 8 minutes (foam and gas formation). Cooling with an ice/water bath is used to keep the temperature below 28° C. More dry dioxane is added (10 ml) and the suspension stirred at an ambient temperature overnight. Progress of reaction is followed by $^1$H-NMR of a sample (obtained by a work-up of a small sample as described below), indicating about 30% of starting material left. In order to drive the reaction forward, two additional additions of the alcoholate of 4-methyl-1-pentanol following the same protocol as given under B): For the first addition, 0.5 times of the amount given under A) is used and stirring continued for 1 hour. For the second addition, 0.3 times the amount described under A) is used and stirring continued for 2.5 hours. Water is then added (50 ml, pH about 10) and the mixture extracted with ether (2×80 ml). The combined organic phases are then dried over sodium sulfate, filtered and the solvent is removed in vacuo to give 6.70 g of an orange-brown oil. Purification by flash chromatography over silica gel with hexane/ethyl acetate 98:2 (v:v) gives 2.70 g of a mixture of the title compound (15%) along with 6-methoxy-2-(4-methyl-pentyloxy)-3-nitro-pyridine (85%, shown below). This mixture is used as such for the following nitro reduction to obtain the corresponding aniline derivatives.

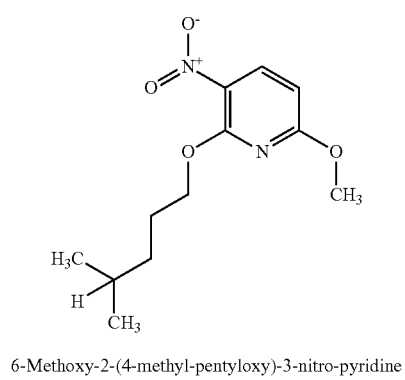 [SMILES: COc1ccc([N+](=O)[O-])c(OCCCC(C)C)n1]

6-Methoxy-2-(4-methyl-pentyloxy)-3-nitro-pyridine $^1$H NMR (400 MHz, CDCl$_3$) title compound: δ 0.92 (d, 6H), 1.37 (m, 2H), 1.62 (m, 1H), 1.85 (m, 2H), 4.10 (s, 3H), 4.37 (t, 2H), 6.35 (d, 1H), 8.33 (d, 1H).

$^1$H NMR (400 MHz, CDCl$_3$) isomer: δ 0.92 (d, 6H), 1.37 (m, 2H), 1.62 (m, 1H), 1.85 (m, 2H), 3.99 (s, 3H), 4.48 (t, 2H), 6.34 (d, 1H), 8.32 (d, 1H).

LC: UV Detection: 220 nm; R$_t$=2.12 min (both components).

TLC: Plates: Merck DC-Plates, silica gel F$_{254}$, saturated atmosphere in developing tank, UV detection, eluent: heptane/ethyl acetate 9:1 NM; R$_f$ of title compound and isomer=0.35, R$_f$ of starting material=0.33.

Example P30

Preparation of 2-Methoxy-6-(4-methyl-pentyloxy)-pyridin-3-ylamine and 6-Methoxy-2-(4-methyl-pentyloxy)-Pyridin-3-ylamine

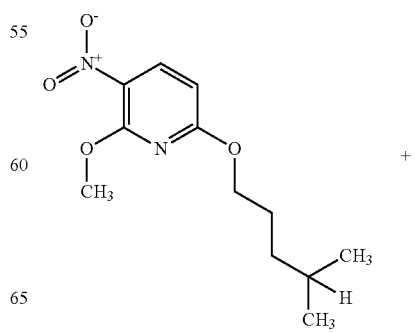

79
-continued

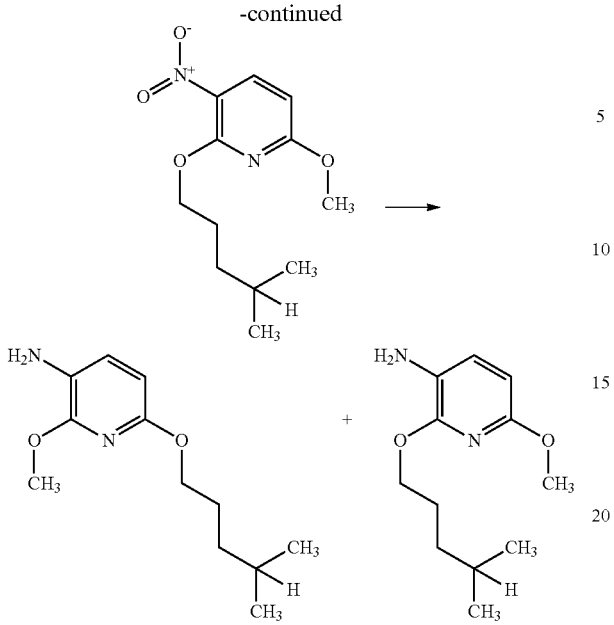

In a 10 ml single-necked round-bottomed flask with a condensor, 400 mg of a mixture consisting of 2-methoxy-6-(4-methyl-pentyloxy)-3-nitro-pyridine (15%) and 6-methoxy-2-(4-methyl-pentyloxy)-3-nitro-pyridine (85%) is suspended in methanol (1.50 ml). Under stirring and cooling with an ice/water bath, 37% ageous hydrochloric acid (0.66 ml) is added. After removing the cooling bath, tin powder (280 mg) is added. The resulting suspension is then stirred under heating to reflux for 3.5 h. Then, the mixture is allowed to reach room temperature and the methanol is removed in vacuo. To the resulting dark green gum, 2 molar aqueous sodium hydroxide solution is added (10 ml, pH about 12). Extraction is carried out using ethyl acetate (2×20 ml). The organic layer is dried over sodium sulfate, filtered and the solvent is removed in vacuo to give 310 mg of a yellow oil. The raw material is purified by chromatography on silica gel (eluent: hexanes/ethyl acetate, gradient from 1:0 to 98:2 (v:v)). 30 mg of the title compound (8.5%) is obtained in the form of a brown oil.

Title Compound $^1$H NMR (400 MHz, CDCl$_3$): δ 0.90 (d, 6H), 1.31 (m, 2H), 1.60 (m, 1H), 1.75 (m, 2H), 3.37 (broad, 2H), 3.95 (s, 3H), 4.14 (t, 2H), 6.15 (d, 1H), 6.93 (d, 1H).

LC: UV Detection: 220 nm; R$_f$=1.69 min.

TLC: Plates: Merck DC-Plates, silica gel F$_{254}$, saturated atmosphere in developing tank, UV detection, eluent: heptane/ethyl acetate 9:1 (v:v); R$_f$ of title compound=0.10, R$_f$ of starting material=0.35.

Along with the title compound, 250 mg of the isomeric 6-methoxy-2-(4-methyl-pentyloxy)-pyridin-3-ylamine in the form of a orange-brown oil is isolated as well (71%).

$^1$H NMR (400 MHz, CDCl$_3$): δ 0.91 (d, 6H), 1.33 (m, 2H), 1.61 (m, 1H), 1.79 (m, 2H), 3.38 (broad, 2H), 3.82 (s, 3H), 4.32 (t, 2H), 6.14 (d, 1H), 6.94 (d, 1H).

LC: UV Detection: 220 nm; R$_f$=1.72 min.

TLC: Plates: Merck DC-Plates, silica gel F$_{254}$, saturated atmosphere in developing tank, UV detection, eluent: heptane/ethyl acetate 9:1 (v:v); R$_f$=0.15.

80
Example P31

Preparation of 3-Chloro-6-methoxy-2-(4-methyl-pentyloxy)-5-nitro-pyridine and 3-Chloro-2-methoxy-6-(4-methyl-pentyloxy)-5-nitro-pyridine

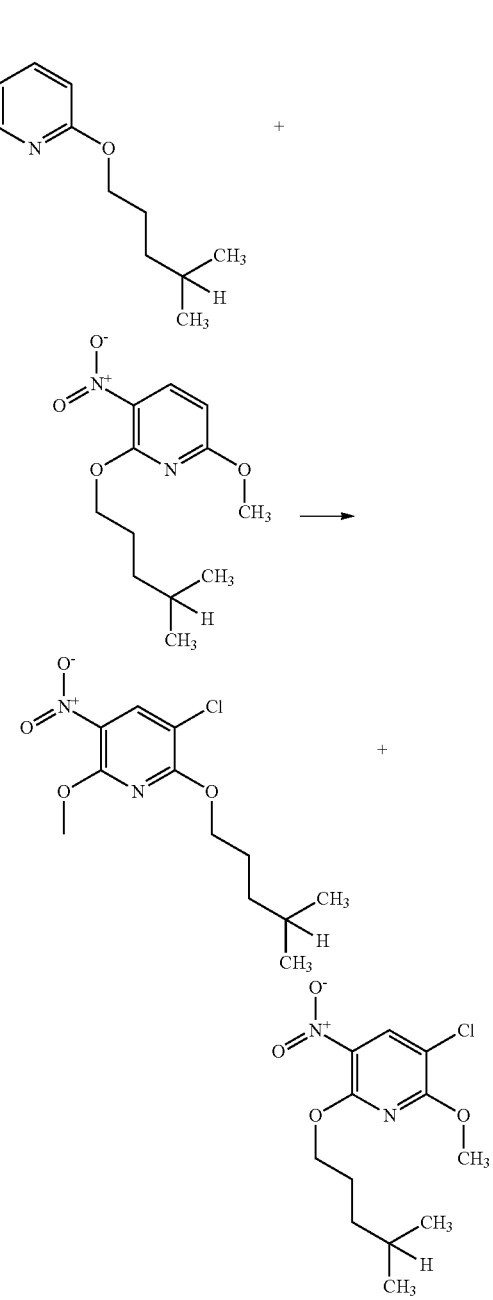

In a 10 ml three-necked round-bottomed flask equipped with a condenser, 2-methoxy-6-(4-methyl-pentyloxy)-3-nitro-pyridine (15%) and 6-methoxy-2-(4-methyl-pentyloxy)-3-nitro-pyridine (85%) (250 mg) is dissolved in dry acetonitril (1.00 ml) and stirred at room temperature. Under stirring, N-chlorosuccinimide (131 mg) is added. Stirring is continued for 3.5 h under heating to reflux. After cooling to room temperature, water is added (5 ml, pH about 6) and extraction is done using ether (2×10 ml). The organic layer is washed with a 10% ageous sodium bisulfite solution (10 ml). After drying over sodium sulfate, the organic layer is filtered and the solvent removed in vacuo to give a 250 mg of a yellow solid. After chromatography on silica gel (eluent: hexanes/ethyl acetate 99:1 (v:v)), 230 mg of a dark red oil is obtained that has the following composition:

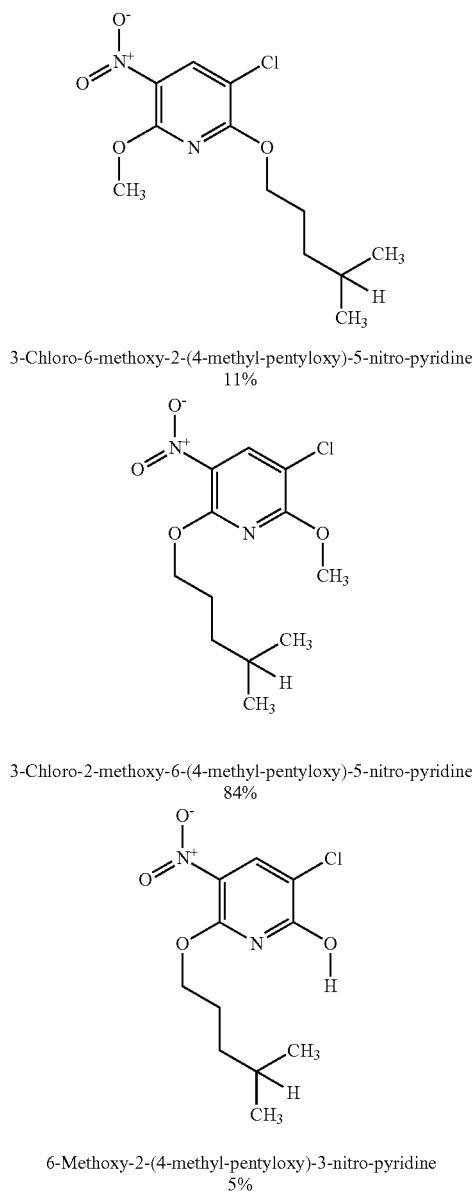

3-Chloro-6-methoxy-2-(4-methyl-pentyloxy)-5-nitro-pyridine
11%

3-Chloro-2-methoxy-6-(4-methyl-pentyloxy)-5-nitro-pyridine
84%

6-Methoxy-2-(4-methyl-pentyloxy)-3-nitro-pyridine
5%

$^1$H NMR (400 MHz, CDCl$_3$) of title compound: δ 0.92 (d, 6H), 1.36 (m, 2H), 1.62 (m, 1H), 1.85 (m, 2H), 4.10 (s, 3H), 4.46 (t, 2H), 8.42 (s, 1H).

$^1$H NMR (400 MHz, CDCl$_3$) of 3-chloro-2-methoxy-6-(4-methyl-pentyloxy)-5-nitro-pyridine: δ 0.92 (d, 6H), 1.36 (m, 2H), 1.62 (m, 1H), 1.85 (m, 2H), 4.08 (s, 3H), 4.47 (t, 2H), 8.41 (s, 1H).

TLC: Plates: Merck DC-Plates, silica gel F$_{254}$, saturated atmosphere in developing tank, UV detection, eluent: heptane/ethyl acetate 9:1 (v:v); R$_f$ of title compound and of 3-chloro-2-methoxy-6-(4-methyl-pentyloxy)-5-nitro-pyridine=0.43, R$_f$ of starting material=0.35.

Example P32

Preparation of 5-Chloro-2-methoxy-6-(4-methyl-pentyloxy)-pyridin-3-ylamine, 5-Chloro-6-methoxy-2-(4-methyl-pentyloxy)-pyridin-3-ylamine and 6-Methoxy-2-(4-methyl-pentyloxy)-pyridin-3-ylamine

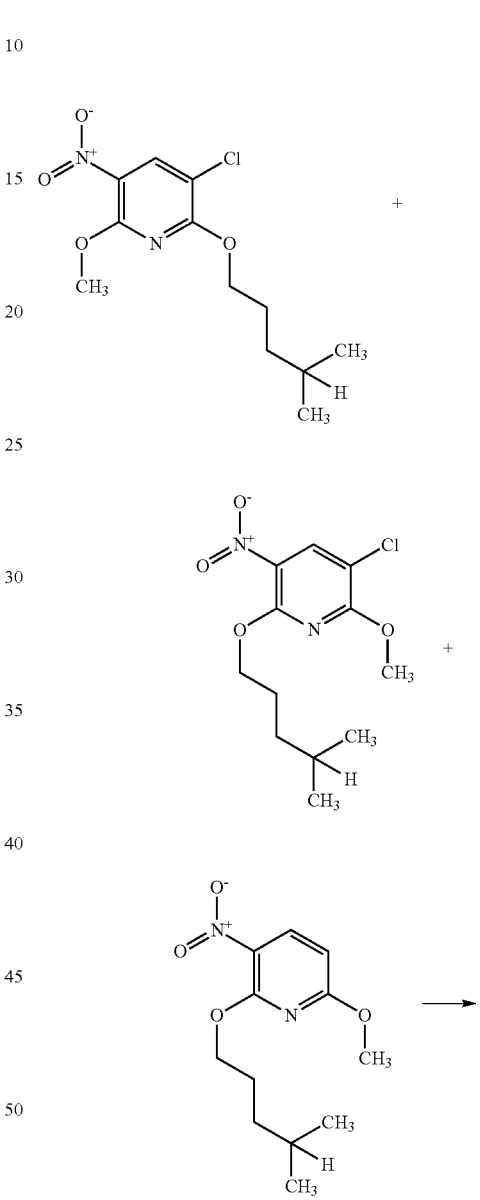

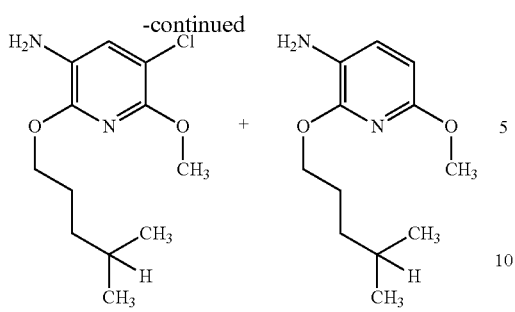

In a 50 ml single-necked round-bottomed flask with a condensor, 220 mg of a mixture consisting of 3-chloro-6-methoxy-2-(4-methyl-pentyloxy)-5-nitro-pyridine (11%), 3-chloro-2-methoxy-6-(4-methyl-pentyloxy)-5-nitro-pyridine (84%) and 6-methoxy-2-(4-methyl-pentyloxy)-3-nitro-pyridine (5%) is suspended in methanol (1.50 ml). Under stirring and cooling with an ice/water bath, 37% ageous hydrochloric acid (0.32 ml) is added. After removing the cooling bath, tin powder (181 mg) is added. The resulting suspension is then stirred under heating to reflux for 2.5 hours. Following the course of the reaction by thin layer chromatography indicated that no starting materials are left. The mixture is then allowed to reach room temperature and the methanol is removed in vacuo. To the resulting yellow solid, 2 molar ageous sodium hydroxide solution is added (5 ml, pH about 12). Extraction is carried out using ethyl acetate (2×10 ml). The organic layer is dried over sodium sulfate, filtered and the solvent is removed in vacuo to give 170 mg of a yellow oil. The raw material is purified by chromatography on silica gel (eluent: hexanes/ethyl acetate 97:3 (v:v)). This gives 170 mg of 5-chloro-6-methoxy-2-(4-methyl-pentyloxy)-pyridin-3-ylamine in pure form, along with 20 mg of a mixture of 5-chloro-2-methoxy-6-(4-methyl-pentyloxy)-pyridin-3-ylamine (62%) and 6-methoxy-2-(4-methyl-pentyloxy)-pyridin-3-ylamine (38%). The mixture was used as such for the transformation to obtain the corresponding amidine derivatives.

Title compound (5-chloro-6-methoxy-2-(4-methyl-pentyloxy)-pyridin-3-ylamine)
$^1$H NMR (400 MHz, CDCl$_3$): δ 0.91 (d, 6H), 1.33 (m, 2H), 1.61 (m, 1H), 1.78 (m, 2H), 3.42 (broad, 2H), 3.91 (s, 3H), 4.31 (t, 2H), 6.99 (s, 1H).
LC: UV Detection: 220 nm; R$_f$=2.07 min.
TLC: Plates: Merck DC-Plates, silica gel F$_{254}$, saturated atmosphere in developing tank, UV detection, eluent: heptane/ethyl acetate 9:1 (v:v); R$_f$ of isomer=0.28, R$_f$ of starting material=0.43.

For the mixture consisting of:
5-chloro-2-methoxy-6-(4-methyl-pentyloxy)-pyridin-3-ylamine (62%)
$^1$H NMR (400 MHz, CDCl$_3$): δ 0.91 (d, 6H), 1.32 (m, 2H), 1.61 (m, 1H), 1.79 (m, 2H), 3.40 (broad, 2H), 3.93 (s, 3H), 4.27 (t, 2H), 6.98 (s, 1H).
LC: UV Detection: 220 nm; R$_f$=2.09 min.
TLC: Plates: Merck DC-Plates, silica gel F$_{254}$, saturated atmosphere in developing tank, UV detection, eluent: heptane/ethyl acetate 9:1 (v:v); R$_f$ of title compound=0.18, R$_f$ of starting material=0.43.
6-methoxy-2-(4-methyl-pentyloxy)-pyridin-3-ylamine (38%)
$^1$H NMR (400 MHz, CDCl$_3$): δ 0.91 (d, 6H), 1.33 (m, 2H), 1.61 (m, 1H), 1.79 (m, 2H), 3.40 (broad, 2H), 3.82 (s, 3H), 4.32 (t, 2H), 6.14 (d, 1H), 6.94 (d, 1H).
LC: UV Detection: 220 nm; R$_f$=1.72 min.
TLC: Plates: Merck DC-Plates, silica gel F$_{254}$, saturated atmosphere in developing tank, UV detection, eluent: heptane/ethyl acetate 9:1 (v:v); R$_f$ of title compound=0.15, R$_f$ of starting material=0.35.

Example P33

Preparation of 3-Nitro-2-phenyl-pyridine

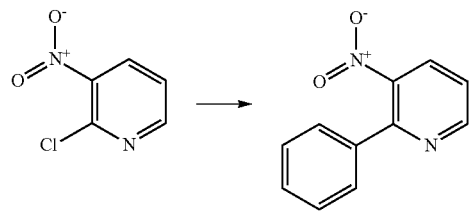 [SMILES: O=[N+]([O-])c1cccnc1Cl ; O=[N+]([O-])c1cccnc1-c1ccccc1]

In a 250 mL single-necked round-bottomed flask equipped with a condensor, 10.0 g of 2-chloro-3-nitro-pyridine (CA registry number 5470-18-8) is dissolved in 75.0 ml of toluene and 9.3 ml of ethanol under argon. Then, 19.18 g of potassium carbonate in 12.0 ml of water is added, followed by 7.69 g of phenyl boronic acid. After stirring for 15 minutes under a flow of argon, 2.19 g of tetrakis(triphenylphosphine)palladium is added. The mixture is then stirred for 20 hours under heating to reflux. The dark brown mixture is then cooled down to ambient temperature, followed by the addition of 100 ml of saturated aqueous NH$_4$Cl solution. This mixture is extracted with AcOEt (2×100 ml). The organic phase is dried over Na$_2$SO$_4$, filtered and concentrated in vacuo to give 15.26 g of a dark brown oil. After purification by flash chromatography [silica gel cartridge (20 g, 60 ml) of a solid deposition with hexane/ethyl acetate 3:2 (v:v), 12.23 g of the title compound is obtained as a brown oil.
title compound is obtained as a brown oil.
$^1$H NMR (400 MHz, CDCl$_3$): δ 7.46 (m, 4H), 7.56 (m, 2H), 8.13 (dd, 1H), 8.85 (dd, 1H).
LC: UV Detection: 220 nm; R$_f$=1.54 min.
TLC: Plates: Merck DC-Plates, silica gel F$_{254}$, saturated atmosphere in developing tank, UV detection, eluent: heptane/ethyl acetate 1:1 (v:v); R$_f$ of title compound=0.44, R$_f$ of starting material=0.44.

Example P34

Preparation of 3-Nitro-2-phenyl-pyridine-1-oxide

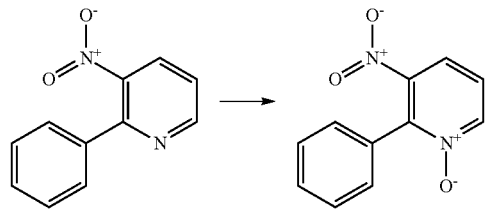 [SMILES: O=[N+]([O-])c1cccnc1-c1ccccc1 ; O=[N+]([O-])c1ccc[n+]([O-])c1-c1ccccc1]

In a 250 mL three-necked round-bottomed flask equipped with a thermometer, droppingbfunnel and a condensor, 11.62 g of 3-nitro-2-phenyl-pyridine is dissolved in 58.0 ml of

85 dichloromethane. Then, 13.65 g of H₂O₂ urea adduct is added. Under cooling with an ice/water bath, 16.40 ml trifluoroacetic acid anhydride is added dropwise over 25 minutes (temperature below 12° C.). After stirring at 10° C. for 45 minutes, the cooling bath is removed and the mixture is stirred at an ambient temperature for 18 hours. Afterwards, 150 ml of water is added (pH about 1) and extraction is carried out with dichloromethane (3×100 ml). After washing the organic phase with 10% aqueous sodium sulfite solution, it is dried over Na₂SO₄. After purification by chromatography on a pad of silica gel (eluent: first dichloromethane, then ethyl acetate), 9.45 g of the title compound is obtained as a yellow-green solid (MP: 116-117° C.).

¹H NMR (400 MHz, CDCl₃): δ 7.42 (m, 3H), 7.50 (m, 3H), 7.64 (dd, 1H), 8.50 (dd, 1H).

LC: UV Detection: 220 nm; $R_f$=1.12 min.

TLC: Plates: Merck DC-Plates, silica gel F₂₅₄, saturated atmosphere in developing tank, UV detection, eluent: heptane/ethyl acetate 1:1 (v:v); $R_f$ of title compound=0.05, $R_f$ of starting material=0.44.

Example P35

Preparation of 6-Chloro-3-nitro-2-phenyl-pyridine

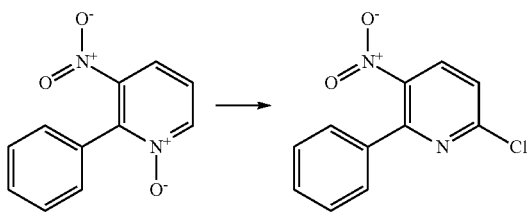 [SMILES: O=[N+]([O-])c1ccc[n+]([O-])c1-c1ccccc1 ; O=[N+]([O-])c1ccc(Cl)nc1-c1ccccc1]

In a 100 ml single-necked round-bottomed flask equipped with a condenser, 5.00 g of 3-nitro-2-phenyl-pyridine-1-oxide is dissolved in 25.0 ml dry 1,2-dichloroethane. Phosphorous oxide chloride (3.18 ml) is added carefully (yellow-orange solution). This mixture is then stirred under heating to reflux for 17 h. After cooling the mixture to ambient temperature. Ice/water is added then. The extraction is carried out with dichloromethane (2×50 ml). After washing with brine, the organic phase is dried over sodium sulfate, filtered and concentrated in vacuo. Purification by flash chromatography over a silica gel cartridge (25 g, 150 ml) of a solid deposition with hexane/ethyl acetate 4:1 (v:v) gives 2.61 g of the title compound as a yellow oil.

¹H NMR (400 MHz, CDCl₃): δ 7.46 (m, 4H), 7.56 (m, 2H), 8.10 (d, 1H).

LC: UV Detection: 220 nm; $R_f$=1.78 min.

TLC: Plates: Merck DC-Plates, silica gel F₂₅₄, saturated atmosphere in developing tank, UV detection, eluent: heptane/ethyl acetate 1:1 (v:v); $R_f$ of title compound=0.59, $R_f$ of starting material=0.05.

86

Example P36

Preparation of 2-Chloro-6-methyl-5-nitro-nicotinonitril

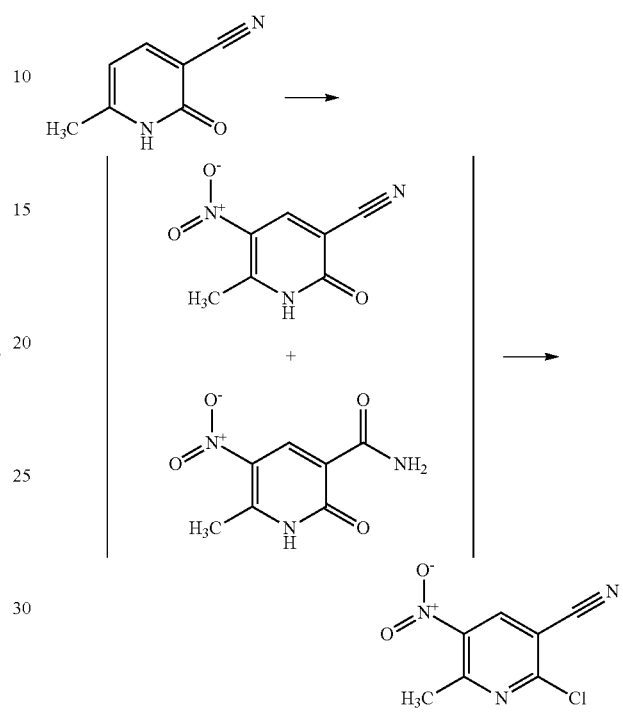

In a 200 ml five-necked reaction flask equipped with a mechanical stirrer, dropping funnel, thermometer and a condensor, 10.00 g of 6-methyl-2-oxo-1,2-dihydro-pyridine-3-carbonitrile (CA registry number: 4241-27-4) is added slowly to 75.0 ml concentrated sulfuric acid (exothermic). While stirring and cooling with an ice/water bath, mixed acid reagent (freshly prepared from 5.0 ml of concentrated sulfuric and 3.40 ml of fuming nitric acid) is added dropwise over 10 minutes. This mixture is first allowed to reach 25° C. and then stirred at about this temperature (under occasional cooling initially with an ice/water bath) for 4 hours. The mixture is then carefully poured into ice and add then water (250 ml volume altogether). A precipitate begins to form. After filtration, washing with water and drying 750 mg of a yellow solid is isolated being a mixture of 6-methyl-5-nitro-2-oxo-1,2-dihydropyridine-3-carbonitrile (39%) and 6-methyl-5-nitro-2-oxo-1,2-dihydropyridine-3-carboxylic acid amide (61%). This is used directly for the following step.

In a 50 ml single-necked round-bottomed flask equipped with a condenser, the mixture described above is suspended in 3.80 ml of phosphorous oxide chloride. Under stirring this mixture is heated under reflux for 23.5 hours (dark brown solution).

After cooling the mixture to ambient temperature, it is concentrated in vacuo at 50° C. The resulting gum is treated with ice followed by an excess of saturated aqueous sodium bicarbonate solution. The extraction is carried out with AcOEt (3×20 ml). The organic phase is dried over sodium sulfate, filtered and concentrated in vacuo to get 600 mg of a brown solid. Purification by flash chromatography over a silica gel cartridge (20 g, 60 ml) of a solid deposition with hexane/ethyl acetate 9:1 (v:v) gives 510 mg of the title compound as a light yellow solid (MP: 94-95° C.).

$^1$H NMR (400 MHz, CDCl$_3$): δ 2.95 (s, 3H), 8.60 (s, 1H).

TLC: Plates: Merck DC-Plates, silica gel F$_{254}$, saturated atmosphere in developing tank, UV detection, eluent: heptane/ethyl acetate 1:4 (v:v); R$_f$ of title compound=0.68, R$_f$ of starting material=0.

Example P37

Preparation of 2-(4-Chloro-3-trifluoromethyl-phenoxy)-6-methyl-5-nitro-nicotinonitrile

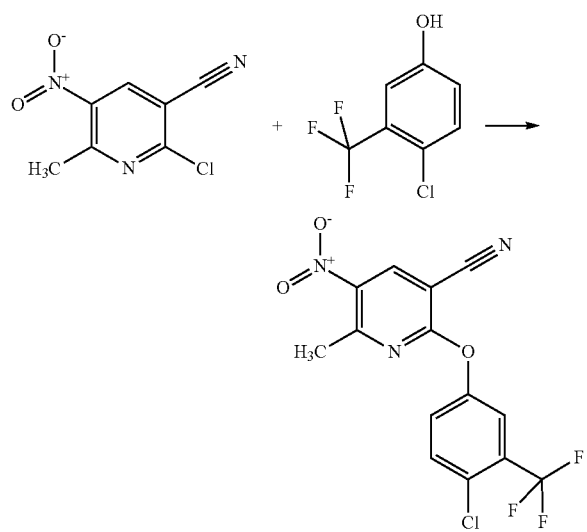

In a 50 ml single-necked round-bottomed flask, 990 mg 4-chloro-3-trifluoromethyl-phenol is dissolved in 5.00 ml of dry dioxane. Afterwards, 1.73 ml of Hünig's base is added under stirring, followed by 1.00 g of 2-chloro-6-methyl-5-nitro-nicotinonitrile and stirring continued at an ambient temperature for 24 hours (dark violet suspension). Afterwards, the mixture is filtered through a pad of silica gel on a sintered glass filter disk, followed by washing with dichloromethane. The combined organic phases are concentrated in vacuo to give 2.32 g of a dark violet gum. After purification by chromatography [silica gel cartridge (50 g, 150 ml), eluent: hexanes/ethyl acetate 4:1 (v:v)], 1.53 g of the title compound are obtained in the form of a orange solid (MP: 110-111° C.).

$^1$H NMR (400 MHz, CDCl$_3$): δ 2.77 (s, 3H), 7.34 (dd, 1H), 7.60 (m, 2H), 8.72 (s, 1H).

LC: UV Detection: 220 nm; R$_t$=2.08 min.

TLC: Plates: Merck DC-Plates, silica gel F$_{254}$, saturated atmosphere in developing tank, UV detection, eluent: heptane/ethyl acetate 2:1 (v:v); R$_f$ of title compound=0.54, R$_f$ of starting material=0.52.

Example P38

Preparation of 6-Methyl-2-(4-methyl-pentyloxy)-5-nitro-nicotinonitrile

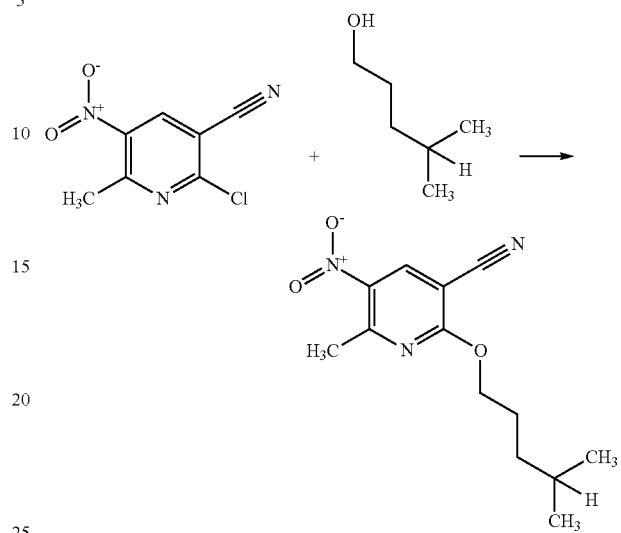

In a 12 ml Supelco vessel, to 0.95 ml of 4-methyl-pentan-1-ol is added 1.00 g of 2-chloro-6-methyl-5-nitro-nicotinonitrile. After closing the vessel with a septum, the mixture is stirred under heating to reflux (oil bath temperature of 130° C.). The progress of the reaction is monitored by thin layer chromatography. After 46 hours, an additional 0.53 ml of 4-methyl-pentan-1-ol is added and stirring continued under the specified conditions. After a heating period of 118 hours in total, the mixture is allowed to come to an ambient temperature. Then, the volatiles are removed in vacuo at a temperature of 50° C. to give 1.08 g of a brown oil. After purification by chromatography [silica gel cartridge (50 g, 100 ml), eluent: hexanes/ethyl acetate 95:5 (v:v)], 690 mg of the title compound are obtained in the form of a yellow oil.

$^1$H NMR (400 MHz, CDCl$_3$): δ 0.93 (d, 6H), 1.34 (m, 2H), 1.62 (m, 1H), 1.85 (m, 2H), 2.87 (s, 3H), 4.52 (t, 2H), 8.59 (s, 1H).

TLC: Plates: Merck DC-Plates, silica gel F$_{254}$, saturated atmosphere in developing tank, UV detection, eluent: heptane/ethyl acetate 2:1 (v:v); R$_f$ of title compound=0.59, R$_f$ of starting material=0.52.

Example P39

Preparation of 3-Bromo-4-methyl-5-nitro-1H-pyridin-2-one

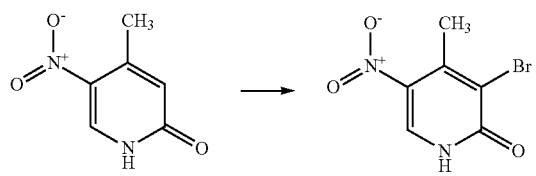

In a 1000 ml three-necked round-bottomed flask, 5.00 g of 4-methyl-5-nitro-1H-pyridin-2-one (CA registry number: 21901-41-7) is suspended in 500 ml of water. Under stirring, the mixture is kept at a temperature of 40° C. while 1.83 ml of elemental bromine is added dropwise. Stirring at 40° C. is continued for an additional 4 hours. Afterwards, the mixture is cooled to 10° C. and the resulting precipitate collected by filtration and washed with water (4×). After drying, 6.65 g of the title compound is obtained in the form of a beige solid (MP: 237-240° C.).

Example P40

Preparation of 3-Bromo-2-chloro-4-methyl-5-nitro-pyridine

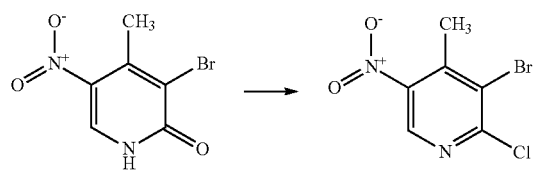

In a 25 ml single-necked round-bottomed flask, to 1.72 ml phosphorous oxide chloride kept at a temperature of 5° C., 0.857 ml quinoline and 3.40 g of 3-bromo-4-methyl-5-nitro-1H-pyridin-2-one are added consecutively. The resulting beige suspension is stirred under heating to 120° C. whereupon a brown solution is obtained. Stirring is continued for 2 hours. Afterwards, the solution is cooled down to an ambient temperature and poured into water. The resulting precipitate is collected by filtration, the filter cake washed with water (4×) and dried to give 3.15 g of the title compound in the form of a brown solid (MP: 60-62° C.).

Example P41

Preparation of 3-Bromo-2-(4-chloro-3-trifluoromethyl-phenoxy)-4-methyl-5-nitro-pyridine

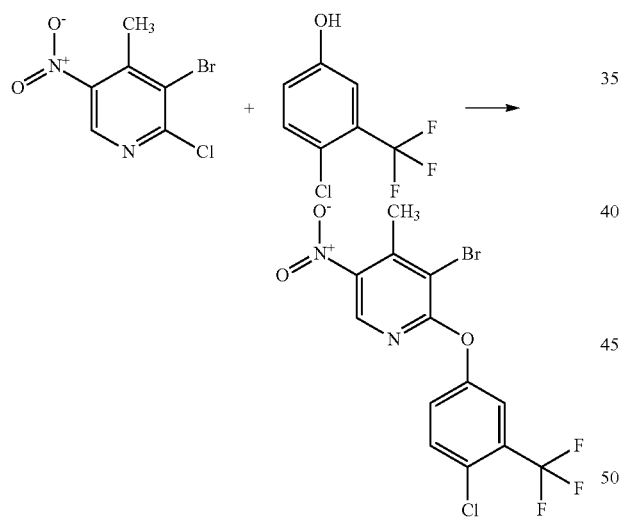

In a 250 ml three-necked round-bottomed flask, 4.00 g 4-chloro-3-trifluoromethyl-phenol is dissolved in 80 ml of dry methyl-ethyl-ketone. 3.85 g potassium carbonate followed by 4.70 g of 3-bromo-2-chloro-4-methyl-5-nitro-pyridine are added. The resulting brown suspension is heated to 80° C. under stirring for 3 hours. Afterwards, the green suspension is allowed to reach an ambient temperature and it then poured into water. The mixture is extracted with ethyl acetate (3×50 ml). The combined organic phases are washed with brine, dried over sodium sulfate, filtered and the solvent removed in vacuo. After purification of the raw product on silica gel with cyclohexane/ethyl actetae 19:1 (v:v) 7.36 g of the title compound are obtained as a light yellow gum that solidifies upon standing (MP: 73-74° C.).

Example P42

Preparation of 244-Chloro-3-trifluoromethyl-phenoxy)-3,4-dimethyl-5-nitro-pyridine

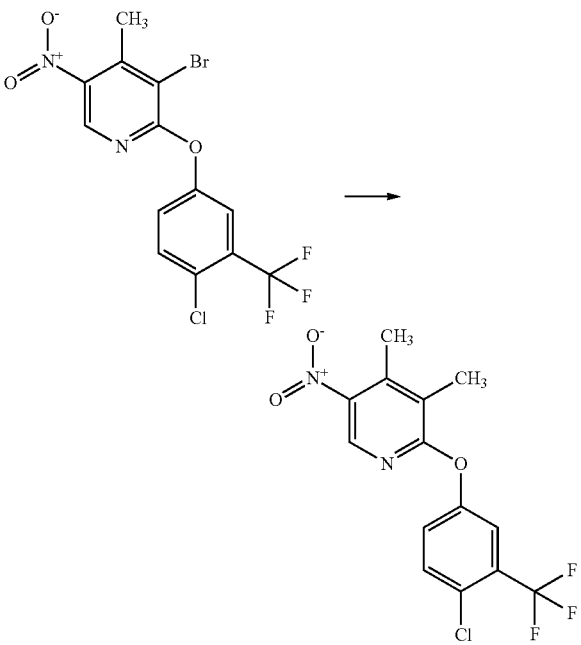

Example P43

Preparation of N-[5-Bromo-2-methyl-6-(4-methyl-pentyloxy)-pyridin-3-yl]-formimidic acid methyl ester

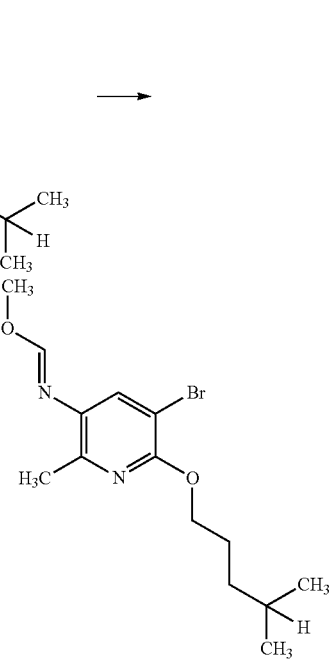

In a 50 ml single-necked round-bottomed flask, 3.00 g 5-bromo-2-methyl-6-(4-methyl-pentyloxy)-pyridin-3-ylamine is dissolved in 10 ml of trimethyl-orthoformate.

Under stirring the solution is heated to reflux for 8 hours. Afterwards, the reaction mixture is allowed to reach an ambient temperature and the volatile components are removed in vacuo at 50° C. to give 3.38 g of the title compound in the form of a brown oil.

$^1$H NMR (400 MHz, CDCl$_3$): δ 0.91-0.94(d,6H, CH$_3$), 1.31-1.41(m,2H, CH$_2$), 1.56-1.73(m,1H, CH), 1.76-1.80(m, 2H, CH$_2$), 2.35(s,3H, CH$_3$), 4.28(s,3H, CH$_3$), 4.33-4.36(t, 2H, CH$_2$), 7.26(s,1H), 7.75(s,1H).

TLC: Plates: Merck DC-Platten, Kieselgel F$_{254}$, saturated atmosphere in developing tank, UV detection, eluent: cyclohexane/ethyl acetate 1:1 (v:v); R$_f$ of title compound=0.73.

Example P44

Preparation of N-[5-Bromo-2-methyl-6-(4-methyl-pentyloxy)-pyridin-3-yl]-N'-ethyl-formamidine

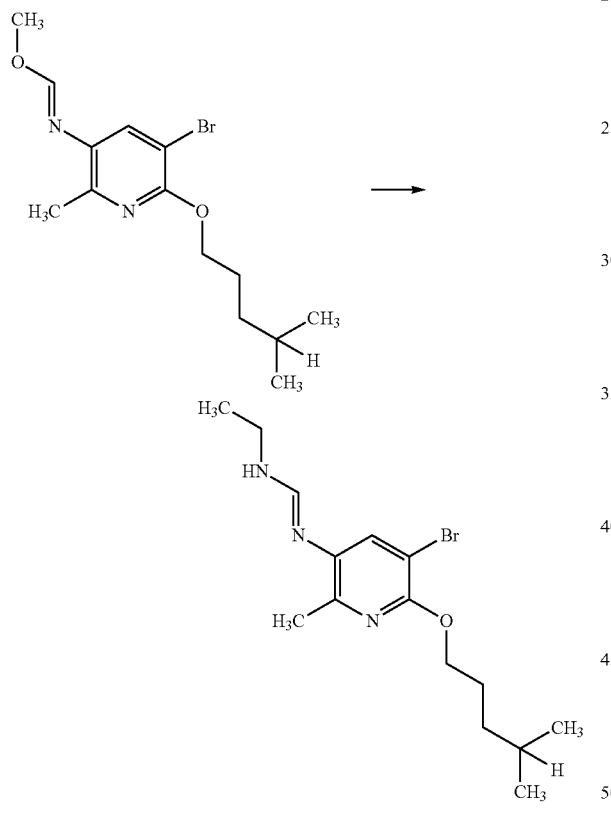

In a 50 ml single-necked round-bottomed flask, 540 mg of N-[5-Bromo-2-methyl-6-(4-methyl-pentyloxy)-pyridin-3-yl]-formimidic acid methyl ester is dissolved in 6.60 ml of dry dichloromethane. Under stirring at an ambient temperature, 214 mg of ethylamine hydrochloride along with 0.45 ml of Hünig's base are added. Stirring is continued at room temperature for 20 hours. Then, the volatiles are removed in vacuo at 50° C. After purification on silica gel (eluent: heptane/ethyl acetate 8:1 (v:v) with 5% triethylamine) to give 530 mg of the title compound in the form of a brown oil.

$^1$H NMR (400 MHz, CDCl$_3$): δ 0.88-0.89 (d,6H, CH$_3$), 1.22-1.28 (t, 3H, CH$_3$) 1.30-1.36(m,2H, CH$_2$), 1.57-1.68(m, 1H, CH), 1.75-1.82(m,2H, CH$_2$), 3.32-3.40(broad, 2H, CH$_2$) 2.35(s,3H, CH$_3$), 4.30-4.34(t,2H, CH$_2$), 4.34-4.71(broad, 1H, NH) 7.28(s,1H), 7.45(s,1H).

TLC: Plates: Merck DC-Platten, Kieselgel F$_{254}$, saturated atmosphere in developing tank, UV detection, eluent: cyclohexane/ethyl acetate 1:1+5% Triethylamine (v:v); R$_f$ of title compound=0.24.

Example P45

Preparation of N-[5-Bromo-2-methyl-6-(4-methyl-pentyloxy)-Pyridin-3-yl]-N,N-diethyl-formamidine

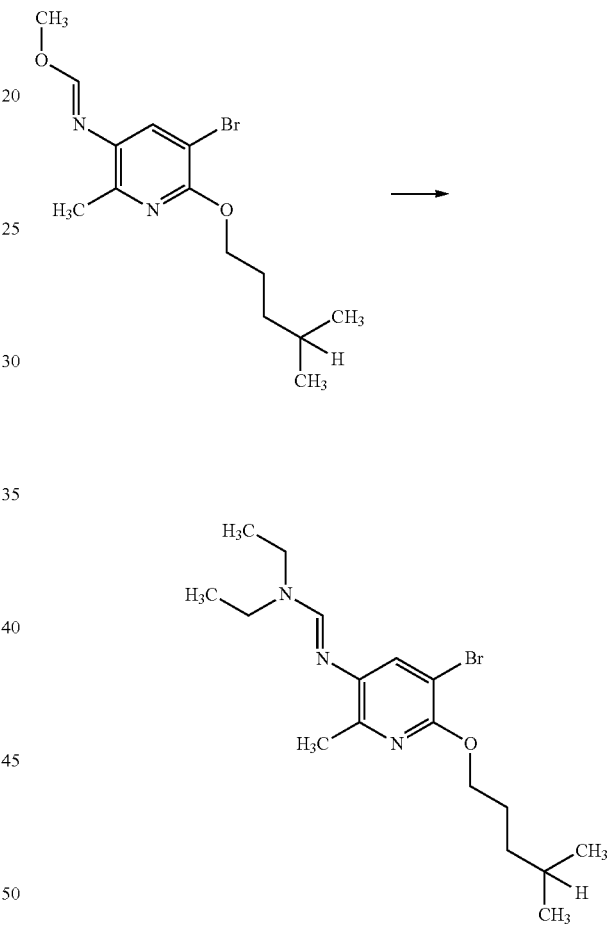

In a 50 ml single-necked round-bottomed flask, 540 mg of N-[5-Bromo-2-methyl-6-(4-methyl-pentyloxy)-pyridin-3-yl]-formimidic acid methyl ester is dissolved in 6.60 ml of dry dichloromethane. Under stirring at an ambient temperature, 0.273 ml of diethylamine is added. Stirring is continued for 44 hours at an ambient temperature.

LC of a sample indicated that about 40% of starting material is still present.

An additional amount of diethylamine is added and stirring is continued for an additional 24 hours. Then, the volatiles are removed in vacuo at 50° C. After purification on silica gel (eluent: heptane/ethyl acetate 8:1 (v:v) with 5% triethylamine) 530 mg of the title compound are obtained in the form of a yellow oil.

$^1$H NMR (400 MHz, CDCl$_3$): δ 0.92-0.0.94 (d,6H, CH$_3$), 1.20-1.25 (t,6H, CH$_3$) 1.31-1.39(m,2H, CH$_2$), 1.57-1.67(m, 1H, CH), 1.74-1.82(m,2H, CH$_2$), 2.34(s,3H, CH$_3$) 3.19-3.49 (broad, 4H, CH$_2$), 4.28-4.34(t,2H, CH$_2$), 7.30(s,1H), 7.36(s, 1H).

TLC: Plates: Merck DC-Platten, Kieselgel F$_{254}$, saturated atmosphere in developing tank, UV detection, eluent: cyclohexane/ethyl acetate 1:1 (v:v); R$_f$ of title compound=0.66.

Example P46

Preparation of 3-Bromo-5-isothiocyannato-6-methyl-2-(4-methyl-pentyloxy)-pyridine

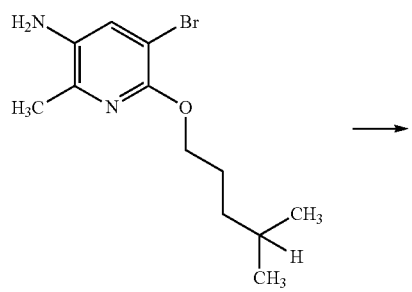

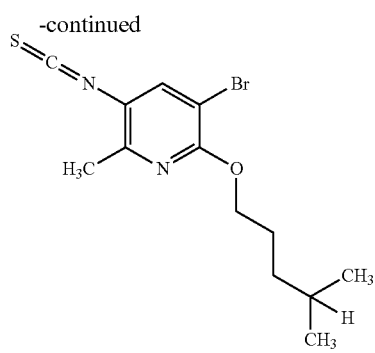

In a 50 ml single-necked round-bottomed flask, 800 mg of 5-Bromo-2-methyl-6-(4-methyl-pentyloxy)-pyridin-3-ylamine in 1.00 ml of dry dichloromethane (light yellow solution). Under stirring at a temperature below 5° C. (ice/water bath), first triethylamine (46.6 ml) followed by thiophosgene (ClCSCl) (28.5 ml are added dropwise. Stirring is continued at the same temperature for 1.25 hours. Then, water (10 ml) is added and the extraction is carried out with diethyl ether (2×10 ml). After washing with brine, the organic phase is dried over sodium sulfate, filtered and concentrated in vacuo to give 130 mg of a yellow oil. The material is used as such for the next step.

Example P47

Preparation of 3-[5-Bromo-2-methyl-6-(4-methyl-pentyloxy)-pyridin-3-yl]-1-isopropyl-1-methyl-thiourea

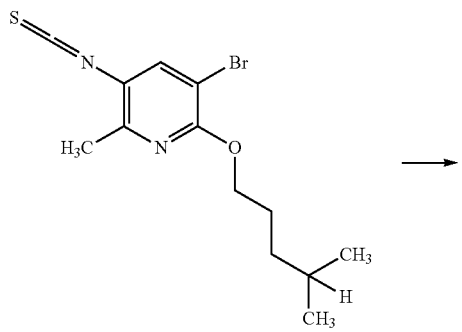

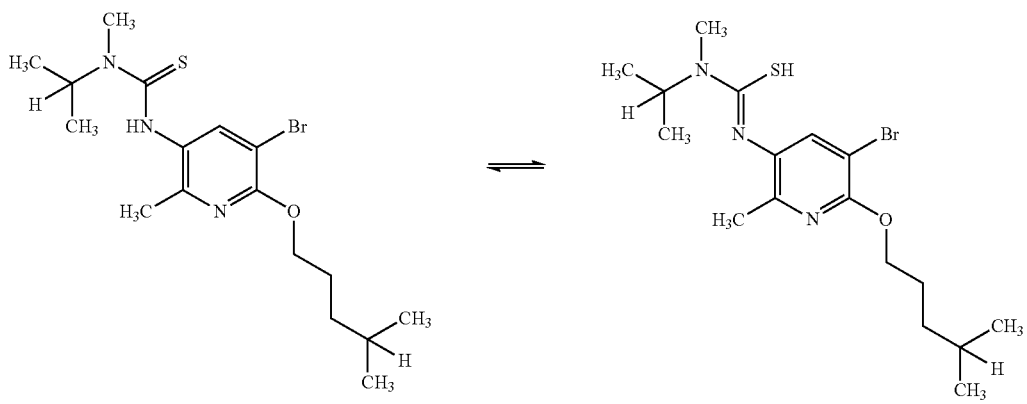

In a 50 ml single-necked round-bottomed flask, 920 mg of 3-bromo-5-isothiocyannato-6-methyl-2-(4-methyl-pentyloxy)-pyridine oxide is dissolved in 1.00 ml dry chloroform. Under stirring, isopropyl-ethyl-amine (20.4 mg) is added dropwise at an ambient temperature. Stirring is continued at the same temperature for 45 minutes. Then, 5.00 ml of water is added to the resulting orange solution. The extraction is carried out with diethyl ether (2×10 ml). After washing with brine, the organic phase is dried over sodium sulfate, filtered and concentrated in vacuo to give 140 mg of a brown oil. Purification by flash chromatography over a silica gel cartridge (20 g, 60 ml) of a solid deposition with hexane/ethyl acetate 95:5 (v:v) gives 60.0 mg of the title compound as a yellow oil.

$^1$H NMR (400 MHz, CDCl$_3$): δ 0.92 (d, 6H), 1.24 (d, 6H), 1.34 (m, 2H), 1.63 (m, 1H), 1.80 (m, 2H), 2.34 (s, 3H), 3.08 (s, 3H), 4.34 (t, 2H), 5.48 (broad, 1H), 6.70 (broad, 1H), 7.70 (s, 1H).

LC: UV Detection: 220 nm; R$_t$=2.19 min.

TLC: Plates: Merck DC-Plates, silica gel F$_{254}$, saturated atmosphere in developing tank, UV detection, eluent: heptane/ethyl acetate 4:1 (v:v); R$_f$ of title compound=0.22, R$_f$ of starting material=0.67.

Example P48

Preparation of 5-Amino-2-imidazol-1-yl-6-methyl-nicotinonitrile

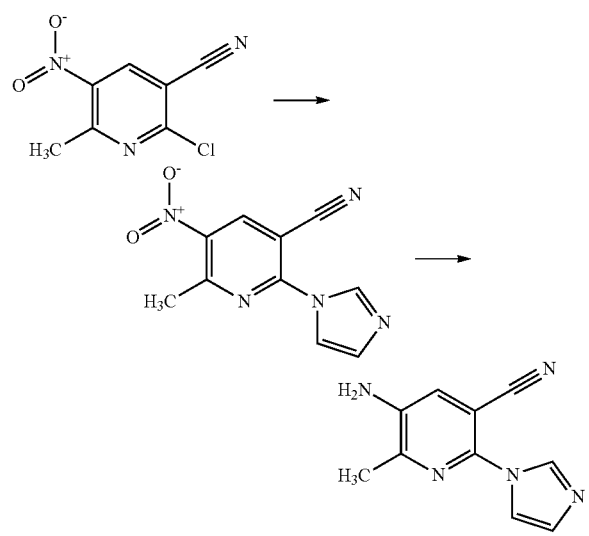

In a 5 ml Supelco vessel, 200 mg of 2-chloro-6-methyl-5-nitro-nicotinonitrile (140 mg) is solubilized in dry dioxane (1.00 ml). After adding 138 mg of imidazole, the mixture was stirred for 70 hours at an ambient temperature. The, the suspension was filtered over a pad of silica gel, the filter cake washed with ethyl acetate and the combined organic phases concentrated in vacuo to give 240 mg of orange-brown solid.

In a 50 ml single-necked round-bottomed flask, this solid (240 mg) is dissolved in methanol (1.00 ml). Under stirring and cooling with an ice/water bath, 1.00 mol of an ageous 27% hydrochloric acid is added dropwise. After removing the cooling bath, tin powder is added (186 mg). The green-gray suspension is stirred under heating to reflux for 2.45 hours. Afterwards, the heating bath is removed and the mixture stirred at an ambient temperature overnight. Then, the volatiles are removed in vacuo and 20 ml of a 4 molar ageous sodium hydroxide solution is added. The extraction is done with ethyl acetate (3×15 ml). The organic layer is dried over sodium sulfate, filtered and the solvent is removed in vacuo to give 160 mg of an orange-brown solid.

MS: ES+: 200 (M+H)$^+$; ES−: 198 (M−H)$^+$

LC Methodology Used

Method 1

HP 1100 HPLC from Agilent: solvent degasser, quaternary pump, heated column compartment and diode-array detector.

Column: Phenomenex Gemini C18, 3 ⊓m particle size, 110 Angström, 30×3 mm,

Temp: 60° C.

DAD Wavelength range (nm): 200 to 500

Solvent Gradient: (same for all methods)

A=water+0.05% HCOOH

B=Acetonitril/Methanol (4:1, v/v)+0.04% HCOOH

| Time | A % | B % | Flow (ml/min) |
|------|-----|-----|---------------|
| 0.00 | 95.0 | 5.0 | 1.700 |
| 2.00 | 0.0 | 100.0 | 1.700 |
| 2.80 | 0.0 | 100.0 | 1.700 |
| 2.90 | 95.0 | 5.0 | 1.700 |
| 3.10 | 95.0 | 5.0 | 1.700 |

Method 3

HP 1100 HPLC from Agilent: solvent degasser, binary pump, heated column compartment and diode-array detector.

Column: Phenomenex Gemini C18, 3 ⊓m particle size, 110 Angström, 30×3 mm,

Temp: 60° C.

DAD Wavelength range (nm): 200 to 500

Solvent Gradient: (same as above)

Method 4

HP 1100 HPLC from Agilent: solvent degasser, binary pump, heated column compartment and wavelength detector.

Column: Phenomenex Gemini C18, 3 nm particle size, 110 Angström, 30×3 mm

Temp: 60° C.

Solvent Gradient: (same as above)

MS. Spectra were recorded on a ZMD (Micromass, Manchester UK) or a ZQ (Waters Corp. Milford, Mass., USA) mass spectrometer equipped with an electrospray source (ESI; source temperature 80 to 100° C.; desolvation temperature 200 to 250° C.; cone voltage 30 V; cone gas flow 50 L/Hr, desolvation gas flow 400 to 600 L/Hr, mass range: 150 to 1000 Da).

The compounds according to the following tables can be prepared analogously. The examples which follow are intended to illustrate the invention and show preferred compounds of formula I and X.

TABLE P

Physical data of compounds of formula I and X:

| Compound No. | Structures | MS/NMR/melting point in ° C. |
|---|---|---|
| P.01 | 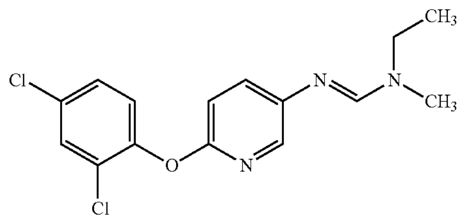 [SMILES: CCN(C)/C=N/c1ccc(Oc2ccc(Cl)cc2Cl)nc1] | $^1$H NMR (400 MHz, CDCl$_3$): δ 1.18-1.23(t, 3H, CH$_3$), 2.98(s, 3H, CH$_3$), 3.25-3.51(m$_{br}$, 2H, CH$_2$), 6.84-6.89(d, 1H), 7.09(d, 1H), 7.23(dxd, 1H), 7.35(dxd, 1H), 7.45(d, 1H), 7.50(s$_{br}$, 1H), 7.75(d, 1H). |
| P.02 | 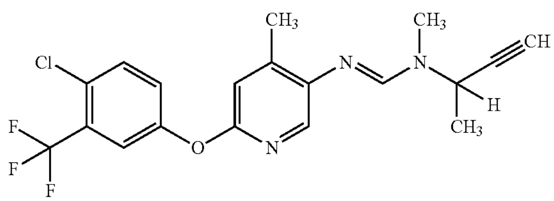 [SMILES: C#CC(C)N(C)/C=N/c1cnc(Oc2ccc(Cl)c(C(F)(F)F)c2)cc1C] | 1H NMR (400 MHz, CDCl$_3$): δ 1.38 + 1.48(2d, 3H, CH$_3$), 2.20(s, 3H, CH3), 2.30 + 2.40(d, 1H, CH), 2.89 + 2.98(2s, 3H, CH$_3$), 4.43 + 5.38(2m, 1H, CH), 6.72(s, 1H), 7.15(dxd, 1H), 7.38(d, 1H), 7.42(d, 1H), 7.62(s, 1H), 7.98 + 8.15(2s, 1H). |
| P.03 | 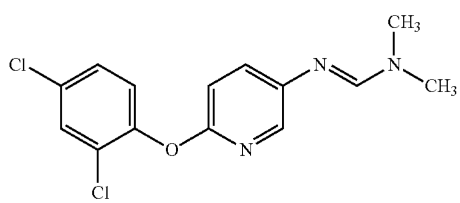 [SMILES: CN(C)/C=N/c1ccc(Oc2ccc(Cl)cc2Cl)nc1] | 1H NMR (500 MHz, CD3CN): δ 2.92(s, 3H, CH$_3$), 2.97(s, 3H, CH$_3$), 6.88(d, 1H), 7.13(d, 1H), 7.32(dxd, 1H), 7.36(dxd, 1H), 7.55(d, 1H), 7.60(s, 1H), 7.63(d, 1H). |
| P.04 | 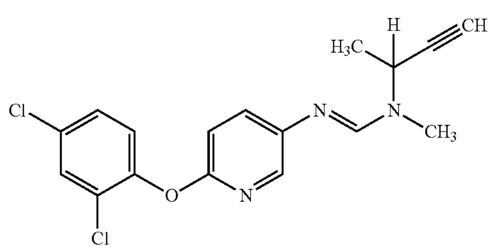 [SMILES: C#CC(C)N(C)/C=N/c1ccc(Oc2ccc(Cl)cc2Cl)nc1] | gum |
| P.05 | 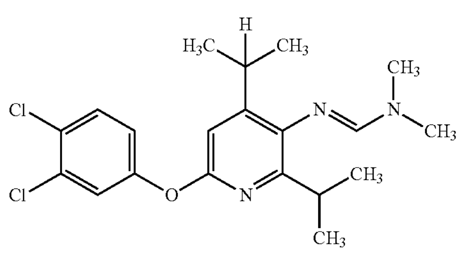 [SMILES: CC(C)c1cc(Oc2ccc(Cl)c(Cl)c2)nc(C(C)C)c1/N=C/N(C)C] | 1H NMR (400 MHz, CDCl$_3$): δ 1.11-1.17(2q, 12H, 4xCH$_3$), 3.20(s, 6H, 2xCH$_3$), 3.08-3.20(m, 2H), 6.08(s, 1H), 6.85(dxd, 1H), 7.14(s, 1H), 7.28(d, 1H), 7.37(d, 1H). |
| P.06 | 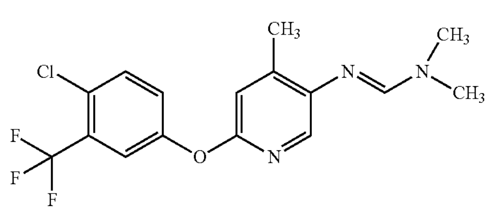 [SMILES: Cc1cc(Oc2ccc(Cl)c(C(F)(F)F)c2)ncc1/N=C/N(C)C] | gum |

TABLE P-continued

Physical data of compounds of formula I and X:

| Compound No. | Structures | MS/NMR/melting point in °C. |
|---|---|---|
| P.07 | 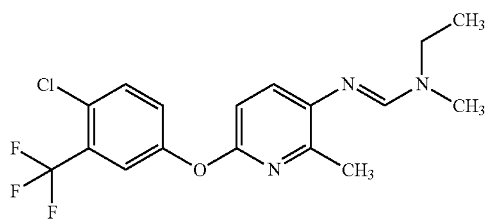 [SMILES: CCN(C)/C=N/c1ccc(Oc2ccc(Cl)c(C(F)(F)F)c2)nc1C] | gum |
| P.08 | 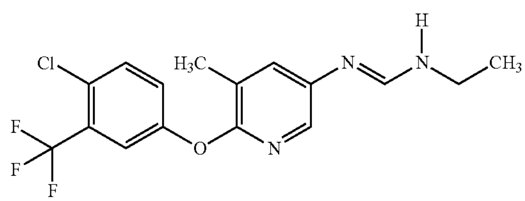 [SMILES: CCN/C=N/c1cnc(Oc2ccc(Cl)c(C(F)(F)F)c2)c(C)c1] | gum |
| P.09 | 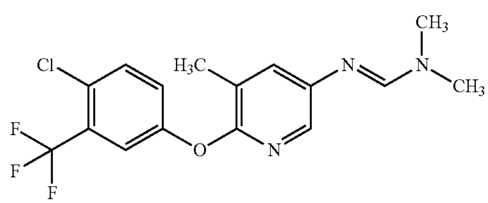 [SMILES: Cc1cc(/N=C/N(C)C)cnc1Oc1ccc(Cl)c(C(F)(F)F)c1] | gum |
| P.10 | 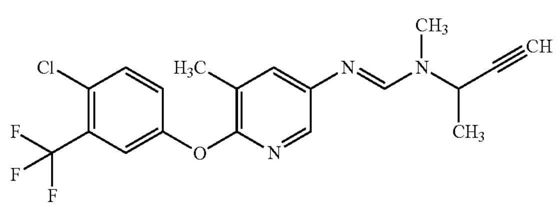 [SMILES: C#CC(C)N(C)/C=N/c1cnc(Oc2ccc(Cl)c(C(F)(F)F)c2)c(C)c1] | gum |
| P.11 | 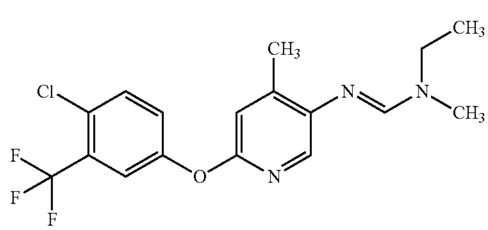 [SMILES: CCN(C)/C=N/c1cnc(Oc2ccc(Cl)c(C(F)(F)F)c2)cc1C] | 1H NMR (400 MHz, CDCl3): δ 1.19-1.24(t, 3, CH$_3$), 2.30(s, 3H, CH$_3$), 3.00(s, 3H, CH$_3$), 3.28-3.53(m, 2H, CH$_3$), 6.78(s, 1H), 7.19(dxd, 1H), 7.39-7.45(m, 3H), 7.54(s, 1H). |
| P.12 | 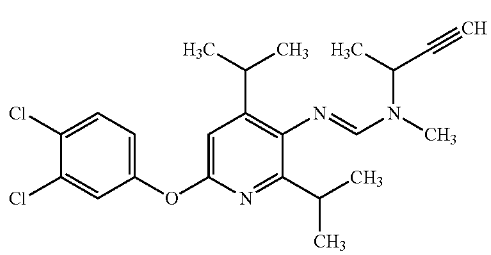 [SMILES: C#CC(C)N(C)/C=N/c1c(C(C)C)cc(Oc2ccc(Cl)c(Cl)c2)nc1C(C)C] | gum |

TABLE P-continued

Physical data of compounds of formula I and X:

| Compound No. | Structures | MS/NMR/melting point in ° C. |
|---|---|---|
| P.13 | 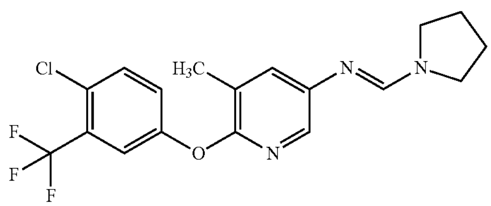 [SMILES: Cc1cc(/N=C/N2CCCC2)cnc1Oc1ccc(Cl)c(C(F)(F)F)c1] | 1H NMR (400 MHz, CDCl₃): δ 1.95(mbr, 4H, 2xCH₂), 2.28(s, 3H, CH₃), 3.50-3.55(m, 4H, 2xCH₂), 7.17(dxd, 1H), 7.23(d, 1H), 7.39(d, 1H), 7.55(d, 1H), 7.64(d, 1H), 7.75(s, 1H). |
| P.14 | 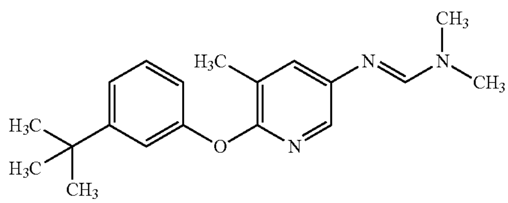 [SMILES: Cc1cc(/N=C/N(C)C)cnc1Oc1cccc(C(C)(C)C)c1] | gum |
| P.15 | 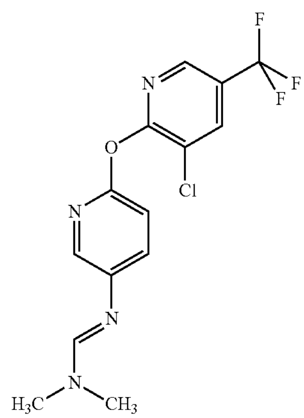 [SMILES: CN(C)/C=N/c1ccc(Oc2ncc(C(F)(F)F)cc2Cl)nc1] | gum |
| P.16 | 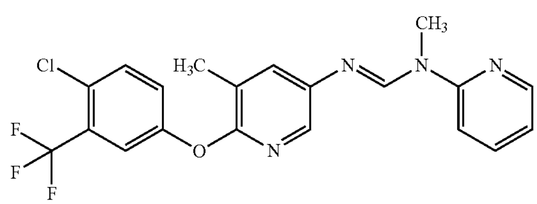 [SMILES: Cc1cc(/N=C/N(C)c2ccccn2)cnc1Oc1ccc(Cl)c(C(F)(F)F)c1] | 1H NMR (400 MHz, CDCl₃): δ 2.34(t, 3, CH₃), 3.53(s, 3H, CH₃), 6.96(d, 1H), 7.00(dxd, 1H), 7.21(dxd, 1H), 7.38(d, 1H), 7.45-7.51(m, 2H), 7.68-7.72(m, 1H), 7.79(d, 1H), 8.33(dxd, 1H), 9.11(s, 1H). |
| P.17 | 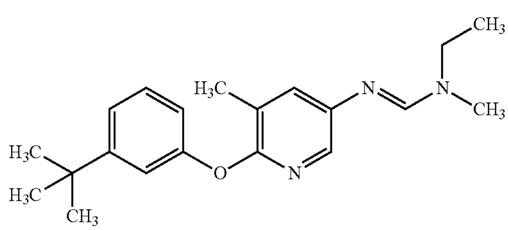 [SMILES: CCN(C)/C=N/c1cnc(Oc2cccc(C(C)(C)C)c2)c(C)c1] | 1H NMR (400 MHz, CDCl₃): δ 1.19-1.24(t, 3, CH₃), 1.30(s, 9H, 3xCH₃), 2.28(s, 3H, CH₃), 3.00(s, 3H, CH₃), 3.25-3.35(mbr, 2H, CH₂), 6.80(dxd, 1H), 7.08-7.12(m, 2H), 7.20-7.27(m, 2H), 7.53(sbr, 1H), 7.67(d, 1H). |
| p.18. | 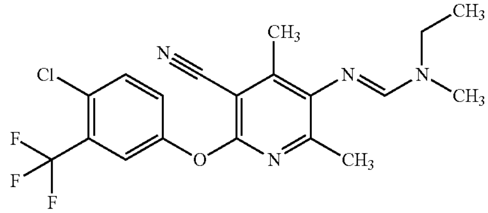 [SMILES: CCN(C)/C=N/c1c(C)nc(Oc2ccc(Cl)c(C(F)(F)F)c2)c(C#N)c1C] | gum |

TABLE P-continued

Physical data of compounds of formula I and X:

| Compound No. | Structures | MS/NMR/melting point in ° C. |
|---|---|---|
| P.19 | 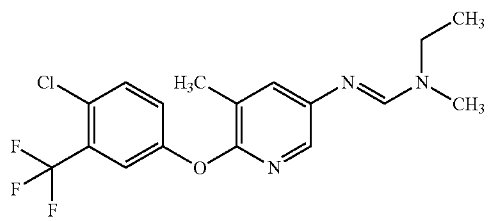 [SMILES: CCN(C)/C=N/c1cnc(Oc2ccc(Cl)c(C(F)(F)F)c2)c(C)c1] | 1H NMR (400 MHz, CDCl₃): δ 1.19-1.24(t, 3, CH₃), 2.28(s, 3H, CH₃), 3.00(s, 3H, CH₃), 3.28-3.53(m, 2H, CH₃), 7.15-7.26(m, 2H), 7.40(d, 1H), 7.46(d, 1H), 7.55(sbr, 1H), 7.65(d, 1H). |
| P.20 | 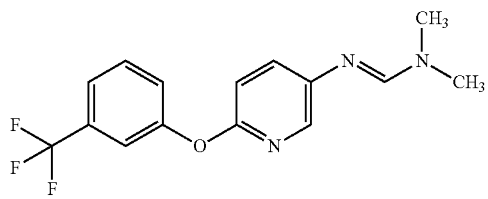 [SMILES: CN(C)/C=N/c1ccc(Oc2cccc(C(F)(F)F)c2)nc1] | 1H NMR (500 MHz, CD₃CN): δ 2.94(s, 3H, CH₃), 2.98(s, 3H, CH₃), 6.90(d, 1H), 7.30(m, 1H), 7.36-7.40(2m, 2H), 7.46(m, 1H), 7.54(m, 1H), 7.62(s, 1H), 7.72(d, 1H). |
| P.21 | 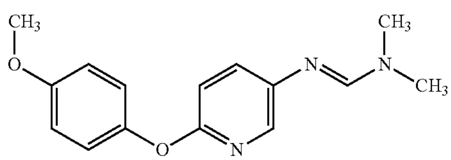 [SMILES: COc1ccc(Oc2ccc(/N=C/N(C)C)cn2)cc1] | 1H NMR (500 MHz, CD₃CN): δ 2.92(s, 3H, CH₃), 2.97(s, 3H, CH₃), 3.75(s, 3H, OCH₃), 6.75(d, 1H), 6.91(d, 2H), 6.98(d, 2H), 7.30(dxd, 1H), 7.58(s, 1H), 7.65(d, 1H). |
| P.22 | 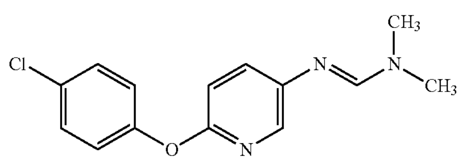 [SMILES: CN(C)/C=N/c1ccc(Oc2ccc(Cl)cc2)nc1] | 1H NMR (500 MHz, CD₃CN): δ 2.90(s, 3H, CH₃), 2.97(s, 3H, CH₃), 6.84(d, 1H), 7.02(d, 2H), 7.34(d, 2H), 7.35(dxd, 1H), 7.60(s, 1H), 7.70(d, 1H). |
| P.23 | 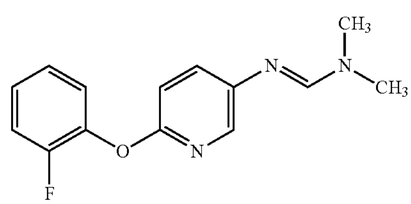 [SMILES: CN(C)/C=N/c1ccc(Oc2ccccc2F)nc1] | 1H NMR (500 MHz, CD₃CN): δ 2.90(s, 3H, CH₃), 2.97(s, 3H, CH₃), 6.87(d, 1H), 7.15-7.23(2m, 4H), 7.35(dxd, 1H), 7.58(s, 1H), 7.81(d, 1H). |
| P.24 | 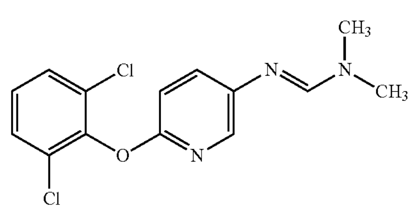 [SMILES: CN(C)/C=N/c1ccc(Oc2c(Cl)cccc2Cl)nc1] | 1H NMR (500 MHz, CD₃CN): δ 2.90(s, 3H, CH3), 2.96(s, 3H, CH₃), 6.93(d, 1H), 7.21(t, 1H), 7.38(dxd, 1H), 7.45(d, 2H), 7.54(d, 1H), 7.58(s, 1H). |
| P.25 | 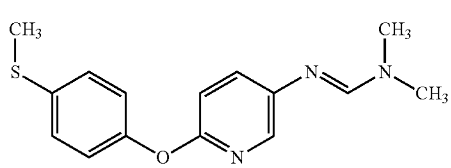 [SMILES: CSc1ccc(Oc2ccc(/N=C/N(C)C)cn2)cc1] | 1H NMR (500 MHz, CD₃CN): δ 2.45(s, 3H, SCH₃), 2.92(s, 3H, CH₃), 2.97(s, 3H, CH₃), 6.82(d, 1H), 7.02(d, 2H), 7.28(d, 2H), 7.35(dxd, 1H), 7.60(s, 1H), 7.70(d, 1H). |

TABLE P-continued

Physical data of compounds of formula I and X:

| Compound No. | Structures | MS/NMR/melting point in °C. |
|---|---|---|
| P.26 | 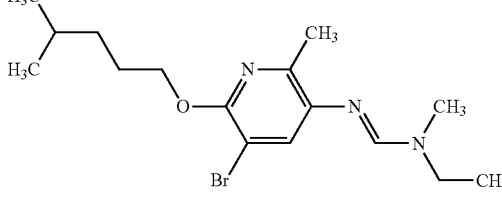 | 1H NMR (400 MHz, CDCl₃): δ 0.91(d, 6H), 1.15-1.40(m, m, 5 H), 1.61(m, 1H), 1.78(m, 2H), 2.38(s, 3H), 3.04(broad, 3H), 3.25-3.60(broad, 2H), 4.30(t, 2H), 7.28(s, 1H), 7.30-7.50(broad, 1H). |
| P.27 | 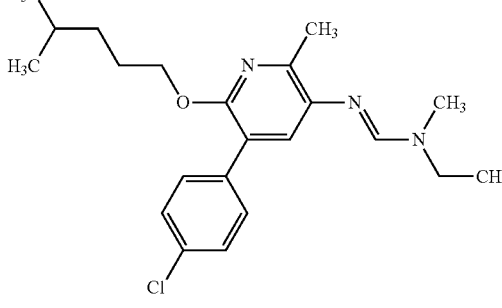 | 1H NMR (400 MHz, CDCl₃): δ 0.88(d, 6H); 1.20(t, 3H), 1.23(m, 2H), 1.58(m, 1H), 1.72(m, 2H), 2.44(s, 3H), 3.02(s, 3H), 3.15-3.60(broad, 2H), 4.29(t, 2H), 7.06(s, 1H), 7.34(d, 2H), 7.42(broad, 1H), 7.52(d, 2H). |
| P.28 | 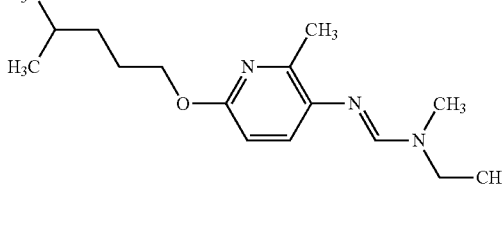 | 1H NMR (400 MHz, CDCl₃): δ 0.90(d, 6H), 1.20(t, 3H), 1.33(m, 2H), 1.60(m, 1H); 1.76(m, 2H), 2.41(s, 3H), 2.99(s, 3H), 3.20-3.50(broad, 1H), 3.35(broad, 1H), 4.18(t, 2H), 6.46(d, 1H), 7.01(d, 1H), 7.38(broad, 1H). |
| P.29 | 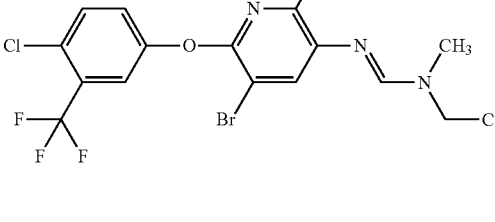 | 1H NMR (400 MHz, CDCl₃): δ 1.15-1.35(broad, 3H), 2.34(s, 3H), 3.03(s, 3H), 3.25-3.60(broad, 2H), 7.16 and 7.19(dd, 1H), 7.35(s, 1H), 7.42(m, 1H), 7.45(m, 1H), 7.30-7.55(broad, 1H). |
| P.30 | 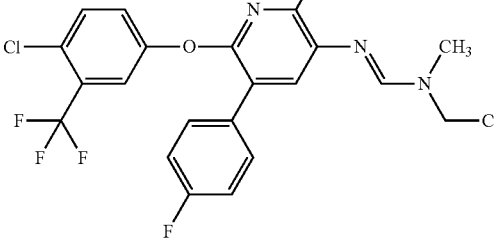 | RP HPLC: Retention time of compound: 1.55 minutes |

TABLE P-continued

Physical data of compounds of formula I and X:

| Compound No. | Structures | MS/NMR/melting point in °C. |
|---|---|---|
| P.31 | 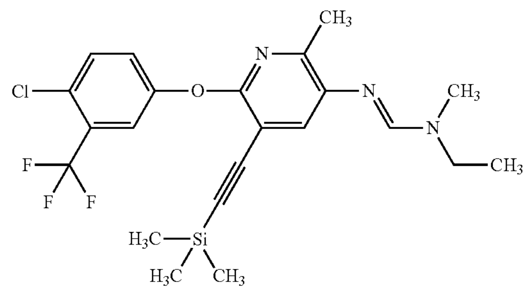 [SMILES: CCN(C)/C=N/c1cc(C#C[Si](C)(C)C)c(Oc2ccc(Cl)c(C(F)(F)F)c2)nc1C] | RP HPLC: retention time of compound: 1.61 minutes |
| P.32 | 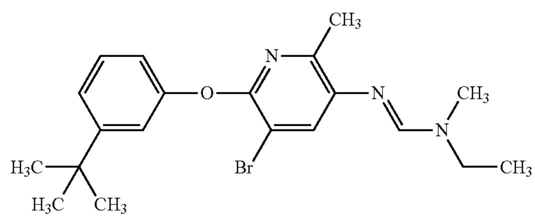 [SMILES: CCN(C)/C=N/c1cc(Br)c(Oc2cccc(C(C)(C)C)c2)nc1C] | RP HPLC: retention time of compound: 1.46 and 1.49 minutes |
| P.33 | 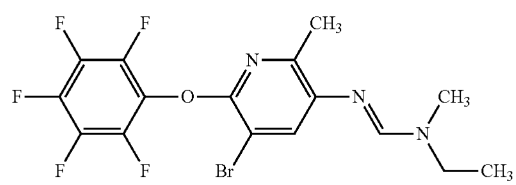 [SMILES: CCN(C)/C=N/c1cc(Br)c(Oc2c(F)c(F)c(F)c(F)c2F)nc1C] | RP HPLC: retention time of compound: 1.44 minutes |
| P.34 | 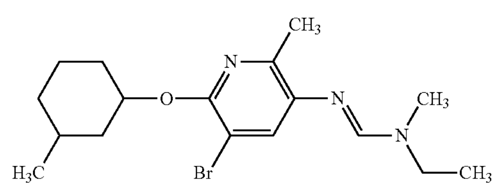 | RP HPLC: retention time of compound: 1.38 minutes |
| P.35 | 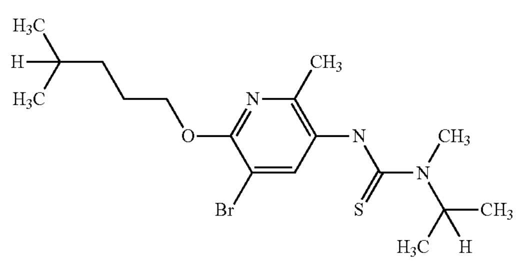 [SMILES: Cc1nc(OCCCC(C)C)c(Br)cc1NC(=S)N(C)C(C)C] | RP HPLC: retention time of compound: 2.19 minutes |
| P.36 | 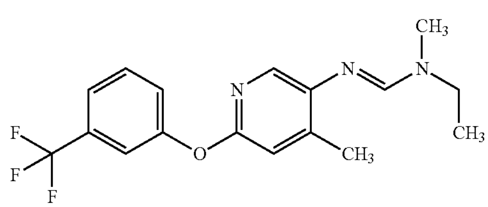 [SMILES: CCN(C)/C=N/c1cnc(Oc2cccc(C(F)(F)F)c2)cc1C] | RP HPLC: retention time of compound: 1.11 minutes |

TABLE P-continued

Physical data of compounds of formula I and X:

| Compound No. | Structures | MS/NMR/melting point in ° C. |
|---|---|---|
| P.37 | (structure) | 78-79° C.<br>intermediate (formula X) |
| P.38 | (structure) | RP HPLC: retention time of compound: 1.35 minutes |
| P.39 | (structure) | 93-94° C. |
| P.40 | (structure) | 155-156° C. |
| P.41 | (structure) | 142-143° C. |
| P.42 | (structure) | 92-93° C. |

TABLE P-continued
Physical data of compounds of formula I and X:
| Compound No. | Structures | MS/NMR/melting point in ° C. |
|---|---|---|
| P.43 | 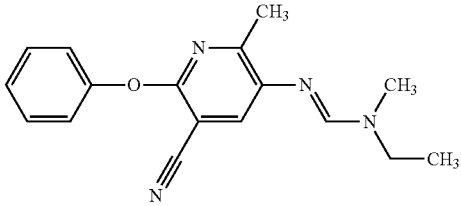 [SMILES: CCN(C)/C=N/c1cc(C#N)c(Oc2ccccc2)nc1C] | 66-67° C. |
| P.44 | 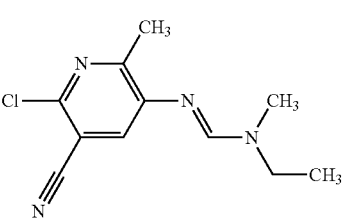 | 91-92° C.<br>intermediate (formula X) |
| P.45 | 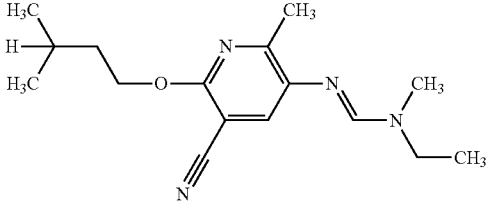 [SMILES: CCN(C)/C=N/c1cc(C#N)c(OCCC(C)C)nc1C] | RP HPLC: retention time of compound: 1.27 minutes |
| P.46 | 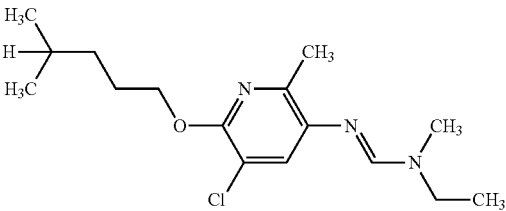 | RP HPLC: retention time of compound: 1.42 minutes |
| P.47 | 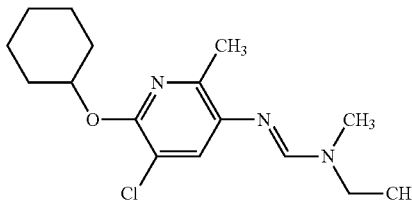 | RP HPLC: retention time of compound: 1.45 minutes |
| P.48 | 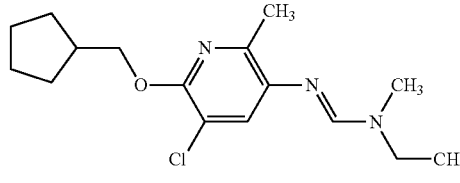 | RP HPLC: retention time of compound: 1.50 minutes |
| P.49 | 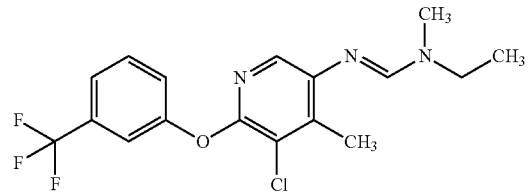 [SMILES: CCN(C)/C=N/c1cnc(Oc2cccc(C(F)(F)F)c2)c(Cl)c1C] | 72-73° C. |

TABLE P-continued

Physical data of compounds of formula I and X:

| Compound No. | Structures | MS/NMR/melting point in °C. |
|---|---|---|
| P.50 | (structure) | 82-83° C. |
| P.51 | (structure) | 70-71° C. |
| P.52 | (structure) | 81-82° C. |
| P.53 | (structure) | RP HPLC: retention time of compound: 1.43 minutes |
| P.54 | (structure) | RP HPLC: retention time of compound: 1.51 minutes |
| P.55 | (structure) | RP HPLC: retention time of compound: 2.31 minutes |
| P.56 | (structure) | RP HPLC: retention time of compound: 2.27 minutes |

TABLE P-continued

Physical data of compounds of formula I and X:

| Compound No. | Structures | MS/NMR/melting point in °C. |
|---|---|---|
| P.57 | (structure) | 74-75° C. |
| P.58 | (structure) | RP HPLC: retention time of compound: 1.31 minutes |
| P.59 | (structure) | RP HPLC: retention time of compound: 1.40 minutes |
| P.60 | (structure) | MS (M + 1) 2.96 intermediate (formula X) |
| P.61 | (structure) | RP HPLC: retention time of compound: 1.42 minutes |
| P.62 | (structure) | RP HPLC: retention time of compound: 1.36 minutes |

TABLE P-continued

Physical data of compounds of formula I and X:

| Compound No. | Structures | MS/NMR/melting point in ° C. |
|---|---|---|
| P.63 | 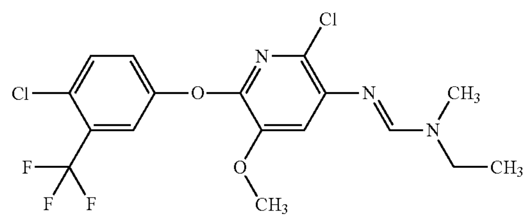 [SMILES: CCN(C)/C=N/c1cc(OC)c(Oc2ccc(Cl)c(C(F)(F)F)c2)nc1Cl] | 80-82° C. |
| P.64 | 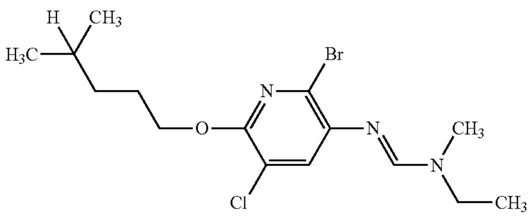 [SMILES: CCN(C)/C=N/c1cc(Cl)c(OCCCC(C)C)nc1Br] | RP HPLC: retention time of compound: 1.65 minutes |
| P.65 | 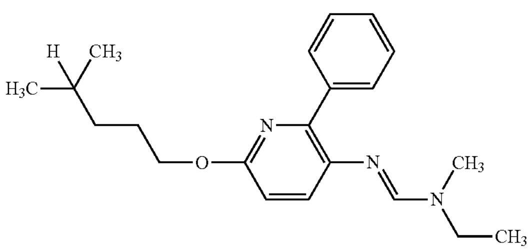 [SMILES: CCN(C)/C=N/c1ccc(OCCCC(C)C)nc1-c1ccccc1] | RP HPLC: retention time of compound: 1.41 minutes |
| P.66 | 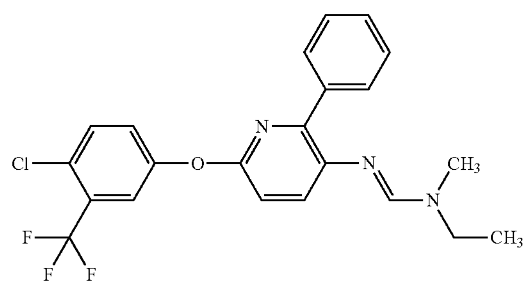 [SMILES: CCN(C)/C=N/c1ccc(Oc2ccc(Cl)c(C(F)(F)F)c2)nc1-c1ccccc1] | RP HPLC: retention time of compound: 1.45 minutes |
| P.67 | 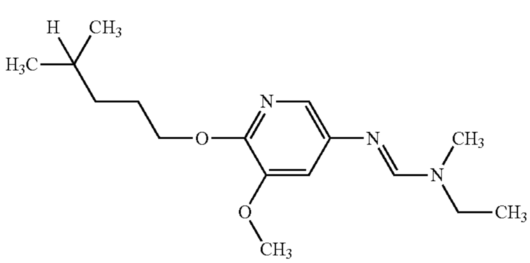 | RP HPLC: retention time of compound: 1.20 minutes |
| P.68 | 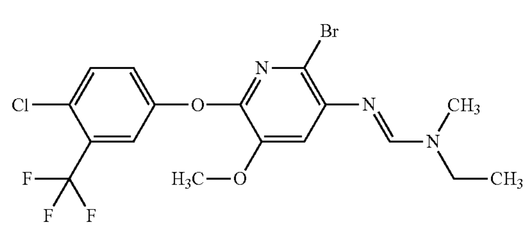 [SMILES: CCN(C)/C=N/c1cc(OC)c(Oc2ccc(Cl)c(C(F)(F)F)c2)nc1Br] | 84-85° C. |

TABLE P-continued

Physical data of compounds of formula I and X:

| Compound No. | Structures | MS/NMR/melting point in ° C. |
|---|---|---|
| P.69 | 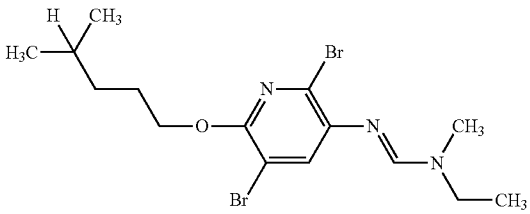 [SMILES: CCN(C)/C=N/c1cc(Br)c(OCCCC(C)C)nc1Br] | RP HPLC: retention time of compound: 1.72 minutes |
| P.70 | 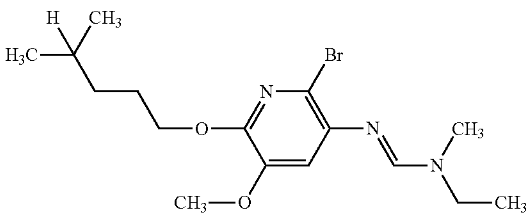 [SMILES: CCN(C)/C=N/c1cc(OC)c(OCCCC(C)C)nc1Br] | RP HPLC: retention time of compound: 1.32 minutes |
| P.71 | 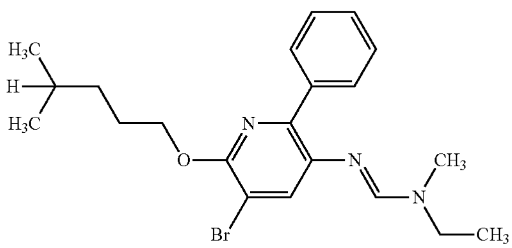 [SMILES: CCN(C)/C=N/c1cc(Br)c(OCCCC(C)C)nc1-c1ccccc1] | RP HPLC: retention time of compound: 1.60 minutes |
| P.72 | 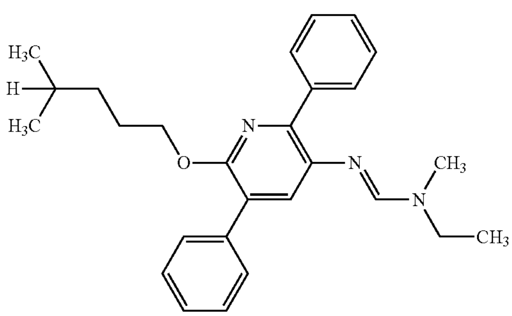 [SMILES: CCN(C)/C=N/c1cc(-c2ccccc2)c(OCCCC(C)C)nc1-c1ccccc1] | RP HPLC: retention time of compound: 1.61 minutes |
| P.73 | 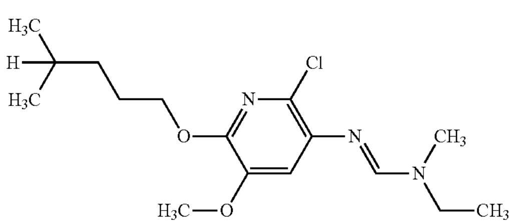 [SMILES: CCN(C)/C=N/c1cc(OC)c(OCCCC(C)C)nc1Cl] | RP HPLC: retention time of compound: 1.33 minutes |
| P.74 | 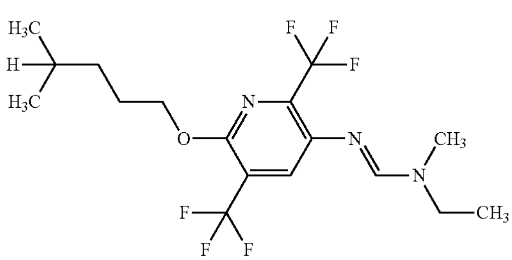 [SMILES: CCN(C)/C=N/c1cc(C(F)(F)F)c(OCCCC(C)C)nc1C(F)(F)F] | RP HPLC: retention time of compound: 2.24 minutes |

TABLE P-continued

Physical data of compounds of formula I and X:

| Compound No. | Structures | MS/NMR/melting point in ° C. |
|---|---|---|
| P.75 | 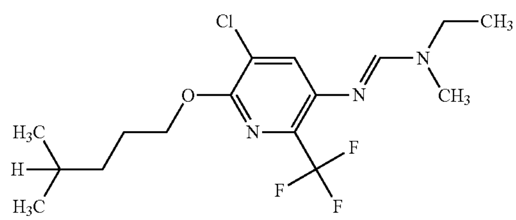 [SMILES: CCN(C)/C=N/c1cc(Cl)c(OCCCC(C)C)nc1C(F)(F)F] | RP HPLC: retention time of compound: 2.10 minutes |
| P.76 | 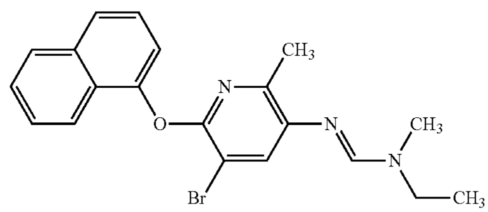 [SMILES: CCN(C)/C=N/c1cc(Br)c(Oc2cccc3ccccc23)nc1C] | RP HPLC: retention time of compound: 1.35 minutes |
| P.77 | 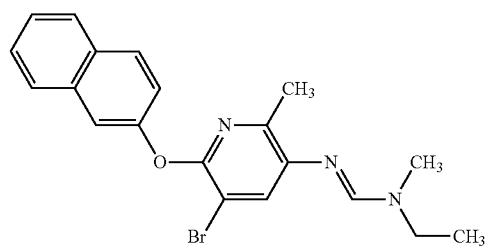 [SMILES: CCN(C)/C=N/c1cc(Br)c(Oc2ccc3ccccc3c2)nc1C] | RP HPLC: retention time of compound: 1.37 minutes |
| P.78 | 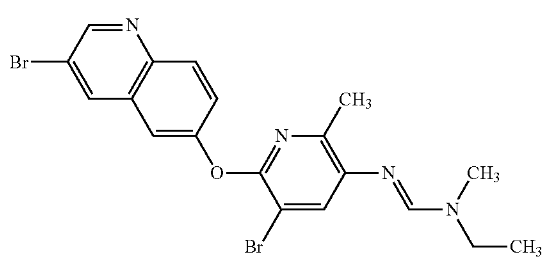 [SMILES: CCN(C)/C=N/c1cc(Br)c(Oc2cc(Cl)c3ncc(Br)cc3c2)nc1C] | 123-125° C. |
| P.79 | 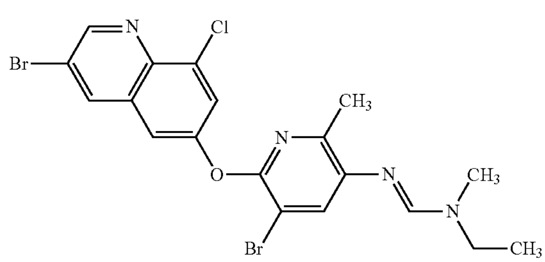 | RP HPLC: retention time of compound: 1.46 minutes |
| P.80 | 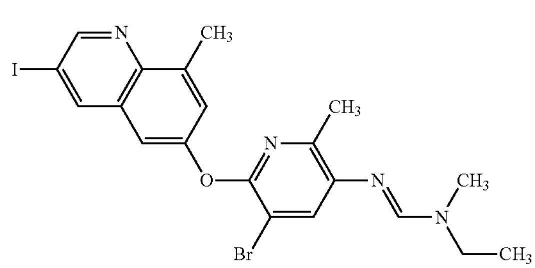 [SMILES: CCN(C)/C=N/c1cc(Br)c(Oc2cc(C)c3ncc(I)cc3c2)nc1C] | RP HPLC: retention time of compound: 1.50 minutes |

TABLE P-continued

Physical data of compounds of formula I and X:

| Compound No. | Structures | MS/NMR/melting point in °C. |
|---|---|---|
| P.81 | [structure] | RP HPLC: retention time of compound: 2.22 minutes |
| P.82 | [structure] | RP HPLC: retention time of compound: 1.39 minutes |

Table A discloses 526 sets of meanings of the variables $R_1$, $R_2$, $R_5$ and $R_6$ in a compound of formula I.

TABLE A

Meanings for $R_1$, $R_2$, $R_5$ and $R_6$:

| Line | $R_1$ | $R_2$ | $R_6$ | $R_5$ |
|---|---|---|---|---|
| A.1.1 | CH$_3$ | CH$_2$CH$_3$ | H | [structure] |
| A.1.2 | CH$_3$ | CH$_2$CH$_3$ | H | [structure] |
| A.1.3 | CH$_3$ | CH$_2$CH$_3$ | H | [structure] |
| A.1.4 | CH$_3$ | CH$_2$CH$_3$ | H | [structure] |

TABLE A-continued
Meanings for $R_1$, $R_2$, $R_5$ and $R_6$:
| Line | $R_1$ | $R_2$ | $R_6$ | $R_5$ |
|------|-------|-------|-------|-------|
| A.1.5 | CH$_3$ | CH$_2$CH$_3$ | H | 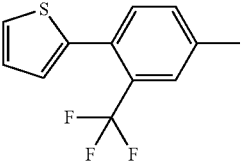 |
| A.1.6 | CH$_3$ | CH$_2$CH$_3$ | H | 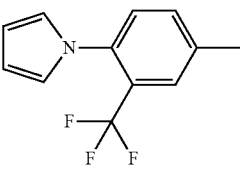 |
| A.1.7 | CH$_3$ | CH$_2$CH$_3$ | H | 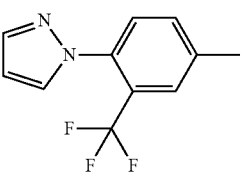 |
| A.1.8 | CH$_3$ | CH$_2$CH$_3$ | H | 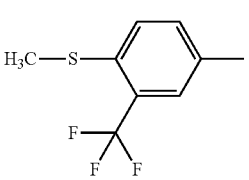 |
| A.1.9 | CH$_3$ | CH$_2$CH$_3$ | H | 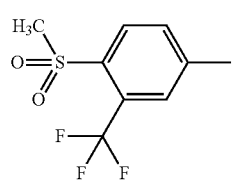 |
| A.1.10 | CH$_3$ | CH$_2$CH$_3$ | H | 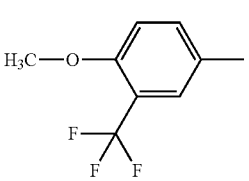 |
| A.1.11 | CH$_3$ | CH$_2$CH$_3$ | H | 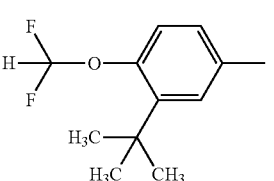 |
| A.1.12 | CH$_3$ | CH$_2$CH$_3$ | H | 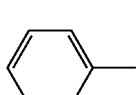 |
| A.1.13 | CH$_3$ | CH$_2$CH$_3$ | H | 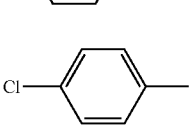 |

TABLE A-continued
Meanings for $R_1$, $R_2$, $R_5$ and $R_6$:
| Line | $R_1$ | $R_2$ | $R_6$ | $R_5$ |
|---|---|---|---|---|
| A.1.14 | $CH_3$ | $CH_2CH_3$ | H | 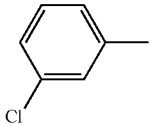 |
| A.1.15 | $CH_3$ | $CH_2CH_3$ | H | 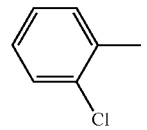 |
| A.1.16 | $CH_3$ | $CH_2CH_3$ | H | 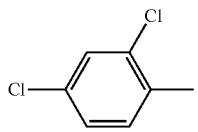 |
| A.1.17 | $CH_3$ | $CH_2CH_3$ | H | 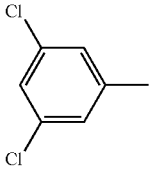 |
| A.1.18 | $CH_3$ | $CH_2CH_3$ | H | 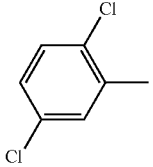 |
| A.1.19 | $CH_3$ | $CH_2CH_3$ | H | 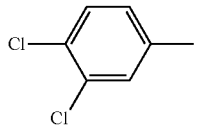 |
| A.1.20 | $CH_3$ | $CH_2CH_3$ | H | 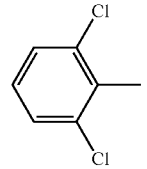 |
| A.1.21 | $CH_3$ | $CH_2CH_3$ | H | 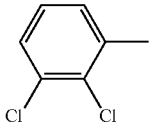 |
| A.1.22 | $CH_3$ | $CH_2CH_3$ | H | 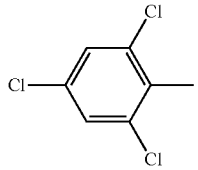 |

TABLE A-continued

Meanings for $R_1$, $R_2$, $R_5$ and $R_6$:

| Line | $R_1$ | $R_2$ | $R_6$ | $R_5$ |
|---|---|---|---|---|
| A.1.23 | $CH_3$ | $CH_2CH_3$ | H | 4-methylphenyl |
| A.1.24 | $CH_3$ | $CH_2CH_3$ | H | 3-methylphenyl |
| A.1.25 | $CH_3$ | $CH_2CH_3$ | H | 2-methylphenyl |
| A.1.26 | $CH_3$ | $CH_2CH_3$ | H | 3-chloro-4-methylphenyl |
| A.1.27 | $CH_3$ | $CH_2CH_3$ | H | 4-chloro-3-methylphenyl |
| A.1.28 | $CH_3$ | $CH_2CH_3$ | H | 3,4-dimethylphenyl |
| A.1.29 | $CH_3$ | $CH_2CH_3$ | H | 2,4-dimethylphenyl |
| A.1.30 | $CH_3$ | $CH_2CH_3$ | H | 4-fluorophenyl |
| A.1.31 | $CH_3$ | $CH_2CH_3$ | H | 3-fluorophenyl |
| A.1.32 | $CH_3$ | $CH_2CH_3$ | H | 2-fluorophenyl |

TABLE A-continued
Meanings for $R_1$, $R_2$, $R_5$ and $R_6$:
| Line | $R_1$ | $R_2$ | $R_6$ | $R_5$ |
|---|---|---|---|---|
| A.1.33 | $CH_3$ | $CH_2CH_3$ | H | 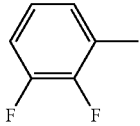 |
| A.1.34 | $CH_3$ | $CH_2CH_3$ | H | 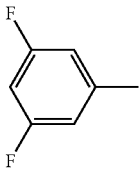 |
| A.1.35 | $CH_3$ | $CH_2CH_3$ | H | 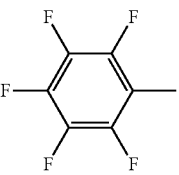 |
| A.1.36 | $CH_3$ | $CH_2CH_3$ | H | 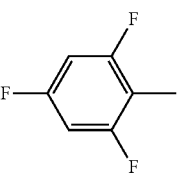 |
| A.1.37 | $CH_3$ | $CH_2CH_3$ | H | 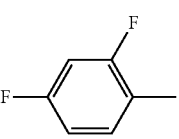 |
| A.1.38 | $CH_3$ | $CH_2CH_3$ | H | 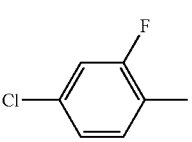 |
| A.1.39 | $CH_3$ | $CH_2CH_3$ | H | 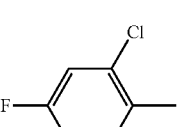 |
| A.1.40 | $CH_3$ | $CH_2CH_3$ | H | 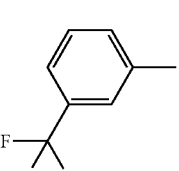 |
| A.1.41 | $CH_3$ | $CH_2CH_3$ | H | 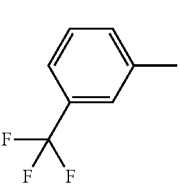 |

TABLE A-continued
Meanings for $R_1$, $R_2$, $R_5$ and $R_6$:
| Line | $R_1$ | $R_2$ | $R_6$ | $R_5$ |
|------|-------|-------|-------|-------|
| A.1.42 | CH$_3$ | CH$_2$CH$_3$ | H | 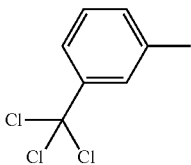 |
| A.1.43 | CH$_3$ | CH$_2$CH$_3$ | H | 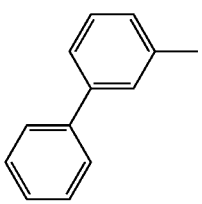 |
| A.1.44 | CH$_3$ | CH$_2$CH$_3$ | H | 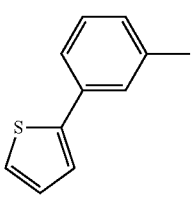 |
| A.1.45 | CH$_3$ | CH$_2$CH$_3$ | H | 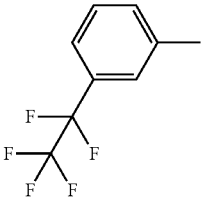 |
| A.1.46 | CH$_3$ | CH$_2$CH$_3$ | H | 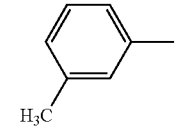 |
| A.1.47 | CH$_3$ | CH$_2$CH$_3$ | H | 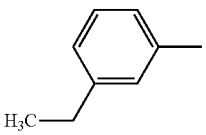 |
| A.1.48 | CH$_3$ | CH$_2$CH$_3$ | H | 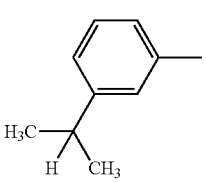 |
| A.1.49 | CH$_3$ | CH$_2$CH$_3$ | H | 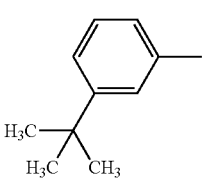 |

TABLE A-continued
Meanings for $R_1$, $R_2$, $R_5$ and $R_6$:
| Line | $R_1$ | $R_2$ | $R_6$ | $R_5$ |
|---|---|---|---|---|
| A.1.50 | $CH_3$ | $CH_2CH_3$ | H | 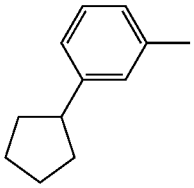 |
| A.1.51 | $CH_3$ | $CH_2CH_3$ | H | 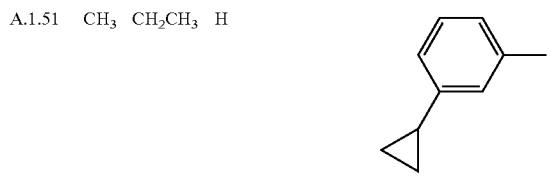 |
| A.1.52 | $CH_3$ | $CH_2CH_3$ | H | 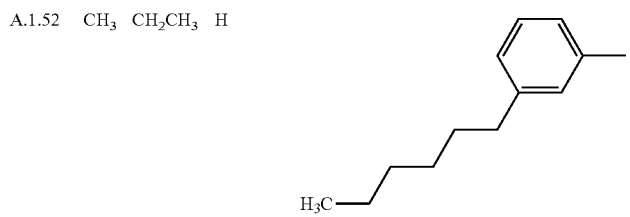 |
| A.1.53 | $CH_3$ | $CH_2CH_3$ | H | 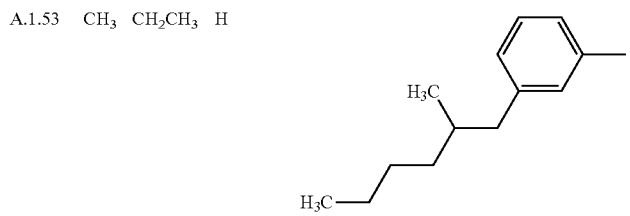 |
| A.1.54 | $CH_3$ | $CH_2CH_3$ | H | 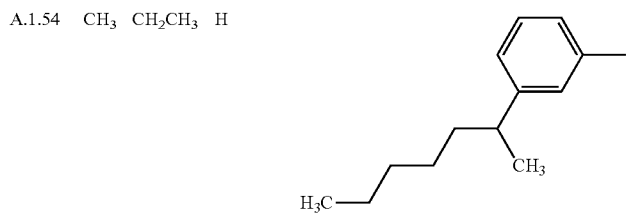 |
| A.1.55 | $CH_3$ | $CH_2CH_3$ | H | 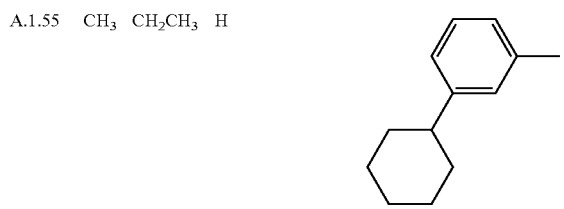 |
| A.1.56 | $CH_3$ | $CH_2CH_3$ | H | 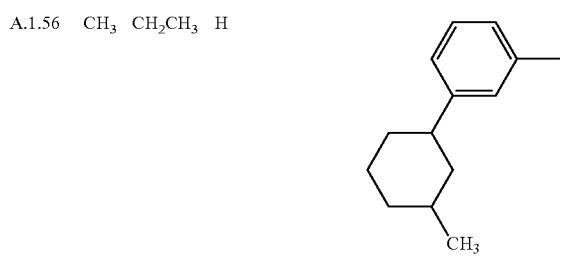 |

TABLE A-continued
Meanings for $R_1$, $R_2$, $R_5$ and $R_6$:
| Line | $R_1$ | $R_2$ | $R_6$ | $R_5$ |
|---|---|---|---|---|
| A.1.57 | $CH_3$ | $CH_2CH_3$ | H | 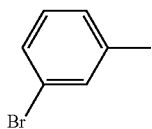 |
| A.1.58 | $CH_3$ | $CH_2CH_3$ | H | 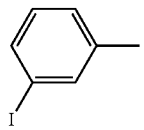 |
| A.1.59 | $CH_3$ | $CH_2CH_3$ | H | 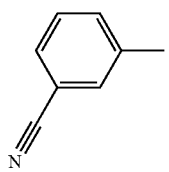 |
| A.1.60 | $CH_3$ | $CH_2CH_3$ | H | 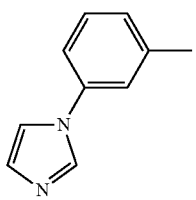 |
| A.1.61 | $CH_3$ | $CH_2CH_3$ | H | 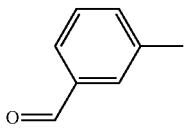 |
| A.1.62 | $CH_3$ | $CH_2CH_3$ | H | 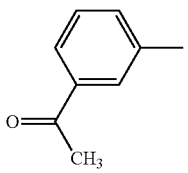 |
| A.1.63 | $CH_3$ | $CH_2CH_3$ | H | 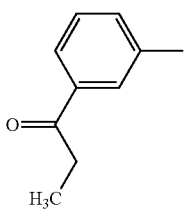 |
| A.1.64 | $CH_3$ | $CH_2CH_3$ | H | 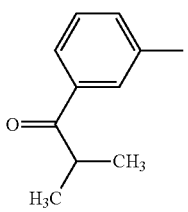 |

TABLE A-continued

Meanings for $R_1$, $R_2$, $R_5$ and $R_6$:

| Line | $R_1$ | $R_2$ | $R_6$ | $R_5$ |
|---|---|---|---|---|
| A.1.65 | $CH_3$ | $CH_2CH_3$ | H | 3-(cyclohexylcarbonyl)benzoyl group (3-methylphenyl with C(=O)-cyclohexyl at meta) |
| A.1.66 | $CH_3$ | $CH_2CH_3$ | H | 3-methylphenyl with C(=O)CF$_3$ at meta |
| A.1.67 | $CH_3$ | $CH_2CH_3$ | H | 3-aminophenyl (H$_2$N-) |
| A.1.68 | $CH_3$ | $CH_2CH_3$ | H | 3-(N,N-dimethylamino)phenyl |
| A.1.69 | $CH_3$ | $CH_2CH_3$ | H | 3-[N-methyl-N-(isobutyryl)amino]phenyl |
| A.1.70 | $CH_3$ | $CH_2CH_3$ | H | 3-[N-allyl-N-(methylsulfonyl)amino]phenyl |
| A.1.71 | $CH_3$ | $CH_2CH_3$ | H | 3-(tert-butylamino)phenyl |

TABLE A-continued

Meanings for $R_1$, $R_2$, $R_5$ and $R_6$:

| Line | $R_1$ | $R_2$ | $R_6$ | $R_5$ |
|---|---|---|---|---|
| A.1.72 | $CH_3$ | $CH_2CH_3$ | H | 2-methyl-6-(trifluoromethyl)phenyl |
| A.1.73 | $CH_3$ | $CH_2CH_3$ | H | 3,5-bis(trifluoromethyl)phenyl |
| A.1.74 | $CH_3$ | $CH_2CH_3$ | H | 4-methyl-2-(trifluoromethyl)-... (with $H_3C$ substituent) |
| A.1.75 | $CH_3$ | $CH_2CH_3$ | H | 4-chloro-3-(trifluoromethyl)phenyl |
| A.1.76 | $CH_3$ | $CH_2CH_3$ | H | 4-bromo-3-(trifluoromethyl)phenyl |
| A.1.77 | $CH_3$ | $CH_2CH_3$ | H | 4-cyano-3-(trifluoromethyl)phenyl |
| A.1.78 | $CH_3$ | $CH_2CH_3$ | H | 4-ethyl-3-(trifluoromethyl)phenyl |
| A.1.79 | $CH_3$ | $CH_2CH_3$ | H | 3-chloro-5-(trifluoromethyl)phenyl |

TABLE A-continued

Meanings for $R_1$, $R_2$, $R_5$ and $R_6$:

| Line | $R_1$ | $R_2$ | $R_6$ | $R_5$ |
|---|---|---|---|---|
| A.1.80 | $CH_3$ | $CH_2CH_3$ | H | 4-chloro-3-methyl-5-(trifluoromethyl)phenyl |
| A.1.81 | $CH_3$ | $CH_2CH_3$ | H | 4-(trifluoromethyl)phenyl |
| A.1.82 | $CH_3$ | $CH_2CH_3$ | H | 3-tert-butylphenyl |
| A.1.83 | $CH_3$ | $CH_2CH_3$ | H | 4-tert-butylphenyl |
| A.1.84 | $CH_3$ | $CH_2CH_3$ | H | 3-isopropylphenyl |
| A.1.85 | $CH_3$ | $CH_2CH_3$ | H | 4-isopropylphenyl |
| A.1.86 | $CH_3$ | $CH_2CH_3$ | H | 2-ethyl-4-methyl-1-propylphenyl |
| A.1.87 | $CH_3$ | $CH_2CH_3$ | H | 2-tert-butyl-4-methylphenyl |
| A.1.88 | $CH_3$ | $CH_2CH_3$ | H | 2-tert-butyl-4-chlorophenyl |

TABLE A-continued
Meanings for $R_1$, $R_2$, $R_5$ and $R_6$:
| Line | $R_1$ | $R_2$ | $R_6$ | $R_5$ |
|---|---|---|---|---|
| A.1.89 | $CH_3$ | $CH_2CH_3$ | H | 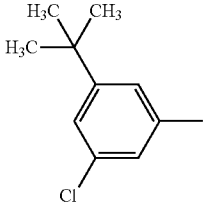 |
| A.1.190 | $CH_3$ | $CH_2CH_3$ | H | 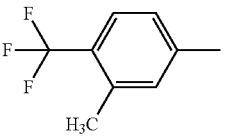 |
| A.1.91 | $CH_3$ | $CH_2CH_3$ | H | 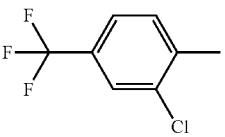 |
| A.1.92 | $CH_3$ | $CH_2CH_3$ | H | 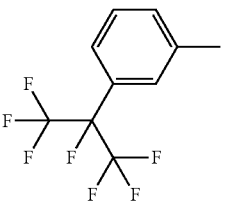 |
| A.1.93 | $CH_3$ | $CH_2CH_3$ | H | 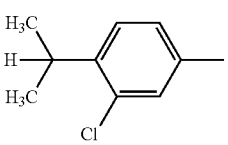 |
| A.1.94 | $CH_3$ | $CH_2CH_3$ | H | 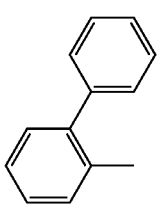 |
| A.1.95 | $CH_3$ | $CH_2CH_3$ | H | 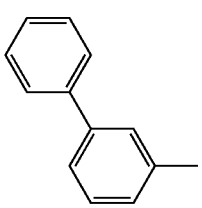 |
| A.1.96 | $CH_3$ | $CH_2CH_3$ | H | 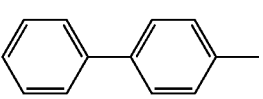 |

TABLE A-continued

Meanings for $R_1$, $R_2$, $R_5$ and $R_6$:

| Line | $R_1$ | $R_2$ | $R_6$ | $R_5$ |
|---|---|---|---|---|
| A.1.97 | $CH_3$ | $CH_2CH_3$ | H | 3'-chloro-3-biphenylyl |
| A.1.98 | $CH_3$ | $CH_2CH_3$ | H | 4-methyl-3-phenylphenyl (with $H_3C$ substituent) |
| A.1.99 | $CH_3$ | $CH_2CH_3$ | H | 4-chloro-3-phenylphenyl (with Cl substituent) |
| A.1.100 | $CH_3$ | $CH_2CH_3$ | H | 4-bromo-3-phenylphenyl (with Br substituent) |
| A.1.101 | $CH_3$ | $CH_2CH_3$ | H | 3-(carboxy)phenyl (—C(=O)OH) |
| A.1.102 | $CH_3$ | $CH_2CH_3$ | H | 3-(methoxycarbonyl)phenyl (—C(=O)O—$CH_3$) |
| A.1.103 | $CH_3$ | $CH_2CH_3$ | H | 3-(ethoxycarbonyl)phenyl (—C(=O)O—$CH_2CH_3$) |

TABLE A-continued

Meanings for $R_1$, $R_2$, $R_5$ and $R_6$:

| Line | $R_1$ | $R_2$ | $R_6$ | $R_5$ |
|---|---|---|---|---|
| A.1.104 | $CH_3$ | $CH_2CH_3$ | H | 3-methylbenzoate of n-pentyl |
| A.1.105 | $CH_3$ | $CH_2CH_3$ | H | 3-methylbenzoate of isopropyl |
| A.1.106 | $CH_3$ | $CH_2CH_3$ | H | 3-methylbenzoate of tert-butyl |
| A.1.107 | $CH_3$ | $CH_2CH_3$ | H | 3-methylbenzoate of pentan-2-yl |
| A.1.108 | $CH_3$ | $CH_2CH_3$ | H | 3-methylbenzoate of allyl |
| A.1.109 | $CH_3$ | $CH_2CH_3$ | H | 3-methylbenzoate of but-3-en-2-yl |
| A.1.110 | $CH_3$ | $CH_2CH_3$ | H | 3-methylbenzoate of propargyl |

TABLE A-continued
Meanings for $R_1$, $R_2$, $R_5$ and $R_6$:
| Line | $R_1$ | $R_2$ | $R_6$ | $R_5$ |
|---|---|---|---|---|
| A.1.111 | $CH_3$ | $CH_2CH_3$ | H | 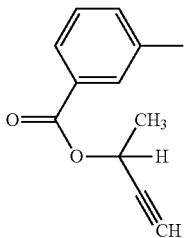 |
| A.1.112 | $CH_3$ | $CH_2CH_3$ | H | 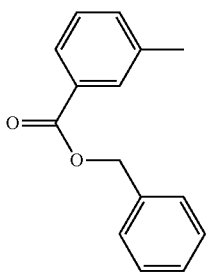 |
| A.1.113 | $CH_3$ | $CH_2CH_3$ | H | 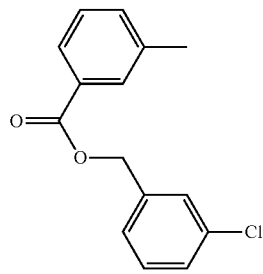 |
| A.1.114 | $CH_3$ | $CH_2CH_3$ | H | 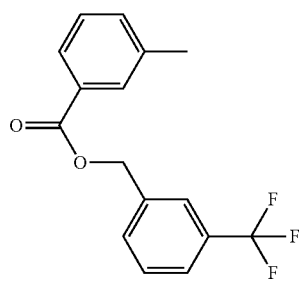 |
| A.1.115 | $CH_3$ | $CH_2CH_3$ | H | 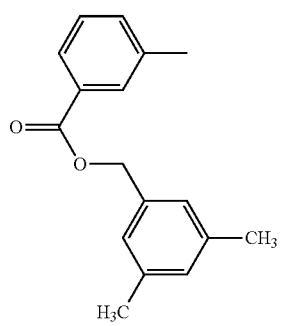 |

TABLE A-continued

Meanings for $R_1$, $R_2$, $R_5$ and $R_6$:

| Line | $R_1$ | $R_2$ | $R_6$ | $R_5$ |
|---|---|---|---|---|
| A.1.116 | $CH_3$ | $CH_2CH_3$ | H | 3-methyl-benzamide (C(O)NH$_2$) |
| A.1.117 | $CH_3$ | $CH_2CH_3$ | H | 3-methyl-N-ethylbenzamide |
| A.1.118 | $CH_3$ | $CH_2CH_3$ | H | 3-methyl-N,N-diethylbenzamide |
| A.1.119 | $CH_3$ | $CH_2CH_3$ | H | 3-methyl-N-allyl-N-ethylbenzamide |
| A.1.120 | $CH_3$ | $CH_2CH_3$ | H | 3-methyl-N-benzylbenzamide |
| A.1.121 | $CH_3$ | $CH_2CH_3$ | H | 3-methyl-N-benzyl-N-methylbenzamide |

TABLE A-continued

Meanings for $R_1$, $R_2$, $R_5$ and $R_6$:

| Line | $R_1$ | $R_2$ | $R_6$ | $R_5$ |
|---|---|---|---|---|
| A.1.122 | $CH_3$ | $CH_2CH_3$ | H | 3-(1H-tetrazol-5-yl)phenyl |
| A.1.123 | $CH_3$ | $CH_2CH_3$ | H | 3-(1-methyl-1H-tetrazol-5-yl)phenyl |
| A.1.124 | $CH_3$ | $CH_2CH_3$ | H | 3-(thiazol-2-yl)phenyl |
| A.1.125 | $CH_3$ | $CH_2CH_3$ | H | 3-(thiocarbamoyl)phenyl |
| A.1.126 | $CH_3$ | $CH_2CH_3$ | H | 2,2-difluoro-benzo[1,3]dioxol-4-yl |
| A.1.127 | $CH_3$ | $CH_2CH_3$ | H | 2,2-dichloro-benzo[1,3]dioxol-4-yl |
| A.1.128 | $CH_3$ | $CH_2CH_3$ | H | 2,2-dimethyl-benzo[1,3]dioxol-4-yl |

TABLE A-continued

Meanings for $R_1$, $R_2$, $R_5$ and $R_6$:

| Line | $R_1$ | $R_2$ | $R_6$ | $R_5$ |
|---|---|---|---|---|
| A.1.129 | $CH_3$ | $CH_2CH_3$ | H | 2-methyl-benzo[1,3]dioxole-2-yl (H, $CH_3$ at 2-position) |
| A.1.130 | $CH_3$ | $CH_2CH_3$ | H | 2-methyl-2-cyano-benzo[1,3]dioxol-4-yl ($H_3C$, $C\equiv N$ at 2-position) |
| A.1.131 | $CH_3$ | $CH_2CH_3$ | H | 6-chloro-2,2-difluoro-benzo[1,3]dioxol-4-yl |
| A.1.132 | $CH_3$ | $CH_2CH_3$ | H | 6-methyl-2,2-difluoro-benzo[1,3]dioxol-4-yl |
| A.1.133 | $CH_3$ | $CH_2CH_3$ | H | 2-oxo-benzo[1,3]dioxol-4-yl |
| A.1.134 | $CH_3$ | $CH_2CH_3$ | H | 2-thioxo-benzo[1,3]dioxol-4-yl |

TABLE A-continued

Meanings for $R_1$, $R_2$, $R_5$ and $R_6$:

| Line | $R_1$ | $R_2$ | $R_6$ | $R_5$ |
|---|---|---|---|---|
| A.1.135 | $CH_3$ | $CH_2CH_3$ | H | 6-chloro-4-methyl-2H-1,3-benzodioxole-2-thione |
| A.1.136 | $CH_3$ | $CH_2CH_3$ | H | 4,6-dimethyl-2H-1,3-benzodioxol-2-one |
| A.1.137 | $CH_3$ | $CH_2CH_3$ | H | 4,6-dimethyl-2H-1,3-benzodioxole-2-thione |
| A.1.138 | $CH_3$ | $CH_2CH_3$ | H | 4-chloro-2,2-difluoro-7-methyl-2H-1,3-benzodioxole |
| A.1.139 | $CH_3$ | $CH_2CH_3$ | H | 5-chloro-2,2-difluoro-4-methyl-2H-1,3-benzodioxole |
| A.1.140 | $CH_3$ | $CH_2CH_3$ | H | 5-methyl-2H-1,3-benzodioxole |
| A.1.141 | $CH_3$ | $CH_2CH_3$ | H | 2,2-difluoro-5-methyl-2H-1,3-benzodioxole |

TABLE A-continued
| Line | $R_1$ | $R_2$ | $R_6$ | $R_5$ |
|---|---|---|---|---|
| A.1.142 | $CH_3$ | $CH_2CH_3$ | H | 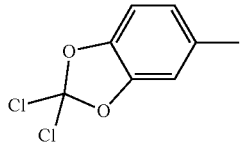 |
| A.1.143 | $CH_3$ | $CH_2CH_3$ | H | 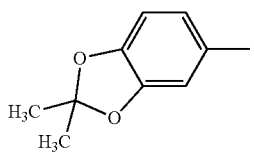 |
| A.1.144 | $CH_3$ | $CH_2CH_3$ | H | 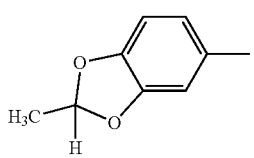 |
| A.1.145 | $CH_3$ | $CH_2CH_3$ | H | 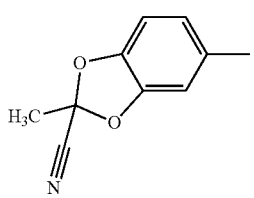 |
| A.1.146 | $CH_3$ | $CH_2CH_3$ | H | 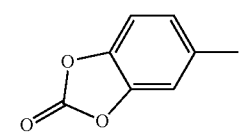 |
| A.1.147 | $CH_3$ | $CH_2CH_3$ | H | 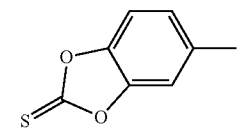 |
| A.1.148 | $CH_3$ | $CH_2CH_3$ | H | 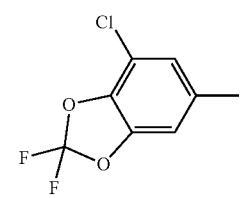 |
| A.1.149 | $CH_3$ | $CH_2CH_3$ | H | 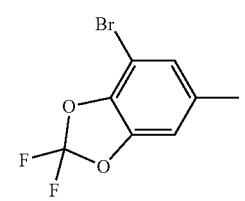 |

TABLE A-continued

Meanings for $R_1$, $R_2$, $R_5$ and $R_6$:

| Line | $R_1$ | $R_2$ | $R_6$ | $R_5$ |
|---|---|---|---|---|
| A.1.150 | $CH_3$ | $CH_2CH_3$ | H | 7-chloro-2,2-dichloro-5-methyl-1,3-benzodioxole |
| A.1.151 | $CH_3$ | $CH_2CH_3$ | H | 7-methyl-2,2-difluoro-5-methyl-1,3-benzodioxole |
| A.1.152 | $CH_3$ | $CH_2CH_3$ | H | 7-chloro-5-methyl-1,3-benzodioxol-2-one |
| A.1.153 | $CH_3$ | $CH_2CH_3$ | H | 6-methyl-1H-indole |
| A.1.154 | $CH_3$ | $CH_2CH_3$ | H | 6-methyl-1-methyl-1H-indole |
| A.1.155 | $CH_3$ | $CH_2CH_3$ | H | 6-methyl-1-allyl-1H-indole |
| A.1.156 | $CH_3$ | $CH_2CH_3$ | H | 4-methyl-1-methyl-1H-indole |

TABLE A-continued
| | | Meanings for $R_1$, $R_2$, $R_5$ and $R_6$: | | |
|---|---|---|---|---|
| Line | $R_1$ | $R_2$ | $R_6$ | $R_5$ |
| A.1.157 | $CH_3$ | $CH_2CH_3$ | H | 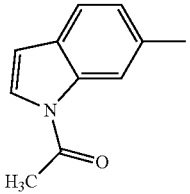 |
| A.1.158 | $CH_3$ | $CH_2CH_3$ | H | 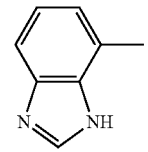 |
| A.1.159 | $CH_3$ | $CH_2CH_3$ | H | 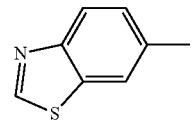 |
| A.1.60 | $CH_3$ | $CH_2CH_3$ | H | 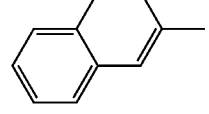 |
| A.1.161 | $CH_3$ | $CH_2CH_3$ | H | 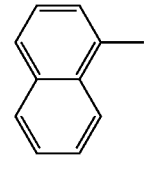 |
| A.1.162 | $CH_3$ | $CH_2CH_3$ | H | 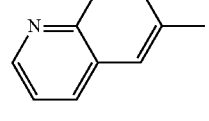 |
| A.1.163 | $CH_3$ | $CH_2CH_3$ | H | 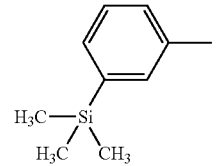 |
| A.1.164 | $CH_3$ | $CH_2CH_3$ | H | 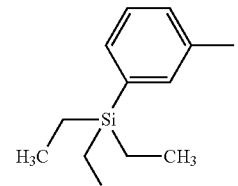 |

TABLE A-continued
| Line | $R_1$ | $R_2$ | $R_6$ | $R_5$ |
|---|---|---|---|---|
| A.1.165 | $CH_3$ | $CH_2CH_3$ | H | 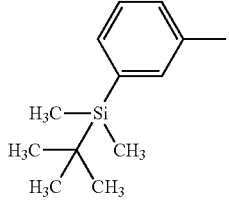 |
| A.1.166 | $CH_3$ | $CH_2CH_3$ | H | 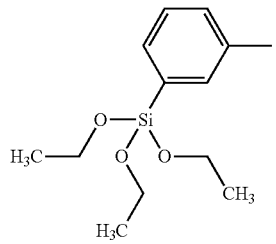 |
| A.1.167 | $CH_3$ | $CH_2CH_3$ | H | 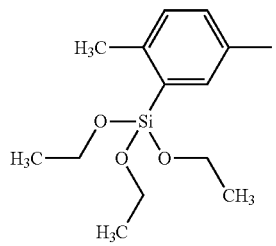 |
| A.1.168 | $CH_3$ | $CH_2CH_3$ | H | 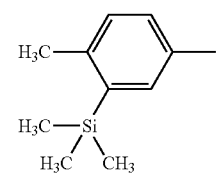 |
| A.1.169 | $CH_3$ | $CH_2CH_3$ | H | 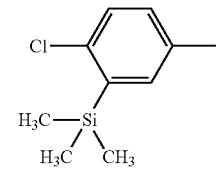 |
| A.1.170 | $CH_3$ | $CH_2CH_3$ | H | 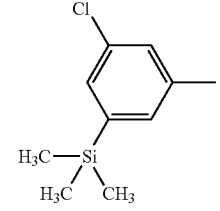 |
| A.1.171 | $CH_3$ | $CH_2CH_3$ | H | 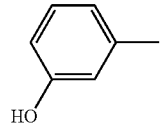 |

TABLE A-continued

Meanings for $R_1$, $R_2$, $R_5$ and $R_6$:

| Line | $R_1$ | $R_2$ | $R_6$ | $R_5$ |
|---|---|---|---|---|
| A.1.172 | $CH_3$ | $CH_2CH_3$ | H | 3-methoxyphenyl |
| A.1.173 | $CH_3$ | $CH_2CH_3$ | H | 3-ethoxyphenyl |
| A.1.174 | $CH_3$ | $CH_2CH_3$ | H | 3-isopropoxyphenyl |
| A.1.175 | $CH_3$ | $CH_2CH_3$ | H | 3-(n-pentyloxy)phenyl |
| A.1.176 | $CH_3$ | $CH_2CH_3$ | H | 3-(hexan-2-yloxy)phenyl |
| A.1.177 | $CH_3$ | $CH_2CH_3$ | H | 3-(tert-butoxy)phenyl |
| A.1.178 | $CH_3$ | $CH_2CH_3$ | H | 3-(cyclopentylmethoxy)phenyl |

TABLE A-continued
Meanings for $R_1$, $R_2$, $R_5$ and $R_6$:
| Line | $R_1$ | $R_2$ | $R_6$ | $R_5$ |
|---|---|---|---|---|
| A.1.79 | $CH_3$ | $CH_2CH_3$ | H | 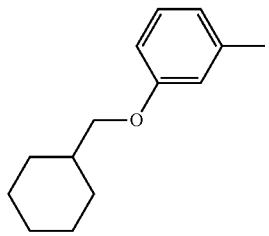 |
| A.1.180 | $CH_3$ | $CH_2CH_3$ | H | 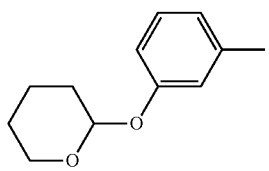 |
| A.1.181 | $CH_3$ | $CH_2CH_3$ | H | 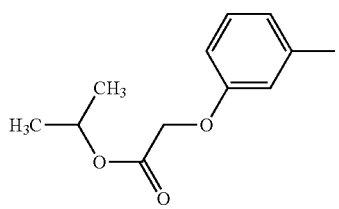 |
| A.1.182 | $CH_3$ | $CH_2CH_3$ | H | 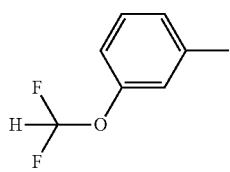 |
| A.1.183 | $CH_3$ | $CH_2CH_3$ | H | 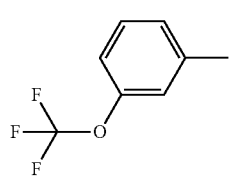 |
| A.1.184 | $CH_3$ | $CH_2CH_3$ | H | 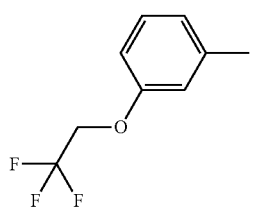 |
| A.1.185 | $CH_3$ | $CH_2CH_3$ | H | 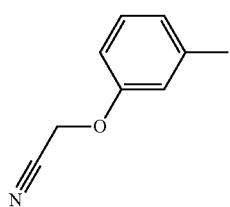 |

TABLE A-continued
Meanings for $R_1$, $R_2$, $R_5$ and $R_6$:
| Line | $R_1$ | $R_2$ | $R_6$ | $R_5$ |
|---|---|---|---|---|
| A.1.186 | $CH_3$ | $CH_2CH_3$ | H | 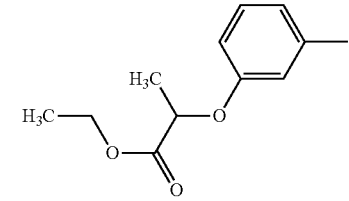 |
| A.1.187 | $CH_3$ | $CH_2CH_3$ | H | 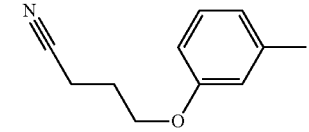 |
| A.1.188 | $CH_3$ | $CH_2CH_3$ | H | 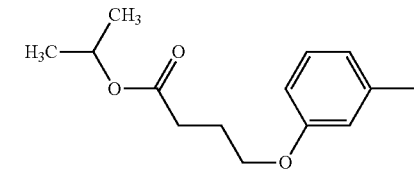 |
| A.1.189 | $CH_3$ | $CH_2CH_3$ | H | 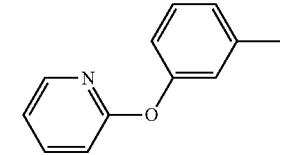 |
| A.1.190 | $CH_3$ | $CH_2CH_3$ | H | 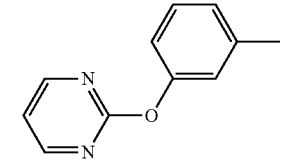 |
| A.1.191 | $CH_3$ | $CH_2CH_3$ | H | 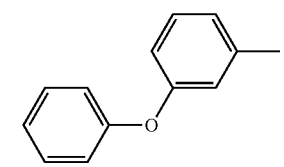 |
| A.1.192 | $CH_3$ | $CH_2CH_3$ | H | 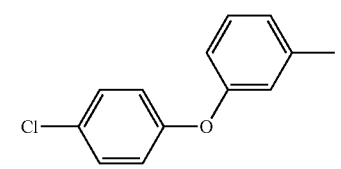 |
| A.1.193 | $CH_3$ | $CH_2CH_3$ | H | 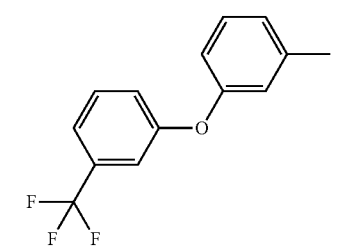 |

TABLE A-continued
| Meanings for $R_1$, $R_2$, $R_5$ and $R_6$: | | | | |
|---|---|---|---|---|
| Line | $R_1$ | $R_2$ | $R_6$ | $R_5$ |
| A.1.194 | $CH_3$ | $CH_2CH_3$ | H | 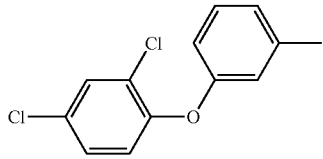 |
| A.1.195 | $CH_3$ | $CH_2CH_3$ | H | 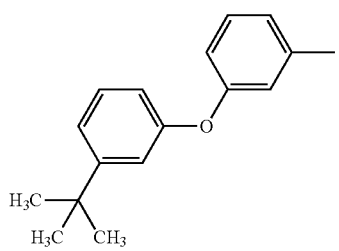 |
| A.1.196 | $CH_3$ | $CH_2CH_3$ | H | 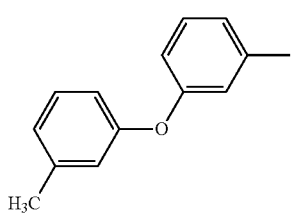 |
| A.1.197 | $CH_3$ | $CH_2CH_3$ | H | 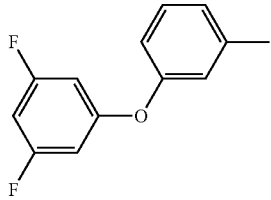 |
| A.1.198 | $CH_3$ | $CH_2CH_3$ | H | 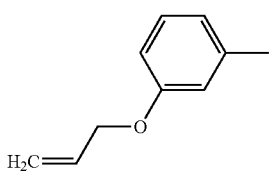 |
| A.1.199 | $CH_3$ | $CH_2CH_3$ | H | 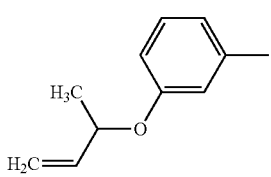 |
| A.1.200 | $CH_3$ | $CH_2CH_3$ | H | 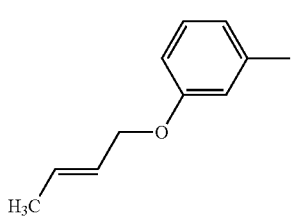 |

TABLE A-continued
Meanings for $R_1$, $R_2$, $R_5$ and $R_6$:
| Line | $R_1$ | $R_2$ | $R_6$ | $R_5$ |
|---|---|---|---|---|
| A.1.201 | $CH_3$ | $CH_2CH_3$ | H | 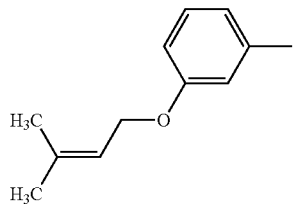 |
| A.1.202 | $CH_3$ | $CH_2CH_3$ | H | 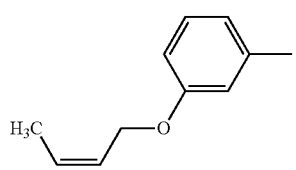 |
| A.1.203 | $CH_3$ | $CH_2CH_3$ | H | 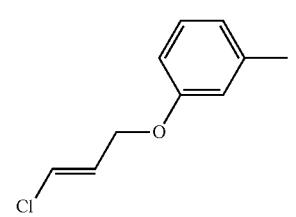 |
| A.1.204 | $CH_3$ | $CH_2CH_3$ | H | 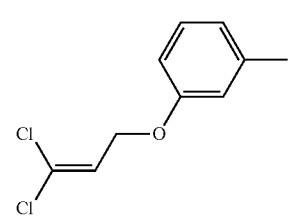 |
| A.1.205 | $CH_3$ | $CH_2CH_3$ | H | 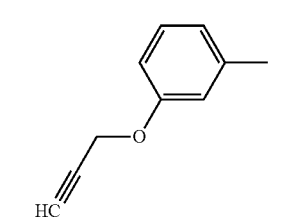 |
| A.1.206 | $CH_3$ | $CH_2HC_3$ | H | 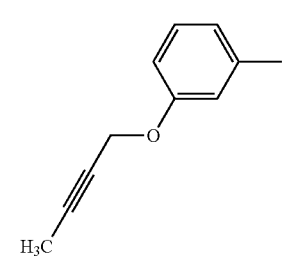 |
| A.1.207 | $CH_3$ | $CH_2CH_3$ | H | 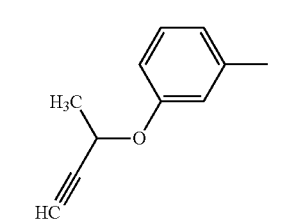 |

TABLE A-continued
| Line | $R_1$ | $R_2$ | $R_6$ | $R_5$ |
|---|---|---|---|---|
| A.1.208 | $CH_3$ | $CH_2CH_3$ | H | 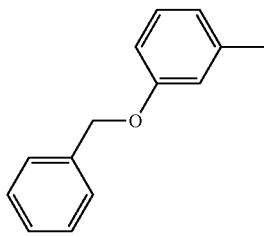 |
| A.1.209 | $CH_3$ | $CH_2CH_3$ | H | 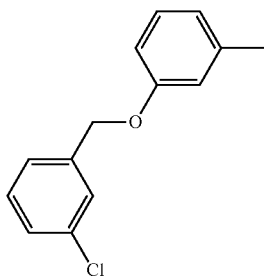 |
| A.1.210 | $CH_3$ | $CH_2CH_3$ | H | 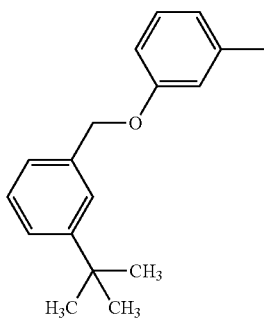 |
| A.1.211 | $CH_3$ | $CH_2CH_3$ | H | 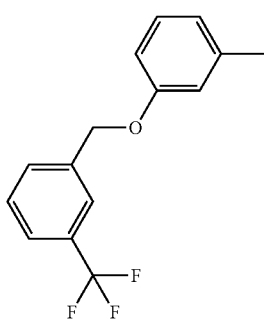 |
| A.1.212 | $CH_3$ | $CH_2CH_3$ | H | 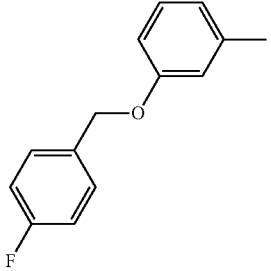 |

TABLE A-continued
Meanings for $R_1$, $R_2$, $R_5$ and $R_6$:
| Line | $R_1$ | $R_2$ | $R_6$ | $R_5$ |
|---|---|---|---|---|
| A.1.213 | $CH_3$ | $CH_2CH_3$ | H | 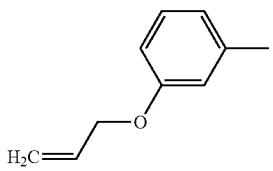 |
| A.1.214 | $CH_3$ | $CH_2CH_3$ | H | 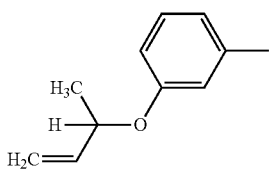 |
| A.1.215 | $CH_3$ | $CH_2CH_3$ | H | 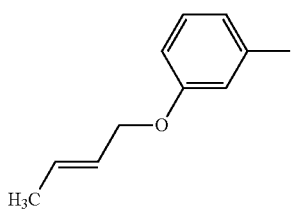 |
| A.1.216 | $CH_3$ | $CH_2CH_3$ | H | 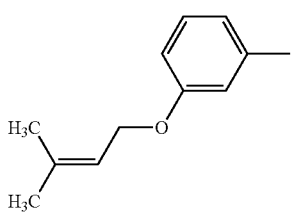 |
| A.1.217 | $CH_3$ | $CH_2CH_3$ | H | 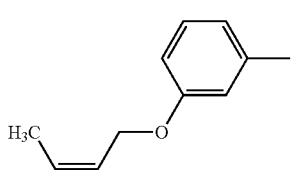 |
| A.1.218 | $CH_3$ | $CH_2CH_3$ | H | 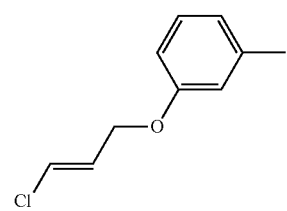 |
| A.1.219 | $CH_3$ | $CH_2CH_3$ | H | 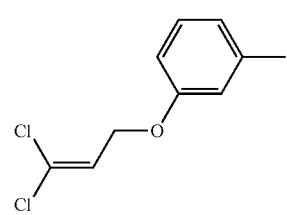 |

TABLE A-continued
Meanings for $R_1$, $R_2$, $R_5$ and $R_6$:
| Line | $R_1$ | $R_2$ | $R_6$ | $R_5$ |
|---|---|---|---|---|
| A.1.220 | $CH_3$ | $CH_2CH_3$ | H | 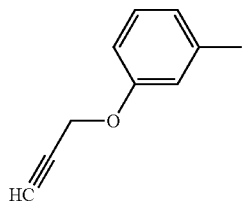 |
| A.1.221 | $CH_3$ | $CH_2CH_3$ | H | 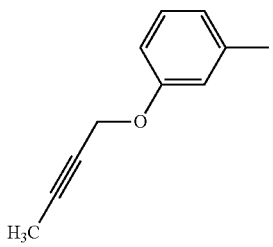 |
| A.1.222 | $CH_3$ | $CH_2CH_3$ | H | 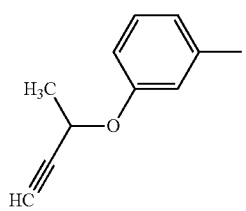 |
| A.1.223 | $CH_3$ | $CH_2CH_3$ | H | 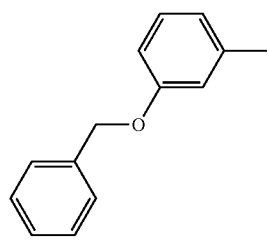 |
| A.1.224 | $CH_3$ | $CH_2CH_3$ | H | 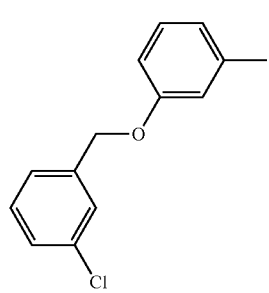 |

TABLE A-continued
Meanings for $R_1$, $R_2$, $R_5$ and $R_6$:
| Line | $R_1$ | $R_2$ | $R_6$ | $R_5$ |
|---|---|---|---|---|
| A.1.225 | $CH_3$ | $CH_2CH_3$ | H | 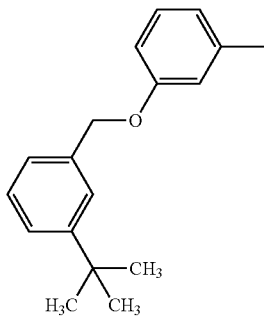 |
| A.1.226 | $CH_3$ | $CH_2CH_3$ | H | 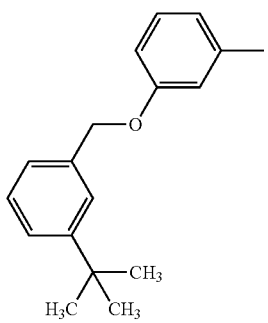 |
| A.1.227 | $CH_3$ | $CH_2CH_3$ | H | 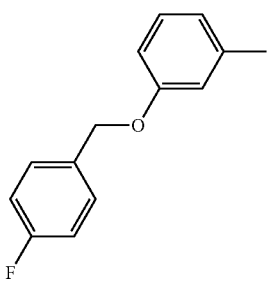 |
| A.1.228 | $CH_3$ | $CH_2CH_3$ | H | 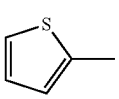 |
| A.1.229 | $CH_3$ | $CH_2CH_3$ | H | 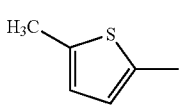 |
| A.1.230 | $CH_3$ | $CH_2CH_3$ | H | 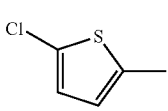 |
| A.1.231 | $CH_3$ | $CH_2CH_3$ | H | 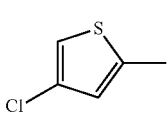 |
| A.1.232 | $CH_3$ | $CH_2CH_3$ | H | H— |

TABLE A-continued

Meanings for $R_1$, $R_2$, $R_5$ and $R_6$:

| Line | $R_1$ | $R_2$ | $R_6$ | $R_5$ |
|---|---|---|---|---|
| A.1.233 | $CH_3$ | $CH_2CH_3$ | H | trimethylsilyl |
| A.1.234 | $CH_3$ | $CH_2CH_3$ | H | tert-butyl(dimethyl)silyl |
| A.1.235 | $CH_3$ | $CH_2CH_3$ | H | triethylsilyl |
| A.1.236 | $CH_3$ | $CH_2CH_3$ | H | triisopropylsilyl |
| A.1.237 | $CH_3$ | $CH_2CH_3$ | H | dimethyl(phenyl)silyl |
| A.1.238 | $CH_3$ | $CH_2CH_3$ | H | tripropylsilyl |
| A.1.239 | $CH_3$ | $CH_2CH_3$ | H | butyl(dimethyl)silyl |
| A.1.240 | $CH_3$ | $CH_2CH_3$ | H | isobutyl(dimethyl)silyl |
| A.1.241 | $CH_3$ | $CH_2CH_3$ | H | benzyl(dimethyl)silyl |

TABLE A-continued

Meanings for $R_1$, $R_2$, $R_5$ and $R_6$:

| Line | $R_1$ | $R_2$ | $R_6$ | $R_5$ |
|---|---|---|---|---|
| A.1.242 | $CH_3$ | $CH_2CH_3$ | H | 3-chlorophenyl-Si(CH$_3$)$_2$– |
| A.1.243 | $CH_3$ | $CH_2CH_3$ | H | 3-(trifluoromethyl)phenyl-Si(CH$_3$)$_2$– |
| A.1.244 | $CH_3$ | $CH_2CH_3$ | H | Si(OCH$_2$CH$_3$)$_3$– |
| A.1.245 | $CH_3$ | $CH_2CH_3$ | H | H$_3$C— |
| A.1.246 | $CH_3$ | $CH_2CH_3$ | H | CH$_3$CH$_2$– |
| A.1.247 | $CH_3$ | $CH_2CH_3$ | H | CH$_3$CH$_2$CH$_2$– |
| A.1.248 | $CH_3$ | $CH_2CH_3$ | H | CH$_3$(CH$_2$)$_3$– |
| A.1.249 | $CH_3$ | $CH_2CH_3$ | H | CH$_3$(CH$_2$)$_4$– |
| A.1.250 | $CH_3$ | $CH_2CH_3$ | H | CH$_3$(CH$_2$)$_7$– |
| A.1.251 | $CH_3$ | $CH_2CH_3$ | H | (CH$_3$)$_3$C– |
| A.1.252 | $CH_3$ | $CH_2CH_3$ | H | (CH$_3$)$_2$CHCH$_2$– |
| A.1.253 | $CH_3$ | $CH_2CH_3$ | H | (CH$_3$)$_2$CHCH(CH$_3$)– |
| A.1.254 | $CH_3$ | $CH_2CH_3$ | H | CH$_3$CH$_2$CH(CH$_3$)CH$_2$– |

TABLE A-continued
| | | Meanings for $R_1$, $R_2$, $R_5$ and $R_6$: | | |
|---|---|---|---|---|
| Line | $R_1$ | $R_2$ | $R_6$ | $R_5$ |
| A.1.255 | $CH_3$ | $CH_2CH_3$ | H | 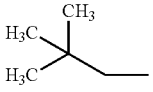 |
| A.1.256 | $CH_3$ | $CH_2CH_3$ | H | 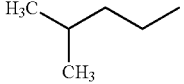 |
| A.1.257 | $CH_3$ | $CH_2CH_3$ | H | 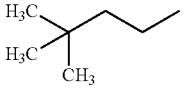 |
| A.1.258 | $CH_3$ | $CH_2CH_3$ | H | 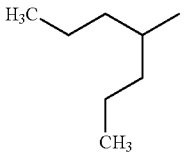 |
| A.1.259 | $CH_3$ | $CH_2CH_3$ | H | 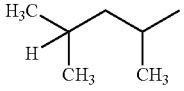 |
| A.1.260 | $CH_3$ | $CH_2CH_3$ | H | 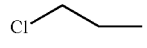 |
| A.1.261 | $CH_3$ | $CH_2CH_3$ | H | 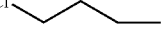 |
| A.1.262 | $CH_3$ | $CH_2CH_3$ | H |  |
| A.1.263 | $CH_3$ | $CH_2CH_3$ | H | 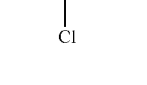 |
| A.1.264 | $CH_3$ | $CH_2CH_3$ | H | 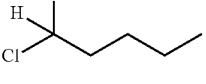 |
| A.1.265 | $CH_3$ | $CH_2CH_3$ | H | 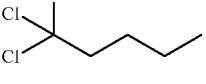 |
| A.1.266 | $CH_3$ | $CH_2CH_3$ | H | 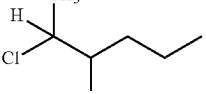 |
| A.1.267 | $CH_3$ | $CH_2CH_3$ | H | 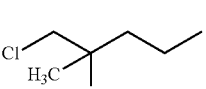 |

TABLE A-continued

Meanings for $R_1$, $R_2$, $R_5$ and $R_6$:

| Line | $R_1$ | $R_2$ | $R_6$ | $R_5$ |
|---|---|---|---|---|
| A.1.268 | $CH_3$ | $CH_2CH_3$ | H | 1-chloro-2-chloro-3-methylpentyl |
| A.1.269 | $CH_3$ | $CH_2CH_3$ | H | 1-chloro-2-chlorohexyl |
| A.1.270 | $CH_3$ | $CH_2CH_3$ | H | 3,3,3-trifluoropropyl derivative |
| A.1.271 | $CH_3$ | $CH_2CH_3$ | H | 2,2,2-trifluoropentyl derivative |
| A.1.272 | $CH_3$ | $CH_2CH_3$ | H | 1,1-difluoro-3-methylpentyl |
| A.1.273 | $CH_3$ | $CH_2CH_3$ | H | cyclopropyl |
| A.1.274 | $CH_3$ | $CH_2CH_3$ | H | cyclopentyl |
| A.1.275 | $CH_3$ | $CH_2CH_3$ | H | 3-methylcyclopentyl |
| A.1.276 | $CH_3$ | $CH_2CH_3$ | H | 3,3-dimethylcyclopentyl |
| A.1.277 | $CH_3$ | $CH_2CH_3$ | H | 3-methylcyclopentenyl |
| A.1.278 | $CH_3$ | $CH_2CH_3$ | H | cyclohexyl |
| A.1.279 | $CH_3$ | $CH_2CH_3$ | H | 3-methylcyclohexyl |

TABLE A-continued

Meanings for $R_1$, $R_2$, $R_5$ and $R_6$:

| Line | $R_1$ | $R_2$ | $R_6$ | $R_5$ |
|---|---|---|---|---|
| A.1.280 | $CH_3$ | $CH_2CH_3$ | H | 2,3-dimethylcyclohexyl |
| A.1.281 | $CH_3$ | $CH_2CH_3$ | H | 4,4-dimethylcyclohexyl (gem-dimethyl) |
| A.1.282 | $CH_3$ | $CH_2CH_3$ | H | 4-methylcyclohex-1-enyl (methyl) |
| A.1.283 | $CH_3$ | $CH_2CH_3$ | H | cycloheptyl |
| A.1.284 | $CH_3$ | $CH_2CH_3$ | H | methylcycloheptyl |
| A.1.285 | $CH_3$ | $CH_2CH_3$ | H | cycloheptenyl |
| A.1.286 | $CH_3$ | $CH_2CH_3$ | H | benzo[1,3]dioxol-4-yl-methyl |
| A.1.287 | $CH_3$ | $CH_2CH_3$ | H | cyclopropylmethyl |
| A.1.288 | $CH_3$ | $CH_2CH_3$ | H | cyclopentylmethyl |
| A.1.289 | $CH_3$ | $CH_2CH_3$ | H | (3-methylcyclopentyl)methyl |
| A.1.290 | $CH_3$ | $CH_2CH_3$ | H | (2-methylcyclopent-2-enyl)methyl |

TABLE A-continued
Meanings for $R_1$, $R_2$, $R_5$ and $R_6$:
| Line | $R_1$ | $R_2$ | $R_6$ | $R_5$ |
|---|---|---|---|---|
| A.1.291 | $CH_3$ | $CH_2CH_3$ | H | 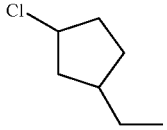 |
| A.1.292 | $CH_3$ | $CH_2CH_3$ | H | 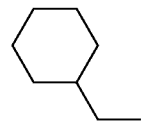 |
| A.1.293 | $CH_3$ | $CH_2CH_3$ | H |  |
| A.1.294 | $CH_3$ | $CH_2CH_3$ | H | 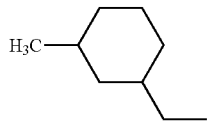 |
| A.1.295 | $CH_3$ | $CH_2CH_3$ | H | 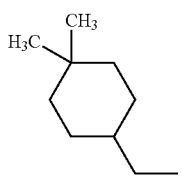 |
| A.1.296 | $CH_3$ | $CH_2CH_3$ | H | 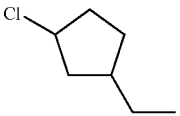 |
| A.1.297 | $CH_3$ | $CH_2CH_3$ | H | 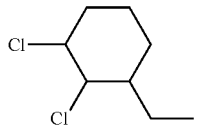 |
| A.1.298 | $CH_3$ | $CH_2CH_3$ | H | 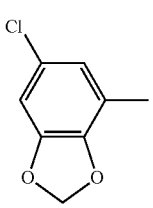 |
| A.1.299 | $CH_3$ | $CH_2CH_3$ | H | 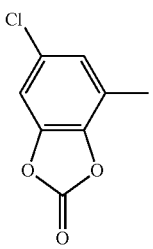 |

TABLE A-continued
Meanings for $R_1$, $R_2$, $R_5$ and $R_6$:
| Line | $R_1$ | $R_2$ | $R_6$ | $R_5$ |
|---|---|---|---|---|
| A.1.300 | $CH_3$ | $CH_2CH_3$ | H | 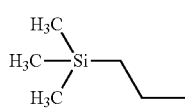 |
| A.1.301 | $CH_3$ | $CH_2CH_3$ | H | 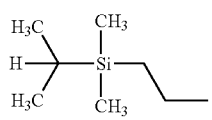 |
| A.1.302 | $CH_3$ | $CH_2CH_3$ | H | 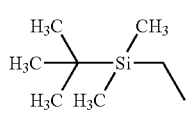 |
| A.1.303 | $CH_3$ | $CH_2CH_3$ | H | 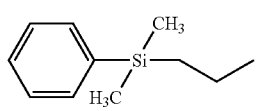 |
| A.1.304 | $CH_3$ | $CH_2CH_3$ | H | 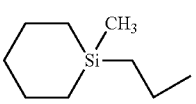 |
| A.1.305 | $CH_3$ | $CH_2CH_3$ | H | 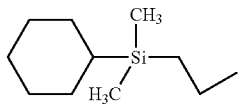 |
| A.1.306 | $CH_3$ | $CH_2CH_3$ | H | 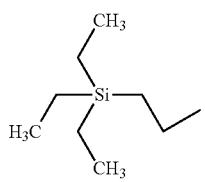 |
| A.1.307 | $CH_3$ | $CH_2CH_3$ | H | 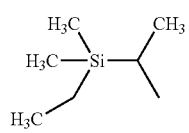 |
| A.1.308 | $CH_3$ | $CH_2CH_3$ | H | 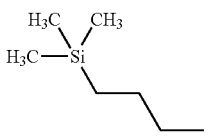 |
| A.1.309 | $CH_3$ | $CH_2CH_3$ | H | 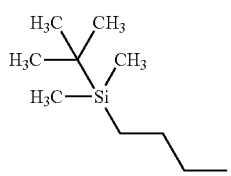 |

TABLE A-continued
Meanings for $R_1$, $R_2$, $R_5$ and $R_6$:
| Line | $R_1$ | $R_2$ | $R_6$ | $R_5$ |
|---|---|---|---|---|
| A.1.310 | CH$_3$ | CH$_2$CH$_3$ | H | 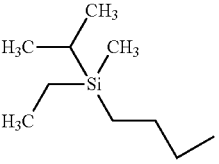 |
| A.1.311 | CH$_3$ | CH$_2$CH$_3$ | H | 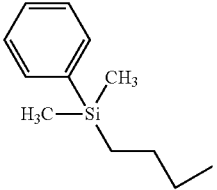 |
| A.1.312 | CH$_3$ | CH$_2$CH$_3$ | H | 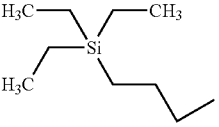 |
| A.1.313 | CH$_3$ | CH$_2$CH$_3$ | H | 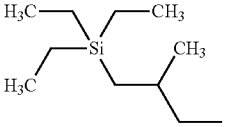 |
| A.1.314 | CH$_3$ | CH$_2$CH$_3$ | H | 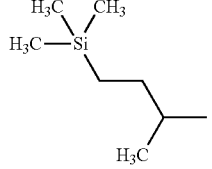 |
| A.1.315 | CH$_3$ | CH$_2$CH$_3$ | H | 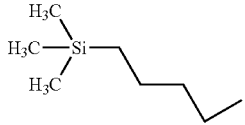 |
| A.1.316 | CH$_3$ | CH$_2$CH$_3$ | H | 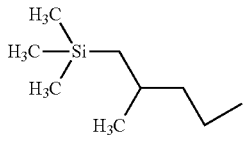 |
| A.1.317 | CH$_3$ | CH$_2$CH$_3$ | H | 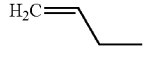 |
| A.1.318 | CH$_3$ | CH$_2$CH$_3$ | H | 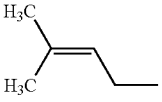 |
| A.1.319 | CH$_3$ | CH$_2$CH$_3$ | H | 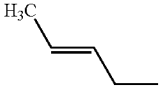 |

TABLE A-continued

Meanings for $R_1$, $R_2$, $R_5$ and $R_6$:

| Line | $R_1$ | $R_2$ | $R_6$ | $R_5$ |
|---|---|---|---|---|
| A.1.320 | $CH_3$ | $CH_2CH_3$ | H | cis-CH$_3$CH=CHCH$_2$CH$_3$ (pent-2-enyl, Z) |
| A.1.321 | $CH_3$ | $CH_2CH_3$ | H | (CH$_3$)$_2$CH-CH=CH-CH$_2$- |
| A.1.322 | $CH_3$ | $CH_2CH_3$ | H | Cl$_2$C=CH-CH$_2$CH$_3$ |
| A.1.323 | $CH_3$ | $CH_2CH_3$ | H | ClCH=CH-CH$_2$CH$_3$ |
| A.1.324 | $CH_3$ | $CH_2CH_3$ | H | (CH$_3$)$_3$C-CH=CH-CH$_2$- |
| A.1.325 | $CH_3$ | $CH_2CH_3$ | H | CH$_2$=C(CH$_3$)-CH$_2$CH$_3$ |
| A.1.326 | $CH_3$ | $CH_2CH_3$ | H | (CH$_3$)(CH$_3$CH$_2$)C=CH-CH$_2$CH$_3$ |
| A.1.327 | $CH_3$ | $CH_2CH_3$ | H | Ph-CH=CH-CH$_2$CH$_3$ |
| A.1.328 | $CH_3$ | $CH_2CH_3$ | H | 3-Cl-C$_6$H$_4$-CH=CH-CH$_2$CH$_3$ |
| A.1.329 | $CH_3$ | $CH_2CH_3$ | H | 3-CF$_3$-C$_6$H$_4$-CH=CH-CH$_2$CH$_3$ |
| A.1.330 | $CH_3$ | $CH_2CH_3$ | H | Ph-CH=CH-CH$_2$CH$_3$ (Z) |

TABLE A-continued

Meanings for $R_1$, $R_2$, $R_5$ and $R_6$:

| Line | $R_1$ | $R_2$ | $R_6$ | $R_5$ |
|---|---|---|---|---|
| A.1.331 | $CH_3$ | $CH_2CH_3$ | H | $H_2C=CH-CH_2-CH_2-CH_3$ |
| A.1.332 | $CH_3$ | $CH_2CH_3$ | H | $(H_3C)(CH_3)C=CH-CH_2-CH_2-CH_3$ |
| A.1.333 | $CH_3$ | $CH_2CH_3$ | H | $H_3C-CH_2-CH_2-CH=CH-CH_2-CH_3$ |
| A.1.334 | $CH_3$ | $CH_2CH_3$ | H | $Ph-CH=CH-CH_2-CH_2-CH_3$ |
| A.1.335 | $CH_3$ | $CH_2CH_3$ | H | $H_2C=C(CH_3)-$ |
| A.1.336 | $CH_3$ | $CH_2CH_3$ | H | $H_2C=CH-CH_2-CH(CH_3)-$ |
| A.1.337 | $CH_3$ | $CH_2CH_3$ | H | $H_3C-C(=O)-CH_2-CH_2-$ |
| A.1.338 | $CH_3$ | $CH_2CH_3$ | H | $H_3C-CH_2-C(=O)-CH_2-CH_2-$ |
| A.1.339 | $CH_3$ | $CH_2CH_3$ | H | $H_3C-CH_2-CH_2-C(=O)-CH_2-CH_2-$ |
| A.1.340 | $CH_3$ | $CH_2CH_3$ | H | $(H_3C)_2CH-C(=O)-CH_2-CH_2-$ |
| A.1.341 | $CH_3$ | $CH_2CH_3$ | H | $(H_3C)_3C-C(=O)-CH_2-CH_2-$ |
| A.1.342 | $CH_3$ | $CH_2CH_3$ | H | $H_3C-CH_2-CH_2-CH_2-C(=O)-CH_2-CH_2-$ |
| A.1.343 | $CH_3$ | $CH_2CH_3$ | H | $(H_3C)_2CH-CH_2-C(=O)-CH_2-CH_2-$ |

TABLE A-continued

Meanings for $R_1$, $R_2$, $R_5$ and $R_6$:

| Line | $R_1$ | $R_2$ | $R_6$ | $R_5$ |
|---|---|---|---|---|
| A.1.344 | $CH_3$ | $CH_2CH_3$ | H | hexan-3-one (H₃C–CH₂–C(=O)–CH₂–CH₂–CH₃) |
| A.1.345 | $CH_3$ | $CH_2CH_3$ | H | 1-penten-3-one (H₂C=CH–C(=O)–CH₂–CH₃) |
| A.1.346 | $CH_3$ | $CH_2CH_3$ | H | pentan-2-one (H₃C–C(=O)–CH₂–CH₂–CH₃) |
| A.1.347 | $CH_3$ | $CH_2CH_3$ | H | 2-methylhexan-3-one ((H₃C)₂CH–C(=O)–CH₂–CH₂–CH₃) |
| A.1.348 | $CH_3$ | $CH_2CH_3$ | H | HO–CH₂–CH₂–CH₃ |
| A.1.349 | $CH_3$ | $CH_2CH_3$ | H | H₃C–O–CH₂–CH₂–CH₃ |
| A.1.350 | $CH_3$ | $CH_2CH_3$ | H | H₃C–CH₂–O–CH₂–CH₂–CH₃ |
| A.1.351 | $CH_3$ | $CH_2CH_3$ | H | (H₃C)₂CH–O–CH₂–CH₂–CH₃ |
| A.1.352 | $CH_3$ | $CH_2CH_3$ | H | (H₃C)₃C–O–CH₂–CH₂–CH₃ |
| A.1.353 | $CH_3$ | $CH_2CH_3$ | H | H₂C=CH–CH₂–O–CH₂–CH₂–CH₃ |
| A.1.354 | $CH_3$ | $CH_2CH_3$ | H | H₂C=C(CH₃)–CH₂–O–CH₂–CH₂–CH₃ |
| A.1.355 | $CH_3$ | $CH_2CH_3$ | H | H₃C–CH₂–O–CH₂–CH(CH₃)₂ |

TABLE A-continued
Meanings for $R_1$, $R_2$, $R_5$ and $R_6$:
| Line | $R_1$ | $R_2$ | $R_6$ | $R_5$ |
|---|---|---|---|---|
| A.1.356 | CH$_3$ | CH$_2$CH$_3$ | H | 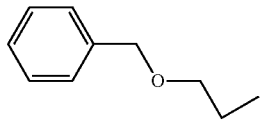 |
| A.1.357 | CH$_3$ | CH$_2$CH$_3$ | H | 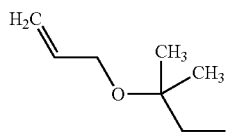 |
| A.1.358 | CH$_3$ | CH$_2$CH$_3$ | H | 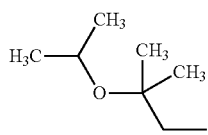 |
| A.1.359 | CH$_3$ | CH$_2$CH$_3$ | H | 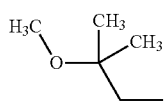 |
| A.1.360 | CH$_3$ | CH$_2$CH$_3$ | H | 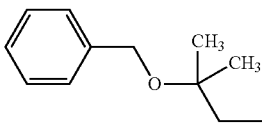 |
| A.1.361 | CH$_3$ | CH$_2$CH$_3$ | H | 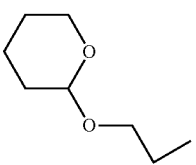 |
| A.1.362 | CH$_3$ | CH$_2$CH$_3$ | H | 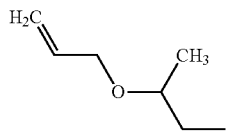 |
| A.1.363 | CH$_3$ | CH$_2$CH$_3$ | H | 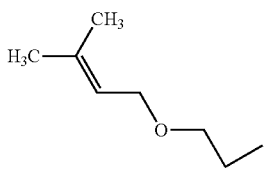 |
| A.1.364 | CH$_3$ | CH$_2$CH$_3$ | H | 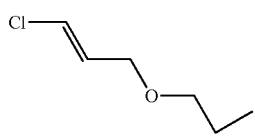 |

TABLE A-continued

Meanings for $R_1$, $R_2$, $R_5$ and $R_6$:

| Line | $R_1$ | $R_2$ | $R_6$ | $R_5$ |
|---|---|---|---|---|
| A.1.365 | $CH_3$ | $CH_2CH_3$ | H | 3,3-dichloro-2-propenyloxypropyl |
| A.1.366 | $CH_3$ | $CH_2CH_3$ | H | 3-phenoxypropyl |
| A.1.367 | $CH_3$ | $CH_2CH_3$ | H | 3-(3-chlorophenoxy)propyl |
| A.1.368 | $CH_3$ | $CH_2CH_3$ | H | 3-(3-trifluoromethylphenoxy)propyl |
| A.1.369 | $CH_3$ | $CH_2CH_3$ | H | 2-(pyridin-2-yloxy)ethyl |
| A.1.370 | $CH_3$ | $CH_2CH_3$ | H | 2-(6-chloropyridin-2-yloxy)ethyl |
| A.1.371 | $CH_3$ | $CH_2CH_3$ | H | 4-ethoxybutyl |
| A.1.372 | $CH_3$ | $CH_2CH_3$ | H | 2-methyl-3-ethoxybutyl... |

TABLE A-continued
Meanings for $R_1$, $R_2$, $R_5$ and $R_6$:
| Line | $R_1$ | $R_2$ | $R_6$ | $R_5$ |
|---|---|---|---|---|
| A.1.373 | $CH_3$ | $CH_2CH_3$ | H | 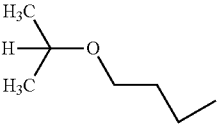 |
| A.1.374 | $CH_3$ | $CH_2CH_3$ | H | 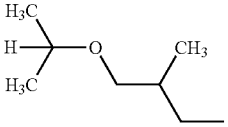 |
| A.1.375 | $CH_3$ | $CH_2CH_3$ | H | 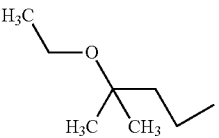 |
| A.1.376 | $CH_3$ | $CH_2CH_3$ | H | 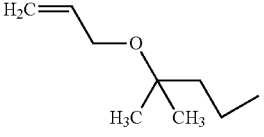 |
| A.1.377 | $CH_3$ | $CH_2CH_3$ | H | 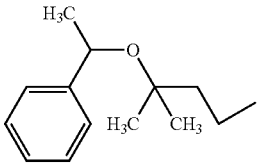 |
| A.1.378 | $CH_3$ | $CH_2CH_3$ | H | 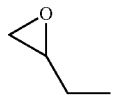 |
| A.1.379 | $CH_3$ | $CH_2CH_3$ | H | 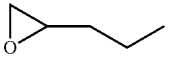 |
| A.1.380 | $CH_3$ | $CH_2CH_3$ | H | 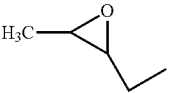 |
| A.1.381 | $CH_3$ | $CH_2CH_3$ | H | 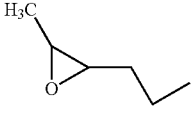 |
| A.1.382 | $CH_3$ | $CH_2CH_3$ | H | 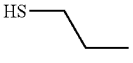 |
| A.1.383 | $CH_3$ | $CH_2CH_3$ | H | 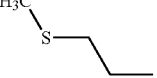 |

TABLE A-continued
Meanings for $R_1$, $R_2$, $R_5$ and $R_6$:
| Line | $R_1$ | $R_2$ | $R_6$ | $R_5$ |
|---|---|---|---|---|
| A.1.384 | $CH_3$ | $CH_2CH_3$ | H | 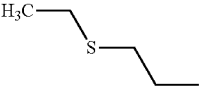 |
| A.1.385 | $CH_3$ | $CH_2CH_3$ | H | 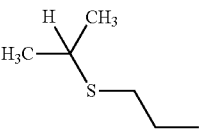 |
| A.1.386 | $CH_3$ | $CH_2CH_3$ | H | 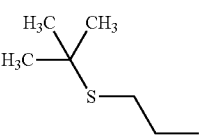 |
| A.1.387 | $CH_3$ | $CH_2CH_3$ | H | 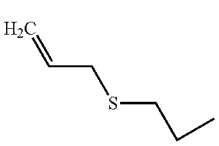 |
| A.1.388 | $CH_3$ | $CH_2CH_3$ | H | 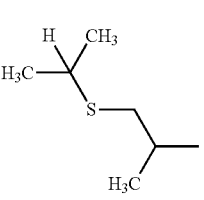 |
| A.1.389 | $CH_3$ | $CH_2CH_3$ | H | 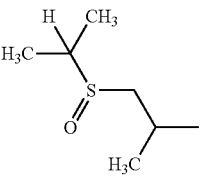 |
| A.1.390 | $CH_3$ | $CH_2CH_3$ | H | 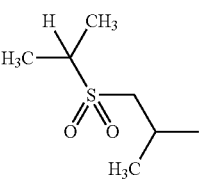 |
| A.1.391 | $CH_3$ | $CH_2CH_3$ | H | 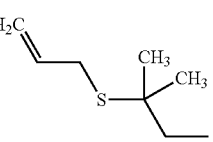 |
| A.1.392 | $CH_3$ | $CH_2CH_3$ | H | 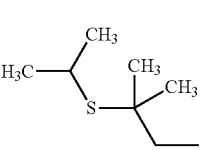 |

TABLE A-continued
Meanings for $R_1$, $R_2$, $R_5$ and $R_6$:
| Line | $R_1$ | $R_2$ | $R_6$ | $R_5$ |
|---|---|---|---|---|
| A.1.393 | $CH_3$ | $CH_2CH_3$ | H | 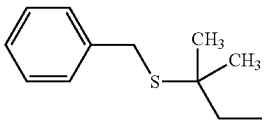 |
| A.1.394 | $CH_3$ | $CH_2CH_3$ | H |  |
| A.1.395 | $CH_3$ | $CH_2CH_3$ | H | 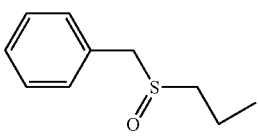 |
| A.1.396 | $CH_3$ | $CH_2CH_3$ | H | 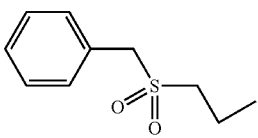 |
| A.1.397 | $CH_3$ | $CH_2CH_3$ | H | 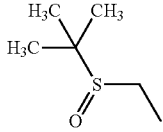 |
| A.1.398 | $CH_3$ | $CH_2CH_3$ | H | 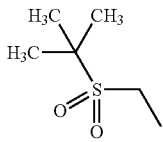 |
| A.1.399 | $CH_3$ | $CH_2CH_3$ | H | 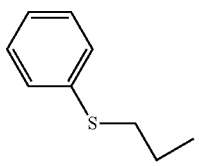 |
| A.1.400 | $CH_3$ | $CH_2CH_3$ | H | 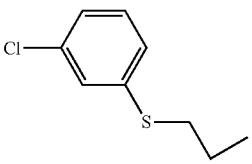 |
| A.1.401 | $CH_3$ | $CH_2CH_3$ | H | 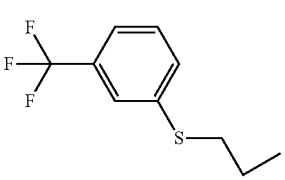 |

TABLE A-continued
Meanings for $R_1$, $R_2$, $R_5$ and $R_6$:
| Line | $R_1$ | $R_2$ | $R_6$ | $R_5$ |
|---|---|---|---|---|
| A.1.402 | $CH_3$ | $CH_2CH_3$ | H | 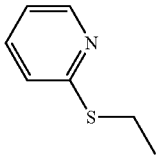 |
| A.1.403 | $CH_3$ | $CH_2CH_3$ | H | 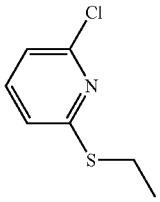 |
| A.1.404 | $CH_3$ | $CH_2CH_3$ | H | 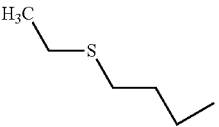 |
| A.1.405 | $CH_3$ | $CH_2CH_3$ | H | 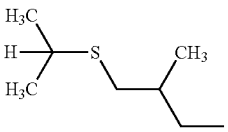 |
| A.1.406 | $CH_3$ | $CH_2CH_3$ | H | 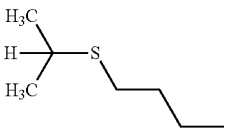 |
| A.1.407 | $CH_3$ | $CH_2CH_3$ | H | 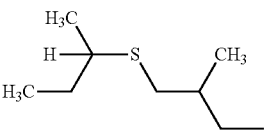 |
| A.1.408 | $CH_3$ | $CH_2CH_3$ | H | 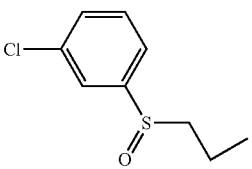 |
| A.1.409 | $CH_3$ | $CH_2CH_3$ | H | 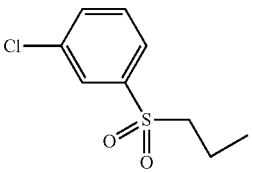 |
| A.1.410 | $CH_3$ | $CH_2CH_3$ | H | 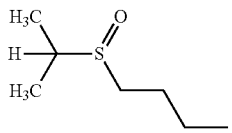 |

TABLE A-continued

Meanings for $R_1$, $R_2$, $R_5$ and $R_6$:

| Line | $R_1$ | $R_2$ | $R_6$ | $R_5$ |
|---|---|---|---|---|
| A.1.411 | $CH_3$ | $CH_2CH_3$ | H | isopropyl-CH-SO$_2$-butyl |
| A.1.412 | $CH_3$ | $CH_2CH_3$ | H | $H_3C-S-C(CH_3)_2-CH_2CH_2CH_3$ |
| A.1.413 | $CH_3$ | $CH_2CH_3$ | H | $H_3C-S(O)-C(CH_3)_2-CH_2CH_2CH_3$ |
| A.1.414 | $CH_3$ | $CH_2CH_3$ | H | $H_3C-SO_2-C(CH_3)_2-CH_2CH_2CH_3$ |
| A.1.415 | $CH_3$ | $CH_2CH_3$ | H | thiiranyl-propyl |
| A.1.416 | $CH_3$ | $CH_2CH_3$ | H | HC≡C-CH$_2$-CH$_2$- |
| A.1.417 | $CH_3$ | $CH_2CH_3$ | H | HC≡C-CH(CH$_3$)- |
| A.1.418 | $CH_3$ | $CH_2CH_3$ | H | HC≡C-C(CH$_3$)$_2$- |
| A.1.419 | $CH_3$ | $CH_2CH_3$ | H | $H_3C$-C≡C-CH$_2$-CH$_2$- |
| A.1.420 | $CH_3$ | $CH_2CH_3$ | H | $(CH_3)_2CH$-C≡C-CH$_2$- |

TABLE A-continued

Meanings for $R_1$, $R_2$, $R_5$ and $R_6$:

| Line | $R_1$ | $R_2$ | $R_6$ | $R_5$ |
|---|---|---|---|---|
| A.1.421 | $CH_3$ | $CH_2CH_3$ | H | benzyl |
| A.1.422 | $CH_3$ | $CH_2CH_3$ | H | 3-methylbenzyl |
| A.1.423 | $CH_3$ | $CH_2CH_3$ | H | 3-chlorobenzyl |
| A.1.424 | $CH_3$ | $CH_2CH_3$ | H | 4-chlorobenzyl |
| A.1.425 | $CH_3$ | $CH_2CH_3$ | H | 2-chlorobenzyl |
| A.1.426 | $CH_3$ | $CH_2CH_3$ | H | 2,4-dichlorobenzyl |
| A.1.427 | $CH_3$ | $CH_2CH_3$ | H | 3,4-dichlorobenzyl |
| A.1.428 | $CH_3$ | $CH_2CH_3$ | H | 3,5-dichlorobenzyl |
| A.1.429 | $CH_3$ | $CH_2CH_3$ | H | 4-(trifluoromethyl)benzyl |

TABLE A-continued
Meanings for $R_1$, $R_2$, $R_5$ and $R_6$:
| Line | $R_1$ | $R_2$ | $R_6$ | $R_5$ |
|---|---|---|---|---|
| A.1.430 | $CH_3$ | $CH_2CH_3$ | H | 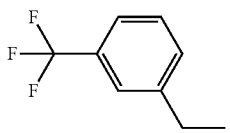 |
| A.1.431 | $CH_3$ | $CH_2CH_3$ | H | 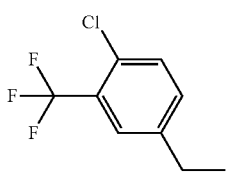 |
| A.1.432 | $CH_3$ | $CH_2CH_3$ | H | 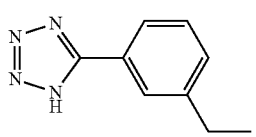 |
| A.1.433 | $CH_3$ | $CH_2CH_3$ | H | 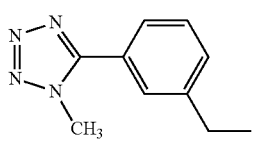 |
| A.1.434 | $CH_3$ | $CH_2CH_3$ | H | 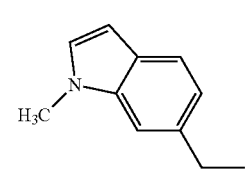 |
| A.1.435 | $CH_3$ | $CH_2CH_3$ | H | 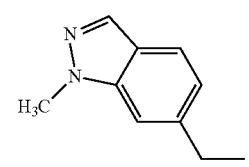 |
| A.1.436 | $CH_3$ | $CH_2CH_3$ | H | 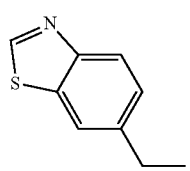 |

TABLE A

Meanings for $R_1$, $R_2$, $R_5$ and $R_6$ (continued):

| Line | $\begin{array}{c} R_1 \\ -N=\!\!\!\!\!\overset{|}{\underset{R_6}{C}}\!\!-N\!\!<\!\!\begin{array}{c}R_1\\R_2\end{array} \end{array}$ | $R_5$ |
|---|---|---|
| A.1.437 | –N=CH–N(CH₃)(CH₂CH₃) | 4-Cl-3-CF₃-phenyl |
| A.1.438 | –N=CH–N(CH₂CH₃)₂ | 4-Cl-3-CF₃-phenyl |
| A.1.439 | –N=CH–N(CH₃)(cyclopropyl) | 4-Cl-3-CF₃-phenyl |
| A.1.440 | –N=CH–N(CH₃)(CH₂CH=CH₂) | 4-Cl-3-CF₃-phenyl |
| A.1.441 | –N=CH–(azetidin-1-yl) | 4-Cl-3-CF₃-phenyl |
| A.1.442 | –N=CH–(2-methylazetidin-1-yl) | 4-Cl-3-CF₃-phenyl |
| A.1.443 | –N=CH–(aziridin-1-yl) | 4-Cl-3-CF₃-phenyl |
| A.1.444 | –N=CH–(2-methylaziridin-1-yl) | 4-Cl-3-CF₃-phenyl |
| A.1.445 | –N=C(CH₃)–N(CH₃)(CH₂CH₃) | 4-Cl-3-CF₃-phenyl |
| A.1.446 | –N=C(Cl)–N(CH₃)(CH₂CH₃) | 4-Cl-3-CF₃-phenyl |
| A.1.447 | –N=C(CH₃)–N(CH₂CH₃)₂ | 4-Cl-3-CF₃-phenyl |
| A.1.448 | –N=CH–N(CH₃)(CH₂C≡CH) | 4-Cl-3-CF₃-phenyl |
| A.1.449 | –N=CH–N(CH₃)(CH(CH₃)C≡CH) | 4-Cl-3-CF₃-phenyl |
| A.1.450 | –N=CH–N(CH₃)(C(CH₃)₃) | 4-Cl-3-CF₃-phenyl |
| A.1.451 | –N=CH–(2,3-dimethylaziridin-1-yl) | 4-Cl-3-CF₃-phenyl |
| A.1.452 | –N=CH–(pyrrolidin-1-yl) | 4-Cl-3-CF₃-phenyl |

TABLE A-continued
Meanings for $R_1$, $R_2$, $R_5$ and $R_6$ (continued):
| Line | 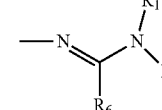 | $R_5$ |
|---|---|---|
| A.1.453 | 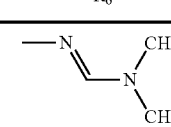 | 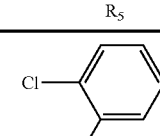 |
| A.1.454 | 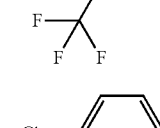 | 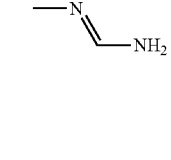 |
| A.1.455 | 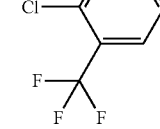 | 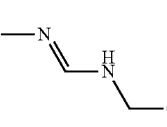 |
| A.1.456 | 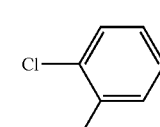 | 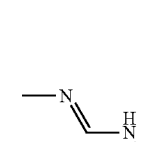 |
| A.1.457 | 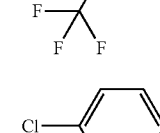 | 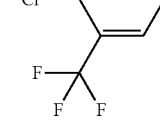 |
| A.1.458 | 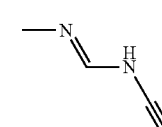 | 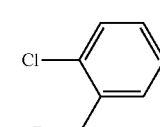 |
| A.1.459 | 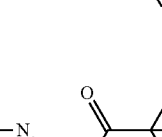 | 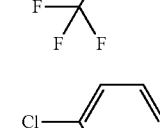 |
| A.1.460 | 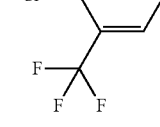 | 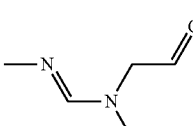 |
TABLE A-continued
Meanings for $R_1$, $R_2$, $R_5$ and $R_6$ (continued):
| Line | 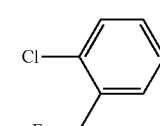 | $R_5$ |
|---|---|---|
| A.1.461 | | |
| A.1.462 | | |
| A.1.463 | | |
| A.1.464 | | |
| A.1.465 | | |
| A.1.466 | | |
| A.1.467 | | |
| A.1.468 | 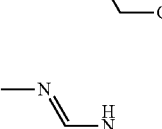 | 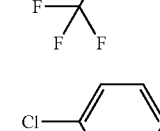 |

TABLE A-continued
Meanings for R₁, R₂, R₅ and R₆ (continued):
| Line | R₆ | R₅ |
|---|---|---|
| A.1.469 | 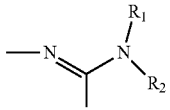 | 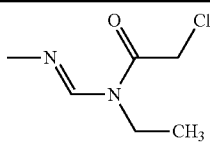 |
| A.1.470 | 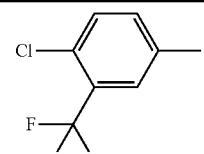 | 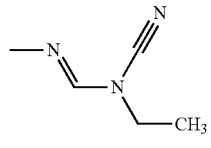 |
| A.1.471 | 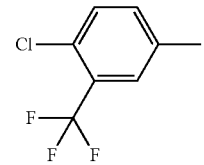 | 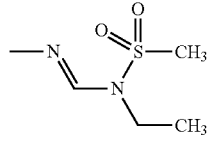 |
| A.1.472 | 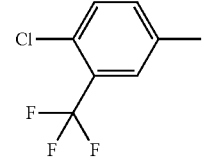 | 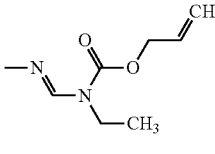 |
| A.1.473 | 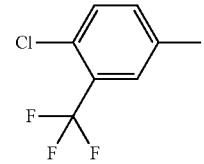 | 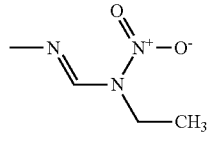 |
| A.1.474 | 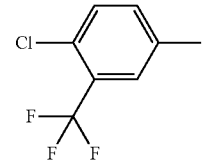 | 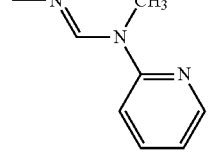 |
| A.1.475 | 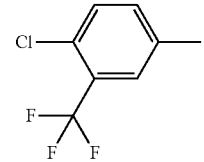 | 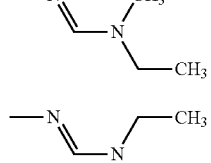 |
| A.1.476 | 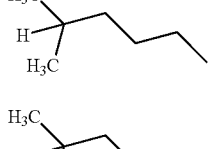 | 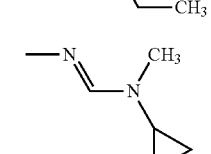 |
| A.1.477 | 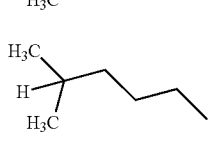 | 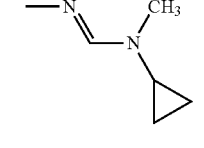 |
| A.1.478 | 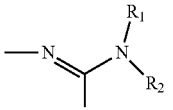 | 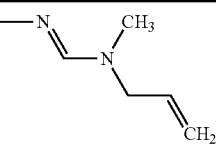 |
| A.1.479 | 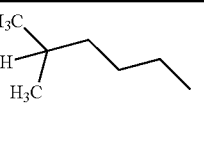 | 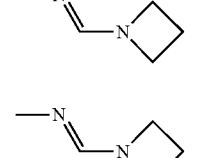 |
| A.1.480 | 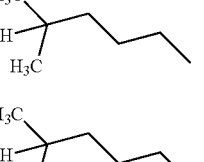 | 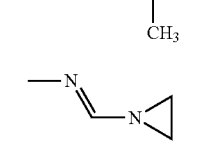 |
| A.1.481 | 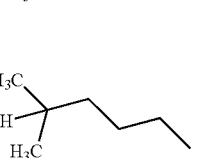 | 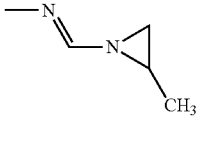 |
| A.1.482 | 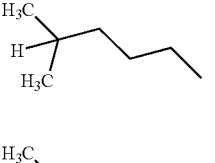 | 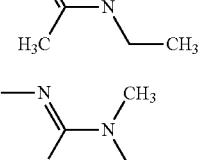 |
| A.1.483 |  | 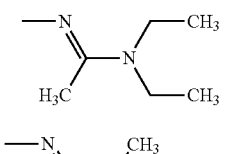 |
| A.1.484 | 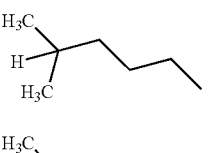 | 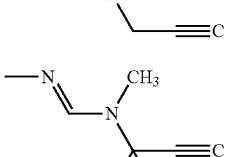 |
| A.1.485 | 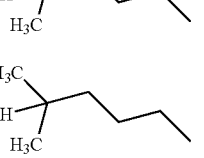 | 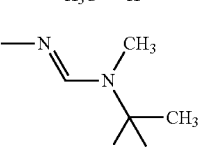 |
| A.1.486 | 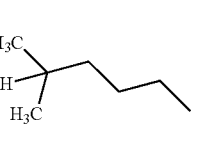 | 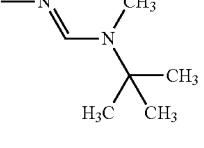 |
| A.1.487 | 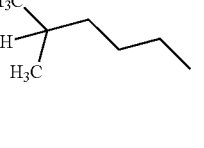 | 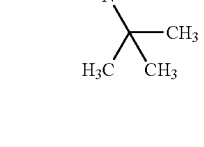 |
| A.1.488 | 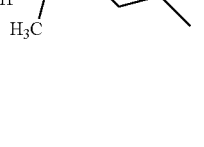 | 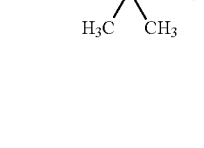 |

TABLE A-continued

Meanings for $R_1$, $R_2$, $R_5$ and $R_6$ (continued):

| Line | $R_6\text{-N=C(R_1)(N(R_2))}$ structure | $R_5$ |
|---|---|---|
| A.1.489 | N=CH–N(aziridine with 2,3-dimethyl) | 2-methylhexyl (H3C, H, H3C, chain) |
| A.1.490 | N=CH–N(pyrrolidine) | 2-methylhexyl |
| A.1.491 | N=CH–N(3-methylpyrrolidine) | 2-methylhexyl |
| A.1.492 | N=CH–N(2,5-dihydropyrrole) | 2-methylhexyl |
| A.1.493 | N=CH–N(piperidine) | 2-methylhexyl |
| A.1.494 | N=CH–N(morpholine) | 2-methylhexyl |
| A.1.495 | N=CH–N(thiomorpholine) | 2-methylhexyl |
| A.1.496 | N=CH–N(2-methylpyrrolidine) | 2-methylhexyl |
| A.1.497 | N=CH–N(2-methylpiperidine) | 2-methylhexyl |
| A.1.498 | N=CH–N(3-methylpiperidine) | 2-methylhexyl |
| A.1.499 | N=CH–N(CH3)2 | 2-methylhexyl |
| A.1.500 | N=CH–NH2 | 2-methylhexyl |
| A.1.501 | N=CH–NH–CH3 (ethyl shown: N-H, CH3) | 2-methylhexyl |
| A.1.502 | N=CH–NH–CH3 | 2-methylhexyl |
| A.1.503 | N=CH–NH–CN | 2-methylhexyl |
| A.1.504 | N=CH–N(C(O)C(CH3)3)(CH2CH3) | 2-methylhexyl |
| A.1.505 | N=CH–N(CH2CH=CH2)(CH2CH3) | 2-methylhexyl |
| A.1.506 | N=CH–NH–C(O)CH3 | 2-methylhexyl |
| A.1.507 | N=CH–N(C(O)CH2Cl)(CH2CH3) | 2-methylhexyl |
| A.1.508 | N=CH–N(CN)(CH2CH3) | 2-methylhexyl |
| A.1.509 | N=CH–N(S(O)2CH3)(CH2CH3) | 2-methylhexyl |

TABLE A-continued
Meanings for R₁, R₂, R₅ and R₆ (continued):
| Line | R₆ | R₅ |
|---|---|---|
| A.1.510 | 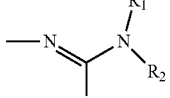 | 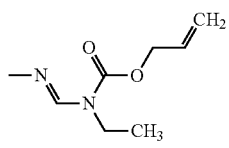 |
| A.1.511 | 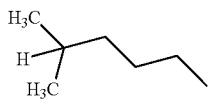 | 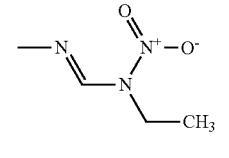 |
| A.1.512 | 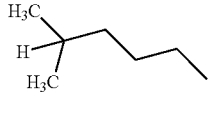 | 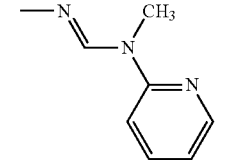 |
| A.1.513 | 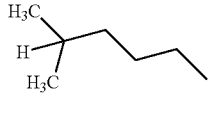 | 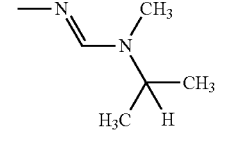 |
| A.1.514 | 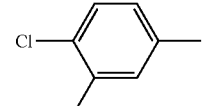 | 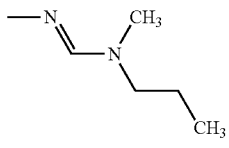 |
| A.1.515 | 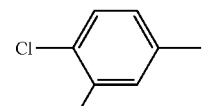 | 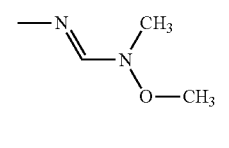 |
| A.1.516 | 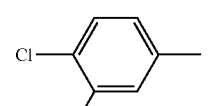 | 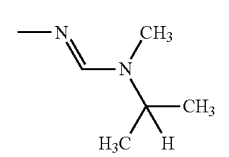 |
| A.1.517 | 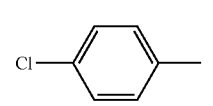 | 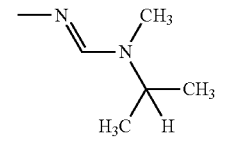 |
| A.1.518 | 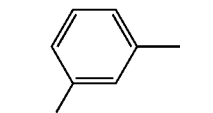 | 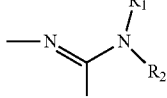 |
| A.1.519 | 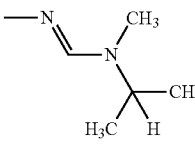 | 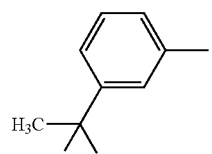 |
| A.1.520 | 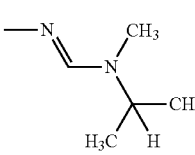 | 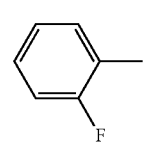 |
| A.1.521 | 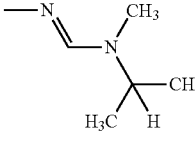 | 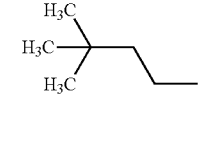 |
| A.1.522 | 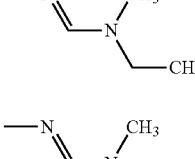 | 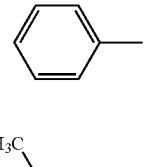 |
| A.1.523 | 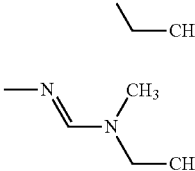 | 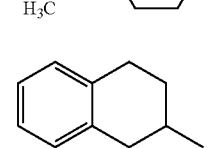 |
| A.1.524 | 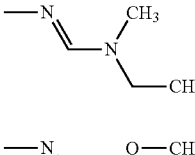 | 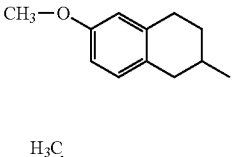 |
| A.1.525 | 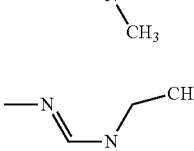 | 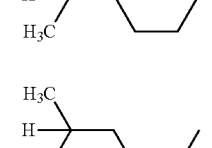 |
| A.1.526 | 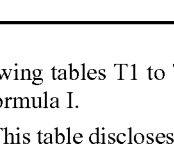 | 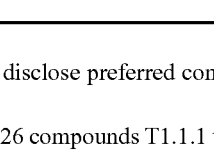 |
The following tables T1 to T151 disclose preferred compounds of formula I.
Table 1: This table discloses the 526 compounds T1.1.1 to T1.1.526 of the formula

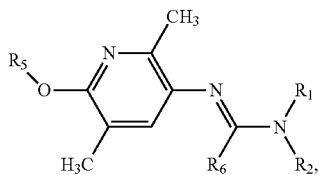
(T1)

in which, for each of these 526 specific compounds, each of the variables $R_1$, $R_2$, $R_5$ and $R_6$ has the specific meaning given in the corresponding line, appropriately selected from the 526 lines A.1.1 to A.1.526 of Table A. For example, the specific compound T1.1.13 is the compound of the formula T1, in which each of the variables $R_1$, $R_2$, $R_5$ and $R_6$ has the specific meaning given in the line A.1.13 of Table A:

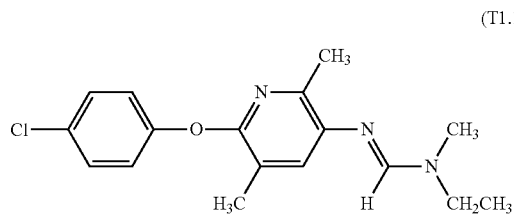
(T1.1.13)

According to the same system, also all of the other 511 specific compounds disclosed in the Table 1 as well as all of the specific compounds disclosed in the Tables 2 to T151 are specified analogously.

Table 2: This table discloses the 526 compounds T2.1.1 to T2.1.526 of the formula

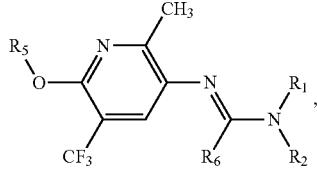
(T2)

in which, for each of these 526 specific compounds, each of the variables $R_1$, $R_2$, $R_5$ and $R_6$ has the specific meaning given in the corresponding line, appropriately selected from the 526 lines A.1.1 to A.1.526 of Table A.

Table 3: This table discloses the 526 compounds T3.1.1 to T3.1.526 of the formula

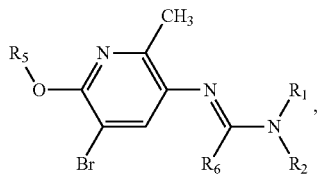
(T3)

in which, for each of these 526 specific compounds, each of the variables $R_1$, $R_2$, $R_5$ and $R_6$ has the specific meaning given in the corresponding line, appropriately selected from the 526 lines A.1.1 to A.1.526 of Table A.

Table 4: This table discloses the 526 compounds T4.1.1 to T4.1.526 of the formula

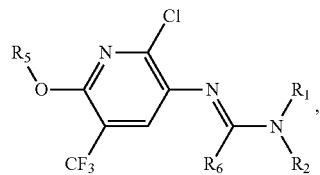
(T4)

in which, for each of these 526 specific compounds, each of the variables $R_1$, $R_2$, $R_5$ and $R_6$ has the specific meaning given in the corresponding line, appropriately selected from the 526 lines A.1.1 to A.1.526 of Table A.

Table 5: This table discloses the 526 compounds T5.1.1 to T5.1.526 of the formula

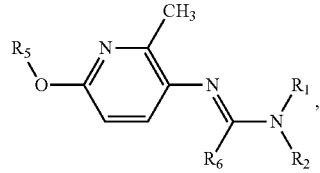
(T5)

in which, for each of these 526 specific compounds, each of the variables $R_1$, $R_2$, $R_5$ and $R_6$ has the specific meaning given in the corresponding line, appropriately selected from the 526 lines A.1.1 to A.1.526 of Table A.

Table 6: This table discloses the 526 compounds T6.1.1 to T6.1.526 of the formula

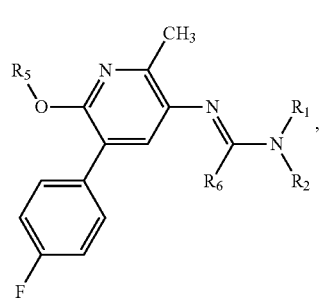
(T6)

in which, for each of these 526 specific compounds, each of the variables $R_1$, $R_2$, $R_5$ and $R_6$ has the specific meaning given in the corresponding line, appropriately selected from the 526 lines A.1.1 to A.1.526 of Table A.

Table 7: This table discloses the 526 compounds T7.1.1 to T7.1.526 of the formula

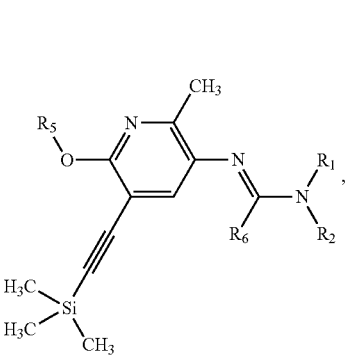
(T7)

in which, for each of these 526 specific compounds, each of the variables $R_1$, $R_2$, $R_5$ and $R_6$ has the specific meaning given in the corresponding line, appropriately selected from the 526 lines A.1.1 to A.1.526 of Table A.

Table 8: This table discloses the 526 compounds T8.1.1 to T8.1.526 of the formula

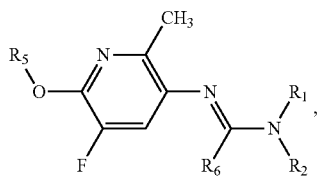
(T8)

in which, for each of these 526 specific compounds, each of the variables $R_1$, $R_2$, $R_5$ and $R_6$ has the specific meaning given in the corresponding line, appropriately selected from the 526 lines A.1.1 to A.1.526 of Table A.

Table 9: This table discloses the 526 compounds T9.1.1 to T9.1.526 of the formula

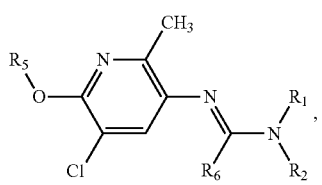
(T9)

in which, for each of these 526 specific compounds, each of the variables $R_1$, $R_2$, $R_5$ and $R_6$ has the specific meaning given in the corresponding line, appropriately selected from the 526 lines A.1.1 to A.1.526 of Table A.

Table 10: This table discloses the 526 compounds T10.1.1 to T10.1.526 of the formula

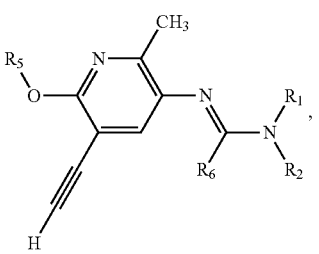
(T10)

in which, for each of these 526 specific compounds, each of the variables $R_1$, $R_2$, $R_5$ and $R_6$ has the specific meaning given in the corresponding line, appropriately selected from the 526 lines A.1.1 to A.1.526 of Table A.

Table 11: This table discloses the 526 compounds T11.1.1 to T11.1.526 of the formula

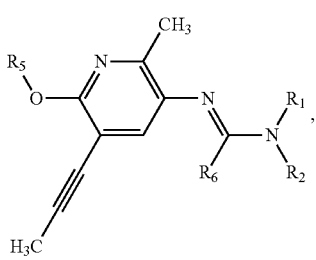
(T11)

in which, for each of these 526 specific compounds, each of the variables $R_1$, $R_2$, $R_5$ and $R_6$ has the specific meaning given in the corresponding line, appropriately selected from the 526 lines A.1.1 to A.1.526 of Table A.

Table 12: This table discloses the 526 compounds T12.1.1 to T12.1.526 of the formula

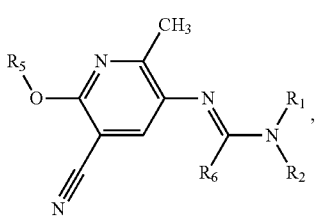
(T12)

in which, for each of these 526 specific compounds, each of the variables $R_1$, $R_2$, $R_5$ and $R_6$ has the specific meaning given in the corresponding line, appropriately selected from the 526 lines A.1.1 to A.1.526 of Table A.

Table 13: This table discloses the 526 compounds T13.1.1 to T13.1.526 of the formula

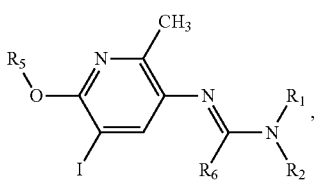
(T13)

in which, for each of these 526 specific compounds, each of the variables $R_1$, $R_2$, $R_5$ and $R_6$ has the specific meaning given in the corresponding line, appropriately selected from the 526 lines A.1.1 to A.1.526 of Table A.

Table 14: This table discloses the 526 compounds T14.1.1 to T14.1.526 of the formula

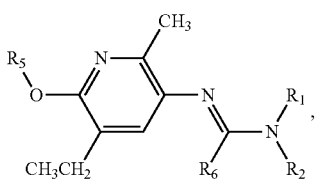
(T14)

in which, for each of these 526 specific compounds, each of the variables $R_1$, $R_2$, $R_5$ and $R_6$ has the specific meaning given in the corresponding line, appropriately selected from the 526 lines A.1.1 to A.1.526 of Table A.

Table 15: This table discloses the 526 compounds T15.1.1 to T15.1.526 of the formula

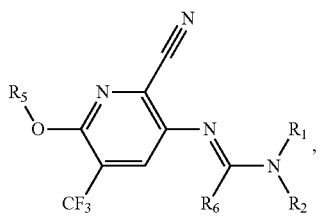
(T15)

in which, for each of these 526 specific compounds, each of the variables $R_1$, $R_2$, $R_5$ and $R_6$ has the specific meaning given in the corresponding line, appropriately selected from the 526 lines A.1.1 to A.1.526 of Table A.

Table 16: This table discloses the 526 compounds T16.1.1 to T16.1.526 of the formula

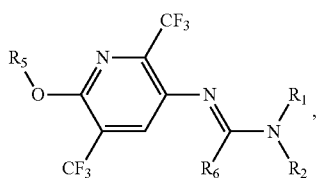
(T16)

in which, for each of these 526 specific compounds, each of the variables $R_1$, $R_2$, $R_5$ and $R_6$ has the specific meaning given in the corresponding line, appropriately selected from the 526 lines A.1.1 to A.1.526 of Table A.

Table 17: This table discloses the 526 compounds T17.1.1 to T17.1.526 of the formula

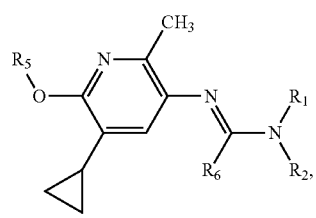
(T17)

in which, for each of these 526 specific compounds, each of the variables $R_1$, $R_2$, $R_5$ and $R_6$ has the specific meaning given in the corresponding line, appropriately selected from the 526 lines A.1.1 to A.1.526 of Table A.

Table 18: This table discloses the 526 compounds T18.1.1 to T18.1.526 of the formula

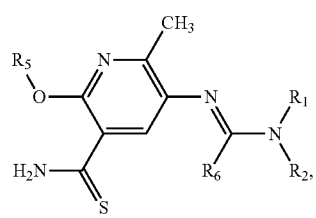
(T18)

in which, for each of these 526 specific compounds, each of the variables $R_1$, $R_2$, $R_5$ and $R_6$ has the specific meaning given in the corresponding line, appropriately selected from the 526 lines A.1.1 to A.1.526 of Table A.

Table 19: This table discloses the 526 compounds T19.1.1 to T19.1.526 of the formula

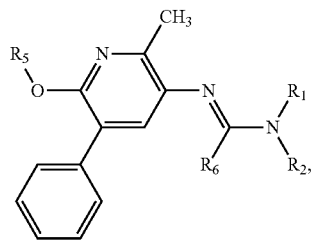
(T19)

in which, for each of these 526 specific compounds, each of the variables $R_1$, $R_2$, $R_5$ and $R_6$ has the specific meaning given in the corresponding line, appropriately selected from the 526 lines A.1.1 to A.1.526 of Table A.

Table 20: This table discloses the 526 compounds T20.1.1 to T20.1.526 of the formula

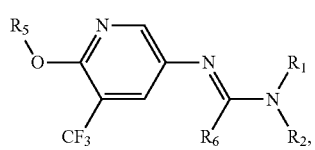
(T20)

in which, for each of these 526 specific compounds, each of the variables $R_1$, $R_2$, $R_5$ and $R_6$ has the specific meaning given in the corresponding line, appropriately selected from the 526 lines A.1.1 to A.1.526 of Table A.

Table 21: This table discloses the 526 compounds T21.1.1 to T21.1.526 of the formula

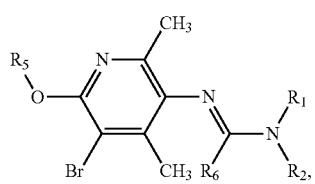
(T21)

in which, for each of these 526 specific compounds, each of the variables $R_1$, $R_2$, $R_5$ and $R_6$ has the specific meaning given in the corresponding line, appropriately selected from the 526 lines A.1.1 to A.1.526 of Table A.

Table 22: This table discloses the 526 compounds T22.1.1 to T22.1.526 of the formula

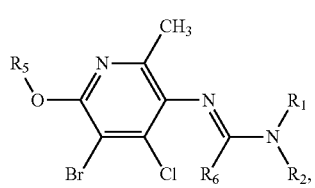
(T22)

in which, for each of these 526 specific compounds, each of the variables $R_1$, $R_2$, $R_5$ and $R_6$ has the specific meaning given in the corresponding line, appropriately selected from the 526 lines A.1.1 to A.1.526 of Table A.

Table 23: This table discloses the 526 compounds T23.1.1 to T23.1.526 of the formula

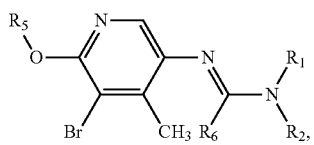

(T23)

in which, for each of these 526 specific compounds, each of the variables $R_1$, $R_2$, $R_5$ and $R_6$ has the specific meaning given in the corresponding line, appropriately selected from the 526 lines A.1.1 to A.1.526 of Table A.

Table 24: This table discloses the 526 compounds T24.1.1 to T24.1.526 of the formula

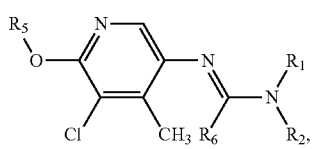

(T24)

in which, for each of these 526 specific compounds, each of the variables $R_1$, $R_2$, $R_5$ and $R_6$ has the specific meaning given in the corresponding line, appropriately selected from the 526 lines A.1.1 to A.1.526 of Table A.

Table 25: This table discloses the 526 compounds T25.1.1 to T25.1.526 of the formula

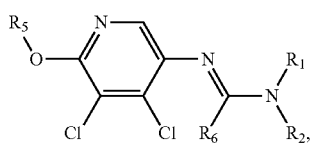

(T25)

in which, for each of these 526 specific compounds, each of the variables $R_1$, $R_2$, $R_5$ and $R_6$ has the specific meaning given in the corresponding line, appropriately selected from the 526 lines A.1.1 to A.1.526 of Table A.

Table 26: This table discloses the 526 compounds T26.1.1 to T26.1.526 of the formula

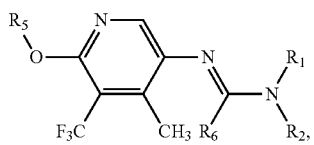

(T26)

in which, for each of these 526 specific compounds, each of the variables $R_1$, $R_2$, $R_5$ and $R_6$ has the specific meaning given in the corresponding line, appropriately selected from the 526 lines A.1.1 to A.1.526 of Table A.

Table 27: This table discloses the 526 compounds T27.1.1 to T27.1.526 of the formula

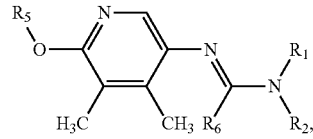

(T27)

in which, for each of these 526 specific compounds, each of the variables $R_1$, $R_2$, $R_5$ and $R_6$ has the specific meaning given in the corresponding line, appropriately selected from the 526 lines A.1.1 to A.1.526 of Table A.

Table 28: This table discloses the 526 compounds T28.1.1 to T28.1.526 of the formula

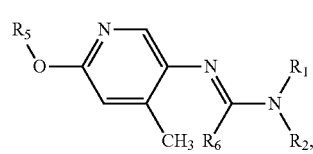

(T28)

in which, for each of these 526 specific compounds, each of the variables $R_1$, $R_2$, $R_5$ and $R_6$ has the specific meaning given in the corresponding line, appropriately selected from the 526 lines A.1.1 to A.1.526 of Table A.

Table 29: This table discloses the 526 compounds T29.1.1 to T29.1.526 of the formula

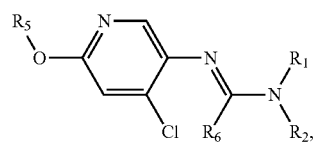

(T29)

in which, for each of these 526 specific compounds, each of the variables $R_1$, $R_2$, $R_5$ and $R_6$ has the specific meaning given in the corresponding line, appropriately selected from the 526 lines A.1.1 to A.1.526 of Table A.

Table 30: This table discloses the 526 compounds T30.1.1 to T30.1.526 of the formula

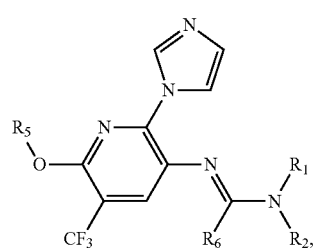

(T30)

in which, for each of these 526 specific compounds, each of the variables $R_1$, $R_2$, $R_5$ and $R_6$ has the specific meaning given in the corresponding line, appropriately selected from the 526 lines A.1.1 to A.1.526 of Table A.

Table 31: This table discloses the 526 compounds T31.1.1 to T31.1.526 of the formula (T31)

in which, for each of these 526 specific compounds, each of the variables $R_1$, $R_2$, $R_5$ and $R_6$ has the specific meaning given in the corresponding line, appropriately selected from the 526 lines A.1.1 to A.1.526 of Table A.

Table 32: This table discloses the 526 compounds T32.1.1 to T32.1.526 of the formula (T32)

in which, for each of these 526 specific compounds, each of the variables $R_1$, $R_2$, $R_5$ and $R_6$ has the specific meaning given in the corresponding line, appropriately selected from the 526 lines A.1.1 to A.1.526 of Table A.

Table 33: This table discloses the 526 compounds T33.1.1 to T33.1.526 of the formula (T33)

in which, for each of these 526 specific compounds, each of the variables $R_1$, $R_2$, $R_5$ and $R_6$ has the specific meaning given in the corresponding line, appropriately selected from the 526 lines A.1.1 to A.1.526 of Table A.

Table 34: This table discloses the 526 compounds T34.1.1 to T34.1.526 of the formula (T34)

in which, for each of these 526 specific compounds, each of the variables $R_1$, $R_2$, $R_5$ and $R_6$ has the specific meaning given in the corresponding line, appropriately selected from the 526 lines A.1.1 to A.1.526 of Table A.

Table 35: This table discloses the 526 compounds T35.1.1 to T35.1.526 of the formula (T35)

in which, for each of these 526 specific compounds, each of the variables $R_1$, $R_2$, $R_5$ and $R_6$ has the specific meaning given in the corresponding line, appropriately selected from the 526 lines A.1.1 to A.1.526 of Table A.

Table 36: This table discloses the 526 compounds T36.1.1 to T36.1.526 of the formula (T36)

in which, for each of these 526 specific compounds, each of the variables $R_1$, $R_2$, $R_5$ and $R_6$ has the specific meaning given in the corresponding line, appropriately selected from the 526 lines A.1.1 to A.1.526 of Table A.

Table 37: This table discloses the 526 compounds T37.1.1 to T37.1.526 of the formula (T37)

in which, for each of these 526 specific compounds, each of the variables $R_1$, $R_2$, $R_5$ and $R_6$ has the specific meaning given in the corresponding line, appropriately selected from the 526 lines A.1.1 to A.1.526 of Table A.

Table 38: This table discloses the 526 compounds T38.1.1 to T38.1.526 of the formula (T38)

in which, for each of these 526 specific compounds, each of the variables $R_1$, $R_2$, $R_5$ and $R_6$ has the specific meaning given in the corresponding line, appropriately selected from the 526 lines A.1.1 to A.1.526 of Table A.

Table 39: This table discloses the 526 compounds T39.1.1 to T39.1.526 of the formula

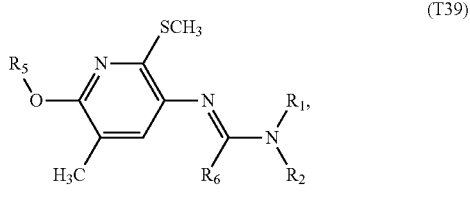
(T39)

in which, for each of these 526 specific compounds, each of the variables $R_1$, $R_2$, $R_5$ and $R_6$ has the specific meaning given in the corresponding line, appropriately selected from the 526 lines A.1.1 to A.1.526 of Table A.

Table 40: This table discloses the 526 compounds T40.1.1 to T40.1.526 of the formula

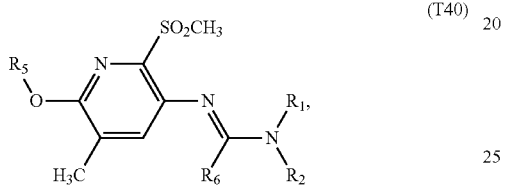
(T40)

in which, for each of these 526 specific compounds, each of the variables $R_1$, $R_2$, $R_5$ and $R_6$ has the specific meaning given in the corresponding line, appropriately selected from the 526 lines A.1.1 to A.1.526 of Table A.

Table 41: This table discloses the 526 compounds T41.1.1 to T41.1.526 of the formula

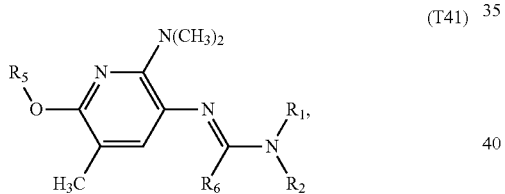
(T41)

in which, for each of these 526 specific compounds, each of the variables $R_1$, $R_2$, $R_5$ and $R_6$ has the specific meaning given in the corresponding line, appropriately selected from the 526 lines A.1.1 to A.1.526 of Table A.

Table 42: This table discloses the 526 compounds T42.1.1 to T42.1.526 of the formula

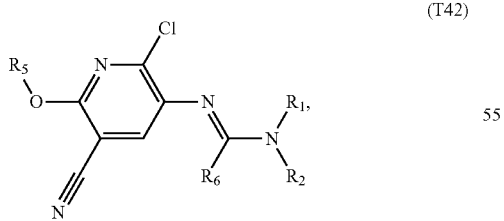
(T42)

in which, for each of these 526 specific compounds, each of the variables $R_1$, $R_2$, $R_5$ and $R_6$ has the specific meaning given in the corresponding line, appropriately selected from the 526 lines A.1.1 to A.1.526 of Table A.

Table 43: This table discloses the 526 compounds T43.1.1 to T43.1.526 of the formula

(T43)

in which, for each of these 526 specific compounds, each of the variables $R_1$, $R_2$, $R_5$ and $R_6$ has the specific meaning given in the corresponding line, appropriately selected from the 526 lines A.1.1 to A.1.526 of Table A.

Table 44: This table discloses the 526 compounds T44.1.1 to T44.1.526 of the formula

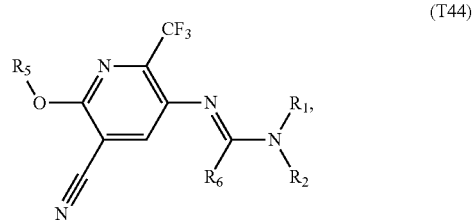
(T44)

in which, for each of these 526 specific compounds, each of the variables $R_1$, $R_2$, $R_5$ and $R_6$ has the specific meaning given in the corresponding line, appropriately selected from the 526 lines A.1.1 to A.1.526 of Table A.

Table 45: This table discloses the 526 compounds T45.1.1 to T45.1.526 of the formula

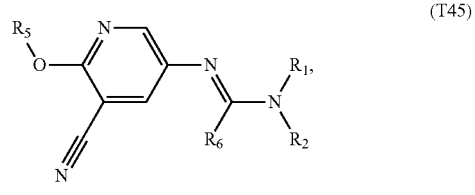
(T45)

in which, for each of these 526 specific compounds, each of the variables $R_1$, $R_2$, $R_5$ and $R_6$ has the specific meaning given in the corresponding line, appropriately selected from the 526 lines A.1.1 to A.1.526 of Table A.

Table 46: his table discloses the 526 compounds T46.1.1 to T46.1.526 of the formula

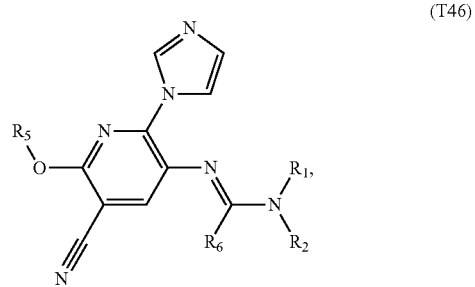
(T46)

in which, for each of these 526 specific compounds, each of the variables $R_1$, $R_2$, $R_5$ and $R_6$ has the specific meaning given in the corresponding line, appropriately selected from the 526 lines A.1.1 to A.1.526 of Table A.

Table 47: This table discloses the 526 compounds T47.1.1 to T47.1.526 of the formula

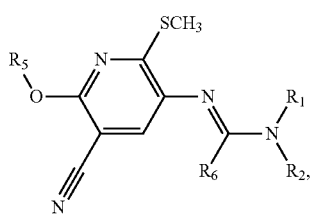
(T47)

in which, for each of these 526 specific compounds, each of the variables $R_1$, $R_2$, $R_5$ and $R_6$ has the specific meaning given in the corresponding line, appropriately selected from the 526 lines A.1.1 to A.1.526 of Table A.

Table 48: This table discloses the 526 compounds T48.1.1 to T48.1.526 of the formula

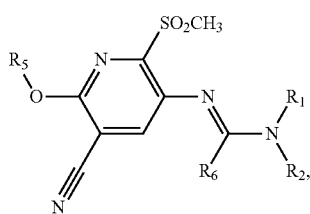
(T48)

in which, for each of these 526 specific compounds, each of the variables $R_1$, $R_2$, $R_5$ and $R_6$ has the specific meaning given in the corresponding line, appropriately selected from the 526 lines A.1.1 to A.1.526 of Table A.

Table 49: This table discloses the 526 compounds T49.1.1 to T49.1.526 of the formula

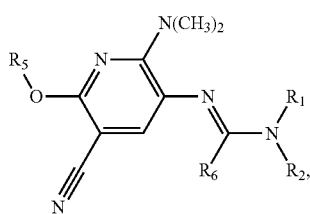
(T49)

in which, for each of these 526 specific compounds, each of the variables $R_1$, $R_2$, $R_5$ and $R_6$ has the specific meaning given in the corresponding line, appropriately selected from the 526 lines A.1.1 to A.1.526 of Table A.

Table 50: This table discloses the 526 compounds T50.1.1 to T50.1.526 of the formula

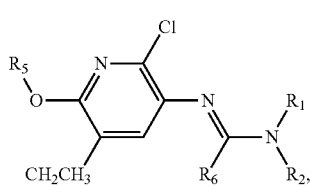
(T50)

in which, for each of these 526 specific compounds, each of the variables $R_1$, $R_2$, $R_5$ and $R_6$ has the specific meaning given in the corresponding line, appropriately selected from the 526 lines A.1.1 to A.1.526 of Table A.

Table 51: This table discloses the 526 compounds T51.1.1 to T51.1.526 of the formula

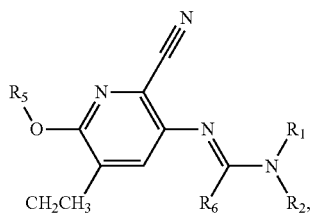
(T51)

in which, for each of these 526 specific compounds, each of the variables $R_1$, $R_2$, $R_5$ and $R_6$ has the specific meaning given in the corresponding line, appropriately selected from the 526 lines A.1.1 to A.1.526 of Table A.

Table 52: This table discloses the 526 compounds T52.1.1 to T52.1.526 of the formula

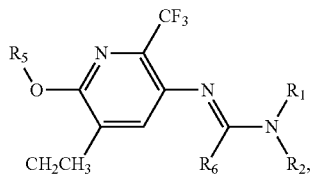
(T52)

in which, for each of these 526 specific compounds, each of the variables $R_1$, $R_2$, $R_5$ and $R_6$ has the specific meaning given in the corresponding line, appropriately selected from the 526 lines A.1.1 to A.1.526 of Table A.

Table 53: This table discloses the 526 compounds T53.1.1 to T53.1.526 of the formula

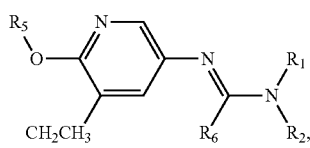
(T53)

in which, for each of these 526 specific compounds, each of the variables $R_1$, $R_2$, $R_5$ and $R_6$ has the specific meaning given in the corresponding line, appropriately selected from the 526 lines A.1.1 to A.1.526 of Table A.

Table 54: This table discloses the 526 compounds T54.1.1 to T54.1.526 of the formula

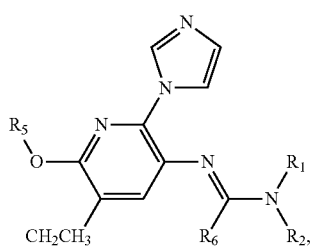
(T54)

in which, for each of these 526 specific compounds, each of the variables $R_1$, $R_2$, $R_5$ and $R_6$ has the specific meaning given Table 55: This table discloses the 526 compounds T55.1.1 to T55.1.526 of the formula

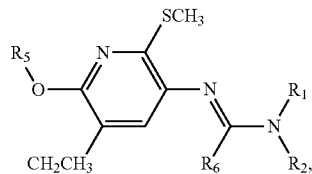
(T55)

in which, for each of these 526 specific compounds, each of the variables $R_1$, $R_2$, $R_5$ and $R_6$ has the specific meaning given in the corresponding line, appropriately selected from the 526 lines A.1.1 to A.1.526 of Table A.

Table 56: This table discloses the 526 compounds T56.1.1 to T56.1.526 of the formula

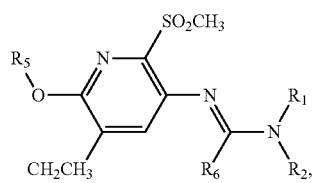
(T56)

in which, for each of these 526 specific compounds, each of the variables $R_1$, $R_2$, $R_5$ and $R_6$ has the specific meaning given in the corresponding line, appropriately selected from the 526 lines A.1.1 to A.1.526 of Table A.

Table 57: This table discloses the 526 compounds T57.1.1 to T57.1.526 of the formula

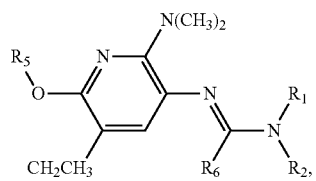
(T57)

in which, for each of these 526 specific compounds, each of the variables $R_1$, $R_2$, $R_5$ and $R_6$ has the specific meaning given in the corresponding line, appropriately selected from the 526 lines A.1.1 to A.1.526 of Table A.

Table 58: This table discloses the 526 compounds T58.1.1 to T58.1.526 of the formula

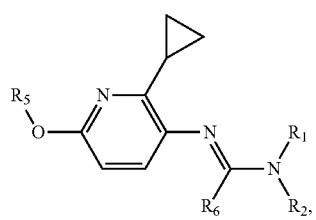
(T58)

in which, for each of these 526 specific compounds, each of the variables $R_1$, $R_2$, $R_5$ and $R_6$ has the specific meaning given in the corresponding line, appropriately selected from the 526 lines A.1.1 to A.1.526 of Table A.

Table 59: This table discloses the 526 compounds T59.1.1 to T59.1.526 of the formula

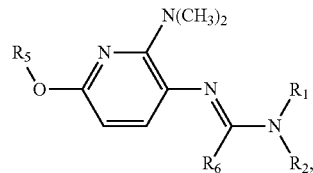
(T59)

in which, for each of these 526 specific compounds, each of the variables $R_1$, $R_2$, $R_5$ and $R_6$ has the specific meaning given in the corresponding line, appropriately selected from the 526 lines A.1.1 to A.1.526 of Table A.

Table 60: This table discloses the 526 compounds T60.1.1 to T60.1.526 of the formula

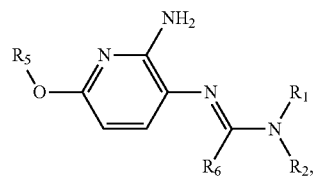
(T60)

in which, for each of these 526 specific compounds, each of the variables $R_1$, $R_2$, $R_5$ and $R_6$ has the specific meaning given in the corresponding line, appropriately selected from the 526 lines A.1.1 to A.1.526 of Table A.

Table 61: This table discloses the 526 compounds T61.1.1 to T61.1.526 of the formula

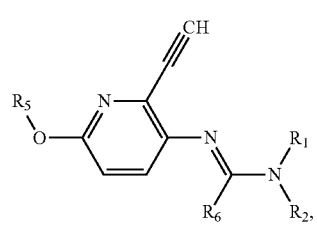
(T61)

in which, for each of these 526 specific compounds, each of the variables $R_1$, $R_2$, $R_5$ and $R_6$ has the specific meaning given in the corresponding line, appropriately selected from the 526 lines A.1.1 to A.1.526 of Table A.

Table 62: This table discloses the 526 compounds T62.1.1 to T62.1.526 of the formula

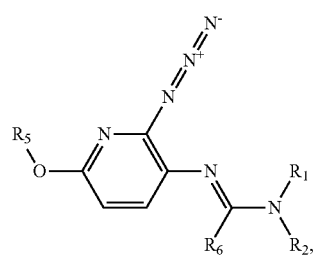
(T62)

in which, for each of these 526 specific compounds, each of the variables $R_1$, $R_2$, $R_5$ and $R_6$ has the specific meaning given in the corresponding line, appropriately selected from the 526 lines A.1.1 to A.1.526 of Table A.

Table 63: This table discloses the 526 compounds T63.1.1 to T63.1.526 of the formula

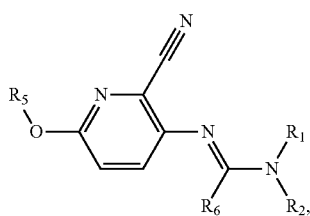
(T63)

in which, for each of these 526 specific compounds, each of the variables $R_1$, $R_2$, $R_5$ and $R_6$ has the specific meaning given in the corresponding line, appropriately selected from the 526 lines A.1.1 to A.1.526 of Table A.

Table 64: This table discloses the 526 compounds T64.1.1 to T64.1.526 of the formula

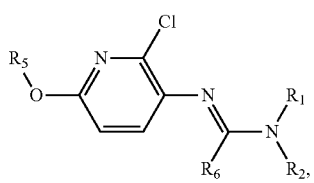
(T64)

in which, for each of these 526 specific compounds, each of the variables $R_1$, $R_2$, $R_5$ and $R_6$ has the specific meaning given in the corresponding line, appropriately selected from the 526 lines A.1.1 to A.1.526 of Table A.

Table 65: This table discloses the 526 compounds T65.1.1 to T65.1.526 of the formula

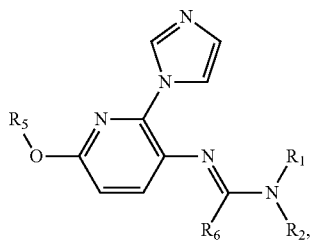
(T65)

in which, for each of these 526 specific compounds, each of the variables $R_1$, $R_2$, $R_5$ and $R_6$ has the specific meaning given in the corresponding line, appropriately selected from the 526 lines A.1.1 to A.1.526 of Table A.

Table 66: This table discloses the 526 compounds T66.1.1 to T66.1.526 of the formula

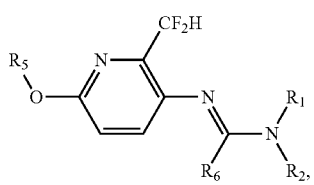
(T66)

in which, for each of these 526 specific compounds, each of the variables $R_1$, $R_2$, $R_5$ and $R_6$ has the specific meaning given in the corresponding line, appropriately selected from the 526 lines A.1.1 to A.1.526 of Table A.

Table 67: This table discloses the 526 compounds T67.1.1 to T67.1.526 of the formula

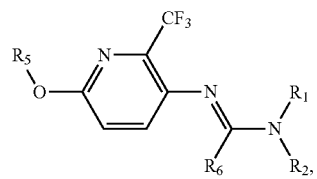
(T67)

in which, for each of these 526 specific compounds, each of the variables $R_1$, $R_2$, $R_5$ and $R_6$ has the specific meaning given in the corresponding line, appropriately selected from the 526 lines A.1.1 to A.1.526 of Table A.

Table 68: This table discloses the 526 compounds T68.1.1 to T68.1.526 of the formula

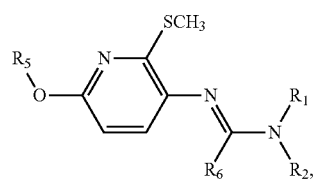
(T68)

in which, for each of these 526 specific compounds, each of the variables $R_1$, $R_2$, $R_5$ and $R_6$ has the specific meaning given in the corresponding line, appropriately selected from the 526 lines A.1.1 to A.1.526 of Table A.

Table 69: This table discloses the 526 compounds T69.1.1 to T69.1.526 of the formula

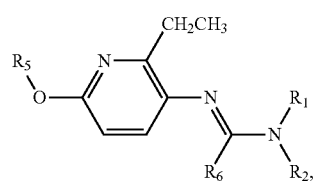
(T69)

in which, for each of these 526 specific compounds, each of the variables $R_1$, $R_2$, $R_5$ and $R_6$ has the specific meaning given in the corresponding line, appropriately selected from the 526 lines A.1.1 to A.1.526 of Table A.

Table 70: This table discloses the 526 compounds T70.1.1 to T70.1.526 of the formula

(T70)

in which, for each of these 526 specific compounds, each of the variables $R_1$, $R_2$, $R_5$ and $R_6$ has the specific meaning given in the corresponding line, appropriately selected from the 526 lines A.1.1 to A.1.526 of Table A.

Table 71: This table discloses the 526 compounds T71.1.1 to T71.1.526 of the formula

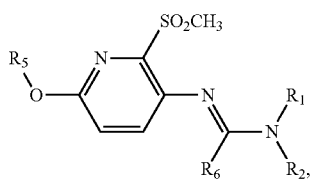

(T71)

in which, for each of these 526 specific compounds, each of the variables $R_1, R_2, R_5$ and $R_6$ has the specific meaning given in the corresponding line, appropriately selected from the 526 lines A.1.1 to A.1.526 of Table A.

Table 72: This table discloses the 526 compounds T72.1.1 to T72.1.526 of the formula

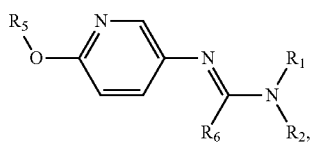

(T72)

in which, for each of these 526 specific compounds, each of the variables $R_1, R_2, R_5$ and $R_6$ has the specific meaning given in the corresponding line, appropriately selected from the 526 lines A.1.1 to A.1.526 of Table A.

Table 73: This table discloses the 526 compounds T73.1.1 to T73.1.526 of the formula

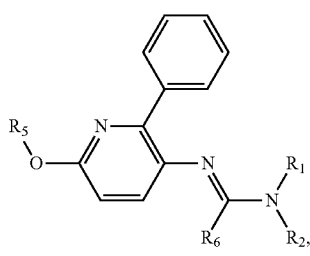

(T73)

in which, for each of these 526 specific compounds, each of the variables $R_1, R_2, R_5$ and $R_6$ has the specific meaning given in the corresponding line, appropriately selected from the 526 lines A.1.1 to A.1.526 of Table A.

Table 74: This table discloses the 526 compounds T74.1.1 to T74.1.526 of the formula

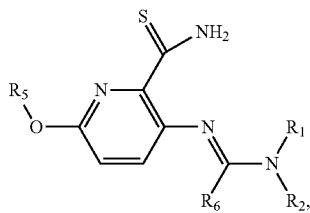

(T74)

in which, for each of these 526 specific compounds, each of the variables $R_1, R_2, R_5$ and $R_6$ has the specific meaning given in the corresponding line, appropriately selected from the 526 lines A.1.1 to A.1.526 of Table A.

Table 75: This table discloses the 526 compounds T75.1.1 to T75.1.526 of the formula

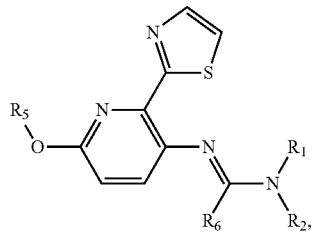

(T75)

in which, for each of these 526 specific compounds, each of the variables $R_1, R_2, R_5$ and $R_6$ has the specific meaning given in the corresponding line, appropriately selected from the 526 lines A.1.1 to A.1.526 of Table A.

Table 76: This table discloses the 526 compounds T76.1.1 to T76.1.526 of the formula

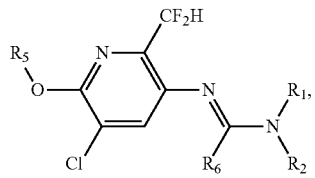

(T76)

in which, for each of these 526 specific compounds, each of the variables $R_1, R_2, R_5$ and $R_6$ has the specific meaning given in the corresponding line, appropriately selected from the 526 lines A.1.1 to A.1.526 of Table A.

Table 77: This table discloses the 526 compounds T77.1.1 to T77.1.526 of the formula (T77)

in which, for each of these 526 specific compounds, each of the variables $R_1, R_2, R_5$ and $R_6$ has the specific meaning given in the corresponding line, appropriately selected from the 526 lines A.1.1 to A.1.526 of Table A.

Table 78: This table discloses the 526 compounds T78.1.1 to T78.1.526 of the formula

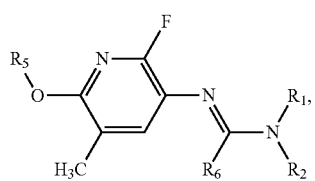

(T78)

in which, for each of these 526 specific compounds, each of the variables $R_1, R_2, R_5$ and $R_6$ has the specific meaning given in the corresponding line, appropriately selected from the 526 lines A.1.1 to A.1.526 of Table A.

Table 79: This table discloses the 526 compounds T79.1.1 to T79.1.526 of the formula

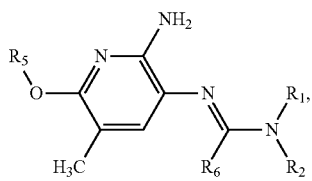

(T79)

in which, for each of these 526 specific compounds, each of the variables $R_1$, $R_2$, $R_5$ and $R_6$ has the specific meaning given in the corresponding line, appropriately selected from the 526 lines A.1.1 to A.1.526 of Table A.

Table 80: This table discloses the 526 compounds T80.1.1 to T80.1.526 of the formula

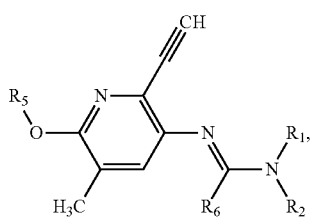

(T80)

in which, for each of these 526 specific compounds, each of the variables $R_1$, $R_2$, $R_5$ and $R_6$ has the specific meaning given in the corresponding line, appropriately selected from the 526 lines A.1.1 to A.1.526 of Table A.

Table 81: This table discloses the 526 compounds T81.1.1 to T81.1.526 of the formula

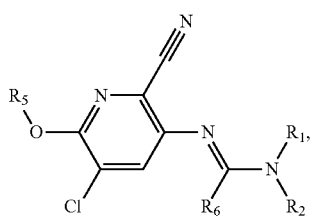

(T81)

in which, for each of these 526 specific compounds, each of the variables $R_1$, $R_2$, $R_5$ and $R_6$ has the specific meaning given in the corresponding line, appropriately selected from the 526 lines A.1.1 to A.1.526 of Table A.

Table 82: This table discloses the 526 compounds T82.1.1 to T82.1.526 of the formula

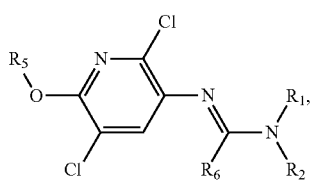

(T82)

in which, for each of these 526 specific compounds, each of the variables $R_1$, $R_2$, $R_5$ and $R_6$ has the specific meaning given in the corresponding line, appropriately selected from the 526 lines A.1.1 to A.1.526 of Table A.

Table 83: This table discloses the 526 compounds T83.1.1 to T83.1.526 of the formula

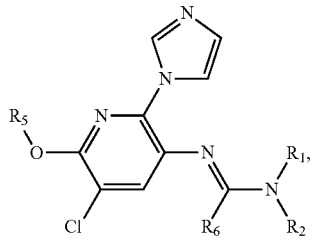

(T83)

in which, for each of these 526 specific compounds, each of the variables $R_1$, $R_2$, $R_5$ and $R_6$ has the specific meaning given in the corresponding line, appropriately selected from the 526 lines A.1.1 to A.1.526 of Table A.

Table 84: This table discloses the 526 compounds T84.1.1 to T84.1.526 of the formula

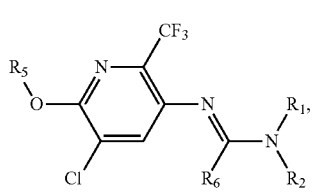

(T84)

in which, for each of these 526 specific compounds, each of the variables $R_1$, $R_2$, $R_5$ and $R_6$ has the specific meaning given in the corresponding line, appropriately selected from the 526 lines A.1.1 to A.1.526 of Table A.

Table 85: This table discloses the 526 compounds T85.1.1 to T85.1.526 of the formula

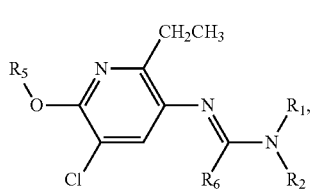

(T85)

in which, for each of these 526 specific compounds, each of the variables $R_1$, $R_2$, $R_5$ and $R_6$ has the specific meaning given in the corresponding line, appropriately selected from the 526 lines A.1.1 to A.1.526 of Table A.

Table 86: This table discloses the 526 compounds T86.1.1 to T86.1.526 of the formula

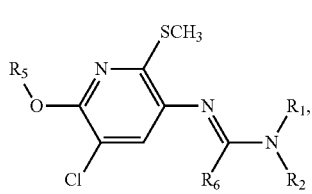

(T86)

in which, for each of these 526 specific compounds, each of the variables $R_1$, $R_2$, $R_5$ and $R_6$ has the specific meaning given in the corresponding line, appropriately selected from the 526 lines A.1.1 to A.1.526 of Table A.

Table 87: This table discloses the 526 compounds T87.1.1 to T87.1.526 of the formula

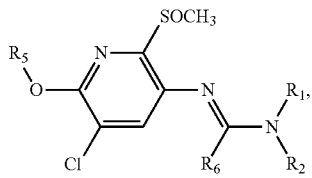
(T87)

in which, for each of these 526 specific compounds, each of the variables $R_1$, $R_2$, $R_5$ and $R_6$ has the specific meaning given in the corresponding line, appropriately selected from the 526 lines A.1.1 to A.1.526 of Table A.

Table 88: This table discloses the 526 compounds T88.1.1 to T88.1.526 of the formula

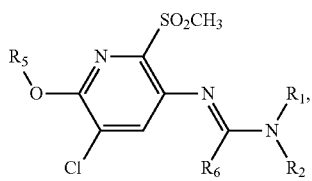
(T88)

in which, for each of these 526 specific compounds, each of the variables $R_1$, $R_2$, $R_5$ and $R_6$ has the specific meaning given in the corresponding line, appropriately selected from the 526 lines A.1.1 to A.1.526 of Table A.

Table 89: This table discloses the 526 compounds T89.1.1 to T89.1.526 of the formula

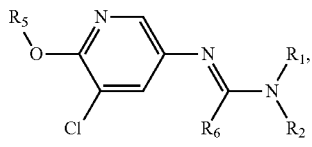
(T89)

in which, for each of these 526 specific compounds, each of the variables $R_1$, $R_2$, $R_5$ and $R_6$ has the specific meaning given in the corresponding line, appropriately selected from the 526 lines A.1.1 to A.1.526 of Table A.

Table 90: This table discloses the 526 compounds T90.1.1 to T90.1.526 of the formula

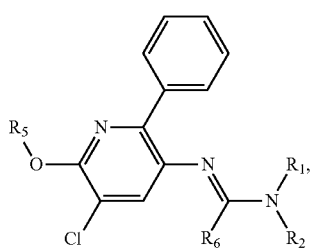
(T90)

in which, for each of these 526 specific compounds, each of the variables $R_1$, $R_2$, $R_5$ and $R_6$ has the specific meaning given in the corresponding line, appropriately selected from the 526 lines A.1.1 to A.1.526 of Table A.

Table 91: This table discloses the 526 compounds T91.1.1 to T91.1.526 of the formula

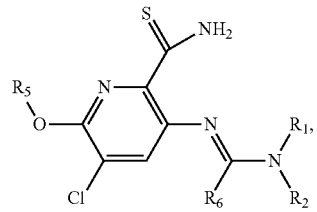
(T91)

in which, for each of these 526 specific compounds, each of the variables $R_1$, $R_2$, $R_5$ and $R_6$ has the specific meaning given in the corresponding line, appropriately selected from the 526 lines A.1.1 to A.1.526 of Table A.

Table 92: This table discloses the 526 compounds T92.1.1 to T92.1.526 of the formula

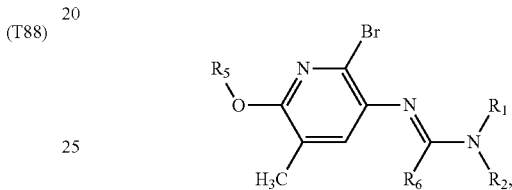
(T92)

in which, for each of these 526 specific compounds, each of the variables $R_1$, $R_2$, $R_5$ and $R_6$ has the specific meaning given in the corresponding line, appropriately selected from the 526 lines A.1.1 to A.1.526 of Table A.

Table 93: This table discloses the 526 compounds T93.1.1 to T93.1.526 of the formula

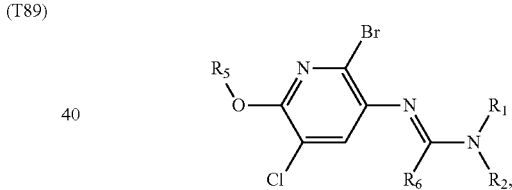
(T93)

in which, for each of these 526 specific compounds, each of the variables $R_1$, $R_2$, $R_5$ and $R_6$ has the specific meaning given in the corresponding line, appropriately selected from the 526 lines A.1.1 to A.1.526 of Table A.

Table 94: This table discloses the 526 compounds T94.1.1 to T94.1.526 of the formula

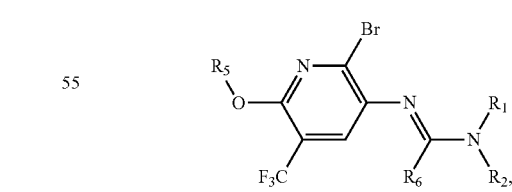
(T94)

in which, for each of these 526 specific compounds, each of the variables $R_1$, $R_2$, $R_5$ and $R_6$ has the specific meaning given in the corresponding line, appropriately selected from the 526 lines A.1.1 to A.1.526 of Table A.

Table 95: This table discloses the 526 compounds T95.1.1 to T95.1.526 of the formula (T95)

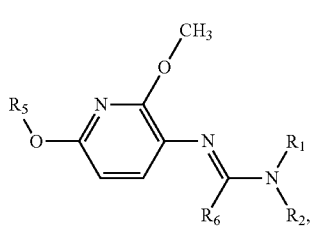

in which, for each of these 526 specific compounds, each of the variables $R_1$, $R_2$, $R_5$ and $R_6$ has the specific meaning given in the corresponding line, appropriately selected from the 526 lines A.1.1 to A.1.526 of Table A.

Table 96: This table discloses the 526 compounds T96.1.1 to T96.1.526 of the formula (T96)

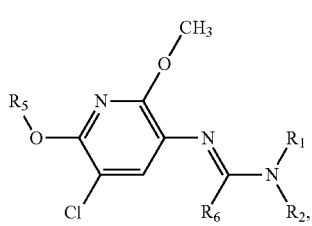

in which, for each of these 526 specific compounds, each of the variables $R_1$, $R_2$, $R_5$ and $R_6$ has the specific meaning given in the corresponding line, appropriately selected from the 526 lines A.1.1 to A.1.526 of Table A.

Table 97: This table discloses the 526 compounds T97.1.1 to T97.1.526 of the formula (T97)

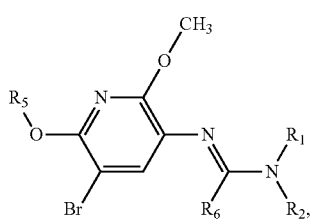

in which, for each of these 526 specific compounds, each of the variables $R_1$, $R_2$, $R_5$ and $R_6$ has the specific meaning given in the corresponding line, appropriately selected from the 526 lines A.1.1 to A.1.526 of Table A.

Table 98: This table discloses the 526 compounds T98.1.1 to T98.1.526 of the formula (T98)

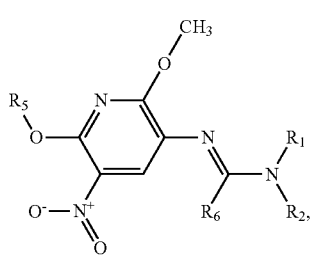

in which, for each of these 526 specific compounds, each of the variables $R_1$, $R_2$, $R_5$ and $R_6$ has the specific meaning given in the corresponding line, appropriately selected from the 526 lines A.1.1 to A.1.526 of Table A.

Table 99: This table discloses the 526 compounds T99.1.1 to T99.1.526 of the formula (T99)

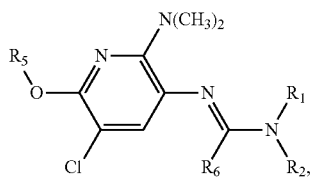

in which, for each of these 526 specific compounds, each of the variables $R_1$, $R_2$, $R_5$ and $R_6$ has the specific meaning given in the corresponding line, appropriately selected from the 526 lines A.1.1 to A.1.526 of Table A.

Table 100: This table discloses the 526 compounds T100.1.1 to T100.1.526 of the formula (T100)

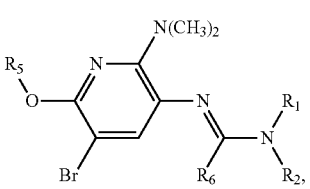

in which, for each of these 526 specific compounds, each of the variables $R_1$, $R_2$, $R_5$ and $R_6$ has the specific meaning given in the corresponding line, appropriately selected from the 526 lines A.1.1 to A.1.526 of Table A.

Table 101: This table discloses the 526 compounds T101.1.1 to T101.1.526 of the formula (T101)

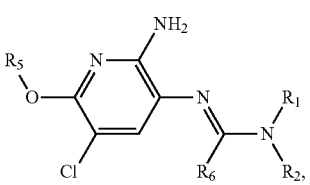

in which, for each of these 526 specific compounds, each of the variables $R_1$, $R_2$, $R_5$ and $R_6$ has the specific meaning given in the corresponding line, appropriately selected from the 526 lines A.1.1 to A.1.526 of Table A.

Table 102: This table discloses the 526 compounds T102.1.1 to T102.1.526 of the formula (T102)

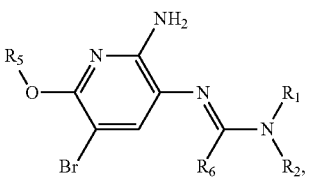

in which, for each of these 526 specific compounds, each of the variables $R_1$, $R_2$, $R_5$ and $R_6$ has the specific meaning given in the corresponding line, appropriately selected from the 526 lines A.1.1 to A.1.526 of Table A.

Table 103: This table discloses the 526 compounds T103.1.1 to T103.1.526 of the formula

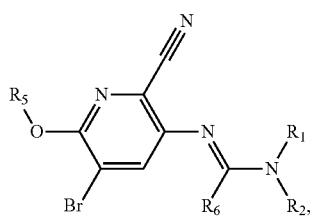
(T103)

in which, for each of these 526 specific compounds, each of the variables $R_1$, $R_2$, $R_5$ and $R_6$ has the specific meaning given in the corresponding line, appropriately selected from the 526 lines A.1.1 to A.1.526 of Table A.

Table 104: This table discloses the 526 compounds T104.1.1 to T104.1.526 of the formula

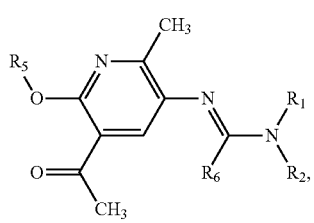
(T104)

in which, for each of these 526 specific compounds, each of the variables $R_1$, $R_2$, $R_5$ and $R_6$ has the specific meaning given in the corresponding line, appropriately selected from the 526 lines A.1.1 to A.1.526 of Table A.

Table 105: This table discloses the 526 compounds T105.1.1 to T105.1.526 of the formula

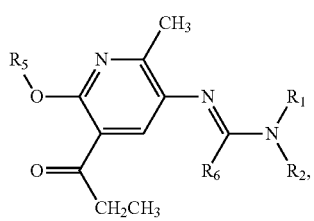
(T105)

in which, for each of these 526 specific compounds, each of the variables $R_1$, $R_2$, $R_5$ and $R_6$ has the specific meaning given in the corresponding line, appropriately selected from the 526 lines A.1.1 to A.1.526 of Table A.

Table 106: This table discloses the 526 compounds T106.1.1 to T106.1.526 of the formula

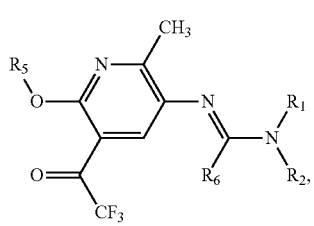
(T106)

in which, for each of these 526 specific compounds, each of the variables $R_1$, $R_2$, $R_5$ and $R_6$ has the specific meaning given in the corresponding line, appropriately selected from the 526 lines A.1.1 to A.1.526 of Table A.

Table 107: This table discloses the 526 compounds T107.1.1 to T107.1.526 of the formula

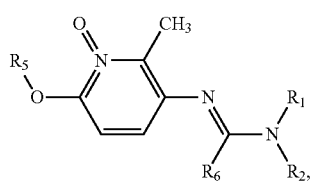
(T107)

in which, for each of these 526 specific compounds, each of the variables $R_1$, $R_2$, $R_5$ and $R_6$ has the specific meaning given in the corresponding line, appropriately selected from the 526 lines A.1.1 to A.1.526 of Table A.

Table 108: This table discloses the 526 compounds T108.1.1 to T108.1.526 of the formula

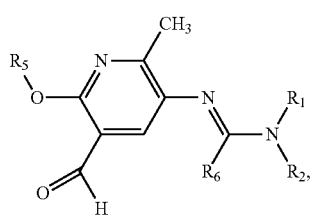
(T108)

in which, for each of these 526 specific compounds, each of the variables $R_1$, $R_2$, $R_5$ and $R_6$ has the specific meaning given in the corresponding line, appropriately selected from the 526 lines A.1.1 to A.1.526 of Table A.

Table 109: This table discloses the 526 compounds T109.1.1 to T109.1.526 of the formula

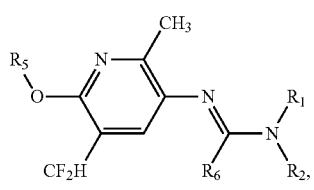
(T109)

in which, for each of these 526 specific compounds, each of the variables $R_1$, $R_2$, $R_5$ and $R_6$ has the specific meaning given in the corresponding line, appropriately selected from the 526 lines A.1.1 to A.1.526 of Table A.

Table 110: This table discloses the 526 compounds T110.1.1 to T110.1.526 of the formula

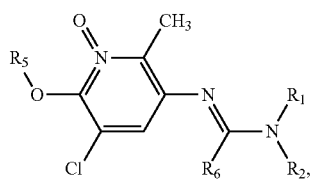
(T110)

Table 111: This table discloses the 526 compounds T111.1.1 to T111.1.526 of the formula

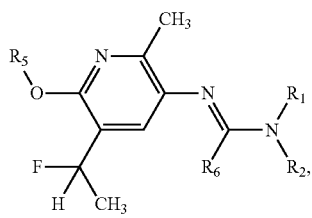
(T111)

in which, for each of these 526 specific compounds, each of the variables $R_1$, $R_2$, $R_5$ and $R_6$ has the specific meaning given in the corresponding line, appropriately selected from the 526 lines A.1.1 to A.1.526 of Table A.

Table 112: This table discloses the 526 compounds T112.1.1 to T112.1.526 of the formula

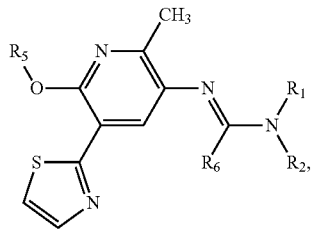
(T112)

in which, for each of these 526 specific compounds, each of the variables $R_1$, $R_2$, $R_5$ and $R_6$ has the specific meaning given in the corresponding line, appropriately selected from the 526 lines A.1.1 to A.1.526 of Table A.

Table 113: This table discloses the 526 compounds T113.1.1 to T113.1.526 of the formula

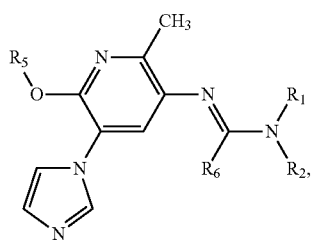
(T113)

in which, for each of these 526 specific compounds, each of the variables $R_1$, $R_2$, $R_5$ and $R_6$ has the specific meaning given in the corresponding line, appropriately selected from the 526 lines A.1.1 to A.1.526 of Table A.

Table 114: This table discloses the 526 compounds T114.1.1 to T114.1.526 of the formula

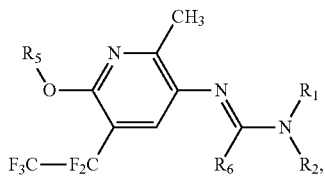
(T114)

in which, for each of these 526 specific compounds, each of the variables $R_1$, $R_2$, $R_5$ and $R_6$ has the specific meaning given in the corresponding line, appropriately selected from the 526 lines A.1.1 to A.1.526 of Table A.

Table 115: This table discloses the 526 compounds T115.1.1 to T115.1.526 of the formula

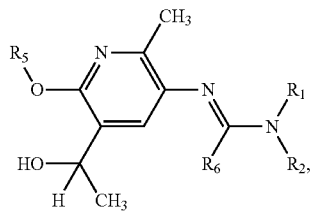
(T115)

in which, for each of these 526 specific compounds, each of the variables $R_1$, $R_2$, $R_5$ and $R_6$ has the specific meaning given in the corresponding line, appropriately selected from the 526 lines A.1.1 to A.1.526 of Table A.

Table 116: This table discloses the 526 compounds T116.1.1 to T116.1.526 of the formula

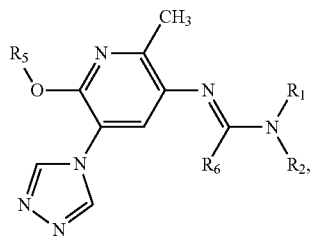
(T116)

in which, for each of these 526 specific compounds, each of the variables $R_1$, $R_2$, $R_5$ and $R_6$ has the specific meaning given in the corresponding line, appropriately selected from the 526 lines A.1.1 to A.1.526 of Table A.

Table 117: This table discloses the 526 compounds T117.1.1 to T117.1.526 of the formula

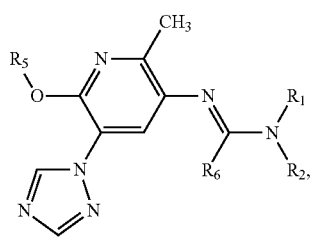
(T117)

in which, for each of these 526 specific compounds, each of the variables $R_1$, $R_2$, $R_5$ and $R_6$ has the specific meaning given Table 118: This table discloses the 526 compounds T118.1.1 to T118.1.526 of the formula

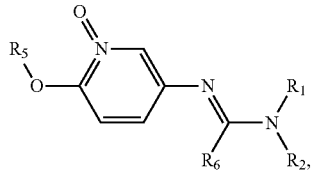
(T118)

in which, for each of these 526 specific compounds, each of the variables $R_1$, $R_2$, $R_5$ and $R_6$ has the specific meaning given in the corresponding line, appropriately selected from the 526 lines A.1.1 to A.1.526 of Table A.

Table 119: This table discloses the 526 compounds T119.1.1 to T119.1.526 of the formula

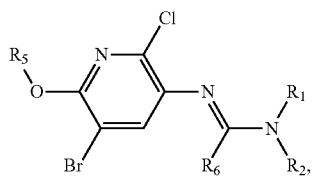
(T119)

in which, for each of these 526 specific compounds, each of the variables $R_1$, $R_2$, $R_5$ and $R_6$ has the specific meaning given in the corresponding line, appropriately selected from the 526 lines A.1.1 to A.1.526 of Table A.

Table 120: This table discloses the 526 compounds T120.1.1 to T120.1.526 of the formula

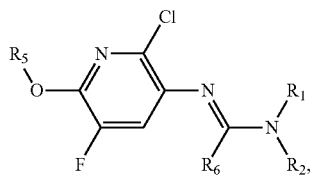
(T120)

in which, for each of these 526 specific compounds, each of the variables $R_1$, $R_2$, $R_5$ and $R_6$ has the specific meaning given in the corresponding line, appropriately selected from the 526 lines A.1.1 to A.1.526 of Table A.

Table 121: This table discloses the 526 compounds T121.1.1 to T121.1.526 of the formula

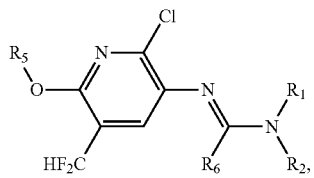
(T121)

in which, for each of these 526 specific compounds, each of the variables $R_1$, $R_2$, $R_5$ and $R_6$ has the specific meaning given in the corresponding line, appropriately selected from the 526 lines A.1.1 to A.1.526 of Table A.

Table 122: This table discloses the 526 compounds T122.1.1 to T122.1.526 of the formula

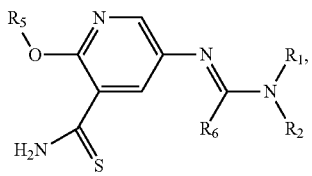
(T122)

in which, for each of these 526 specific compounds, each of the variables $R_1$, $R_2$, $R_5$ and $R_6$ has the specific meaning given in the corresponding line, appropriately selected from the 526 lines A.1.1 to A.1.526 of Table A.

Table 123: This table discloses the 526 compounds T123.1.1 to T123.1.526 of the formula

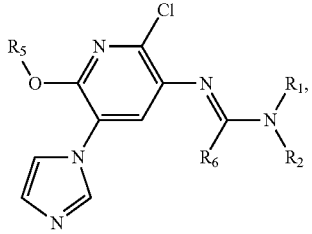
(T123)

in which, for each of these 526 specific compounds, each of the variables $R_1$, $R_2$, $R_5$ and $R_6$ has the specific meaning given in the corresponding line, appropriately selected from the 526 lines A.1.1 to A.1.526 of Table A.

Table 124: This table discloses the 526 compounds T124.1.1 to T124.1.526 of the formula

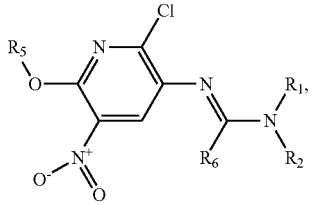
(T124)

in which, for each of these 526 specific compounds, each of the variables $R_1$, $R_2$, $R_5$ and $R_6$ has the specific meaning given in the corresponding line, appropriately selected from the 526 lines A.1.1 to A.1.526 of Table A.

Table 125: This table discloses the 526 compounds T125.1.1 to T125.1.526 of the formula

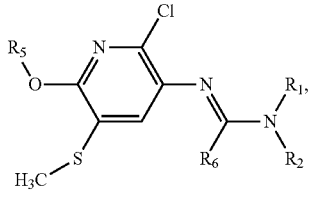
(T125)

in which, for each of these 526 specific compounds, each of the variables $R_1$, $R_2$, $R_5$ and $R_6$ has the specific meaning given in the corresponding line, appropriately selected from the 526 lines A.1.1 to A.1.526 of Table A.

Table 126: This table discloses the 526 compounds T126.1.1 to T126.1.526 of the formula

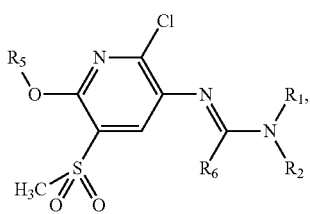

(T126)

in which, for each of these 526 specific compounds, each of the variables $R_1$, $R_2$, $R_5$ and $R_6$ has the specific meaning given in the corresponding line, appropriately selected from the 526 lines A.1.1 to A.1.526 of Table A.

Table 127: This table discloses the 526 compounds T127.1.1 to T127.1.526 of the formula

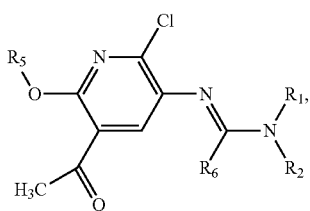

(T127)

in which, for each of these 526 specific compounds, each of the variables $R_1$, $R_2$, $R_5$ and $R_6$ has the specific meaning given in the corresponding line, appropriately selected from the 526 lines A.1.1 to A.1.526 of Table A.

Table 128: This table discloses the 526 compounds T128.1.1 to T128.1.526 of the formula

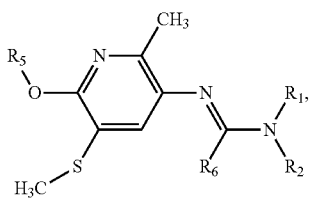

(T128)

in which, for each of these 526 specific compounds, each of the variables $R_1$, $R_2$, $R_5$ and $R_6$ has the specific meaning given in the corresponding line, appropriately selected from the 526 lines A.1.1 to A.1.526 of Table A.

Table 129: This table discloses the 526 compounds T129.1.1 to T129.1.526 of the formula

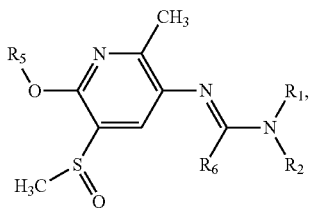

(T129)

in which, for each of these 526 specific compounds, each of the variables $R_1$, $R_2$, $R_5$ and $R_6$ has the specific meaning given in the corresponding line, appropriately selected from the 526 lines A.1.1 to A.1.526 of Table A.

Table 130: This table discloses the 526 compounds T130.1.1 to T130.1.526 of the formula

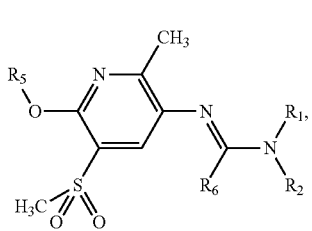

(T130)

in which, for each of these 526 specific compounds, each of the variables $R_1$, $R_2$, $R_5$ and $R_6$ has the specific meaning given in the corresponding line, appropriately selected from the 526 lines A.1.1 to A.1.526 of Table A.

Table 131: This table discloses the 526 compounds T131.1.1 to T131.1.526 of the formula

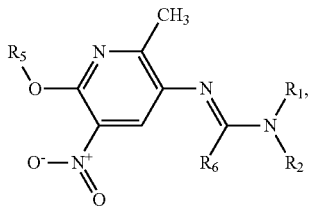

(T131)

in which, for each of these 526 specific compounds, each of the variables $R_1$, $R_2$, $R_5$ and $R_6$ has the specific meaning given in the corresponding line, appropriately selected from the 526 lines A.1.1 to A.1.526 of Table A.

Table 132: This table discloses the 526 compounds T132.1.1 to T132.1.526 of the formula

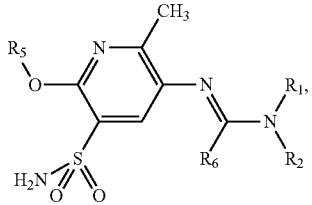

(T132)

in which, for each of these 526 specific compounds, each of the variables $R_1$, $R_2$, $R_5$ and $R_6$ has the specific meaning given in the corresponding line, appropriately selected from the 526 lines A.1.1 to A.1.526 of Table A.

Table 133: This table discloses the 526 compounds T133.1.1 to T133.1.526 of the formula

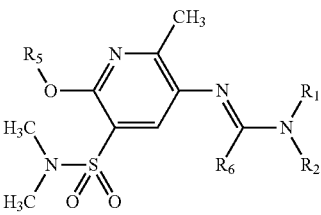

(T133)

in which, for each of these 526 specific compounds, each of the variables $R_1$, $R_2$, $R_5$ and $R_6$ has the specific meaning given in the corresponding line, appropriately selected from the 526 lines A.1.1 to A.1.526 of Table A.

Table 134: This table discloses the 526 compounds T134.1.1 to T134.1.526 of the formula (T134)

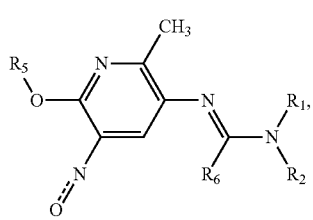

in which, for each of these 526 specific compounds, each of the variables $R_1$, $R_2$, $R_5$ and $R_6$ has the specific meaning given in the corresponding line, appropriately selected from the 526 lines A.1.1 to A.1.526 of Table A.

Table 135: This table discloses the 526 compounds T135.1.1 to T135.1.526 of the formula (T135)

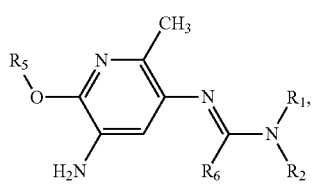

in which, for each of these 526 specific compounds, each of the variables $R_1$, $R_2$, $R_5$ and $R_6$ has the specific meaning given in the corresponding line, appropriately selected from the 526 lines A.1.1 to A.1.526 of Table A.

Table 136: This table discloses the 526 compounds T136.1.1 to T136.1.526 of the formula (T136)

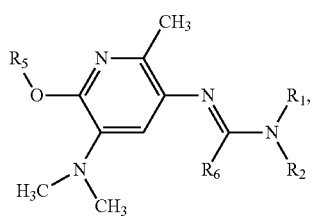

in which, for each of these 526 specific compounds, each of the variables $R_1$, $R_2$, $R_5$ and $R_6$ has the specific meaning given in the corresponding line, appropriately selected from the 526 lines A.1.1 to A.1.526 of Table A.

Table 137: This table discloses the 526 compounds T137.1.1 to T137.1.526 of the formula (T137)

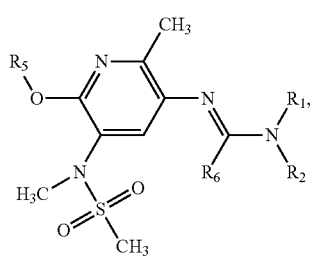

in which, for each of these 526 specific compounds, each of the variables $R_1$, $R_2$, $R_5$ and $R_6$ has the specific meaning given in the corresponding line, appropriately selected from the 526 lines A.1.1 to A.1.526 of Table A.

Table 138: This table discloses the 526 compounds T138.1.1 to T138.1.526 of the formula (T138)

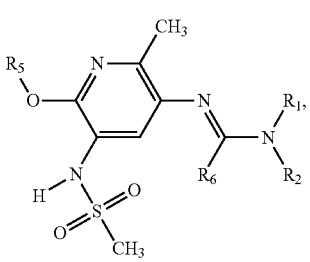

in which, for each of these 526 specific compounds, each of the variables $R_1$, $R_2$, $R_5$ and $R_6$ has the specific meaning given in the corresponding line, appropriately selected from the 526 lines A.1.1 to A.1.526 of Table A.

Table 139: This table discloses the 526 compounds T139.1.1 to T139.1.526 of the formula (T139)

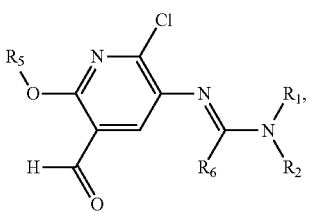

in which, for each of these 526 specific compounds, each of the variables $R_1$, $R_2$, $R_5$ and $R_6$ has the specific meaning given in the corresponding line, appropriately selected from the 526 lines A.1.1 to A.1.526 of Table A.

Table 140: This table discloses the 526 compounds T140.1.1 to T140.1.526 of the formula (T140)

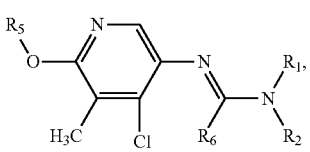

in which, for each of these 526 specific compounds, each of the variables $R_1$, $R_2$, $R_5$ and $R_6$ has the specific meaning given in the corresponding line, appropriately selected from the 526 lines A.1.1 to A.1.526 of Table A.

Table 141: This table discloses the 526 compounds T141.1.1 to T141.1.526 of the formula (T141)

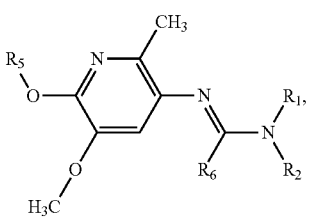

in which, for each of these 526 specific compounds, each of the variables $R_1$, $R_2$, $R_5$ and $R_6$ has the specific meaning given in the corresponding line, appropriately selected from the 526 lines A.1.1 to A.1.526 of Table A.

Table 142: This table discloses the 526 compounds T142.1.1 to T142.1.526 of the formula (T142)

in which, for each of these 526 specific compounds, each of the variables $R_1$, $R_2$, $R_5$ and $R_6$ has the specific meaning given in the corresponding line, appropriately selected from the 526 lines A.1.1 to A.1.526 of Table A.

Table 143: This table discloses the 526 compounds T143.1.1 to T143.1.526 of the formula (T143)

in which, for each of these 526 specific compounds, each of the variables $R_1$, $R_2$, $R_5$ and $R_6$ has the specific meaning given in the corresponding line, appropriately selected from the 526 lines A.1.1 to A.1.526 of Table A.

Table 144: This table discloses the 526 compounds T144.1.1 to T144.1.526 of the formula (T144)

in which, for each of these 526 specific compounds, each of the variables $R_1$, $R_2$, $R_5$ and $R_6$ has the specific meaning given in the corresponding line, appropriately selected from the 526 lines A.1.1 to A.1.526 of Table A.

Table 145: This table discloses the 526 compounds T145.1.1 to T145.1.526 of the formula (T145)

in which, for each of these 526 specific compounds, each of the variables $R_1$, $R_2$, $R_5$ and $R_6$ has the specific meaning given in the corresponding line, appropriately selected from the 526 lines A.1.1 to A.1.526 of Table A.

Table 146: This table discloses the 526 compounds T146.1.1 to T146.1.526 of the formula (T146)

in which, for each of these 526 specific compounds, each of the variables $R_1$, $R_2$, $R_5$ and $R_6$ has the specific meaning given in the corresponding line, appropriately selected from the 526 lines A.1.1 to A.1.526 of Table A.

Table 147: This table discloses the 526 compounds T147.1.1 to T147.1.526 of the formula (T147)

in which, for each of these 526 specific compounds, each of the variables $R_1$, $R_2$, $R_5$ and $R_6$ has the specific meaning given in the corresponding line, appropriately selected from the 526 lines A.1.1 to A.1.526 of Table A.

Table 148: This table discloses the 526 compounds T148.1.1 to T148.1.526 of the formula (T148)

in which, for each of these 526 specific compounds, each of the variables $R_1$, $R_2$, $R_5$ and $R_6$ has the specific meaning given in the corresponding line, appropriately selected from the 526 lines A.1.1 to A.1.526 of Table A.

Table 149: This table discloses the 526 compounds T149.1.1 to T149.1.526 of the formula (T149)

in which, for each of these 526 specific compounds, each of the variables $R_1$, $R_2$, $R_5$ and $R_6$ has the specific meaning given in the corresponding line, appropriately selected from the 526 lines A.1.1 to A.1.526 of Table A.

Table 150: This table discloses the 526 compounds T150.1.1 to T150.1.526 of the formula

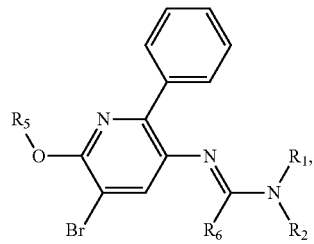

(T150)

in which, for each of these 526 specific compounds, each of the variables $R_1$, $R_2$, $R_5$ and $R_6$ has the specific meaning given in the corresponding line, appropriately selected from the 526 lines A.1.1 to A.1.526 of Table A.

Table 151: This table discloses the 526 compounds T151.1.1 to T151.1.526 of the formula

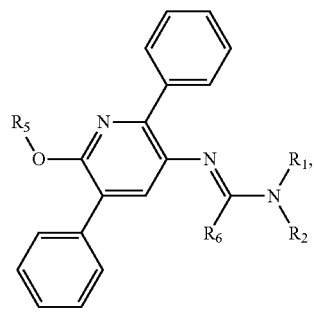

(T151)

in which, for each of these 526 specific compounds, each of the variables $R_1$, $R_2$, $R_5$ and $R_6$ has the specific meaning given in the corresponding line, appropriately selected from the 526 lines A.1.1 to A.1.526 of Table A.

Formulation examples for compounds of formula I:

Example F-1.1 to F-1.3

Emulsifiable Concentrates

| Components | F-1.1 | F-1.2 | F-1.3 |
|---|---|---|---|
| compound of Tables 1 to 151 | 25% | 40% | 50% |
| calcium dodecylbenzenesulfonate | 5% | 8% | 6% |
| castor oil polyethylene glycol ether (36 mol ethylenoxy units) | 5% | — | — |
| tributylphenolpolyethylene glycol ether (30 mol ethylenoxy units) | — | 12% | 4% |
| cyclohexanone | — | 15% | 20% |
| xylene mixture | 65% | 25% | 20% |

Emulsions of any desired concentration can be prepared by diluting such concentrates with water.

Example F-2

Emulsifiable Concentrate

| Components | F-2 |
|---|---|
| compound of Tables 1 to 151 | 10% |
| octylphenolpolyethylene glycol ether (4 to 5 mol ethylenoxy units) | 3% |
| calcium dodecylbenzenesulfonate | 3% |
| castor oil polyglycol ether (36 mol ethylenoxy units) | 4% |
| cyclohexanone | 30% |
| xylene mixture | 50% |

Emulsions of any desired concentration can be prepared by diluting such concentrates with water.

Examples F-3.1 to F-3.4

Solutions

| Components | F-3.1 | F-3.2 | F-3.3 | F-3.4 |
|---|---|---|---|---|
| compound of Tables 1 to 151 | 80% | 10% | 5% | 95% |
| propylene glycol monomethyl ether | 20% | — | — | — |
| polyethylene glycol (relative molecular mass: 400 atomic mass units) | — | 70% | — | — |
| N-methylpyrrolid-2-one | — | 20% | — | — |
| epoxidised coconut oil | — | — | 1% | 5% |
| benzin (boiling range: 160-190°) | — | — | 94% | — |

The solutions are suitable for use in the form of microdrops.

Examples F-4.1 to F-4.4

Granulates

| Components | F-4.1 | F-4.2 | F-4.3 | F-4.4 |
|---|---|---|---|---|
| compound of Tables 1 to 151 | 5% | 10% | 8% | 21% |
| kaolin | 94% | — | 79% | 54% |
| highly dispersed silicic acid | 1% | — | 13% | 7% |
| attapulgite | — | 90% | — | 18% |

The novel compound is dissolved in dichloromethane, the solution is sprayed onto the carrier and the solvent is then removed by distillation under vacuum.

Examples F-5.1 and F-5.2

Dusts

| Components | F-5.1 | F-5.2 |
|---|---|---|
| compound of Tables 1 to 151 | 2% | 5% |
| highly dispersed silicic acid | 1% | 5% |
| talcum | 97% | — |
| kaolin | — | 90% |

Ready for use dusts are obtained by intimately mixing all components.

Examples F-6.1 to F-6.3

Wettable Powders

| Components | F-6.1 | F-6.2 | F-6.3 |
|---|---|---|---|
| compound of Tables 1 to 151 | 25% | 50% | 75% |
| sodium lignin sulfonate | 5% | 5% | — |
| sodium lauryl sulfate | 3% | — | 5% |
| sodium diisobutylnaphthalene sulfonate | — | 6% | 10% |
| octylphenolpolyethylene glycol ether (7 to 8 mol ethylenoxy units) | — | 2% | — |
| highly dispersed silicic acid | 5% | 10% | 10% |
| kaolin | 62% | 27% | — |

All components are mixed and the mixture is thoroughly ground in a suitable mill to give wettable powders which can be diluted with water to suspensions of any desired concentration.

Example F7

Flowable Concentrate for Seed Treatment

| | |
|---|---|
| compound of Tables 1 to 151 | 40% |
| propylene glycol | 5% |
| copolymer butanol PO/EO | 2% |
| tristyrenephenole with 10-20 moles EO | 2% |
| 1,2-benzisothiazolin-3-one (in the form of a 20% solution in water) | 0.5% |
| monoazo-pigment calcium salt | 5% |
| Silicone oil (in the form of a 75% emulsion in water) | 0.2% |
| Water | 45.3% |

The finely ground active ingredient is intimately mixed with the adjuvants, giving a suspension concentrate from which suspensions of any desired dilution can be obtained by dilution with water. Using such dilutions, living plants as well as plant propagation material can be treated and protected against infestation by microorganisms, by spraying, pouring or immersion.

The activity of the compositions according to the invention can be broadened considerably, and adapted to prevailing circumstances, by adding other insecticidally, acaricidally and/or fungicidally active ingredients. The mixtures of the compounds of formula I with other insecticidally, acaricidally and/or fungicidally active ingredients may also have further surprising advantages which can also be described, in a wider sense, as synergistic activity. For example, better tolerance by plants, reduced phytotoxicity, insects can be controlled in their different development stages or better behaviour during their production, for example during grinding or mixing, during their storage or during their use.

Suitable additions to active ingredients here are, for example, representatives of the following classes of active ingredients: organophosphorus compounds, nitrophenol derivatives, thioureas, juvenile hormones, formamidines, benzophenone derivatives, ureas, pyrrole derivatives, carbamates, pyrethroids, chlorinated hydrocarbons, acylureas, pyridyl-methyleneamino derivatives, macrolides, neonicotinoids and Bacillus thuringiensis preparations.

The following mixtures of the compounds of formula I with active ingredients are preferred (the abbreviation "TX" means "one compound selected from the group consisting of the compounds of Table P and the compounds represented by formulae T1 to T151 described in tables 1 to 151 of the present invention"):

an adjuvant selected from the group of substances consisting of petroleum oils (alternative name) (628)+TX,
an acaricide selected from the group of substances consisting of 1,1-bis(4-chlorophenyl)-2-ethoxyethanol (IUPAC name) (910)+TX, 2,4-dichlorophenyl benzenesulfonate (IUPAC/Chemical Abstracts name) (1059)+TX, 2-fluoro-N-methyl-N-1-naphthylacetamide (IUPAC name) (1295)+TX, 4-chlorophenyl phenyl sulfone (IUPAC name) (981)+TX, abamectin (1)+TX, acequinocyl (3)+TX, acetoprole [CCN]+TX, acrinathrin (9)+TX, aldicarb (16)+TX, aldoxycarb (863)+TX, alpha-cypermethrin (202)+TX, amidithion (870)+TX, amidoflumet [CCN]+TX, amidothioate (872)+TX, amiton (875)+TX, amiton hydrogen oxalate (875)+TX, amitraz (24)+TX, aramite (881)+TX, arsenous oxide (882)+TX, AVI 382 (compound code)+TX, AZ 60541 (compound code)+TX, azinphos-ethyl (44)+TX, azinphos-methyl (45)+TX, azobenzene (IUPAC name) (888)+TX, azocyclotin (46)+TX, azothoate (889)+TX, benomyl (62)+TX, benoxafos (alternative name) [CCN]+TX, benzoximate (71)+TX, benzyl benzoate (IUPAC name) [CCN]+TX, bifenazate (74)+TX, bifenthrin (76)+TX, binapacryl (907)+TX, brofenvalerate (alternative name)+TX, bromocyclen (918)+TX, bromophos (920)+TX, bromophos-ethyl (921)+TX, bromopropylate (94)+TX, buprofezin (99)+TX, butocarboxim (103)+TX, butoxycarboxim (104)+TX, butylpyridaben (alternative name)+TX, calcium polysulfide (IUPAC name) (111)+TX, camphechlor (941)+TX, carbanolate (943)+TX, carbaryl (115)+TX, carbofuran (118)+TX, carbophenothion (947)+TX, CGA 50'439 (development code) (125)+TX, chinomethionat (126)+TX, chlorbenside (959)+TX, chlordimeform (964)+TX, chlordimeform hydrochloride (964)+TX, chlorfenapyr (130)+TX, chlorfenethol (968)+TX, chlorfenson (970)+TX, chlorfensulphide (971)+TX, chlorfenvinphos (131)+TX, chlorobenzilate (975)+TX, chloromebuform (977)+TX, chloromethiuron (978)+TX, chloropropylate (983)+TX, chlorpyrifos (145)+TX, chlorpyrifos-methyl (146)+TX, chlorthiophos (994)+TX, cinerin I (696)+TX, cinerin II (696)+TX, cinerins (696)+TX, clofentezine (158)+TX, closantel (alternative name) [CCN]+TX, coumaphos (174)+TX, crotamiton (alternative name) [CCN]+TX, crotoxyphos (1010)+TX, cufraneb (1013)+TX, cyanthoate (1020)+TX, cyflumetofen (CAS Reg. No.: 400882-07-7)+TX, cyhalothrin (196)+TX, cyhexatin (199)+TX, cypermethrin (201)+TX, DCPM (1032)+TX, DDT (219)+TX, demephion (1037)+TX, demephion-O (1037)+TX, demephion-S (1037)+TX, demeton (1038)+TX, demeton-methyl (224)+TX, demeton-O (1038)+TX, demeton-O-methyl (224)+TX, demeton-S (1038)+TX, demeton-5-methyl (224)+TX, demeton-S-methylsulphon (1039)+TX, diafenthiuron (226)+TX, dialifos (1042)+TX, diazinon (227)+TX, dichlofluanid (230)+TX, dichlorvos (236)+TX, dicliphos (alternative name)+TX, dicofol (242)+TX, dicrotophos (243)+TX, dienochlor (1071)+TX, dimefox (1081)+TX, dimethoate (262)+TX, dinactin (alternative name) (653)+TX, dinex (1089)+TX, dinex-diclexine (1089)+TX, dinobuton (269)+TX, dinocap (270)+TX, dinocap-4 [CCN]+TX, dinocap-6 [CCN]+TX, dinocton (1090)+TX, dinopenton (1092)+TX, dinosulfon (1097)+TX, dinoterbon (1098)+TX, dioxathion (1102)+TX, diphenyl sulfone (IUPAC name) (1103)+TX, disulfuram (alternative name) [CCN]+TX, disulfoton (278)+TX, DNOC (282)+TX, dofenapyn (1113)+

TX, doramectin (alternative name) [CCN]+TX, endosulfan (294)+TX, endothion (1121)+TX, EPN (297)+TX, eprinomectin (alternative name) [CCN]+TX, ethion (309)+TX, ethoate-methyl (1134)+TX, etoxazole (320)+TX, etrimfos (1142)+TX, fenazaflor (1147)+TX, fenazaquin (328)+TX, fenbutatin oxide (330)+TX, fenothiocarb (337)+TX, fenpropathrin (342)+TX, fenpyrad (alternative name)+TX, fenpyroximate (345)+TX, fenson (1157)+TX, fentrifanil (1161)+TX, fenvalerate (349)+TX, fipronil (354)+TX, fluacrypyrim (526)+TX, fluazuron (1166)+TX, flubenzimine (1167)+TX, flucycloxuron (366)+TX, flucythrinate (367)+TX, fluenetil (1169)+TX, flufenoxuron (370)+TX, flumethrin (372)+TX, fluorbenside (1174)+TX, fluvalinate (1184)+TX, FMC 1137 (development code) (1185)+TX, formetanate (405)+TX, formetanate hydrochloride (405)+TX, formothion (1192)+TX, formparanate (1193)+TX, gamma-HCH (430)+TX, glyodin (1205)+TX, halfenprox (424)+TX, heptenophos (432)+TX, hexadecyl cyclopropanecarboxylate (IUPAC/Chemical Abstracts name) (1216)+TX, hexythiazox (441)+TX, iodomethane (IUPAC name) (542)+TX, isocarbophos (alternative name) (473)+TX, isopropyl 0-(methoxyaminothiophosphoryl)salicylate (IUPAC name) (473)+TX, ivermectin (alternative name) [CCN]+TX, jasmolin I (696)+TX, jasmolin II (696)+TX, jodfenphos (1248)+TX, lindane (430)+TX, lufenuron (490)+TX, malathion (492)+TX, malonoben (1254)+TX, mecarbam (502)+TX, mephosfolan (1261)+TX, mesulfen (alternative name) [CCN]+TX, methacrifos (1266)+TX, methamidophos (527)+TX, methidathion (529)+TX, methiocarb (530)+TX, methomyl (531)+TX, methyl bromide (537)+TX, metolcarb (550)+TX, mevinphos (556)+TX, mexacarbate (1290)+TX, milbemectin (557)+TX, milbemycin oxime (alternative name) [CCN]+TX, mipafox (1293)+TX, monocrotophos (561)+TX, morphothion (1300)+TX, moxidectin (alternative name) [CCN]+TX, naled (567)+TX, NC-184 (compound code)+TX, NC-526 (compound code)+TX, nifluridide (1309)+TX, nikkomycins (alternative name) [CCN]+TX, nitrilacarb (1526)+TX, nitrilacarb 1:1 zinc chloride complex (1526)+TX, NNI-0101 (compound code)+TX, NNI-0250 (compound code)+TX, omethoate (594)+TX, oxamyl (602)+TX, oxydeprofos (1324)+TX, oxydisulfoton (1325)+TX, pp'-DDT (219)+TX, parathion (615)+TX, permethrin (626)+TX, petroleum oils (alternative name) (628)+TX, phenkapton (1330)+TX, phenthoate (631)+TX, phorate (636)+TX, phosalone (637)+TX, phosfolan (1338)+TX, phosmet (638)+TX, phosphamidon (639)+TX, phoxim (642)+TX, pirimiphos-methyl (652)+TX, polychlorotrpenes (traditional name) (1347)+TX, polynactins (alternative name) (653)+TX, proclonol (1350)+TX, profenofos (662)+TX, promacyl (1354)+TX, propargite (671)+TX, propetamphos (673)+TX, propoxur (678)+TX, prothidathion (1526)+TX, prothoate (1362)+TX, pyrethrin I (696)+TX, pyrethrin II (696)+TX, pyrethrins (696)+TX, pyridaben (699)+TX, pyridaphenthion (701)+TX, pyrimidifen (706)+TX, pyrimitate (1370)+TX, quinalphos (711)+TX, quintiofos (1381)+TX, R-1492 (development code) (1382)+TX, RA-17 (development code) (1383)+TX, rotenone (722)+TX, schradan (1389)+TX, sebufos (alternative name)+TX, selamectin (alternative name) [CCN]+TX, SI-0009 (compound code)+TX, sophamide (1402)+TX, spirodiclofen (738)+TX, spiromesifen (739)+TX, SSI-121 (development code) (1404)+TX, sulfuram (alternative name) [CCN]+TX, sulfluramid (750)+TX, sulfotep (753)+TX, sulfur (754)+TX, SZI-121 (development code) (757)+TX, tau-fluvalinate (398)+TX, tebufenpyrad (763)+TX, TEPP (1417)+TX, terbam (alternative name)+TX, tetrachlorvinphos (777)+TX, tetradifon (786)+TX, tetranactin (alternative name) (653)+TX, tetrasul (1425)+TX, thiafenox (alternative name)+TX, thiocarboxime (1431)+TX, thiofanox (800)+TX, thiometon (801)+TX, thioquinox (1436)+TX, thuringiensin (alternative name) [CCN]+TX, triamiphos (1441)+TX, triarathene (1443)+TX, triazophos (820)+TX, triazuron (alternative name)+TX, trichlorfon (824)+TX, trifenofos (1455)+TX, trinactin (alternative name) (653)+TX, vamidothion (847)+TX, vaniliprole [CCN] and YI-5302 (compound code)+TX, an algicide selected from the group of substances consisting of bethoxazin [CCN]+TX, copper dioctanoate (IUPAC name) (170)+TX, copper sulfate (172)+TX, cybutryne [CCN]+TX, dichlone (1052)+TX, dichlorophen (232)+TX, endothal (295)+TX, fentin (347)+TX, hydrated lime [CCN]+TX, nabam (566)+TX, quinoclamine (714)+TX, quinonamid (1379)+TX, simazine (730)+TX, triphenyltin acetate (IUPAC name) (347) and triphenyltin hydroxide (IUPAC name) (347)+TX, an anthelmintic selected from the group of substances consisting of abamectin (1)+TX, crufomate (1011)+TX, doramectin (alternative name) [CCN]+TX, emamectin (291)+TX, emamectin benzoate (291)+TX, eprinomectin (alternative name) [CCN]+TX, ivermectin (alternative name) [CCN]+TX, milbemycin oxime (alternative name) [CCN]+TX, moxidectin (alternative name) [CCN]+TX, piperazine [CCN]+TX, selamectin (alternative name) [CCN]+TX, spinosad (737) and thiophanate (1435)+TX, an avicide selected from the group of substances consisting of chloralose (127)+TX, endrin (1122)+TX, fenthion (346)+TX, pyridin-4-amine (IUPAC name) (23) and strychnine (745)+TX, a bactericide selected from the group of substances consisting of 1-hydroxy-1H-pyridine-2-thione (IUPAC name) (1222)+TX, 4-(quinoxalin-2-ylamino)benzenesulfonamide (IUPAC name) (748)+TX, 8-hydroxyquinoline sulfate (446)+TX, bronopol (97)+TX, copper dioctanoate (IUPAC name) (170)+TX, copper hydroxide (IUPAC name) (169)+TX, cresol [CCN]+TX, dichlorophen (232)+TX, dipyrithione (1105)+TX, dodicin (1112)+TX, fenaminosulf (1144)+TX, formaldehyde (404)+TX, hydrargaphen (alternative name) [CCN]+TX, kasugamycin (483)+TX, kasugamycin hydrochloride hydrate (483)+TX, nickel bis(dimethyldithiocarbamate) (IUPAC name) (1308)+TX, nitrapyrin (580)+TX, octhilinone (590)+TX, oxolinic acid (606)+TX, oxytetracycline (611)+TX, potassium hydroxyquinoline sulfate (446)+TX, probenazole (658)+TX, streptomycin (744)+TX, streptomycin sesquisulfate (744)+TX, tecloftalam (766)+TX, and thiomersal (alternative name) [CCN]+TX, a biological agent selected from the group of substances consisting of *Adoxophyes orana* GV (alternative name) (12)+TX, *Agrobacterium radiobacter* (alternative name) (13)+TX, *Amblyseius* spp. (alternative name) (19)+TX, *Anagrapha falcifera* NPV (alternative name) (28)+TX, *Anagrus atomus* (alternative name) (29)+TX, *Aphelinus abdominalis* (alternative name) (33)+TX, *Aphidius colemani* (alternative name) (34)+TX, *Aphidoletes aphidimyza* (alternative name) (35)+TX, *Autographa californica* NPV (alternative name) (38)+

TX, *Bacillus firmus* (alternative name) (48)+TX, *Bacillus sphaericus* Neide (scientific name) (49)+TX, *Bacillus thuringiensis* Berliner (scientific name) (51)+TX, *Bacillus thuringiensis* subsp. *aizawai* (scientific name) (51)+TX, *Bacillus thuringiensis* subsp. *israelensis* (scientific name) (51)+TX, *Bacillus thuringiensis* subsp. *japonensis* (scientific name) (51)+TX, *Bacillus thuringiensis* subsp. *kurstaki* (scientific name) (51)+TX, *Bacillus thuringiensis* subsp. *tenebrionis* (scientific name) (51)+TX, *Beauveria bassiana* (alternative name) (53)+TX, *Beauveria brongniartii* (alternative name) (54)+TX, *Chrysoperla carnea* (alternative name) (151)+TX, *Cryptolaemus montrouzieri* (alternative name) (178)+TX, *Cydia pomonella* GV (alternative name) (191)+TX, *Dacnusa sibirica* (alternative name) (212)+TX, *Diglyphus isaea* (alternative name) (254)+TX, *Encarsia formosa* (scientific name) (293)+TX, *Eretmocerus eremicus* (alternative name) (300)+TX, *Helicoverpa zea* NPV (alternative name) (431)+TX, *Heterorhabditis bacteriophora* and *H. megidis* (alternative name) (433)+TX, *Hippodamia convergens* (alternative name) (442)+TX, *Leptomastix dactylopii* (alternative name) (488)+TX, *Macrolophus caliginosus* (alternative name) (491)+TX, *Mamestra brassicae* NPV (alternative name) (494)+TX, *Metaphycus helvolus* (alternative name) (522)+TX, *Metarhizium anisopliae* var. *acridum* (scientific name) (523)+TX, *Metarhizium anisopliae* var. *anisopliae* (scientific name) (523)+TX, *Neodiprion sertifer* NPV and *N. lecontei* NPV (alternative name) (575)+TX, *Orius* spp. (alternative name) (596)+TX, *Paecilomyces fumosoroseus* (alternative name) (613)+TX, *Phytoseiulus persimilis* (alternative name) (644)+TX, *Spodoptera exigua* multicapsid nuclear polyhedrosis virus (scientific name) (741)+TX, *Steinemema bibionis* (alternative name) (742)+TX, *Steinemema carpocapsae* (alternative name) (742)+TX, *Steinemema feltiae* (alternative name) (742)+TX, *Steinemema glaseri* (alternative name) (742)+TX, *Steinemema riobrave* (alternative name) (742)+TX, *Steinemema riobravis* (alternative name) (742)+TX, *Steinemema scapterisci* (alternative name) (742)+TX, *Steinemema* spp. (alternative name) (742)+TX, *Trichogramma* spp. (alternative name) (826)+TX, *Typhlodromus occidentalis* (alternative name) (844) and *Verticillium lecanii* (alternative name) (848)+TX, a soil sterilant selected from the group of substances consisting of iodomethane (IUPAC name) (542) and methyl bromide (537)+TX, a chemosterilant selected from the group of substances consisting of apholate [CCN]+TX, bisazir (alternative name) [CCN]+TX, busulfan (alternative name) [CCN]+TX, diflubenzuron (250)+TX, dimatif (alternative name) [CCN]+TX, hemel [CCN]+TX, hempa [CCN]+TX, metepa [CCN]+TX, methiotepa [CCN]+TX, methyl apholate [CCN]+TX, morzid [CCN]+TX, penfluoron (alternative name) [CCN]+TX, tepa [CCN]+TX, thiohempa (alternative name) [CCN]+TX, thiotepa (alternative name) [CCN]+TX, tretamine (alternative name) [CCN] and uredepa (alternative name) [CCN]+TX, an insect pheromone selected from the group of substances consisting of (E)-dec-5-en-1-yl acetate with (E)-dec-5-en-1-ol (IUPAC name) (222)+TX, (E)-tridec-4-en-1-yl acetate (IUPAC name) (829)+TX, (E)-6-methylhept-2-en-4-ol (IUPAC name) (541)+TX, (E,Z)-tetradeca-4,10-dien-1-yl acetate (IUPAC name) (779)+TX, (Z)-dodec-7-en-1-yl acetate (IUPAC name) (285)+TX, (Z)-hexadec-11-enal (IUPAC name) (436)+TX, (Z)-hexadec-11-en-1-yl acetate (IUPAC name) (437)+TX, (Z)-hexadec-13-en-11-yn-1-yl acetate (IUPAC name) (438)+TX, (Z)-icos-13-en-10-one (IUPAC name) (448)+TX, (Z)-tetradec-7-en-1-al (IUPAC name) (782)+TX, (Z)-tetradec-9-en-1-ol (IUPAC name) (783)+TX, (Z)-tetradec-9-en-1-yl acetate (IUPAC name) (784)+TX, (7E,9Z)-dodeca-7,9-dien-1-yl acetate (IUPAC name) (283)+TX, (9Z,11E)-tetradeca-9,11-dien-1-yl acetate (IUPAC name) (780)+TX, (9Z,12E)-tetradeca-9,12-dien-1-yl acetate (IUPAC name) (781)+TX, 14-methyloctadec-1-ene (IUPAC name) (545)+TX, 4-methylnonan-5-ol with 4-methylnonan-5-one (IUPAC name) (544)+TX, alpha-multistriatin (alternative name) [CCN]+TX, brevicomin (alternative name) [CCN]+TX, codlelure (alternative name) [CCN]+TX, codlemone (alternative name) (167)+TX, cuelure (alternative name) (179)+TX, disparlure (277)+TX, dodec-8-en-1-yl acetate (IUPAC name) (286)+TX, dodec-9-en-1-yl acetate (IUPAC name) (287)+TX, dodeca-8+TX, 10-dien-1-yl acetate (IUPAC name) (284)+TX, dominicalure (alternative name) [CCN]+TX, ethyl 4-methyloctanoate (IUPAC name) (317)+TX, eugenol (alternative name) [CCN]+TX, frontalin (alternative name) [CCN]+TX, gossyplure (alternative name) (420)+TX, grandlure (421)+TX, grandlure I (alternative name) (421)+TX, grandlure II (alternative name) (421)+TX, grandlure III (alternative name) (421)+TX, grandlure IV (alternative name) (421)+TX, hexylure [CCN]+TX, ipsdienol (alternative name) [CCN]+TX, ipsenol (alternative name) [CCN]+TX, japonilure (alternative name) (481)+TX, lineatin (alternative name) [CCN]+TX, litlure (alternative name) [CCN]+TX, looplure (alternative name) [CCN]+TX, medlure [CCN]+TX, megatomoic acid (alternative name) [CCN]+TX, methyl eugenol (alternative name) (526)+TX, muscalure (563)+TX, octadeca-2,13-dien-1-yl acetate (IUPAC name) (588)+TX, octadeca-3,13-dien-1-yl acetate (IUPAC name) (589)+TX, orfralure (alternative name) [CCN]+TX, oryctalure (alternative name) (317)+TX, ostramone (alternative name) [CCN]+TX, siglure [CCN]+TX, sordidin (alternative name) (736)+TX, sulcatol (alternative name) [CCN]+TX, tetradec-11-en-1-yl acetate (IUPAC name) (785)+TX, trimedlure (839)+TX, trimedlure A (alternative name) (839)+TX, trimedlure $B_1$ (alternative name) (839)+TX, trimedlure $B_2$ (alternative name) (839)+TX, trimedlure C (alternative name) (839) and trunc-call (alternative name) [CCN]+TX, an insect repellent selected from the group of substances consisting of 2-(octylthio)-ethanol (IUPAC name) (591)+TX, butopyronoxyl (933)+TX, butoxy(polypropylene glycol) (936)+TX, dibutyl adipate (IUPAC name) (1046)+TX, dibutyl phthalate (1047)+TX, dibutyl succinate (IUPAC name) (1048)+TX, diethyltoluamide [CCN]+TX, dimethyl carbate [CCN]+TX, dimethyl phthalate [CCN]+TX, ethyl hexanediol (1137)+TX, hexamide [CCN]+TX, methoquin-butyl (1276)+TX, methylneodecanamide [CCN]+TX, oxamate [CCN] and picaridin [CCN]+TX, an insecticide selected from the group of substances consisting of 1-dichloro-1-nitroethane (IUPAC/Chemical Abstracts name) (1058)+TX, 1,1-dichloro-2,2-bis(4-ethylphenyl)ethane (IUPAC name) (1056), +TX, 1,2-dichloropropane (IUPAC/Chemical Abstracts name) (1062)+TX, 1,2-dichloropropane with 1,3-dichloropropene (IUPAC name) (1063)+TX, 1-bromo-2-chloroethane (IUPAC/Chemical Abstracts name) (916)+TX, 2,2, 2-trichloro-1-(3,4-dichlorophenyl)ethyl acetate (IUPAC name) (1451)+TX, 2,2-dichlorovinyl 2-ethylsulfinylethyl methyl phosphate (IUPAC name) (1066)+TX, 2-(1,3-dithiolan-2-yl)phenyl dimethylcarbamate (IUPAC/Chemical Abstracts name) (1109)+TX, 2-(2-butoxyethoxy)ethyl thiocyanate (IUPAC/Chemical Abstracts name) (935)+TX, 2-(4,5-dimethyl-1,3-dioxolan-2-yl)phenyl methylcarbamate (IUPAC/Chemical Abstracts name) (1084)+TX, 2-(4-chloro-3,5-xylyloxy) ethanol (IUPAC name) (986)+TX, 2-chlorovinyl diethyl phosphate (IUPAC name) (984)+TX, 2-imidazolidone (IUPAC name) (1225)+TX, 2-isovalerylindan-1,3-dione (IUPAC name) (1246)+TX, 2-methyl(prop-2-ynyl) aminophenyl methylcarbamate (IUPAC name) (1284)+TX, 2-thiocyanatoethyl laurate (IUPAC name) (1433)+TX, 3-bromo-1-chloroprop-1-ene (IUPAC name) (917)+TX, 3-methyl-1-phenylpyrazol-5-yl dimethylcarbamate (IUPAC name) (1283)+TX, 4-methyl(prop-2-ynyl)amino-3,5-xylyl methylcarbamate (IUPAC name) (1285)+TX, 5,5-dimethyl-3-oxocyclohex-1-enyl dimethylcarbamate (IUPAC name) (1085)+TX, abamectin (1)+TX, acephate (2)+TX, acetamiprid (4)+TX, acethion (alternative name) [CCN]+TX, acetoprole [CCN]+TX, acrinathrin (9)+TX, acrylonitrile (IUPAC name) (861)+TX, alanycarb (15)+TX, aldicarb (16)+TX, aldoxycarb (863)+TX, aldrin (864)+TX, allethrin (17)+TX, allosamidin (alternative name) [CCN]+TX, allyxycarb (866)+TX, alpha-cypermethrin (202)+TX, alpha-ecdysone (alternative name) [CCN]+TX, aluminium phosphide (640)+TX, amidithion (870)+TX, amidothioate (872)+TX, aminocarb (873)+TX, amiton (875)+TX, amiton hydrogen oxalate (875)+TX, amitraz (24)+TX, anabasine (877)+TX, athidathion (883)+TX, AVI 382 (compound code)+TX, AZ 60541 (compound code)+TX, azadirachtin (alternative name) (41)+TX, azamethiphos (42)+TX, azinphos-ethyl (44)+TX, azinphos-methyl (45)+TX, azothoate (889)+TX, *Bacillus thuringiensis* delta endotoxins (alternative name) (52)+TX, barium hexafluorosilicate (alternative name) [CCN]+TX, barium polysulfide (IUPAC/Chemical Abstracts name) (892)+TX, barthrin [CCN]+TX, Bayer 22/190 (development code) (893)+TX, Bayer 22408 (development code) (894)+TX, bendiocarb (58)+TX, benfuracarb (60)+TX, bensultap (66)+TX, beta-cyfluthrin (194)+TX, beta-cypermethrin (203)+TX, bifenthrin (76)+TX, bioallethrin (78)+TX, bioallethrin S-cyclopentenyl isomer (alternative name) (79)+TX, bioethanomethrin [CCN]+TX, biopermethrin (908)+TX, bioresmethrin (80)+TX, bis(2-chloroethyl) ether (IUPAC name) (909)+TX, bistrifluoron (83)+TX, borax (86)+TX, brofenvalerate (alternative name)+TX, bromfenvinfos (914)+TX, bromocyclen (918)+TX, bromo-DDT (alternative name) [CCN]+TX, bromophos (920)+TX, bromophos-ethyl (921)+TX, bufencarb (924)+TX, buprofezin (99)+TX, butacarb (926)+TX, butathiofos (927)+TX, butocarboxim (103)+TX, butonate (932)+TX, butoxycarboxim (104)+TX, butylpyridaben (alternative name)+TX, cadusafos (109)+TX, calcium arsenate [CCN]+TX, calcium cyanide (444)+TX, calcium polysulfide (IUPAC name) (111)+TX, camphechlor (941)+TX, carbanolate (943)+TX, carbaryl (115)+TX, carbofuran (118)+TX, carbon disulfide (IUPAC/Chemical Abstracts name) (945)+TX, carbon tetrachloride (IUPAC name) (946)+TX, carbophenothion (947)+TX, carbosulfan (119)+TX, cartap (123)+TX, cartap hydrochloride (123)+TX, cevadine (alternative name) (725)+TX, chlorbicyclen (960)+TX, chlordane (128)+TX, chlordecone (963)+TX, chlordimeform (964)+TX, chlordimeform hydrochloride (964)+TX, chlorethoxyfos (129)+TX, chlorfenapyr (130)+TX, chlorfenvinphos (131)+TX, chlorfluazuron (132)+TX, chlormephos (136)+TX, chloroform [CCN]+TX, chloropicrin (141)+TX, chlorphoxim (989)+TX, chlorprazophos (990)+TX, chlorpyrifos (145)+TX, chlorpyrifos-methyl (146)+TX, chlorthiophos (994)+TX, chromafenozide (150)+TX, cinerin I (696)+TX, cinerin II (696)+TX, cinerins (696)+TX, cis-resmethrin (alternative name)+TX, cismethrin (80)+TX, clocythrin (alternative name)+TX, cloethocarb (999)+TX, closantel (alternative name) [CCN]+TX, clothianidin (165)+TX, copper acetoarsenite [CCN]+TX, copper arsenate [CCN]+TX, copper oleate [CCN]+TX, coumaphos (174)+TX, coumithoate (1006)+TX, crotamiton (alternative name) [CCN]+TX, crotoxyphos (1010)+TX, crufomate (1011)+TX, cryolite (alternative name) (177)+TX, CS 708 (development code) (1012)+TX, cyanofenphos (1019)+TX, cyanophos (184)+TX, cyanthoate (1020)+TX, cyclethrin [CCN]+TX, cycloprothrin (188)+TX, cyfluthrin (193)+TX, cyhalothrin (196)+TX, cypermethrin (201)+TX, cyphenothrin (206)+TX, cyromazine (209)+TX, cythioate (alternative name) [CCN]+TX, d-limonene (alternative name) [CCN]+TX, d-tetramethrin (alternative name) (788)+TX, DAEP (1031)+TX, dazomet (216)+TX, DDT (219)+TX, decarbofuran (1034)+TX, deltamethrin (223)+TX, demephion (1037)+TX, demephion-O (1037)+TX, demephion-S (1037)+TX, demeton (1038)+TX, demeton-methyl (224)+TX, demeton-O (1038)+TX, demeton-O-methyl (224)+TX, demeton-S (1038)+TX, demeton-5-methyl (224)+TX, demeton-5-methylsulphon (1039)+TX, diafenthiuron (226)+TX, dialifos (1042)+TX, diamidafos (1044)+TX, diazinon (227)+TX, dicapthon (1050)+TX, dichlofenthion (1051)+TX, dichlorvos (236)+TX, dicliphos (alternative name)+TX, dicresyl (alternative name) [CCN]+TX, dicrotophos (243)+TX, dicyclanil (244)+TX, dieldrin (1070)+TX, diethyl 5-methylpyrazol-3-yl phosphate (IUPAC name) (1076)+TX, diflubenzuron (250)+TX, dilor (alternative name) [CCN]+TX, dimefluthrin [CCN]+TX, dimefox (1081)+TX, dimetan (1085)+TX, dimethoate (262)+TX, dimethrin (1083)+TX, dimethylvinphos (265)+TX, dimetilan (1086)+TX, dinex (1089)+TX, dinex-diclexine (1089)+TX, dinoprop (1093)+TX, dinosam (1094)+TX, dinoseb (1095)+TX, dinotefuran (271)+TX, diofenolan (1099)+TX, dioxabenzofos (1100)+TX, dioxacarb (1101)+TX, dioxathion (1102)+TX, disulfoton (278)+TX, dithicrofos (1108)+TX, DNOC (282)+TX, doramectin (alternative name) [CCN]+TX, DSP (1115)+TX, ecdysterone (alternative name) [CCN]+TX, EI 1642 (development code) (1118)+TX, emamectin (291)+TX, emamectin benzoate (291)+TX, EMPC (1120)+TX, empenthrin (292)+TX, endosulfan (294)+TX, endothion (1121)+TX, endrin (1122)+TX, EPBP (1123)+TX, EPN (297)+TX, epofenonane (1124)+TX, eprinomectin (alternative name) [CCN]+TX, esfenvalerate (302)+TX, etaphos (alternative name) [CCN]+TX, ethiofencarb (308)+TX, ethion (309)+TX, ethiprole (310)+TX, ethoate-methyl (1134)+TX, ethoprophos (312)+TX, ethyl formate (IUPAC name) [CCN]+TX, ethyl-DDD (alternative name) (1056)+TX, ethylene dibromide (316)+TX, ethylene dichloride (chemical name) (1136)+TX, ethylene oxide [CCN]+TX, etofenprox (319)+TX, etrimfos (1142)+TX, EXD (1143)+TX, famphur (323)+TX, fenamiphos (326)+TX, fenazaflor (1147)+TX, fenchlorphos (1148)+TX, fenethacarb (1149)+TX, fenfluthrin (1150)+TX, fenitrothion (335)+TX, fenobucarb (336)+TX, fenoxacrim (1153)+TX, fenoxycarb (340)+TX, fenpirithrin (1155)+TX, fenpropathrin (342)+TX, fenpyrad (alternative name)+TX, fensulfothion (1158)+TX, fenthion (346)+TX, fenthion-ethyl [CCN]+TX, fenvalerate (349)+TX, fipronil (354)+TX, flonicamid (358)+TX, flubendiamide (CAS. Reg. No.: 272451-65-7)+TX, flucofuron (1168)+TX, flucycloxuron (366)+TX, flucythrinate (367)+TX, fluenetil (1169)+TX, flufenerim [CCN]+TX, flufenoxuron (370)+TX, flufenprox (1171)+TX, flumethrin (372)+TX, fluvalinate (1184)+TX, FMC 1137 (development code) (1185)+TX, fonofos (1191)+TX, formetanate (405)+TX, formetanate hydrochloride (405)+TX, formothion (1192)+TX, formparanate (1193)+TX, fosmethilan (1194)+TX, fospirate (1195)+TX, fosthiazate (408)+TX, fosthietan (1196)+TX, furathiocarb (412)+TX, furethrin (1200)+TX, gamma-cyhalothrin (197)+TX, gamma-HCH (430)+TX, guazatine (422)+TX, guazatine acetates (422)+TX, GY-81 (development code) (423)+TX, halfenprox (424)+TX, halofenozide (425)+TX, HCH (430)+TX, HEOD (1070)+TX, heptachlor (1211)+TX, heptenophos (432)+TX, heterophos [CCN]+TX, hexaflumuron (439)+TX, HHDN (864)+TX, hydramethylnon (443)+TX, hydrogen cyanide (444)+TX, hydroprene (445)+TX, hyquincarb (1223)+TX, imidacloprid (458)+TX, imiprothrin (460)+TX, indoxacarb (465)+TX, iodomethane (IUPAC name) (542)+TX, IPSP (1229)+TX, isazofos (1231)+TX, isobenzan (1232)+TX, isocarbophos (alternative name) (473)+TX, isodrin (1235)+TX, isofenphos (1236)+TX, isolane (1237)+TX, isoprocarb (472)+TX, isopropyl O-(methoxyaminothiophosphoryl)salicylate (IUPAC name) (473)+TX, isoprothiolane (474)+TX, isothioate (1244)+TX, isoxathion (480)+TX, ivermectin (alternative name) [CCN]+TX, jasmolin I (696)+TX, jasmolin II (696)+TX, jodfenphos (1248)+TX, juvenile hormone I (alternative name) [CCN]+TX, juvenile hormone II (alternative name) [CCN]+TX, juvenile hormone III (alternative name) [CCN]+TX, kelevan (1249)+TX, kinoprene (484)+TX, lambda-cyhalothrin (198)+TX, lead arsenate [CCN]+TX, lepimectin (CCN)+TX, leptophos (1250)+TX, lindane (430)+TX, lirimfos (1251)+TX, lufenuron (490)+TX, lythidathion (1253)+TX, m-cumenyl methylcarbamate (IUPAC name) (1014)+TX, magnesium phosphide (IUPAC name) (640)+TX, malathion (492)+TX, malonoben (1254)+TX, mazidox (1255)+TX, mecarbam (502)+TX, mecarphon (1258)+TX, menazon (1260)+TX, mephosfolan (1261)+TX, mercurous chloride (513)+TX, mesulfenfos (1263)+TX, metaflumizone (CCN)+TX, metam (519)+TX, metam-potassium (alternative name) (519)+TX, metam-sodium (519)+TX, methacrifos (1266)+TX, methamidophos (527)+TX, methanesulfonyl fluoride (IUPAC/Chemical Abstracts name) (1268)+TX, methidathion (529)+TX, methiocarb (530)+TX, methocrotophos (1273)+TX, methomyl (531)+TX, methoprene (532)+TX, methoquin-butyl (1276)+TX, methothrin (alternative name) (533)+TX, methoxychlor (534)+TX, methoxyfenozide (535)+TX, methyl bromide (537)+TX, methyl isothiocyanate (543)+TX, methylchloroform (alternative name) [CCN]+TX, methylene chloride [CCN]+TX, metofluthrin [CCN]+TX, metolcarb (550)+TX, metoxadiazone (1288)+TX, mevinphos (556)+TX, mexacarbate (1290)+TX, milbemectin (557)+TX, milbemycin oxime (alternative name) [CCN]+TX, mipafox (1293)+TX, mirex (1294)+TX, monocrotophos (561)+TX, morphothion (1300)+TX, moxidectin (alternative name) [CCN]+TX, naftalofos (alternative name) [CCN]+TX, naled (567)+TX, naphthalene (IUPAC/Chemical Abstracts name) (1303)+TX, NC-170 (development code) (1306)+TX, NC-184 (compound code)+TX, nicotine (578)+TX, nicotine sulfate (578)+TX, nifluridide (1309)+TX, nitenpyram (579)+TX, nithiazine (1311)+TX, nitrilacarb (1526)+TX, nitrilacarb 1:1 zinc chloride complex (1526)+TX, NNI-0101 (compound code)+TX, NNI-0250 (compound code)+TX, nornicotine (traditional name) (1319)+TX, novaluron (585)+TX, noviflumuron (586)+TX, O-5-dichloro-4-iodophenyl O-ethyl ethylphosphonothioate (IUPAC name) (1057)+TX, O,O-diethyl O-4-methyl-2-oxo-2H-chromen-7-yl phosphorothioate (IUPAC name) (1074)+TX, O,O-diethyl O-6-methyl-2-propylpyrimidin-4-yl phosphorothioate (IUPAC name) (1075)+TX, O,O,O',O'-tetrapropyl dithiopyrophosphate (IUPAC name) (1424)+TX, oleic acid (IUPAC name) (593)+TX, omethoate (594)+TX, oxamyl (602)+TX, oxydemeton-methyl (609)+TX, oxydeprofos (1324)+TX, oxydisulfoton (1325)+TX, pp'-DDT (219)+TX, para-dichlorobenzene [CCN]+TX, parathion (615)+TX, parathion-methyl (616)+TX, penfluoron (alternative name) [CCN]+TX, pentachlorophenol (623)+TX, pentachlorophenyl laurate (IUPAC name) (623)+TX, permethrin (626)+TX, petroleum oils (alternative name) (628)+TX, PH 60-38 (development code) (1328)+TX, phenkapton (1330)+TX, phenothrin (630)+TX, phenthoate (631)+TX, phorate (636)+TX, phosalone (637)+TX, phosfolan (1338)+TX, phosmet (638)+TX, phosnichlor (1339)+TX, phosphamidon (639)+TX, phosphine (IUPAC name) (640)+TX, phoxim (642)+TX, phoxim-methyl (1340)+TX, pirimetaphos (1344)+TX, pirimicarb (651)+TX, pirimiphos-ethyl (1345)+TX, pirimiphos-methyl (652)+TX, polychlorodicyclopentadiene isomers (IUPAC name) (1346)+TX, polychloroterpenes (traditional name) (1347)+TX, potassium arsenite [CCN]+TX, potassium thiocyanate [CCN]+TX, prallethrin (655)+TX, precocene I (alternative name) [CCN]+TX, precocene II (alternative name) [CCN]+TX, precocene III (alternative name) [CCN]+TX, primidophos (1349)+TX, profenofos (662)+TX, profluthrin [CCN]+TX, promacyl (1354)+TX, promecarb (1355)+TX, propaphos (1356)+TX, propetamphos (673)+TX, propoxur (678)+TX, prothidathion (1526)+TX, prothiofos (686)+TX, prothoate (1362)+TX, protrifenbute [CCN]+TX, pymetrozine (688)+TX, pyraclofos (689)+TX, pyrazophos (693)+TX, pyresmethrin (1367)+TX, pyrethrin I (696)+TX, pyrethrin II (696)+TX, pyrethrins (696)+TX, pyridaben (699)+TX, pyridalyl (700)+TX, pyridaphenthion (701)+TX, pyrimidifen (706)+TX, pyrimitate (1370)+TX, pyriproxyfen (708)+TX, quassia (alternative name) [CCN]+TX, quinalphos (711)+TX, quinalphos-methyl (1376)+TX, quinothion (1380)+TX, quintiofos (1381)+TX, R-1492 (development code) (1382)+TX, rafoxanide (alternative name) [CCN]+TX, resmethrin (719)+TX, rotenone (722)+TX, RU 15525 (development code) (723)+TX, RU 25475 (development code) (1386)+TX, ryania (alternative name) (1387)+TX, ryanodine (traditional name) (1387)+TX, sabadilla (alternative name) (725)+TX, schradan (1389)+TX, sebufos (alternative name)+TX, selamectin (alternative name) [CCN]+TX, SI-0009 (compound code)+TX, SI-0205 (compound code)+TX, SI-0404 (compound code)+TX, SI-0405 (compound code)+TX, silafluofen (728)+TX, SN 72129 (development code) (1397)+TX, sodium arsenite [CCN]+TX, sodium cyanide (444)+TX, sodium fluoride (IUPAC/Chemical Abstracts name) (1399)+TX, sodium hexafluorosilicate (1400)+TX, sodium pentachlorophenoxide (623)+TX, sodium selenate (IUPAC name) (1401)+TX, sodium thiocyanate [CCN]+TX, sophamide (1402)+TX, spinosad (737)+TX, spiromesifen (739)+TX, spirotetrmat (CCN)+TX, sulcofuron (746)+TX, sulcofuron-sodium (746)+TX, sulfluramid (750)+TX, sulfotep (753)+TX, sulfuryl fluoride (756)+TX, sulprofos (1408)+TX, tar oils (alternative name) (758)+TX, tau-fluvalinate (398)+TX, tazimcarb (1412)+TX, TDE (1414)+TX, tebufenozide (762)+TX, tebufenpyrad (763)+TX, tebupirimfos (764)+TX, teflubenzuron (768)+TX, tefluthrin (769)+TX, temephos (770)+TX, TEPP (1417)+TX, terallethrin (1418)+TX, terbam (alternative name)+TX, terbufos (773)+TX, tetrachloroethane [CCN]+TX, tetrachlorvinphos (777)+TX, tetramethrin (787)+TX, theta-cypermethrin (204)+TX, thiacloprid (791)+TX, thiafenox (alternative name)+TX, thiamethoxam (792)+TX, thicrofos (1428)+TX, thiocarboxime (1431)+TX, thiocyclam (798)+TX, thiocyclam hydrogen oxalate (798)+TX, thiodicarb (799)+TX, thiofanox (800)+TX, thiometon (801)+TX, thionazin (1434)+TX, thiosultap (803)+TX, thiosultap-sodium (803)+TX, thuringiensin (alternative name) [CCN]+TX, tolfenpyrad (809)+TX, tralomethrin (812)+TX, transfluthrin (813)+TX, transpermethrin (1440)+TX, triamiphos (1441)+TX, triazamate (818)+TX, triazophos (820)+TX, triazuron (alternative name)+TX, trichlorfon (824)+TX, trichlormetaphos-3 (alternative name) [CCN]+TX, trichloronat (1452)+TX, trifenofos (1455)+TX, triflumuron (835)+TX, trimethacarb (840)+TX, triprene (1459)+TX, vamidothion (847)+TX, vaniliprole [CCN]+TX, veratridine (alternative name) (725)+TX, veratrine (alternative name) (725)+TX, XMC (853)+TX, xylylcarb (854)+TX, YI-5302 (compound code)+TX, zeta-cypermethrin (205)+TX, zetamethrin (alternative name)+TX, zinc phosphide (640)+TX, zolaprofos (1469) and ZXI 8901 (development code) (858)+TX, a molluscicide selected from the group of substances consisting of bis(tributyltin) oxide (IUPAC name) (913)+TX, bromoacetamide [CCN]+TX, calcium arsenate [CCN]+TX, cloethocarb (999)+TX, copper acetoarsenite [CCN]+TX, copper sulfate (172)+TX, fentin (347)+TX, ferric phosphate (IUPAC name) (352)+TX, metaldehyde (518)+TX, methiocarb (530)+TX, niclosamide (576)+TX, niclosamide-olamine (576)+TX, pentachlorophenol (623)+TX, sodium pentachlorophenoxide (623)+TX, tazimcarb (1412)+TX, thiodicarb (799)+TX, tributyltin oxide (913)+TX, trifenmorph (1454)+TX, trimethacarb (840)+TX, triphenyltin acetate (IUPAC name) (347) and triphenyltin hydroxide (IUPAC name) (347)+TX, a nematicide selected from the group of substances consisting of AKD-3088 (compound code)+TX, 1,2-dibromo-3-chloropropane (IUPAC/Chemical Abstracts name) (1045)+TX, 1,2-dichloropropane (IUPAC/Chemical Abstracts name) (1062)+TX, 1,2-dichloropropane with 1,3-dichloropropene (IUPAC name) (1063)+TX, 1,3-dichloropropene (233)+TX, 3,4-dichlorotetrahydrothiophene 1,1-dioxide (IUPAC/Chemical Abstracts name) (1065)+TX, 3-(4-chlorophenyl)-5-methylrhodanine (IUPAC name) (980)+TX, 5-methyl-6-thioxo-1,3,5-thiadiazinan-3-ylacetic acid (IUPAC name) (1286)+TX, 6-isopentenylaminopurine (alternative name) (210)+TX, abamectin (1)+TX, acetoprole [CCN]+TX, alanycarb (15)+TX, aldicarb (16)+TX, aldoxycarb (863)+TX, AZ 60541 (compound code)+TX, benclothiaz [CCN]+TX, benomyl (62)+TX, butylpyridaben (alternative name)+TX, cadusafos (109)+TX, carbofuran (118)+TX, carbon disulfide (945)+TX, carbosulfan (119)+TX, chloropicrin (141)+TX, chlorpyrifos (145)+TX, cloethocarb (999)+TX, cytokinins (alternative name) (210)+TX, dazomet (216)+TX, DBCP (1045)+TX, DCIP (218)+TX, diamidafos (1044)+TX, dichlofenthion (1051)+TX, dicliphos (alternative name)+TX, dimethoate (262)+TX, doramectin (alternative name) [CCN]+TX, emamectin (291)+TX, emamectin benzoate (291)+TX, eprinomectin (alternative name) [CCN]+TX, ethoprophos (312)+TX, ethylene dibromide (316)+TX, fenamiphos (326)+TX, fenpyrad (alternative name)+TX, fensulfothion (1158)+TX, fosthiazate (408)+TX, fosthietan (1196)+TX, furfural (alternative name) [CCN]+TX, GY-81 (development code) (423)+TX, heterophos [CCN]+TX, iodomethane (IUPAC name) (542)+TX, isamidofos (1230)+TX, isazofos (1231)+TX, ivermectin (alternative name) [CCN]+TX, kinetin (alternative name) (210)+TX, mecarphon (1258)+TX, metam (519)+TX, metam-potassium (alternative name) (519)+TX, metam-sodium (519)+TX, methyl bromide (537)+TX, methyl isothiocyanate (543)+TX, milbemycin oxime (alternative name) [CCN]+TX, moxidectin (alternative name) [CCN]+TX, *Myrothecium verrucaria* composition (alternative name) (565)+TX, NC-184 (compound code)+TX, oxamyl (602)+TX, phorate (636)+TX, phosphamidon (639)+TX, phosphocarb [CCN]+TX, sebufos (alternative name)+TX, selamectin (alternative name) [CCN]+TX, spinosad (737)+TX, terbam (alternative name)+TX, terbufos (773)+TX, tetrachlorothiophene (IUPAC/Chemical Abstracts name) (1422)+TX, thiafenox (alternative name)+TX, thionazin (1434)+TX, triazophos (820)+TX, triazuron (alternative name)+TX, xylenols [CCN]+TX, YI-5302 (compound code) and zeatin (alternative name) (210)+TX, a nitrification inhibitor selected from the group of substances consisting of potassium ethylxanthate [CCN] and nitrapyrin (580)+TX, a plant activator selected from the group of substances consisting of acibenzolar (6)+TX, acibenzolar-5-methyl (6)+TX, probenazole (658) and *Reynoutria sachalinensis* extract (alternative name) (720)+TX, a rodenticide selected from the group of substances consisting of 2-isovalerylindan-1,3-dione (IUPAC name) (1246)+TX, 4-(quinoxalin-2-ylamino)benzenesulfonamide (IUPAC name) (748)+TX, alpha-chlorohydrin [CCN]+TX, aluminium phosphide (640)+TX, antu (880)+TX, arsenous oxide (882)+TX, barium carbonate (891)+TX, bisthiosemi (912)+TX, brodifacoum (89)+TX, bromadiolone (91)+TX, bromethalin (92)+TX, calcium cyanide (444)+TX, chloralose (127)+TX, chlorophacinone (140)+TX, cholecalciferol (alternative name) (850)+TX, coumachlor (1004)+TX, coumafuryl (1005)+TX, coumatetralyl (175)+TX, crimidine (1009)+TX, difenacoum (246)+TX, difethialone (249)+TX, diphacinone (273)+TX, ergocalciferol (301)+TX, flocoumafen (357)+TX, fluoroacetamide (379)+TX, flupropadine (1183)+TX, flupropadine hydrochloride (1183)+TX, gamma-HCH (430)+TX, HCH (430)+TX, hydrogen cyanide (444)+TX, iodomethane (IUPAC name) (542)+TX, lindane (430)+TX, magnesium phosphide (IUPAC name) (640)+TX, methyl bromide (537)+

TX, norbormide (1318)+TX, phosacetim (1336)+TX, phosphine (IUPAC name) (640)+TX, phosphorus [CCN]+TX, pindone (1341)+TX, potassium arsenite [CCN]+TX, pyrinuron (1371)+TX, scilliroside (1390)+TX, sodium arsenite [CCN]+TX, sodium cyanide (444)+TX, sodium fluoroacetate (735)+TX, strychnine (745)+TX, thallium sulfate [CCN]+TX, warfarin (851) and zinc phosphide (640)+TX, a synergist selected from the group of substances consisting of 2-(2-butoxyethoxy)-ethyl piperonylate (IUPAC name) (934)+TX, 5-(1,3-benzodioxol-5-yl)-3-hexylcyclohex-2-enone (IUPAC name) (903)+TX, farnesol with nerolidol (alternative name) (324)+TX, MB-599 (development code) (498)+TX, MGK 264 (development code) (296)+TX, piperonyl butoxide (649)+TX, piprotal (1343)+TX, propyl isomer (1358)+TX, S421 (development code) (724)+TX, sesamex (1393)+TX, sesasmolin (1394) and sulfoxide (1406)+TX, an animal repellent selected from the group of substances consisting of anthraquinone (32)+TX, chloralose (127)+TX, copper naphthenate [CCN]+TX, copper oxychloride (171)+TX, diazinon (227)+TX, dicyclopentadiene (chemical name) (1069)+TX, guazatine (422)+TX, guazatine acetates (422)+TX, methiocarb (530)+TX, pyridin-4-amine (IUPAC name) (23)+TX, thiram (804)+TX, trimethacarb (840)+TX, zinc naphthenate [CCN] and ziram (856)+TX, a virucide selected from the group of substances consisting of imanin (alternative name) [CCN] and ribavirin (alternative name) [CCN]+TX, a wound protectant selected from the group of substances consisting of mercuric oxide (526)+TX, octhilinone (590) and thiophanate-methyl (802)+TX, an insecticide selected from the group consisting of the compound of formula A-1

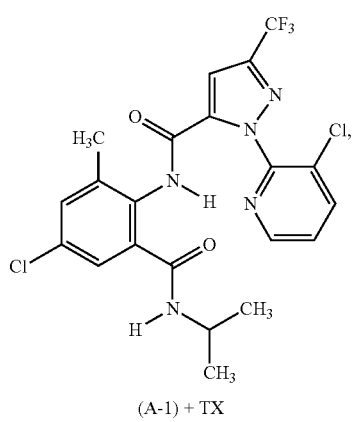

(A-1) + TX

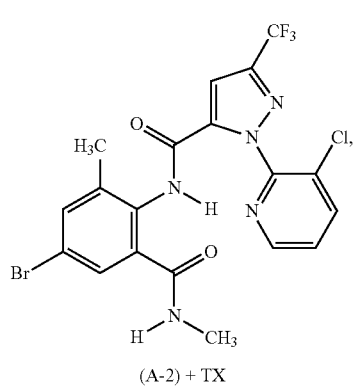

the formula A-2

(A-2) + TX

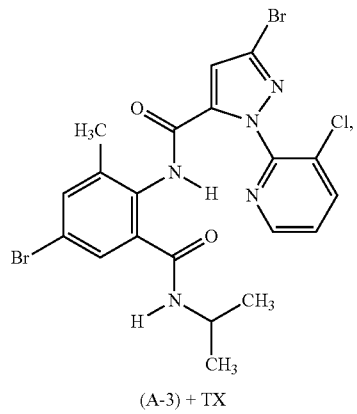

the formula A-3

(A-3) + TX

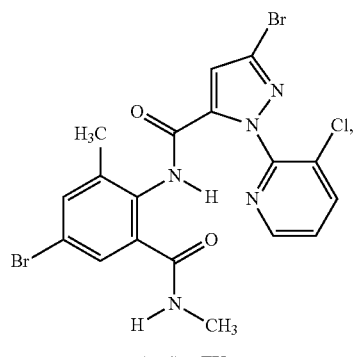

the formula A-4

(A-4) + TX

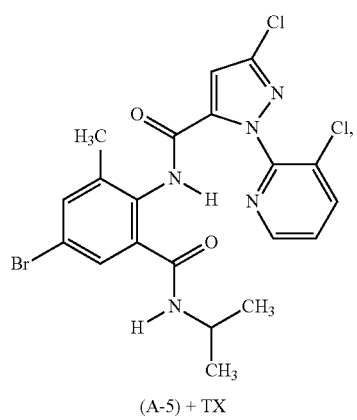

the formula A-5

(A-5) + TX

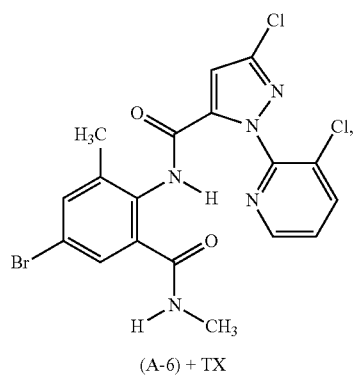

the formula A-6

(A-6) + TX the formula A-7
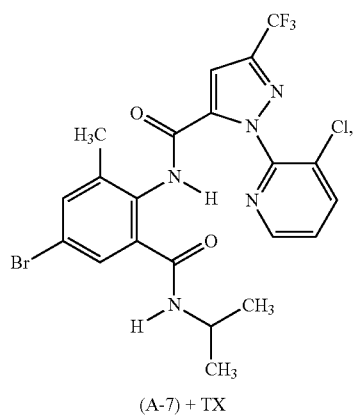
(A-7) + TX
the formula A-8
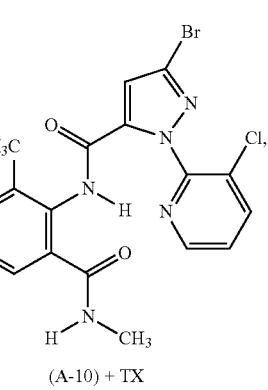
(A-8) + TX
the formula A-9
(A-9) + TX
the formula A-10
(A-10) + TX
the formula A-11
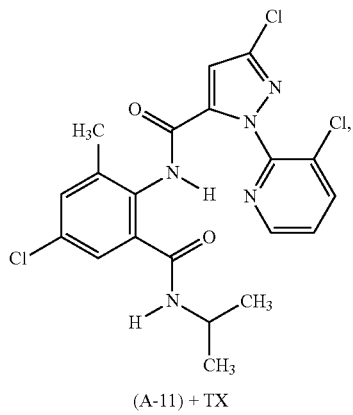
(A-11) + TX
the formula A-12
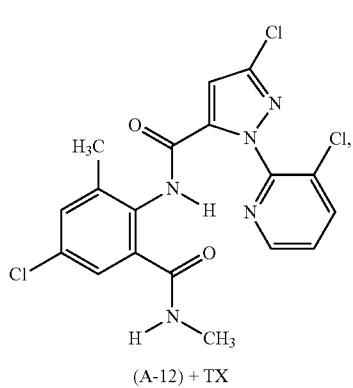
(A-12) + TX
the formula A-13
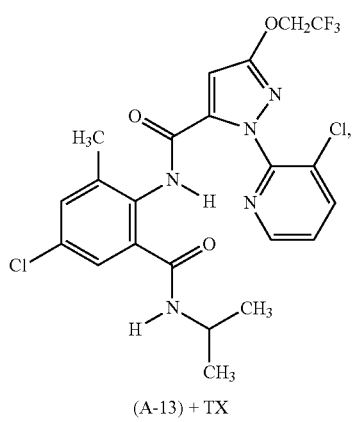
(A-13) + TX
the formula A-14
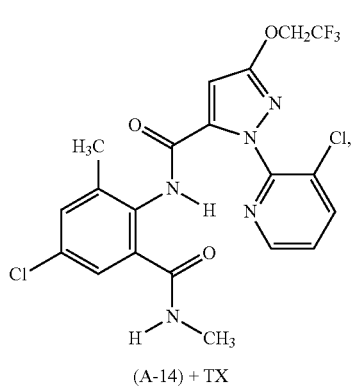
(A-14) + TX the formula A-15
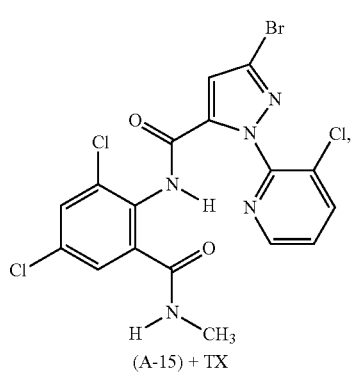
(A-15) + TX
the formula A-16
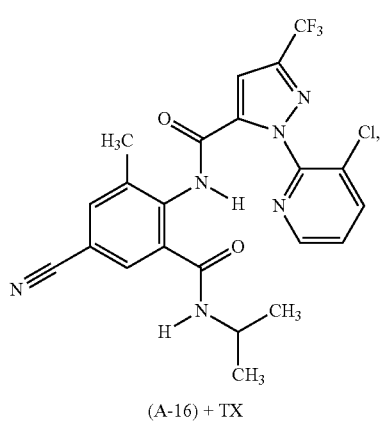
(A-16) + TX
the formula A-17
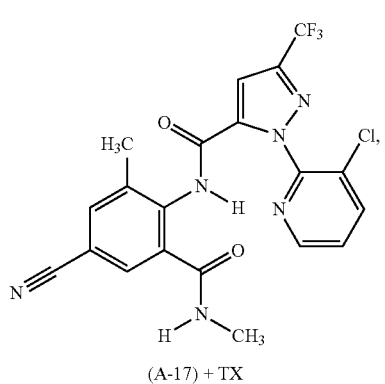
(A-17) + TX
the formula A-18
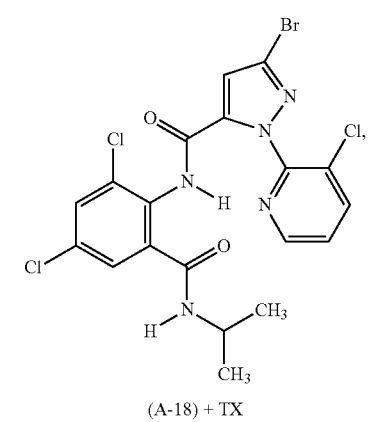
(A-18) + TX
the formula A-19
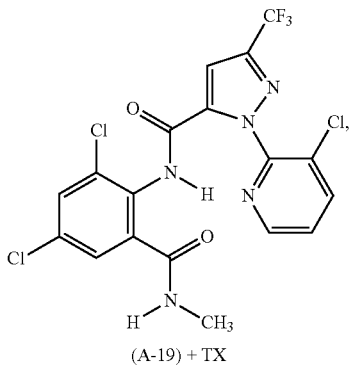
(A-19) + TX
the formula A-20
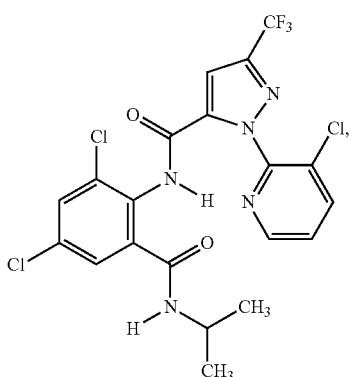
(A-20) + TX
the formula A-21
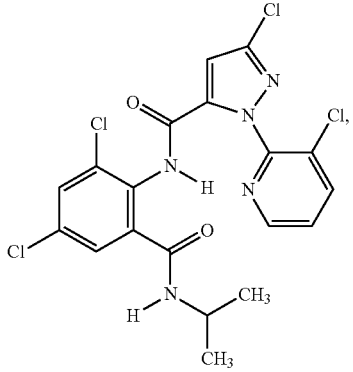
(A-21) + TX
the formula A-22
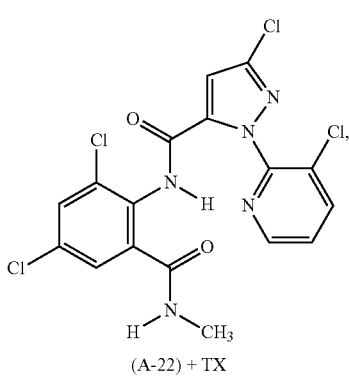
(A-22) + TX -continued

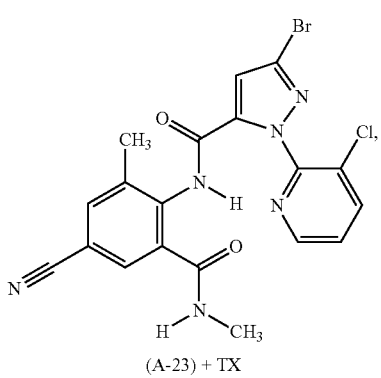

(A-23) + TX

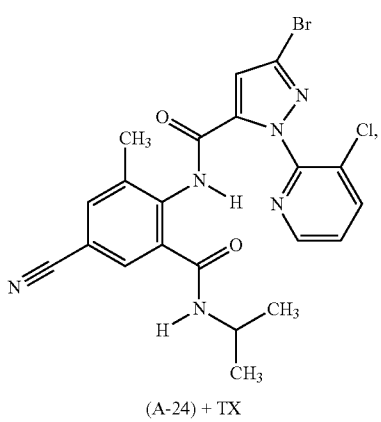

(A-24) + TX

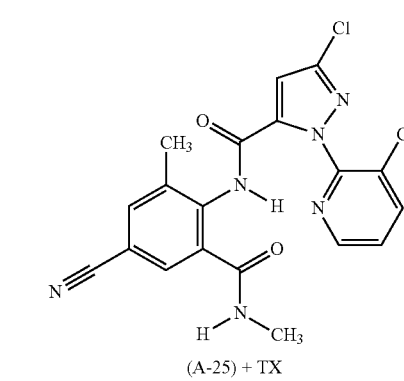

(A-25) + TX

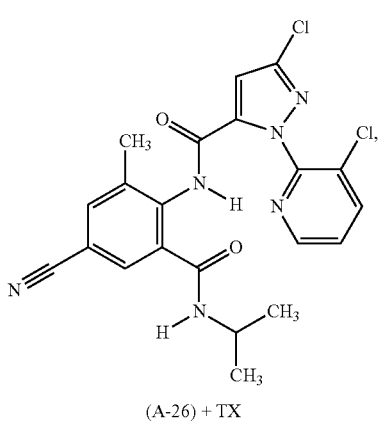

(A-26) + TX and biologically active compounds selected from the group consisting of glyphosate [1071-83-6] and its salts (diammonium [69254-40-6]) isopropylammonium [38641-94-0], monoammonium [40465-66-5], potassium [70901-20-1], sesquisodium [70393-85-0], trimesium [81591-81-3]), glufosinate [52676-47-2] and its salts (e.g. ammonium [77182-82-2], azaconazole (60207-31-0]+TX, bitertanol [70585-36-3]+TX, bromuconazole [116255-48-2]+TX, cyproconazole [94361-06-5]+TX, difenoconazole [119446-68-3]+TX, diniconazole [83657-24-3]+TX, epoxiconazole [106325-08-0]+TX, fenbuconazole [114369-43-6]+TX, fluquinconazole [136426-54-5]+TX, flusilazole [85509-19-9]+TX, flutriafol [76674-21-0]+TX, hexaconazole [79983-71-4]+TX, imazalil [35554-44-0]+TX, imibenconazole [86598-92-7]+TX, ipconazole [125225-28-7]+TX, metconazole [125116-23-6]+TX, myclobutanil [88671-89-0]+TX, pefurazoate [101903-30-4]+TX, penconazole [66246-88-6]+TX, prothioconazole [178928-70-6]+TX, pyrifenox [88283-41-4]+TX, prochloraz [67747-09-5]+TX, propiconazole [60207-90-1]+TX, simeconazole [149508-90-7]+TX, tebuconazole [107534-96-3]+TX, tetraconazole [112281-77-3]+TX, triadimefon [43121-43-3]+TX, triadimenol [55219-65-3]+TX, triflumizole [99387-89-0]+TX, triticonazole [131983-72-7]+TX, ancymidol [12771-68-5]+TX, fenarimol [60168-88-9]+TX, nuarimol [63284-71-9]+TX, bupirimate [41483-43-6]+TX, dimethirimol [5221-53-4]+TX, ethirimol [23947-60-6]+TX, dodemorph [1593-77-7]+TX, fenpropidine [67306-00-7]+TX, fenpropimorph [67564-91-4]+TX, spiroxamine [118134-30-8]+TX, tridemorph [81412-43-3]+TX, cyprodinil [121552-61-2]+TX, mepanipyrim [110235-47-7]+TX, pyrimethanil [53112-28-0]+TX, fenpiclonil [74738-17-3]+TX, fludioxonil [152641-86-1]+TX, benalaxyl [71626-11-4]+TX, furalaxyl [57646-30-7]+TX, metalaxyl [57837-19-1]+TX, R-metalaxyl [70630-17-0]+TX, ofurace [58810-48-3]+TX, oxadixyl [77732-09-3]+TX, benomyl [17804-35-2]+TX, carbendazim [10605-21-7]+TX, debacarb [62732-91-6]+TX, fuberidazole [3878-19-1]+TX, thiabendazole [148-79-8]+TX, chlozolinate [84332-86-5]+TX, dichlozoline [24201-58-9]+TX, iprodione [36734-19-7]+TX, myclozoline [54864-61-8]+TX, procymidone [32809-16-8]+TX, vinclozoline [50471-44-8]+TX, boscalid [188425-85-6]+TX, carboxin [5234-68-4]+TX, fenfuram [24691-80-3]+TX, flutolanil [66332-96-5]+TX, mepronil [55814-41-0]+TX, oxycarboxin [5259-88-1]+TX, penthiopyrad [183675-82-3]+TX, thifluzamide [130000-40-7]+TX, guazatine [108173-90-6]+TX, dodine [2439-10-3] [112-65-2] (free base)+TX, iminoctadine [13516-27-3]+TX, azoxystrobin [131860-33-8]+TX, dimoxystrobin [149961-52-4]+TX, enestroburin {Proc. BCPC, Int. Congr., Glasgow, 2003, 1, 93}+TX, fluoxastrobin [361377-29-9]+TX, kresoxim-methyl [143390-89-0]+TX, metominostrobin [133408-50-1]+TX, trifloxystrobin [141517-21-7]+TX, orysastrobin [248593-16-0]+TX, picoxystrobin [117428-22-5]+TX, pyraclostrobin [175013-18-0]+TX, ferbam [14484-64-1]+TX, mancozeb [8018-01-7]+TX, maneb [12427-38-2]+TX, metiram [9006-42-2]+TX, propineb [12071-83-9]+TX, thiram [137-26-8]+TX, zineb [12122-67-7]+TX, ziram [137-30-4]+TX, captafol [2425-06-1]+TX, captan [133-06-2]+TX, dichlofluanid [1085-98-9]+TX, fluoroimide [41205-21-4]+TX, folpet [133-07-3]+TX, tolylfluanid [731-27-1]+TX, bordeaux mixture [8011-63-0]+TX, copperhydroxid [20427-59-2]+TX, copperoxychlorid [1332-40-7]+TX, coppersulfate [7758-98-7]+TX, copperoxide [1317-39-1]+TX, mancopper [53988-93-5]+TX, oxine-copper [10380-28-6]+TX, dinocap [131-72-6]+TX, nitrothal-isopropyl [10552-74-6]+TX, edifenphos [17109-49-8]+TX, iprobenphos [26087-47-8]+TX, isoprothiolane [50526-35-1]+TX, phosdiphen [36519-00-3]+TX, pyrazophos [13457-18-6]+TX, tolclofos-methyl [57018-04-9]+TX, acibenzolar-5-methyl [135158-54-2]+

TX, anilazine [101-05-3]+TX, benthiavalicarb [413615-35-7]+TX, blasticidin-S [2079-00-7]+TX, chinomethionat [2439-01-2]+TX, chloroneb [2675-77-6]+TX, chlorothalonil [1897-45-6]+TX, cyflufenamid [526409-60-3]+TX, cymoxanil [57966-95-7]+TX, dichlone [117-80-6]+TX, diclocymet [139920-32-4]+TX, diclomezine [62865-36-5]+TX, dicloran [99-30-9]+TX, diethofencarb [87130-20-9]+TX, dimethomorph [110488-70-5]+TX, SYP-L190 (flumorph) [211867-47-9]+TX, dithianon [3347-22-6]+TX, ethaboxam [162650-77-3]+TX, etridiazole [2593-15-9]+TX, famoxadone [131567-57-3]+TX, fenamidone [161326-34-7]+TX, fenoxanil [115852-48-7]+TX, fentin [668-34-8]+TX, ferimzone [89269-64-7]+TX, fluazinam [79622-59-6]+TX, fluopicolide [239110-15-7]+TX, flusulfamide [106917-52-6]+TX, fenhexamid [126833-17-8]+TX, fosetyl-aluminium [39148-24-8]+TX, hymexazol [10004-44-1]+TX, iprovalicarb [140923-17-7]+TX, IKF-916 (cyazofamid) [120116-88-3]+TX, kasugamycin [6980-18-3]+TX, methasulfocarb [66952-49-6]+TX, metrafenone [220899-03-6]+TX, pencycuron [66063-05-6]+TX, phthalide [27355-22-2]+TX, polyoxins [11113-80-7]+TX, probenazole [27605-76-1]+TX, propamocarb [25606-41-1]+TX, proquinazid [189278-12-4]+TX, pyroquilon [57369-32-1]+TX, quinoxyfen [124495-18-7]+TX, quintozene [82-68-8]+TX, sulfur [7704-34-9]+TX, tiadinil [223580-51-6]+TX, triazoxide [72459-58-6]+TX, tricyclazole [41814-78-2]+TX, triforine [26644-46-2]+TX, validamycin [37248-47-8]+TX, zoxamide (RH7281) [156052-68-5]+TX, mandipropamid [374726-62-2]+TX, the compound of formula F-1

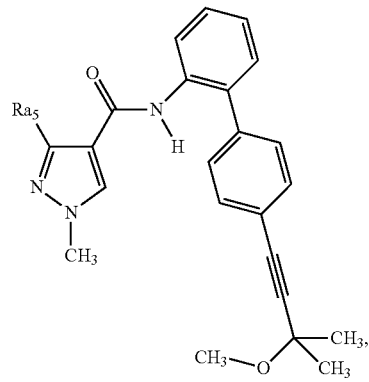

(F-1)

wherein Ra$_5$ is trifluoromethyl or difluoromethyl (WO2004/058723)+TX, the compound of formula F-2

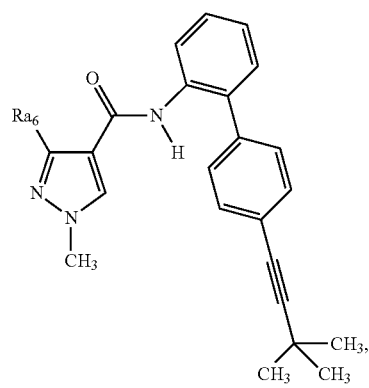

(F-2)

wherein Ra$_6$ is trifluoromethyl or difluoromethyl (WO2004/058723)+TX, the racemic compound of formula F-3 (syn)

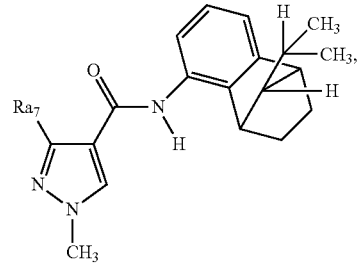

(F-3)

wherein Ra$_7$ is trifluoromethyl or difluoromethyl (WO2004/035589)+TX, the racemic mixture of formula F-4 (anti)

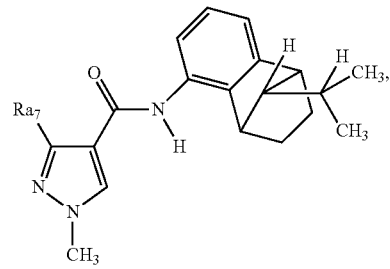

(F-4)

wherein Ra$_7$ is trifluoromethyl or difluoromethyl (WO2004/035589)+TX, the compound of formula F-5

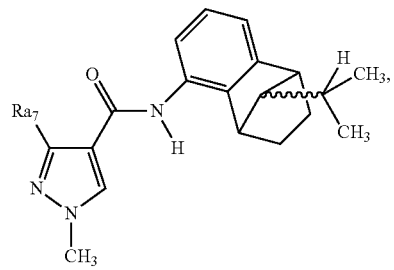

(F-5)

which is an epimeric mixture of racemic compounds of formulae F-3 (syn) and F-4 (anti), wherein the ratio from racemic compounds of formula F-3 (syn) to racemic compounds of formula F-4 (anti) is from 1000:1 to 1:1000 and wherein Ra$_7$ is trifluoromethyl or difluoromethyl (WO2004/035589)+TX, the compound of formula F-6

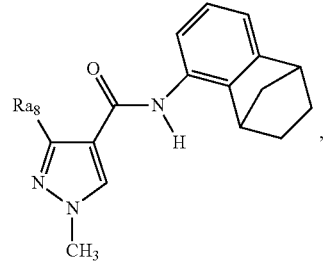

(F-6)

wherein Ra$_8$ is trifluoromethyl or difluoromethyl (WO2004/035589)+TX, the racemic compound of formula F-7 (trans)

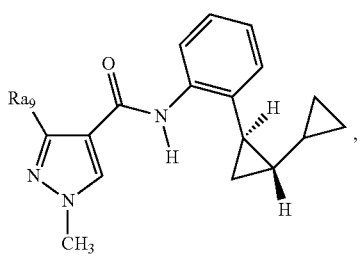

(F-7)

wherein Ra₉ is trifluoromethyl or difluoromethyl (WO03/074491)+TX, the racemic compound of formula F-8 (cis)

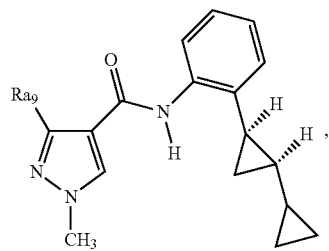

(F-8)

wherein Ra₉ is trifluoromethyl or difluoromethyl (WO03/074491)+TX, the compound of formula F-9

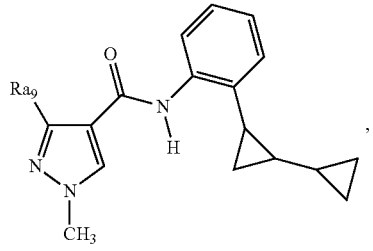

(F-9)

which is a mixture of the racemic compounds of formulae F-7 (trans) and F-8 (cis), wherein the ratio of the racemic compound of formula F-7 (trans) to the racemic compound of formula F-8 (cis) is 2:1 to 100:1; and wherein Ra₉ is trifluoromethyl or difluoromethyl (WO03/074491)+TX, the compound of formula F-10

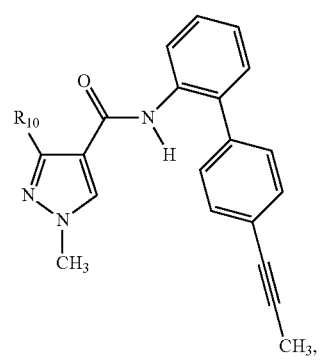

(F-10)

wherein R₁₀ is trifluoromethyl or difluoromethyl (WO2004/058723)+TX, the racemic compound of formula F-11 (trans)

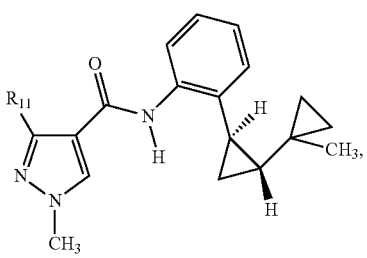

(F-11)

wherein R₁₁ is trifluoromethyl or difluoromethyl (WO 03/074491)+TX, the racemic compound of formula F-12 (cis)

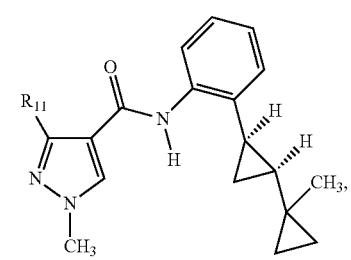

(F-12)

wherein R₁₁ is trifluoromethyl or difluoromethyl (WO 03/074491)+TX, the compound of formula F-13

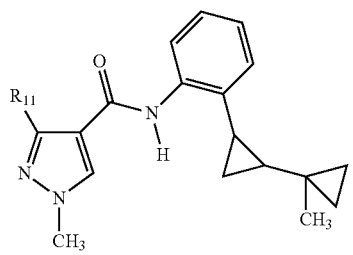

(F-13)

which is a racemic mixture of formulae F-11 (trans) and F-12 (cis), and wherein R₁₁ is trifluoromethyl or difluoromethyl (WO 03/074491)+TX, the compound of formula F-14

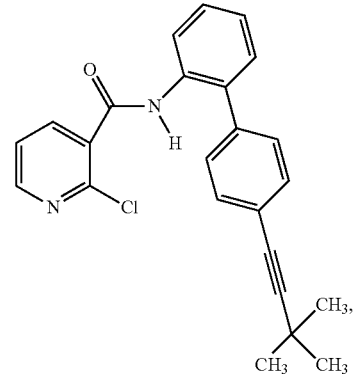

(F-14)

(WO 2004/058723)+TX, and the compound of formula F-15

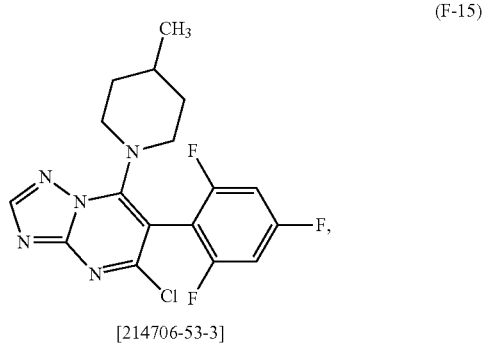 [SMILES: CC1CCN(c2c(-c3c(F)cc(F)cc3F)c(Cl)nc3ncnn23)CC1]

(F-15)

[214706-53-3]

+TX.

The references in brackets behind the active ingredients, e.g. [3878-19-1] refer to the Chemical Abstracts Registry number. The compounds of the formulae A-1 to A-26 are described in WO 03/015518 or in WO 04/067528.The above described mixing partners are known. Where the active ingredients are included in "The Pesticide Manual" [The Pesticide Manual—A World Compendium; Thirteenth Edition; Editor: C. D. S. Tomlin; The British Crop Protection Council], they are described therein under the entry number given in round brackets hereinabove for the particular compound; for example, the compound "abamectin" is described under entry number (1). Where "[CCN]" is added hereinabove to the particular compound, the compound in question is included in the "Compendium of Pesticide Common Names", which is accessible on the internet [A. Wood; Compendium of Pesticide Common Names, Copyright © 1995-2004]; for example, the compound "acetoprole" is described under the internet address http://www.alanwood.net/pesticides/acetoprole.html.

Most of the active ingredients described above are referred to hereinabove by a so-called "common name", the relevant "ISO common name" or another "common name" being used in individual cases. If the designation is not a "common name", the nature of the designation used instead is given in round brackets for the particular compound; in that case, the IUPAC name, the IUPAC/Chemical Abstracts name, a "chemical name", a "traditional name", a "compound name" or a "development code" is used or, if neither one of those designations nor a "common name" is used, an "alternative name" is employed. "CAS Reg. No" means the Chemical Abstracts Registry Number.

The active ingredient mixture of the compounds of formula I selected from tables T1 to T151 with active ingredients described above comprises a compound selected from tables T1 to T151 and an active ingredient as described above preferably in a mixing ratio of from 100:1 to 1:6000, especially from 50:1 to 1:50, more especially in a ratio of from 20:1 to 1:20, even more especially from 10:1 to 1:10, very especially from 5:1 and 1:5, special preference being given to a ratio of from 2:1 to 1:2, and a ratio of from 4:1 to 2:1 being likewise preferred, above all in a ratio of 1:1, or 5:1, or 5:2, or 5:3, or 5:4, or 4:1, or 4:2, or 4:3, or 3:1, or 3:2, or 2:1, or 1:5, or 2:5, or 3:5, or 4:5, or 1:4, or 2:4, or 3:4, or 1:3, or 2:3, or 1:2, or 1:600, or 1:300, or 1:150, or 1:35, or 2:35, or 4:35, or 1:75, or 2:75, or 4:75, or 1:6000, or 1:3000, or 1:1500, or 1:350, or 2:350, or 4:350, or 1:750, or 2:750, or 4:750. Those mixing ratios are understood to include, on the one hand, ratios by weight and also, on other hand, molar ratios.

The mixtures comprising a compound of formula I selected from tables T1 to T151 and one or more active ingredients as described above can be applied, for example, in a single "ready-mix" form, in a combined spray mixture composed from separate formulations of the single active ingredient components, such as a "tank-mix", and in a combined use of the single active ingredients when applied in a sequential manner, i.e. one after the other with a reasonably short period, such as a few hours or days. The order of applying the compounds of formula I selected from tables T1 to T151 and the active ingredients as described above is not essential for working the present invention.

BIOLOGICAL EXAMPLES

Fungicidal Action

Example B-1

Plasmopara viticola: Downy Mildew of Grapevine, Preventative Test

Plasmopara viticola (downy mildew of grapevine): Grape vine leaf disks are placed on agar in multiwell plates (24-well format) and sprayed with the formulated (2% Dimethylsulfoxid, 0.025% Tween 20) test solutions. After drying, the leaf disks are inoculated with a spore suspension of the fungus (80'000 conidia/ml). After appropriate incubation, the preventive fungicidal activity of a compound is assessed 6 days after inoculation as disease damage on the leaf disks and calculated as percent efficacy relative to untreated infected control. (0=no control of Plasmopara viticola, 100% complete control). In this test, compounds listed in Table P above show good activity. In particular compound P.10 shows an activity of at least 50% at an application rate of 200 ppm.

Example B-2

Botrytis cinerea: Gray Mould, Preventative Test

Botrytis cinerea (Gray mould): Bean leaf disks are placed on agar in multiwell plates (24-well format) and sprayed with the formulated (2% Dimethylsulfoxid, 0.025% Tween 20) test solutions. After drying, the leaf disks are inoculated with a spore suspension of the fungus (60'000 conidia/ml). After appropriate incubation, the preventive fungicidal activity of a compound is assessed 3 days after inoculation as disease damage on the leaf disks and calculated as percent efficacy relative to untreated infected control. (0=no control of Botrytis cinerea, 100%=complete control). In this test, compounds listed in Table P above show good activity. In particular compound P.29 shows an activity of at least 50% at an application rate of 200 ppm.

Example B-3

Erysiphe graminis f.sp. tritici: Wheat Powdery Mildew, Preventative Test

Erysiphe graminis f.sp. tritici (Wheat powdery mildew): Wheat leaf segments are placed on agar in multiwell plates (24-well format) and sprayed with the formulated (2% Dimethylsulfoxid, 0.025% Tween 20) test solutions. After drying, the leaf disks are inoculated with spores of the fungus (50 conidia/mm2). After appropriate incubation, the preventive fungicidal activity of a compound is assessed 7 days after inoculation as disease damage on the leaf disks and calculated as percent efficacy relative to untreated infected control. (0=no control of Erysiphe graminis f.sp. tritici, 100%=complete control). In this test, compounds listed in Table P above show good activity. In particular compounds P.07, P.09, P.21, P.22, P.26, P.28, P.29, P.30, P.35, P.59, P.61, P.62, P.63, P.64, P.68, P.69, P.73, P.76, P.77, P.78 and P.82 show an activity of at least 50% at an application rate of 200 ppm.

Example B-4

*Erysiphe graminis* f.sp. *hordei*: Powdery Mildew of Barley, Curative Test

*Erysiphe graminis* f.sp. *hordei* (Barley powdery mildew): Barley leaf segments are placed on agar in multiwell plates (24-well format). The leaf disks are inoculated with spores of the fungus (120 conidia/mm2). After 24 h the leaf disks are sprayed with the formulated (2% Dimethylsulfoxid, 0.025% Tween 20) test solutions. After appropriate incubation, the curative fungicidal activity of a compound is assessed 7 days after inoculation as disease damage on the leaf disks and calculated as percent efficacy relative to untreated infected control (0=no control of *Erysiphe graminis* f.sp. *hordei*, 100%=complete control). In this test, compounds listed in Table P above show good activity. In particular compounds P.01, P.03, P.04, P.06, P.07, P.08, P.11, P.14, P.15, P.16, P.17 and P.19 show an activity of at least 50% at an application rate of 200 ppm.

Example B-5

*Puccinia recondita*: Brown Rust of Wheat, Preventative Test

*Puccinia recondita* (Brown rust): Wheat leaf segments are placed on agar in multiwell plates (24-well format) and sprayed with the formulated (2% Dimethylsulfoxid, 0.025% Tween 20) test solutions. After drying, the leaf disks are inoculated with a spore suspension of the fungus (45'000 conidia/ml). After appropriate incubation, the preventive fungicidal activity of a compound is assessed 8 days after inoculation as disease damage on the leaf disks and calculated as percent efficacy relative to untreated infected control (0=no control of *Puccinia recondita*, 100%=complete control). In this test, compounds listed in Table P above show good activity. In particular compounds P.07, P.11, P.26, P.28, P.29, P.31, P.35, P.51, P.58, P.59, P.61, P.62, P.64, P.70, P.73, P.76, P.77, P.79 and P.82 show an activity of at least 50% at an application rate of 200 ppm.

Example B-6

*Puccinia recondita*: Brown Rust of Wheat, Curative Test

Method Description *Puccinia recondita* (Brown rust): Wheat leaf segments are placed on agar in multiwell plates (24-well format). The leaf disks are then inoculated with a spore suspension of the fungus (45'000 conidia/ml). One day after inoculation the formulated (2% Dimethylsulfoxid, 0.025% Tween 20) test solution is applied. After appropriate incubation, the curative fungicidal activity of a compound is assessed 8 days after inoculation as disease damage on the leaf disks and calculated as percent efficacy relative to untreated infected control (0=no control of *Puccinia recondita*, 100%=complete control). In this test, compounds listed in Table P above show good activity. In particular compounds P.26, P.28, P.29, P.31, P.35, P.36, P.41, P.58, P.59, P.61, P.62, P.64, P.69, P.70,P.73, P.76, P.77, P.81 and P.82 show an activity of at least 50% at an application rate of 200 ppm.

Example B-7

*Phaeosphaeria nodorum*: *Septoria* Leaf Spot of Wheat, Preventative Test

Method Description *Phaeosphaeria nodorum* (syn. *Septoria nodorum, Leptosphaeria nodorum*), glume blotch (Septoria leaf spot): Wheat leaf segments are placed on agar in multiwell plates (24-well format) and sprayed with the formulated (2% Dimethylsulfoxid, 0.025% Tween 20) test solutions. After drying, the leaf disks are inoculated with a spore suspension of the fungus (500'000 conidia/ml). After appropriate incubation, the preventive fungicidal activity of a compound is assessed 4 days after inoculation as disease damage on the leaf disks and calculated as percent efficacy relative to untreated infected control (0=no control of *Phaeosphaeria nodorum*, 100%=complete control). In this test, compounds listed in Table P above show good activity. In particular compounds P.04 and P.29 show an activity of at least 50% at an application rate of 200 ppm.

Example B-8

*Magnaporthe grisea*: Rice Blast Disease, Preventative Test

Method Description *Magnaporthe grisea* (syn. *Pyricularia oryzae*), rice blast disease. Rice leaf segments are placed on agar in multiwell plates (24-well format) and sprayed with the formulated (2% Dimethylsulfoxid, 0.025% Tween 20) test solutions. After drying, the leaf disks are inoculated with a spore suspension of the fungus (90'000 conidia/ml). After appropriate incubation, the preventive fungicidal activity of a compound is assessed 5 days after inoculation as disease damage on the leaf disks and calculated as percent efficacy relative to untreated infected control (0=no control of *Magnaporthe grisea*, 100%=complete control). In this test, compounds listed in Table P above show good activity. In particular compounds P.05, P.08 and P.09 show an activity of at least 50% at an application rate of 200 ppm.

Example B-9

*Pyrenophora teres*: Net Blotch of Barley, Preventative Test

Method Description *Pyrenophora teres* (Net blotch): Barley leaf segments are placed on agar in multiwell plates (24-well format) and sprayed with the formulated (2% Dimethylsulfoxid, 0.025% Tween 20) test solutions. After drying, the leaf disks are inoculated with a spore suspension of the fungus (25'000 conidia/ml). After appropriate incubation, the preventive fungicidal activity of a compound is assessed 4 days after inoculation as disease damage on the leaf disks and calculated as percent efficacy relative to untreated infected control (0=no control of *Pyrenophora teres*, 100%=complete control). In this test, compounds listed in Table P above show good activity. In particular compounds P.05, P.08, P.09, P.46, P.62, P.64, P.69 and P.73 show an activity of at least 50% at an application rate of 200 ppm.

What is claimed is:
1. A compound of formula I

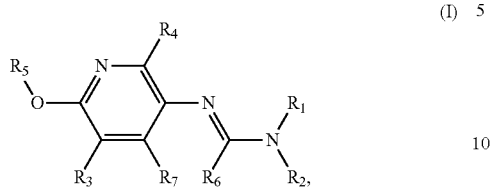

wherein aa) $R_1$ and $R_2$, independently from each other, are hydrogen, cyano, formyl, nitro, $C_1$-$C_7$alkyl, $C_2$-$C_6$alkenyl, $C_2$-$C_6$alkynyl, $C_2$-$C_7$alkylcarbonyl, $C_3$-$C_7$alkenylcarbonyl, $C_4$-$C_9$cycloalkylcarbonyl, $C_1$-$C_6$alkoxy-$C_1$-$C_6$alkyl, $C_1$-$C_6$alkylthio-$C_1$-$C_6$alkyl, $C_2$-$C_7$alkylcarbonyl-$C_1$-$C_6$alkyl, $C_3$-$C_6$alkenyloxy-$C_1$-$C_6$alkyl, $C_3$-$C_6$alkynyloxy-$C_1$-$C_6$alkyl, benzyloxy-$C_1$-$C_6$alkyl, $C_3$-$C_8$cycloalkyl-$C_1$-$C_6$alkyl, $C_2$-$C_7$alkyloxycarbonyl, $C_4$-$C_7$alkenyloxycarbonyl, $C_4$-$C_7$alkynyloxycarbonyl, $C_4$-$C_9$cycloalkyloxycarbonyl, $C_1$-$C_6$alkylsulfonyl, $C_1$-$C_6$haloalkylsulfonyl, $C_1$-$C_6$alkylsulfinyl or $C_1$-$C_6$haloalkylsulfinyl; or ab) $R_1$ and $R_2$, independently from each other, are —Si($R_{51}$)($R_{52}$)($R_{53}$), wherein $R_{51}$, $R_{52}$, $R_{53}$, independently of each other, are halogen, cyano, $C_1$-$C_6$alkyl, $C_2$-$C_6$alkenyl, $C_3$-$C_8$cycloalkyl, $C_5$-$C_8$cycloalkenyl, $C_2$-$C_6$alkynyl, $C_1$-$C_6$alkoxy, benzyl or phenyl; or ac) $R_1$ and $R_2$, independently from each other, are —Si(O$R_{54}$)(O$R_{55}$)(O$R_{56}$), wherein $R_{54}$, $R_{55}$, $R_{56}$, independently of each other, are $C_1$-$C_6$alkyl, $C_3$-$C_6$alkenyl, $C_3$-$C_8$cycloalkyl, $C_3$-$C_6$alkynyl, benzyl or phenyl; or ad) $R_1$ and $R_2$, independently from each other, are phenylsulfonyl, phenylsufinyl, phenylcarbonyl, phenoxycarbonyl, benzyl, benzylcarbonyl or benzyloxycarbonyl; or ae) $R_1$ and $R_2$, independently from each other, are phenylsulfonyl, phenylsufinyl, phenylcarbonyl, phenoxycarbonyl, benzyl, benzylcarbonyl, benzyloxycarbonyl mono- to polysubstituted ae1) by substituents independently selected from the group consisting of hydroxy, mercapto, halogen, cyano, azido, nitro, —SF$_5$, amino, $C_1$-$C_6$alkyl, $C_1$-$C_6$haloalkyl, $C_3$-$C_8$cycloalkyl, $C_3$-$C_8$halocycloalkyl, $C_2$-$C_6$alkenyl, $C_2$-$C_6$haloalkenyl, $C_2$-$C_6$alkynyl, $C_2$-$C_6$haloalkynyl, $C_1$-$C_6$alkoxy, $C_1$-$C_6$haloalkoxy, $C_1$-$C_6$alkoxy$C_1$-$C_6$alkyl, $C_1$-$C_6$alkylthio$C_1$-$C_6$alkyl, $C_3$-$C_6$alkenyloxy, $C_3$-$C_6$haloalkenyloxy, $C_3$-$C_6$alkynyloxy, $C_1$-$C_6$alkylthio, $C_1$-$C_6$haloalkylthio, $C_1$-$C_6$alkylsulfinyl, $C_1$-$C_6$haloalkylsulfinyl, $C_1$-$C_6$alkylsulfonyl, $C_1$-$C_6$haloalkylsulfonyl, benzyloxy, phenoxy, benzyl and phenyl, where benzyloxy, phenoxy, benzyl and phenyl for their part may be mono- to polysubstituted on the phenyl ring by substituents independently selected from the group consisting of halogen, cyano, hydroxy, $C_1$-$C_6$alkyl, $C_1$-$C_6$haloalkyl and $C_1$-$C_6$alkoxy; or ae2) by substituents independently selected from the group consisting of carboxy, —C(=O)—Cl, —C(=O)—F, $C_2$-$C_7$alkoxycarbonyl, $C_2$-$C_7$alkylthiocarbonyl, $C_2$-$C_7$haloalkoxycarbonyl, $C_3$-$C_7$alkenyloxycarbonyl, $C_3$-$C_7$haloalkenyloxycarbonyl, $C_3$-$C_7$alkynyloxycarbonyl, benzyloxycarbonyl and phenoxycarbonyl, where benzyloxycarbonyl and phenoxycarbonyl for their part may be mono- to polysubstituted on the phenyl ring by substituents independently selected form the group consisting of halogen, cyano, hydroxy, $C_1$-$C_6$alkyl, $C_1$-$C_6$haloalkyl and $C_1$-$C_6$alkoxy; or ae3) by substituents independently selected from the group consisting of formyl, $C_2$-$C_7$alkylcarbonyl, $C_2$-$C_7$haloalkylcarbonyl, $C_3$-$C_7$alkenylcarbonyl, phenylcarbonyl and benzylcarbonyl, where phenylcarbonyl and benzylcarbonyl for their part may be mono-to polysubstituted on the phenyl ring by substituents independently selected form the group consisting of halogen, cyano, hydroxy, $C_1$-$C_6$alkyl, $C_1$-$C_6$haloalkyl and $C_1$-$C_6$alkoxy; or ae4) by substituents independently selected from the group consisting of aminosulfonyl, $C_1$-$C_6$alkylaminosulfonyl, N,N-di($C_1$-$C_6$alkyl)aminosulfonyl, —C(=O)N$R_{57}R_{58}$, —C(=S)N$R_{57}R_{58}$ and —N$R_{57}R_{58}$, wherein $R_{57}$ and $R_{58}$, independently of each other, are hydrogen, $C_1$-$C_6$alkyl, $C_1$-$C_6$haloalkyl, $C_3$-$C_6$alkenyl, $C_3$-$C_6$haloalkenyl, $C_3$-$C_6$alkynyl, $C_3$-$C_8$cycloalkyl, $C_3$-$C_8$halocycloalkyl, phenyl or benzyl, where phenyl, benzyl for their part may be mono- to polysubstituted on the phenyl ring by substituents independently selected form the group consisting of halogen, cyano, hydroxy, $C_1$-$C_6$alkyl, $C_1$-$C_6$haloalkyl and $C_1$-$C_6$alkoxy, or $R_{57}$ and $R_{58}$ together with their interconnecting nitrogen atom are aziridino, azetidino, pyrazolino, pyrazolidino, pyrrolino, pyrrolidino, imidazolino, imidazolidino, triazolino, tetrazolino, piperazino, piperidino, morpholino, thiomorpholino, each of which, in turn, may be mono- or polysubstituted by substituents selected from the group consisting of methyl, halogen, cyano and nitro; and substituents at nitrogen atoms in the ring systems being other than halogen; or af) either $R_1$ or $R_2$ is af1) amino, $C_1$-$C_6$alkoxy, $C_3$-$C_6$alkenyloxy, $C_3$-$C_8$cycloalkyloxy, $C_3$-$C_6$alkynyloxy or benzyloxy; or af2) $C_1$-$C_6$alkoxy, $C_3$-$C_6$alkenyloxy, $C_3$-$C_8$cycloalkyloxy, $C_3$-$C_6$alkynyloxy, benzyloxy mono- to polysubstituted by substituents independently selected from the group consisting of halogen, cyano, hydroxy, $C_1$-$C_6$alkyl, $C_1$-$C_6$haloalkyl, $C_1$-$C_6$alkoxy and $C_1$-$C_6$haloalkoxy; or ag) $R_1$ and $R_2$, independently from each other, are $C_1$-$C_7$alkyl, $C_2$-$C_6$alkenyl, $C_2$-$C_6$alkynyl, $C_2$-$C_7$alkylcarbonyl, $C_3$-$C_7$alkenylcarbonyl, $C_4$-$C_9$cycloalkylcarbonyl, $C_1$-$C_6$alkoxy-$C_1$-$C_6$alkyl, $C_1$-$C_6$alkylthio-$C_1$-$C_6$alkyl, $C_3$-$C_6$alkenyloxy-$C_1$-$C_6$alkyl, $C_2$-$C_6$alkylcarbonyl-$C_1$-$C_6$alkyl, $C_3$-$C_6$alkynyloxy-$C_1$-$C_6$alkyl, benzyloxy-$C_1$-$C_6$alkyl, $C_3$-$C_8$cycloalkyl-$C_1$-$C_6$alkyl, $C_2$-$C_7$alkyloxycarbonyl, $C_4$-$C_7$alkenyloxycarbonyl, $C_4$-$C_7$alkynyloxycarbonyl or $C_4$-$C_9$cycloalkyloxycarbonyl, mono- to polysubstituted by substituents independently selected from the group consisting of halogen, cyano, nitro, hydroxy, mercapto, azido, $C_1$-$C_6$alkyl, $C_1$-$C_6$haloalkyl, $C_1$-$C_6$alkoxy, $C_1$-$C_6$haloalkoxy, $C_1$-$C_6$alkylthio, $C_1$-$C_6$alkylsulfinyl, $C_1$-$C_6$alkylsulfonyl, $C_2$-$C_7$alkoxycarbonyl, formyl, $C_2$-$C_7$alkylcarbonyl, —Si($R_{51}$)($R_{52}$)($R_{53}$) and —Si(O$R_{54}$)(O$R_{55}$)(O$R_{56}$); or ah) $R_1$ and $R_2$, independently from each other, are the group A-;

wherein A is a three- to ten-membered monocyclic or fused bicyclic ring system which can be aromatic, partially saturated or fully saturated and can contain 1 to 4 hetero atoms selected from the group consisting of nitrogen, oxygen and sulfur, it not being possible for each ring system to contain more than 2 oxygen atoms and more than 2 sulfur atoms, and it being possible for the three- to ten-membered ring system itself to be mono- or polysubstituted A1) by substituents independently selected from the group consisting of fluoro, bromo, iodo, cyano, nitro, hydroxy, mercapto, nitro, azido, formyl, carboxy, —C(=O)—Cl, =O, =S, —C(=O)—F, $C_1$-$C_6$alkyl, $C_2$-$C_6$alkenyl, $C_2$-$C_6$alkynyl, $C_3$-$C_8$cycloalkyl, $C_5$-$C_8$cycloalkenyl, $C_5$-$C_8$cycloalkynyl, $C_1$-$C_6$haloalkyl, $C_2$-$C_6$haloalkenyl, $C_2$-$C_6$haloalkynyl, $C_3$-$C_8$halocycloalkyl, $C_5$-$C_8$halocycloalkenyl, $C_5$-$C_8$halocycloalkynyl, $C_1$-$C_6$alkoxy, $C_1$-$C_6$haloalkoxy, $C_3$-$C_6$alkenyloxy, $C_3$-$C_6$haloalkenyloxy, $C_3$-$C_6$alkynyloxy, $C_3$-$C_8$cycloalkyloxy, $C_3$-$C_8$halocycloalkyloxy, $C_3$-$C_8$cycloalkenyloxy, $C_3$-$C_8$halocycloalkenyloxy, benzyloxy and phenoxy, where benzyloxy and phenoxy, in turn, may be mono- to polysubstituted by substituents independently selected from the group consisting of halogen, cyano, nitro, hydroxy, mercapto, azido, amino, —$SF_5$, $C_1$-$C_6$alkyl, $C_1$-$C_6$haloalkyl, $C_1$-$C_6$alkoxy, $C_1$-$C_6$haloalkoxy, $C_1$-$C_6$alkoxy$C_1$-$C_6$alkyl, $C_1$-$C_6$alkylthio, $C_1$-$C_6$alkylsulfinyl and $C_1$-$C_6$alkylsulfonyl; or A2) by substituents independently selected from the group consisting of HC(=$NOR_{59}$)—, ($C_1$-$C_6$alkyl)C(=$NOR_{59}$)—, ($C_1$-$C_6$haloalkyl)C(=$NOR_{59}$)—, ($C_1$-$C_6$alkyl)C(=$NOR_{59}$)$C_1$-$C_6$alkyl- and ($C_1$-$C_6$haloalkyl)C(=$NOR_{59}$)$C_1$-$C_6$alkyl-, wherein $R_{59}$ is hydrogen, $C_1$-$C_6$alkyl, $C_1$-$C_6$haloalkyl, $C_3$-$C_6$alkenyl, $C_3$-$C_6$haloalkenyl, $C_3$-$C_6$alkynyl, $C_3$-$C_8$cycloalkyl, $C_3$-$C_8$halocycloalkyl, benzyl and phenyl, and benzyl and phenyl mono- to polysubstituted by halogen, cyano, hydroxy, $C_1$-$C_6$alkyl, $C_1$-$C_6$haloalkyl or $C_1$-$C_6$alkoxy; or A3) by substituents independently selected from the group consisting of $C_1$-$C_6$alkylthio, $C_1$-$C_6$haloalkylthio, $C_1$-$C_6$alkylsulfinyl, $C_1$-$C_6$alkylsulfonyl, ($R_{14}$)S(=O)(=$NR_{13}$)— and ($R_{14}$)($R_{15}$)S(=O)=N—, wherein $R_{13}$ is hydrogen, $C_1$-$C_6$alkyl, $C_1$-$C_6$haloalkyl, $C_3$-$C_6$alkenyl, $C_3$-$C_6$haloalkenyl, $C_3$-$C_6$alkynyl, $C_3$-$C_8$cycloalkyl, $C_3$-$C_8$halocycloalkyl, phenyl or benzyl, or is phenyl or benzyl mono- to polysubstituted by halogen, cyano, hydroxy, $C_1$-$C_6$alkyl, $C_1$-$C_6$haloalkyl or $C_1$-$C_6$alkoxy, and $R_{14}$ and $R_{15}$, independently of each other, are $C_1$-$C_6$alkyl, $C_3$-$C_8$cycloalkyl, $C_1$-$C_6$haloalkyl, $C_3$-$C_8$halocycloalkyl, $C_2$-$C_6$alkenyl, $C_2C_6$haloalkenyl, $C_2$-$C_6$alkynyl, benzyl or phenyl, or benzyl or phenyl independently of each other, substituted by substituents selected from the group consisting of halogen, cyano, hydroxy, $C_1$-$C_6$alkyl, $C_1$-$C_6$haloalkyl and $C_1$-$C_6$alkoxy; or A4) by substituents independently selected from the group consisting of —$NR_{57}R_{58}$, —C(=O)$NR_{57}R_{58}$ and —C(=S)$NR_{57}R_{58}$; or A5) by substituents independently selected from the group consisting of formyl, $C_2$-$C_7$alkylcarbonyl, $C_2$-$C_7$haloalkylcarbonyl, $C_3$-$C_7$alkenylcarbonyl, $C_3$-$C_7$haloalkenylcarbonyl, $C_4$-$C_9$cycloalkylcarbonyl, $C_4$-$C_9$halocycloalkylcarbonyl, $C_2$-$C_7$alkoxycarbonyl, $C_2$-$C_7$haloalkoxycarbonyl, $C_3$-$C_7$alkenyloxycarbonyl, $C_3$-$C_7$alkynyloxycarbonyl, $C_4$-$C_9$cycloalkoxycarbonyl, $C_2$-$C_7$alkylthiocarbonyl and benzyloxycarbonyl, and benzyloxycarbonyl mono- to polysubstituted by substituents independently selected from the group consisting of halogen, cyano, hydroxy, $C_1$-$C_6$alkyl, $C_1$-$C_6$haloalkyl and $C_1$-$C_6$alkoxy; or A6) by substituents independently selected from the group consisting of —Si($R_{51}$)($R_{52}$)($R_{53}$) and —Si($OR_{54}$)($OR_{55}$)($OR_{56}$); or A7) by substituents independently selected from the group consisting of aminosulfinyl, ($C_1$-$C_6$alkyl)aminosulfonyl, N,N-di($C_1$-$C_6$alkyl)aminosulfonyl, di($C_1$-$C_6$alkyl)amino, ($C_1$-$C_6$alkyl)amino, phenyl, phenoxy, benzyl and benzyloxy, where phenyl, phenoxy, benzyl and benzyloxy for their part may be mono- to polysubstituted on the phenyl ring by substituents independently selected form the group consisting of halogen, cyano, hydroxy, amino, nitro, azido, mercapto, formyl, —$SF_5$, $C_1$-$C_6$alkyl, $C_1$-$C_6$haloalkyl, $C_2$-$C_6$alkenyl, $C_2$-$C_6$haloalkenyl, $C_2$-$C_6$alkynyl, $C_1$-$C_6$alkoxy, $C_1$-$C_6$haloalkoxy, $C_1$-$C_6$alkylthio, $C_1$-$C_6$haloalkylthio, $C_3$-$C_6$alkenylthio, $C_3$-$C_6$haloalkenylthio, $C_3$-$C_6$alkynylthio, $C_1$-$C_3$alkoxy-$C_1$-$C_3$alkylthio, $C_2$-$C_6$alkylcarbonyl-$C_1$-$C_3$alkylthio, $C_2$-$C_6$alkoxycarbonyl-$C_1$-$C_3$6alkylthio, cyano-$C_1$-$C_6$alkylthio, $C_1$-$C_6$alkylsulfinyl, $C_1$-$C_6$haloalkylsulfinyl, $C_1$-$C_6$alkylsulfonyl, $C_1$-$C_6$haloalkylsulfonyl, aminosulfonyl, ($C_1$-$C_6$alkyl)aminosulfonyl, N,N-di($C_1$-$C_6$alkyl)aminosulfonyl, di($C_1$-$C_6$alkyl)amino and ($C_1$-$C_6$alkyl)amino; or ai) $R_1$ and $R_2$, independently from each other, are —C(=O)$NR_{57}R_{58}$; or aj) $R_1$ and $R_2$ together form a $C_2$-$C_6$alkylene bridge which may be mono- to polysubstituted by halogen, cyano, $C_1$-$C_6$alkyl or $C_1$-$C_6$haloalkyl groups; or ak) $R_1$ and $R_2$ together with their interconnecting nitrogen atom are pyrazolino, pyrazolidino, pyrrolino, imidazolino, imidazolidino, triazolino, tetrazolino, piperazino, morpholino, thiomorpholino, each of which, independently of each other, may be mono- to polysubstituted by methyl groups, halogen, cyano and nitro; or al) the fragment

can be

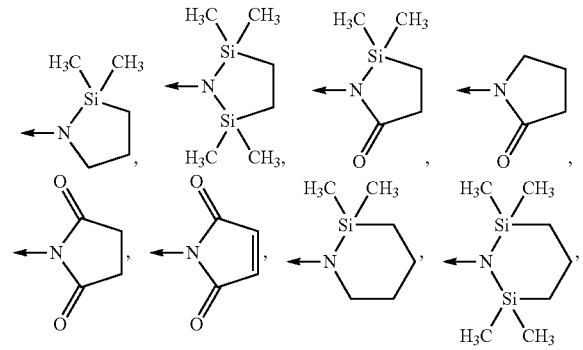

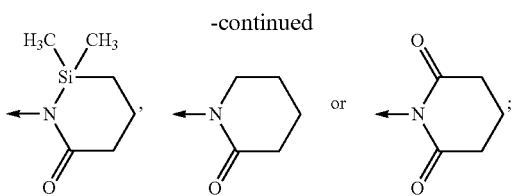

wherein each of the meanings of said fragment can be mono- to polysubstituted by substituents independently selected from the group consisting of halogen, cyano, $C_1$-$C_6$alkyl, $C_1$-$C_6$haloalkyl and $C_1$-$C_6$alkoxy;

ba) $R_3$, $R_4$ and $R_7$, independently from each other, are ba1) hydrogen, halogen, cyano, nitro, mercapto, hydroxy, azido, —$SF_5$, —$NR_{64}R_{65}$, wherein $R_{64}$ and $R_{65}$, independently of each other, are hydrogen, $C_1$-$C_6$alkyl, $C_1$-$C_6$haloalkyl, $C_3$-$C_6$alkenyl, $C_3$-$C_6$haloalkenyl, $C_3$-$C_6$alkynyl, $C_3$-$C_8$cycloalkyl, $C_3$-$C_8$halocycloalkyl, phenyl or benzyl, where phenyl, benzyl for their part may be mono- to polysubstituted on the phenyl ring by substituents independently selected form the group consisting of halogen, cyano, hydroxy, $C_1$-$C_6$alkyl, $C_1$-$C_6$haloalkyl and $C_1$-$C_6$alkoxy, or $R_{64}$ and $R_{65}$ together with their interconnecting nitrogen atom are aziridino, azetidino, pyrazolino, pyrazolidino, pyrrolino, pyrrolidino, imidazolino, imidazolidino, triazolino, tetrazolino, piperazino, piperidino, morpholino, thiomorpholino, each of which, in turn, may be mono- or polysubstituted by substituents selected from the group consisting of methyl, halogen, cyano and nitro; and substituents at nitrogen atoms in the ring systems being other than halogen; or $R_3$, $R_4$ and $R_7$, independently from each other, are —C(=S)NH$_2$, —N=C=O, —N=C=S, amino, $(R_{51})(R_{52})(R_{53})$Si—, $(R_{51})(R_{52})(R_{53})$Si—$(C_1$-$C_6$alkyl)-, $(R_{51})(R_{52})(R_{53})$Si—$(C_2$-$C_6$alkinyl)-, $(OR_{54})(OR_{55})(OR_{56})$Si— or $(OR_{214})(OR_{215})(OR_{216})$Si—$(C_1$-$C_6$alkyl)-; wherein $R_{214}$, $R_{215}$ and $R_{216}$ independently of each other, are halogen, cyano, $C_1$-$C_6$alkyl, $C_2$-$C_6$alkenyl, $C_3$-$C_8$cycloalkyl, $C_5$-$C_8$cycloalkenyl, $C_2$-$C_6$alkynyl, benzyl or phenyl; or $R_3$, $R_4$ and $R_7$, independently from each other, are ba2) $C_1$-$C_6$alkylthio, $C_1$-$C_6$alkylsulfinyl, $C_1$-$C_6$alkylsulfonyl, $C_1$-$C_6$haloalkylthio, $C_1$-$C_6$haloalkylsulfinyl, $C_1$-$C_6$haloalkylsulfonyl, aminosulfinyl, aminosulfonyl, $C_1$-$C_6$alkoxy, $C_1$-$C_6$haloalkoxy, $C_3$-$C_6$alkenyloxy, $C_3$-$C_6$haloalkenyloxy, $C_3$-$C_6$alkinyloxy, $(C_1$-$C_6$alkyl)aminosulfonyl, di$(C_1$-$C_6$alkyl)aminosulfonyl, $C_1$-$C_6$alkoxy, $C_2$-$C_6$alkenyloxy, $C_2$-$C_6$alkynyloxy, $C_1$-$C_6$alkyl-S(=O)($R_{14}$)=N—, ($R_{14}$)S(=O)(=N—$R_{13}$)—, ($R_{14}$)($R_{15}$)S(=O)=N—, —S—$C_3$-$C_6$-alkenyl, —S—$C_3$-$C_6$-alkynyl, —S—$C_3$-$C_8$-cycloalkyl, S-benzyl, or —S—$C_3$-$C_6$-alkenyl, —S—$C_3$-$C_6$-alkynyl, —S—$C_3$-$C_8$-cycloalkyl or S-benzyl; all of which can be mono- to polysubstituted by substituents selected from the group consisting of halogen, cyano, $C_1$-$C_6$-alkyl, $C_1$-$C_6$-haloalkyl, $C_1$-$C_6$-alkoxy; or $R_3$, $R_4$ and $R_7$, independently from each other, are ba3) $C_1$-$C_6$alkyl, $C_2$-$C_6$alkenyl or $C_2$-$C_6$alkynyl, or $C_1$-$C_6$alkyl, $C_2$-$C_6$alkenyl or $C_2$-$C_6$alkynyl mono- to polysubstituted by substituents independently selected from the group consisting of halogen, hydroxy, mercapto, cyano, nitro, $C_1$-$C_6$alkyl, $C_1$-$C_6$haloalkyl, $C_1$-$C_6$alkoxy, $C_1$-$C_6$hydroxyalkyl, tri(alkyl)silyl, $C_1$-$C_6$haloalkoxy, $C_1$-$C_6$alkylthio, $C_1$-$C_6$haloalkylthio, $C_1$-$C_6$alkylsulfinyl, $C_1$-$C_6$haloalkylsulfinyl, $C_1$-$C_6$alkylsulfonyl and $C_1$-$C_6$haloalkylsulfonyl; or $R_3$, $R_4$ and $R_7$, independently from each other, are ba4) formyl, $C_2$-$C_7$alkoxycarbonyl, $C_2$-$C_7$haloalkoxycarbonyl, $C_3$-$C_7$alkenyloxycarbonyl, $C_3$-$C_7$haloalkenyloxycarbonyl, $C_2$-$C_7$alkylcarbonyl, carboxy, —C(=O)—Cl, —C(=O)—F, $C_2$-$C_7$haloalkylcarbonyl, $C_3$-$C_7$alkenylcarbonyl or $C_3$-$C_7$haloalkenylcarbonyl; or $R_3$, $R_4$ and $R_7$, independently from each other, are ba5) phenyl, phenoxy, benzyl or benzyloxy, or phenoxy, benzyl or benzyloxy mono- to polysubstituted by substituents independently selected from the group consisting of halogen, cyano, nitro, hydroxy, mercapto, azido, amino, —$SF_5$, $C_1$-$C_6$alkyl, $C_1$-$C_6$haloalkyl, $C_1$-$C_6$alkoxy, $C_1$-$C_6$haloalkoxy, $C_1$-$C_6$alkylthio, $C_1$-$C_6$alkylsulfinyl and $C_1$-$C_6$alkylsulfonyl; or bb) $R_3$, $R_4$ and $R_7$, independently of each other, are the groups A-, A-O— or A-($C_1$-$C_6$alkyl)-, wherein the group A is as defined above under ah);

ca) $R_5$ is hydrogen, $C_1$-$C_{12}$alkyl, $C_2$-$C_{12}$alkenyl, $C_2$-$C_{12}$alkynyl, $C_1$-$C_{12}$alkylsulfonyl, $C_2$-$C_{12}$alkenylsulfonyl, phenylsulfonyl or benzylsulfonyl, or is $C_1$-$C_{12}$alkyl, $C_2$-$C_{12}$alkenyl, $C_2$-$C_{12}$alkynyl, $C_1$-$C_{12}$alkylsulfonyl, $C_2$-$C_{12}$alkenylsulfonyl, phenylsulfonyl or benzylsulfonyl mono-to polysubstituted by substituents independently selected from the group consisting of halogen, cyano, nitro, hydroxy, mercapto, azido, formyl, $C_2$-$C_7$alkylcarbonyl, $C_2$-$C_7$haloalkylcarbonyl, $C_1$-$C_6$alkyl, $C_1$-$C_6$haloalkyl, $C_1$-$C_6$alkoxy, $C_1$-$C_6$haloalkoxy, $C_1$-$C_6$alkylthio, $C_1$-$C_6$alkylsulfinyl and $C_1$-$C_6$alkylsulfonyl; or cb1) $R_5$ is formyl, $C_2$-$C_{12}$alkylcarbonyl, $C_3$-$C_{12}$alkenylcarbonyl, $C_3$-$C_{12}$alkynylcarbonyl, $C_4$-$C_{12}$cycloalkylcarbonyl, benzylcarbonyl, phenylcarbonyl, $C_2$-$C_{12}$alkoxycarbonyl, $C_4$-$C_{12}$alkenyloxycarbonyl, $C_4$-$C_{12}$alkynyloxycarbonyl, $C_4$-$C_{12}$cycloalkoxycarbonyl, benzyloxycarbonyl or phenoxycarbonyl, or is cb2) $C_2$-$C_{12}$alkylcarbonyl, $C_3$-$C_{12}$alkenylcarbonyl, $C_3$-$C_{12}$alkynylcarbonyl, $C_4$-$C_{12}$cycloalkylcarbonyl, benzylcarbonyl, phenylcarbonyl, $C_2$-$C_{12}$alkoxycarbonyl, $C_4$-$C_{12}$alkenyloxycarbonyl, $C_4$-$C_{12}$alkynyloxycarbonyl, $C_4$-$C_{12}$cycloalkoxycarbonyl, benzyloxycarbonyl or phenoxycarbonyl mono- to polysubstituted by substituents independently selected from the group consisting of halogen, cyano, $C_1$-$C_6$alkyl, $C_1$-$C_6$haloalkyl and $C_1$-$C_6$alkoxy; or cc) $R_5$ is $(R_{51})(R_{52})(R_{53})$Si—, $(R_{51})(R_{52})(R_{53})$Si—$(C_1$-$C_{12}$alkyl)-, $(R_{51})(R_{52})(R_{53})$Si—$(C_3$-$C_8$cycloalkyl)-, $(R_{54}O)(R_{55}O)(R_{56}O)$Si—, $(R_{54}O)(R_{55}O)(R_{56}O)$Si—$(C_1$-$C_{12}$alkyl)- or $(R_{54}O)(R_{55}O)(R_{56}O)$Si—$(C_3$-$C_8$cycloalkyl)-; or cd) $R_5$ is $C_1$-$C_6$alkyl-B—$C_1$-$C_{12}$alkyl-, $C_2$-$C_6$alkenyl-B—$C_1$-$C_{12}$alkyl-, $C_2$-$C_6$alkynyl-B—$C_1$-$C_{12}$alkyl-, $C_3$-$C_8$cycloalkyl-B—$C_1$-$C_{12}$alkyl-, benzyl-B—$C_1$-$C_{12}$alkyl-, phenyl-B—$C_1$-$C_{12}$alkyl-, $C_1$-$C_6$alkyl-B—$C_2$-$C_{12}$alkenyl-, $C_2$-$C_6$alkenyl-B—$C_2$-$C_{12}$alkenyl-, $C_2$-$C_6$alkynyl-B—$C_2$-$C_{12}$alkenyl-, $C_3$-$C_8$ycloalkyl-B—$C_2$-$C_{12}$alkenyl-, benzyl-B—$C_2$-$C_{12}$alkenyl-, phenyl-B—$C_2$-$C_{12}$alkenyl-, $C_1$-$C_6$alkyl-B—$C_2$-$C_{12}$alkynyl-, $C_2$-$C_6$alkenyl-B—$C_2$-$C_{12}$alkynyl-, $C_2$-$C_6$alkynyl-B—$C_2$-$C_{12}$alkynyl-, $C_3$-$C_8$cycloalkyl-B—$C_2$-$C_{12}$alkynyl-, benzyl-B—$C_2$-$C_{12}$alkynyl-, phenyl-B—$C_2$-$C_{12}$alkynyl-, $C_1$-$C_6$alkyl-B—$C_3$-$C_8$cycloalkyl-, $C_2$-$C_6$alkenyl-B—$C_3$-$C_8$cycloalkyl-, $C_2$-$C_6$alkynyl-B—$C_3$-$C_8$cycloalkyl-, $C_3$-$C_8$cycloalkyl-B—$C_3$-$C_8$cycloalkyl-, benzyl-B—$C_3$-$C_{12}$cycloalkyl- or phenyl-B—$C_3$-$C_{12}$cycloalkyl-, wherein the group B is —C(=O)—, —C(=S)—, —C(=NOR$_{59}$)—, —C(R$_{60}$)=NO—, —ON=C(R$_{60}$)—, —O—C(=O)—, —C(=O)—O—, —O—, —S—, —S(=O)—, —S(=O)$_2$—, —S(=O)(=NR$_{13}$)—, —S(=O)(R$_{14}$)=N—, —N=S(=O)(R$_{14}$)—, —N(R$_{62}$)—C=O)—, —C=O)—N(R$_{62}$)—, —N(R$_{62}$)—SO$_2$— or —SO$_2$—N(R$_{62}$)—;

cd1) wherein R$_{60}$ is hydrogen, $C_1$-$C_6$alkyl, $C_3$-$C_8$cycloalkyl, $C_1$-$C_6$haloalkyl, $C_3$-$C_8$halocycloalkyl, $C_2$-$C_6$alkenyl, $C_2$-$C_6$haloalkenyl, $C_2$-$C_6$alkynyl, benzyl or phenyl, or benzyl or phenyl mono- to polysubstituted by substituents independently selected form the group consisting of halogen, cyano, hydroxy, $C_1$-$C_6$alkyl, $C_1$-$C_6$haloalkyl and $C_1$-$C_6$alkoxy, and cd2) R$_{62}$ is hydrogen, $C_1$-$C_6$alkyl, $C_3$-$C_8$cycloalkyl, $C_1$-$C_6$haloalkyl, $C_3$-$C_8$halocycloalkyl, $C_3$-$C_6$alkenyl, $C_3$-$C_6$alkynyl, benzyl or phenyl, or benzyl or phenyl mono- to polysubstituted by substituents independently selected form the group consisting of halogen, cyano, hydroxy, $C_1$-$C_6$alkyl, $C_1$-$C_6$haloalkyl and $C_1$-$C_6$alkoxy; or ce) R$_5$ is $C_1$-$C_6$alkyl-B—$C_1$-$C_{12}$alkyl-, $C_2$-$C_6$alkenyl-B—$C_1$-$C_{12}$alkyl-, $C_2$-$C_6$alkynyl-B—$C_1$-$C_{12}$alkyl-, $C_3$-$C_8$cycloalkyl-B—$C_1$-$C_{12}$alkyl-, benzyl-B—$C_1$-$C_{12}$alkyl-, phenyl-B—$C_1$-$C_{12}$alkyl-, $C_1$-$C_6$alkyl-B—$C_2$-$C_{12}$alkenyl-, $C_2$-$C_6$alkenyl-B—$C_2$-$C_{12}$alkenyl-, $C_2$-$C_6$alkynyl-B—$C_2$-$C_{12}$alkenyl-, $C_3$-$C_8$cycloalkyl-B—$C_2$-$C_{12}$alkenyl-, benzyl-B—$C_2$-$C_{12}$alkenyl-, phenyl-B—$C_2$-$C_{12}$alkenyl-, $C_1$-$C_6$alkyl-B—$C_2$-$C_{12}$alkynyl-, $C_2$-$C_6$alkenyl-B—$C_2$-$C_{12}$alkynyl-, $C_2$-$C_6$alkynyl-B—$C_2$-$C_{12}$alkynyl-, $C_3$-$C_8$cycloalkyl-B—$C_2$-$C_{12}$alkynyl-, benzyl-B—$C_2$-$C_{12}$alkynyl-, phenyl-B—$C_2$-$C_{12}$alkynyl-, $C_1$-$C_6$alkyl-B—$C_3$-$C_8$cycloalkyl-, $C_2$-$C_6$alkenyl-B—$C_3$-$C_8$cycloalkyl-, $C_2$-$C_6$alkynyl-B—$C_3$-$C_8$cycloalkyl-, $C_3$-$C_8$cycloalkyl-B—$C_3$-$C_8$cycloalkyl-, benzyl-B—$C_3$-$C_{12}$cycloalkyl-, phenyl-B—$C_3$-$C_{12}$cycloalkyl-, all of which, in turn, are substituted by substituents independently selected from the group consisting of halogen, cyano, hydroxy, mercapto, $C_1$-$C_6$haloalkyl, $C_1$-$C_6$alkoxy, formyl, $C_2$-$C_6$alkylcarbonyl, $C_1$-$C_6$alkylthio, $C_1$-$C_6$alkylsulfinyl and $C_1$-$C_6$alkylsulfonyl; or cf) R$_5$ is A-, A-($C_1$-$C_6$alkyl)-, A-O—($C_1$-$C_6$alkyl)-, A-($C_2$-$C_6$alkenyl)-, A-O—($C_2$-$C_6$alkenyl)-, A-($C_2$-$C_6$-alkynyl)-, A-O—($C_2$-$C_6$alkynyl)-, A-($C_3$-$C_8$cycloalkyl)- or A-O—($C_3$-$C_8$cycloalkyl)-; wherein the group A is as defined above under ah); or cg) R$_5$ signifies the group —N=C(R$_8$)R$_9$;

cg1) wherein R$_8$ and R$_9$, independently from each other, are hydrogen, halogen, cyano, $C_1$-$C_{12}$alkyl, $C_2$-$C_{12}$alkenyl, $C_2$-$C_{12}$alkinyl, $C_1$-$C_{12}$alkoxy, formyl, $C_2$-$C_{12}$alkylcarbonyl, $C_3$-$C_{12}$alkenylcarbonyl, carboxy, $C_2$-$C_{12}$alkoxycarbonyl or $C_4$-$C_{12}$alkenyloxycarbonyl, or $C_1$-$C_{12}$alkyl, $C_2$-$C_{12}$alkenyl, $C_2$-$C_{12}$alkinyl, $C_1$-$C_{12}$alkoxy, $C_2$-$C_{12}$alkylcarbonyl, $C_3$-$C_{12}$alkenylcarbonyl, $C_2$-$C_{12}$alkoxycarbonyl or $C_4$-$C_{12}$alkenyloxycarbonyl mono- to polysubstituted by substituents independently selected from the group consisting of halogen, cyano, nitro, hydroxy, mercapto, $C_1$-$C_6$alkyl, $C_1$-$C_6$haloalkyl, $C_1$-$C_6$alkoxy, $C_1$-$C_6$haloalkoxy, $C_1$-$C_6$alkylthio, $C_1$-$C_6$alkylsulfinyl and $C_1$-$C_6$alkylsulfonyl; or cg2) R$_8$ and R$_9$ together form a $C_2$-$C_8$alkylene bridge which may optionally be mono- to polysubstituted by substituents independently selected from the group consisting of halogen, cyano, $C_1$-$C_6$alkyl and $C_1$-$C_6$haloalkyl; or cg3) R$_8$ and R$_9$, independently from each other, are the groups A-, A-O— or A-($C_1$-$C_6$alkyl)-;

wherein the group A is as defined above under ah);

d) R$_6$ is hydrogen, fluoro, bromo, chloro, cyano or CHO;

or an agronomically acceptable salt, metallic complex, metalloidic complex, isomer, structural isomer, stereoisomer, diastereoisomer, enantiomer, tautomer or N-oxide thereof.

2. A compound of formula I according to claim 1, wherein R$_1$ and R$_2$, independently of each other, are hydrogen, cyano, $C_1$-$C_6$alkyl, $C_3$-$C_6$cycloalkyl, $C_2$-$C_6$alkenyl, $C_2$-$C_6$alkynyl, benzyl or $C_2$-$C_7$alkylcarbonyl, each of which may be mono- to polysubstituted by substituents independently selected from the group consisting of halogen, $C_1$-$C_6$alkyl, $C_1$-$C_6$haloalkyl, $C_1$-$C_6$alkylthio and $C_1$-$C_6$alkoxy; or R$_1$ and R$_2$ together form a $C_2$-$C_6$alkylene bridge which may be mono- to polysubstituted by methyl groups; or R$_1$ and R$_2$ together with their interconnecting nitrogen atom are pyrazolino, pyrazolidino, pyrrolino, imidazolino, imidazolidino, triazolino, tetrazolino, piperazino, morpholino, thiomorpholino, each of which, independently of each other, may be mono- to polysubstituted by methyl groups; or R$_1$ is hydrogen, cyano, $C_1$-$C_6$alkyl, $C_3$-$C_6$cycloalkyl, $C_2$-$C_6$alkenyl, $C_2$-$C_6$alkynyl, benzyl or $C_2$-$C_7$alkylcarbonyl, each of which may be mono- to polysubstituted by substituents independently selected from the group consisting of halogen, $C_1$-$C_6$alkyl, $C_1$-$C_6$haloalkyl, $C_1$-$C_6$alkylthio and $C_1$-$C_6$alkoxy, and R$_2$ is amino, $C_1$-$C_6$alkoxy, $C_3$-$C_6$alkenyloxy, $C_3$-$C_8$cycloalkyloxy or $C_3$-$C_6$alkynyloxy; or R$_2$ is hydrogen, cyano, $C_1$-$C_6$alkyl, $C_3$-$C_6$cycloalkyl, $C_2$-$C_6$alkenyl, $C_2$-$C_6$alkynyl, benzyl or $C_2$-$C_7$alkylcarbonyl, each of which may be mono- to polysubstituted by substituents independently selected from the group consisting of halogen, $C_1$-$C_6$alkyl, $C_1$-$C_6$haloalkyl, $C_1$-$C_6$alkylthio and $C_1$-$C_6$alkoxy, and R$_1$ is hydroxy, amino, $C_1$-$C_6$alkoxy, $C_3$-$C_6$alkenyloxy, $C_3$-$C_8$cycloalkyloxy or $C_3$-$C_6$alkynyloxy.

3. A compound of formula I according to claim 1, wherein R$_7$ is hydrogen, $C_1$-$C_6$-alkyl, $C_1$-$C_6$-haloalkyl, halogen or cyano.

4. A compound of formula I according to claim 1, wherein R$_4$ is hydrogen, $C_1$-$C_6$-alkyl, $C_1$-$C_6$-haloalkyl, $C_3$-$C_7$cycloalkyl, halogen, cyano, hydroxy, $C_1$-$C_6$alkoxy, amino, azido, mercapto, $C_1$-$C_6$alkylthio, $C_1$-$C_6$alkylsulfinyl, $C_1$-$C_6$alkylsulfonyl, CHO, $C_2$-$C_7$alkylcarbonyl, aziridino, azetidino, pyrazolino, pyrazolidino, pyrrolino, pyrrolidino, imidazolino, imidazolidino, triazolino, tetrazolino, piperazino, piperidino, morpholino, thiomorpholino; or aziridino, azetidino, pyrazolino, pyrazolidino, pyrrolino, pyrrolidino, imidazolino, imidazolidino, triazolino, tetrazolino, piperazino, piperidino, morpholino, thiomorpholino, each of which, in turn, is mono- or polysubstituted by substituents selected from the group consisting of methyl, halogen; or R$_4$ is phenyl, or phenyl which is mono- to polysubstituted by substituents independently selected from the group consisting of halogen, cyano, hydroxy, $C_1$-$C_6$alkyl, $C_1$-$C_6$haloalkyl and $C_1$-$C_6$alkoxy.

5. A compound of formula I according to claim 1, wherein $R_3$ is hydrogen, $C_1$-$C_6$-alkyl, C1-C6-haloalkyl, $C_2$-$C_6$alkenyl, $C_2$-$C_6$alkynyl, $C_3$-$C_7$cycloalkyl, halogen, cyano, azido, nitro, —N=C=O, —N=C=S, —C(=O)NH$_2$, —C(=S)NH2, —C(=O)NH(CH$_3$), —C(=S)NH(CH$_3$), —C(=O)N(CH$_3$)$_2$, —SO$_2$NH$_2$, —SO$_2$NH(CH$_3$), —SO$_2$N(CH$_3$)$_2$, —C(=S)N(CH$_3$)$_2$, —COOH, tri($C_1$-$C_4$alkyl)silyl, tri-($C_1$-$C_4$alkoxy)silyl, hydroxy, $C_1$-$C_6$alkoxy, amino, azido, mercapto, $C_1$-$C_6$alkylamino, $C_2$-$C_{12}$dialkylamino, $C_3$-$C_6$alkenylamino, $C_6$-$C_{12}$dialkenylamino, $C_1$-$C_6$alkyl$C_3$-$C_6$alkenylamino, $C_1$-$C_6$alkylthio, $C_1$-$C_6$alkylsulfinyl, $C_1$-$C_6$alkylsulfonyl, $C_1$-$C_6$haloalkylthio, $C_1$-$C_6$haloalkylsulfinyl, $C_1$-$C_6$haloalkylsulfonyl, CHO, $C_2$-$C_7$alkylcarbonyl, $C_2$-$C_6$alkoxycarbonyl, $C_3$-$C_6$alkenyloxycarbonyl, $C_3$-$C_6$alkynyloxycarbonyl, phenyl, aziridino, azetidino, pyrazolino, pyrazolidino, pyrrolino, pyrrolidino, imidazolino, imidazolidino, triazolino, tetrazolino, piperazino, piperidino, morpholino or thiomorpholino; or $R_3$ is aziridino, azetidino, pyrazolino, pyrazolidino, pyrrolino, pyrrolidino, imidazolino, imidazolidino, triazolino, tetrazolino, piperazino, piperidino, morpholino, thiomorpholino mono- or polysubstituted by substituents independently selected from the group consisting of methyl, halogen and phenyl, or by phenyl which itself can be mono-to polysubstituted by substituents independently selected from the group consisting of halogen, cyano, hydroxy, $C_1$-$C_6$alkyl, $C_1$-$C_6$haloalkyl and $C_1$-$C_6$alkoxy; or $R_3$ is $C_1$-$C_6$-alkyl, $C_2$-$C_6$alkenyl, $C_2$-$C_6$alkynyl, $C_3$-$C_7$cycloalkyl, $C_1$-$C_6$alkoxy, $C_2$-$C_7$alkylcarbonyl, $C_2$-$C_6$alkoxycarbonyl, $C_3$-$C_6$alkenyloxycarbonyl, $C_3$-$C_6$alkynyloxycarbonyl or phenyl, or is phenyl mono- to polysubstituted by substituents independently selected from the group consisting of halogen, cyano, nitro, $C_1$-$C_6$alkyl, $C_1$-$C_6$haloalkyl, hydroxy, $C_1$-$C_6$alkoxy, $C_1$-$C_6$haloakoxy and phenyl, which phenyl in turn may be mono- to polysubstituted by substituents independently selected from the group consisting of halogen, cyano, hydroxy, $C_1$-$C_6$alkyl, $C_1$-$C_6$haloalkyl and $C_1$-$C_6$alkoxy.

6. A compound of formula I according to claim 1, wherein $R_5$ is phenyl, phenyl-$C_1$-$C_{12}$alkyl, phenyl-$C_3$-$C_{12}$cycloalkyl, phenyl-$C_3$-$C_{12}$alkenyl, or phenyl, phenyl-$C_1$-$C_{12}$alkyl, phenyl-$C_3$-$C_{12}$cyclolkyl, phenyl-$C_3$-$C_{12}$alkenyl mono- to polysubstituted by substituents independently selected from the group consisting of fluoro, bromo, iodo, cyano, nitro, amino, azido, hydroxy, mercapto, trialkylsilyl, trialkoxysilyl, CHO, COOH, $C_1$-$C_6$alkyl, $C_1$-$C_6$haloalkyl, $C_1$-$C_6$hydroxyalkyl, $C_3$-$C_8$cycloalkyl, $C_3$-$C_8$cycloalkyl, $C_2$-$C_6$alkenyl, $C_2$-$C_6$haloalkenyl, $C_2$-$C_6$alkynyl, $C_2$-$C_6$haloalkynyl, $C_1$-$C_6$alkoxy, $C_1$-$C_6$haloalkoxy, $C_3$-$C_6$alkenyloxy, $C_3$-$C_6$haloalkenyloxy, $C_3$-$C_6$alkynyloxy, $C_3$-$C_6$cycloalkoxy, $C_3$-$C_6$halocycloalkoxy, $C_1$-$C_6$alkylthio, $C_1$-$C_6$alkylsulfinyl, $C_1$-$C_6$alkylsulfonyl, $C_1$-$C_6$haloalkylthio, $C_1$-$C_6$haloalkylsulfinyl, $C_1$-$C_6$haloalkylsulfonyl, —C(=O)NH$_2$, —C(=S)NH2, —C(=O)NH(CH$_3$), —C(=S)NH(CH$_3$), —C(=O)N(CH$_3$)$_2$, —SO$_2$NH$_2$, —SO$_2$NH(CH$_3$), —SO$_2$N(CH$_3$)$_2$ and —C(=S)N(CH$_3$)$_2$.

7. A compound of formula I according to claim 1, wherein $R_5$ is hydrogen, $(R_{51})(R_{52})(R_{53})$Si—($C_1$-$C_{12}$alkyl)-, tri$C_1$-$C_6$alkylsilyl, phenyl-di$C_1$-$C_6$alkylsilyl, $C_1$-$C_{12}$alkyl, $C_3$-$C_{12}$alkenyl, $C_3$-$C_{12}$alkynyl, $C_3$-$C_{12}$cycloalkyl, $C_3$-$C_{12}$cycloalkyl-$C_1$-$C_{12}$alkyl, $C_5$-$C_{12}$cycloalkenyl, $C_1$-$C_{12}$alkoxy-$C_1$-$C_{12}$alkyl, $C_1$-$C_{12}$alkenyloxy-$C_1$-$C_{12}$alkyl, $C_1$-$C_{12}$alkynyloxy-$C_1$-$C_{12}$alkyl, $C_1$-$C_{12}$alkylthio-$C_1$-$C_{12}$alkyl, $C_1$-$C_{12}$alkylsulfenyl-$C_1$-$C_{12}$alkyl, $C_1$-$C_{12}$alkylsulfonyl-$C_0$-$C_{12}$alkyl, $C_2$-$C_{12}$alkylcarbonyl-$C_0$-$C_{12}$alkyl, $C_3$-$C_{12}$alkenylcarbonyl-$C_0$-$C_{12}$alkyl, $C_2$-$C_{12}$alkoxylcarbonyl-$C_0$-$C_{12}$alkyl, $C_3$-$C_{12}$alkenyloxycarbonyl-$C_0$-$C_{12}$alkyl or $C_3$-$C_{12}$alkynyloxycarbonyl-$C_0$-$C_{12}$alkyl, or $R_5$ is $C_1$-$C_{12}$alkyl, $C_3$-$C_{12}$alkenyl, $C_3$-$C_{12}$alkynyl, $C_3$-$C_{12}$cycloalkyl, $C_3$-$C_{12}$cycloalkyl-$C_1$-$C_{12}$alkyl, $C_5$-$C_{12}$cycloalkenyl, $C_1$-$C_{12}$alkoxy-$C_1$-$C_{12}$alkyl, $C_1$-$C_{12}$alkenyloxy-$C_1$-$C_{12}$alkyl, $C_1$-$C_{12}$alkynyloxy-$C_1$-$C_{12}$alkyl, $C_1$-$C_{12}$alkylthio-$C_1$-$C_{12}$alkyl, $C_1$-$C_{12}$alkylsulfenyl-$C_1$-$C_{12}$alkyl, $C_1$-$C_{12}$alkylsulfonyl-$C_0$-$C_{12}$alkyl, $C_2$-$C_{12}$alkylcarbonyl-$C_0$-$C_{12}$alkyl, $C_3$-$C_{12}$alkenylcarbonyl-$C_0$-$C_{12}$alkyl, $C_2$-$C_{12}$alkoxylcarbonyl-$C_0$-$C_{12}$alkyl, $C_3$-$C_{12}$alkenyloxycarbonyl-$C_0$-$C_{12}$alkyl, $C_3$-$C_{12}$alkynyloxycarbonyl-$C_0$-$C_{12}$alkyl mono- to polysubstituted by substituents independently selected from the group consisting of halogen, cyano, nitro, amino, hydroxy, mercapto, CHO, COOH, $C_1$-$C_6$-trialkylsilyl, tri$C_1$-$C_6$alkoxysilyl, $C_1$-$C_6$alkyl, $C_1$-$C_6$haloalkyl, $C_3$-$C_8$cycloalkyl, $C_3$-$C_8$halocycloalkyl, $C_1$-$C_6$alkenyl, $C_1$-$C_6$haloalkenyl, $C_1$-$C_6$alkoxy, $C_1$-$C_6$haloalkoxy, $C_2$-$C_7$alkylcarbonyl, $C_2$-$C_7$alkoxycarbonyl, $C_2$-$C_7$alkenyloxycarbonyl, $C_2$-$C_7$alkynyloxycarbonyl, $C_1$-$C_6$alkylthio, $C_1$-$C_6$alkylsulfinyl, $C_1$-$C_6$alkylsulfonyl, —C(=O)NH$_2$, —C(=S)NH$_2$, —C(=O)NH(CH$_3$), —C(=S)NH(CH$_3$) and —C(=O)N(CH$_3$)$_2$; and $R_{51}$, $R_{52}$, and $R_{53}$ are as defined in claim 1.

8. A compound of formula I according to claim 1, wherein $R_1$ and $R_2$, independently of each other, are hydrogen, $C_3$-$C_7$cycloalkyl, $C_1$-$C_6$alkyl, $C_2$-$C_6$alkinyl, hydrogen or pyridine;

or $R_1$ and $R_2$ together with their interconnecting nitrogen atom are pyrrolino;

$R_3$ is hydrogen, $C_1$-$C_6$haloalkyl, $C_1$-$C_6$alkyl, halogen, cyano, nitro, $C_1$-$C_4$alkoxy, phenyl, phenyl substituted by halogen, $(R_{51})(R_{52})(R_{53})$Si—($C_2$-$C_6$alkinyl)-, wherein $R_{51}$, $R_{52}$ and $R_{53}$ is as defined in claim 1;

$R_4$ is hydrogen, halogen, phenyl, imidazolyl, amino, $C_1$-$C_6$alkoxy or $C_1$-$C_6$alkyl;

$R_5$ is $C_1$-$C_{12}$alkyl or the group A, wherein

A is a three- to ten-membered monocyclic or fused bicyclic ring system which can be aromatic, partially saturated or fully saturated and can contain 1 to 4 hetero atoms selected from the group consisting of nitrogen, oxygen and sulfur, it not being possible for each ring system to contain more than 2 oxygen atoms and more than 2 sulfur atoms, and it being possible for the three- to ten-membered ring system itself to be mono- or polysubstituted by substituents independently selected from the group consisting of halogen, $C_1$-$C_6$alkyl, $C_1$-$C_6$haloalkyl, $C_1$-$C_6$alkoxy and $C_1$-$C_6$alkylthio;

$R_6$ is hydrogen; and $R_7$ is hydrogen or $C_1$-$C_6$alkyl.

9. A compound of formula I according to claim 8, wherein $R_3$ is hydrogen, $C_1$-$C_6$alkyl, halogen, cyano, nitro, $C_1$-$C_4$alkoxy, phenyl, phenyl substituted by halogen, or $(R_{51})(R_{52})(R_{53})$Si—($C_2$-$C_6$alkinyl)-.

10. A compound of formula I according to claim 1, wherein $R_1$ and $R_2$, independently of each other, are $C_1$-$C_6$alkyl, $C_3$-$C_7$cycloalkyl, $C_2$-$C_6$alkinyl, hydrogen or pyridine;

or $R_1$ and $R_2$ together with their interconnecting nitrogen atom are pyrrolino;

315

$R_3$ is hydrogen, $C_1$-$C_6$alkyl, $C_1$-$C_6$alkoxy, $C_1$-$C_6$haloalkyl, halogen, cyano, phenyl, phenyl substituted by halogen, or is $(R_{51})(R_{52})(R_{53})Si$—$(C_2$-$C_6$alkinyl)-, wherein $R_{51}$, $R_{52}$ and $R_{53}$ is as defined in claim 1;

$R_4$ is hydrogen, halogen, $C_1$-$C_6$alkoxy or $C_1$-$C_6$alkyl;

$R_5$ is $C_1$-$C_6$alkyl, phenyl or $C_1$-$C_6$alkyl, pyridyl or phenyl mono- or disubstituted by substituents selected from the group consisting of halogen, $C_1$-$C_6$alkyl, $C_1$-$C_6$haloalkyl, $C_1$-$C_6$alkoxy and $C_1$-$C_6$alkylthio; or pyridyl mono- or disubstituted by substituents selected from the group consisting of fluoro, bromo, iodo, $C_1$-$C_6$alkyl, $C_1$-$C_6$haloalkyl, $C_1$-$C_6$alkoxy and $C_1$-$C_6$alkylthio;

$R_6$ is hydrogen; and $R_7$ is hydrogen or $C_1$-$C_6$alkyl.

11. A compound of formula I according to claim 10, wherein $R_1$ and $R_2$, independently of each other, are $C_1$-$C_6$alkyl, $C_2$-$C_6$alkinyl, hydrogen or pyridine;

or $R_1$ and $R_2$ together with their interconnecting nitrogen atom are pyrrolino;

$R_3$ is hydrogen, $C_1$-$C_6$alkyl, halogen, cyano, phenyl, phenyl substituted by halogen, or is $(R_{51})(R_{52})(R_{53})Si$-$(C_2$-$C_6$alkinyl)-;

$R_4$ is hydrogen or $C_1$-$C_6$alkyl;

$R_5$ is $C_1$-$C_6$alkyl, phenyl or pyridyl or phenyl mono- or disubstituted by substituents selected from the group consisting of halogen, $C_1$-$C_6$alkyl, $C_1$-$C_6$haloalkyl, $C_1$-$C_6$alkoxy and $C_1$-$C_6$alkylthio or pyridyl mono- or disubstituted by substituents selected from the group consisting of fluoro, bromo, iodo, $C_1$-$C_6$alkyl, $C_1$-$C_6$haloalkyl, $C_1$-$C_6$alkoxy and $C_1$-$C_6$alkylthio.

12. A compound of formula X

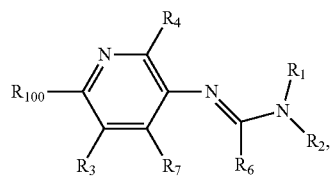

(X)

wherein aa) $R_1$ and $R_2$, independently from each other, are hydrogen, cyano, formyl, nitro, $C_1$-$C_7$alkyl, $C_2$-$C_6$alkenyl $C_2$-$C_6$alkynyl $C_2$-$C_7$alkenylcarbonyl $C_3$-$C_7$alkenylcarbonyl $C_4$-$C_9$cycloalkylcarbonyl, $C_1$-$C_6$alkoxy -$C_1$-$C_6$alkyl, $C_1$-$C_6$alkylthio-$C_1$-$C_6$alkyl, $C_2$-$C_7$alkylcarbonyl-$C_1$-$C_6$alkyl, $C_3C_6$alkenyloxy-$C_1$-$C_6$alkyl, $C_3$-$C_6$alkynyloxy-$C_1$-$C_6$alkyl, benzyloxy-$C_1$-$C_6$alkyl, $C_3$-$C_8$cycloalkyl-$C_1$-$C_6$alkyl, $C_2$-$C_7$alkyloxycarbonyl, $C_4$-$C_7$alkenyloxycarbonyl, $C_4$-$C_7$alkynyloxycarbonyl, $C_4$-$C_9$cycloalkyloxycarbonyl, $C_1$-$C_6$alkylsulfonyl, $C_1$-$C_6$haloalkylsulfonyl, $C_1$-$C_6$alkylsulfinyl or $C_1$-$C_6$haloalkylsulfinyl; or ab) $R_1$ and $R_2$, independently from each other, are —Si$(R_{51})(R_{52})(R_{53})$, wherein $R_{51}$, $R_{52}$, $R_{53}$, independently of each other, are halogen, cyano, $C_1$-$C_6$alkyl, $C_2$-$C_6$alkynyl, $C_3$-$C_8$cycloalkyl, $C_5$-$C_8$cycloalkenyl, $C_2$-$C_6$alkynyl $C_1$-$C_6$alkoxy, benzyl or phenyl; or ac) $R_1$ and $R_2$, independently from each other, are —Si$(OR_{54})(R_{55})(R_{56})$, wherein $R_{54}$, $R_{55}$, $R_{56}$, independently of each other, are $C_1$-$C_6$alkyl, $C_3$-$C_6$alkenyl, $C_3$-$C_8$cycloalkyl, $C_3$-$C_6$alkynyl, benzyl or phenyl; or

316 ad) $R_1$ and $R_2$ independently from each other, are phenylsulfonyl, phenylsufinyl phenylcarbonyl, phenoxycarbonyl, benzyl, benzylcarbonyl or benzyloxycarbonyl; or ae) $R_1$ and $R_2$ independently from each other, are phenylsulfonyl, phenylsufinyl phenylcarbonyl, phenoxycarbonyl, benzyl, benzylcarbonyl, benzyloxycarbonyl mono- to polysubstituted ae1) by substituents independently selected from the group consisting of hydroxy, mercapto, halogen, cyano, azido, nitro, —SF$_5$ amino $C_1$-$C_6$alkyl, $C_1$-$C_6$haloalkyl, $C_3$-$C_8$cycloalkyl, $C_3$-$C_8$halocycloalkyl, $C_2$-$C_6$alkenyl, $C_2$-$C_6$haloalkenyl, $C_2$-$C_6$alkynyl, $C_2C_6$haloalkynyl $C_1$-$C_6$alkoxy $C_1$-$C_6$haloalkoxy $C_1$-$C_6$alkoxy $C_1$-$C_6$alkyl, $C_1$-$C_6$alkylthio$C_1$-$C_6$alkyl, $C_3C_6$alkenyloxy $C_3$-$C_6$haloalkenyloxy $C_3$-$C_6$alkynyloxy, $C_1$-$C_6$alkylthio, $C_1$-$C_6$haloalkylthio, $C_1$-$C_6$alkylsulfinyl $C_1$-$C_6$haloalkylsulfinyl $C_1$-$C_6$alkylsulfonyl $C_1$-$C_6$haloalkylsulfonyl, benzyloxy, phenoxy, benzyl and phenyl, where benzyloxy, phenoxy, benzyl and phenyl for their part may be mono- to polysubstituted on the phenyl ring by substituents independently selected from the group consisting of halogen, cyano, hydroxy, $C_1$-$C_6$ alkyl, $C_1$-$C_6$haloalkoxy and C-$_1$-$C_6$alkoxy; or ae2) by substituents independently selected from the group consisting of carboxy, —C($=$O)—Cl, —C($=$O)—F $C_2$-$C_7$alkoxycarbonyl $C_2$-$C_7$alkylthiocarbonyl, $C_2$-$C_7$haloalkoxycarbonyl, $C_3$-$C_7$alkenyloxycarbonyl, $C_3$-$C_7$haloalkenyloxycarbonyl, $C_3$-$C_7$alkynyloxycarbonyl, benzyloxycarbonyl and phenoxycarbonyl, where benzyloxycarbonyl and phenoxycarbonyl for their part may be mono- to polysubstituted on the phenyl ring by substituents independently selected form the group consisting of halogen, cyano, hydroxy, $C_1$-$C_6$alkyl, $C_1$-$C_6$haloalkyl and $C_1$-$C_6$alkoxy; or ae3) by substituents independently selected from the group consisting of formyl, $C_2$-$C_7$alkylcarbonyl, $C_2$-$C_7$haloalkylcarbonyl, $C_3$-$C_7$alkenylcarbonyl, phenylcarbonyl and benzylcarbonyl, where phenylcarbonyl and benzylcarbonyl for their part may be mono- to polysubstituted on the phenyl ring by substituents independently selected form the group consisting of halogen, cyano, hydroxy, $C_1$-$C_6$alkyl, $C_1$-$C_6$haloalkyl and $C_1$-$C_6$alkoxy; or ae4) by substituents independently selected from the group consisting of aminosulfonyl, $C_1$-$C_6$alkylaminosulfonyl, N N-di($C_1$-$C_6$alkyl)aminosulfonyl, —C($=$O)NR$_{57}$R$_{58}$, —C($=$S)NR$_{57}$R$_{58}$ and —NR$_{57}$R$_{58}$ wherein $R_{57}$ and $R_{58}$, independently of each other are hydrogen $C_1$-$C_6$alkyl, $C_1$-$C_6$haloalkyl, $C_3$-$C_6$alkenyl $C_3$-$C_6$haloalkenyl $C_3$-$C_6$alkynyl $C_3$-$C_8$cycloalkyl, $C_3$-$C_8$halocycloalkyl,I phenyl or benzyl, where phenyl, benzyl for their part may be mono- to polysubstituted on the phenyl ring by substituents independently selected form the group consisting of halogen, cyano, hydroxy, C-$_1$-$C_6$alkyl, C-$_1$-$C_6$haloalkyl and $C_1$-$C_6$alkoxy, or $R_{57}$ and $R_{58}$ together with their interconnecting nitrogen atom are aziridino, azetidino, pyrazolino, pyrazolidino, pyrrolino, pyrrolidino, imidazolino, imidazolidino, triazolino, tetrazolino, piperazino, piperidino, morpholino, thiomorpholino, each of which, in turn, may be mono- or polysubstituted by substituents selected from the group consisting of methyl, halogen, cyano and nitro; and substituents at nitrogen atoms in the ring systems being other than halogen; or af) either $R_1$ or $R_2$ is
af1) amino, $C_1$-$C_6$alkoxy $C_3$-$C_6$alkenyloxy $C_3$-$C_8$cycloalkyloxy, $C_3$-$C_6$alkynyloxy, or benzyloxy; or
af2) $C_1$-$C_6$alkoxy $C_3$-$C_6$alkenyloxy $C_3$-$C_8$cycloalkyloxy $C_3$-$C_6$alkynvloxy, benzyloxy mono- to polysubstituted by substituents independently selected from the group consisting of halogen, cyano, $C_1$-$C_6$alkyl, $C_1$-$C_6$haloalkyl, $C_1$-$C_6$alkoxy and $C_1$-$C_6$haloalkoxy; or
ag) $R_{-1}$ and $R_2$, independently from each other, are $C_1$-$C_7$alkyl, $C_2$-$C_6$alkenyl, $C_2$-$C_6$alkynyl, $C_2$-$C_7$alkylcarbonyl $C_3$-$C_7$alkenylcarbonyl $C_4$-$C_9$cycloalkylcarbonyl, $C_1$-$C_6$alkoxy-$C_1$-$C_6$alkyl, $C_1$-$C_6$alkylthio-$C_1$-$C_6$alkyl, $C_3$-$C_6$alkenyloxy-$C_1$-$C_6$alkyl, $C_2$-$C_6$alkylcarbonyl-$C_1$-$C_6$alkyl, $C_3$-$C_6$alkynyloxy-$C_1$-$C_6$alkyl, benzyloxy-$C_1$-$C_6$alkyl, $C_3$-$C_8$cycloalkyl-$C_1$-$C_6$alkyl, $C_2$-$C_7$alkyloxycarbonyl, $C_4$-$C_7$alkenyloxycarbonyl, $C_4$-$C_7$alkynyloxycarbonyl or $C_4$-$C_9$cycloalkyloxycarbonyl, mono- to polysubstituted by substituents independently selected from the group consisting of halogen, cyano, nitro, hydroxy, mercapto, azido, $C_1$-$C_6$alkyl, $C_1$-$C_6$haloalkyl, $C_1$-$C_6$alkoxy $C_1$-$C_6$haloalkoxy $C_1$-$C_6$alkylthio, $C_1$-$C_6$alkylsulfinyl $C_1$-$C_6$alkylsulfonyl, $C_2$-$C_7$alkoxycarbonyl, formyl, $C_2$-$C_7$alkylcarbonyl, —Si($R_{51}$)($R_{52}$)($R_{53}$) and —Si(OR$_{54}$)(OR$_{55}$)(OR$_{56}$); or
ah) $R_1$ and $R_2$ independently from each other are the group A-; wherein A is a three- to ten-membered monocyclic or fused bicyclic ring system which can be aromatic, partially saturated or fully saturated and can contain 1 to 4 hetero atoms selected from the group consisting of nitrogen, oxygen and sulfur, it not being possible for each ring system to contain more than 2 oxygen atoms and more than 2 sulfur atoms, and it being possible for the three- to ten-membered ring system itself to be mono- or polysubstituted
A1) by substituents independently selected from the group consisting of fluoro, bromo, iodo, cyano, nitro, hydroxy, mercapto, nitro, azido, formyl, carboxy, —C(═O)—Cl, ═O,═S, —C(═O)—F, $C_1$-$C_6$alkyl, $C_2$-$C_6$alkenyl, $C_2$-$C_6$alkynyl, $C_3$-$C_8$cycloalkyl, $C_5$-$C_8$cycloalkenyl $C_5$-$C_8$cycloalkynyl, $C_1$-$C_6$haloalkyl, $C_2$-$C_6$haloalkenylyl $C_2$-$C_6$haloalkynyl $C_3$-$C_8$halocycloalkyl, $C_5$-$C_8$halocycloalkenyl $C_5$-$C_8$halocycloalkynyl $C_1$-$C_6$alkoxy $C_1$-$C_6$haloalkoxy $C_3$-$C_6$alkenyloxy, $C_3$-$C_6$haloalkenylyloxy $C_3$-$C_6$alkynyloxy, $C_3$-$C_8$cycloalkyloxy $C_3$-$C_8$halocycloalkyloxy, $C_3$-$C_8$cycloalkenyloxy, $C_3$-$C_8$halocycloalkenyloxy, benzyloxy phenoxy, where benzyloxy and phenoxy, in turn, may be mono- to polysubstituted by substituents independently selected from the group consisting of halogen, cyano, nitro, hydroxy, mercapto, azido, amino, —SF$_5$, $C_1$-$C_6$alkyl, $C_1$-$C_6$haloalkyl, $C_1$-$C_6$alkoxy, $C_1$-$C_6$haloalkoxy, $C_1$-$C_6$alkoxy$C_1$-$C_6$alkyl, $C_1$-$C_6$alkylthio, $C_1$-$C_6$alkylsulfinyl and $C_1$-$C_6$alkylsulfonyl; or
A2) by substituents independently selected from the group consisting of HC(═NOR$_{59}$)—, ($C_1$-$C_6$alkyl)C(═NOR$_{59}$)—, ($C_1$-$C_6$haloalkyl)C(═NOR$_{59}$)—, ($C_1$-$C_6$alkyl)C(═NOR$_{59}$)$C_1$-$C_6$alkyl- and ($C_1$-$C_6$haloalkyl)C(═NOR$_{69}$K$_1$-$C_6$alkyl-, wherein $R_{59}$ is hydrogen, $C_1$-$C_6$alkyl, $C_1$-$C_6$haloalkyl, $C_3$-$C_6$alkenyl, $C_3$-$C_6$haloalkenylyl, $C_3$-$C_6$alkynyl, $C_3$-$C_8$cycloalkyl, $C_3$-$C_8$halocycloalkyl, benzyl and phenyl, and benzyl and phenyl mono- to polysubstituted by halogen, cyano, hydroxy, $C_1$-$C_6$alkyl, $C_1$-$C_6$haloalkyl or $C_1$-$C_6$alkoxy; or A3) by substituents independently selected from the group consisting of $C_2$-$C_6$alkylthio, $C_1$-$C_6$haloalkylthio, $C_1$-$C_6$alkylsulfinyl $C_1$-$C_6$alkylsulfonyl ($R_{14}$)S(═O)(═NR$_{13}$)— and ($R_{14}$)($R_{15}$)S(═O)═N—, wherein $R_{13}$ is hydrogen, $C_1$-$C_6$alkyl, $C_1$-$C_6$haloalkyl, $C_3$-$C_6$alkenyl, $C_3$-$C_6$haloalkenylyl, $C_3$-$C_6$alkynyl, $C_3$-$C_8$cycloalkyl, $C_3$-$C_8$halocycloalkyl, phenyl or benzyl, or is phenyl or benzyl mono- to polysubstituted by halogen, cyano, hydroxyl, $C_1$-$C_6$alkyl, $C_1$-$C_6$haloalkyl, or $C_1$-$C_6$alkoxy, and $R_{14}$ and $R_5$, independently of each other, are $C_1$-$C_6$alkyl, $C_3$-$C_8$cycloalkyl, $C_1$-$C_6$haloalkyl, $C_3$-$C_8$halocycloalkyl, $C_2$-$C_6$alkenyl $C_2$-$C_6$haloalkenyl $C_2$-$C_6$alkynyl, benzyl or phenyl, or benzyl or phenyl independently of each other, substituted by substituents selected from the group consisting of halogen, cyano, hydroxyl, $C_1$-$C_6$alkyl, $C_1$-$C_6$haloalkyl and $C_1$-$C_6$alkoxy; or
A4) by substituents independently selected from the group consisting of —NR$_{57}$R$_{58}$, —C(═O)NR$_{57}$R$_{58}$ and —C(═S)NR$_{57}$R$_{58}$ or
A5) by substituents independently selected from the group consisting of formyl, $C_2$-$C_7$alkylcarbonyl, $C_2$-$C_7$haloalkylcarbonyl, $C_3$-$C_7$alkenylcarbonyl, $C_3$-$C_7$haloalkenylylcarbonyl, $C_4$-$C_9$cycloalkylcarbonyl, $C_4$-$C_9$halocycloalkylcarbonyl, $C_2$-$C_7$alkoxycarbonyl, $C_2$-$C_7$haloalkoxycarbonyl, $C_3$-$C_7$alkenyloxycarbonyl, $C_3$-$C_7$alkynyloxycarbonyl, $C_4$-$C_9$cycloalkoxycarbonyl, $C_2$-$C_7$alkylthiocarbonyl and benzyloxycarbonyl, and benzyloxycarbonyl mono- to polysubstituted by substituents independently selected from the group consisting of halogen, cyano, hydroxyl, $C_1$-$C_6$haloalkyl and $C_{-1}$-$C_6$alkoxy; or
A6) by substituents independently selected from the group consisting of —Si($R_{51}$)($R_{52}$)($R_{53}$) and —Si(OR$_{54}$OR$_{55}$)(OR$_{56}$); or
A7) by substituents independently selected from the group consisting of
aminosulfinyl, ($C_1$-$C_6$alkyl)aminosulfonyl, N,N-di($C_1$-$C_6$alkyl)aminosulfonyl, di($C_1$-$C_6$alkyl)amino, ($C_1$-$C_6$alkyl)amino, phenyl, phenoxy, benzyl and benzyoxy, where phenyl, phenoxy, benzyl and benzyloxy for their part may be mono- to polysubstituted on the phenyl ring by substituents independently selected form the group consisting of halogen, cyano, hydroxy, amino, nitro, azido, mercapto, formyl, —SF$_5$, $C_1$-$C_6$alkyl, $C_1$-$C_6$haloalkyl, $C_2$-$C_6$alkenyl, $C_2$-$C_6$haloalkenyl, $C_2$-$C_6$alkynyl, $C_1$-$C_6$alkoxy, $C_1$-$C_6$haloalkoxy, $C_1$-$C_6$alkylthio, $C_1$-$C_6$haloalkylthio, $C_3$-$C_6$alkenylthio, $C_3$-$C_6$haloalkenylthio, $C_3$-$C_6$alkynylthio, $C_1$-$C_3$alkoxy-$C_1$-$C_3$alkylthio, $C_2$-$C_6$alkylcarbonyl-$C_1$-$C_3$alkylthio, $C_2$-$C_6$alkoxycarbonyl-$C_1$-$C_3$6alkylthio, cyano-$C_1$-$C_6$alkylthio, $C_1$-$C_6$alkylsulfinyl, $C_1$-$C_6$haloalkylsulfinyl, $C_1$-$C_6$alkylsulfonyl, $C_1$-$C_6$haloalkylsulfonyl, aminosulfonyl, ($C_1$-$C_6$alkyl)aminosulfonyl, N,N-di($C_1$-$C_6$alkyl)aminosulfonyl, di($C_1$-$C_6$alkyl)amino and ($C_1$-$C_6$alkyl)amino; or
ai) $R_1$ and $R_2$, independently from each other, are —C(═O)NR$_{57}$R$_{58}$; or
aj) $R_1$ and $R_2$ together form a $C_2$-$C_6$alkylene bridge which may be mono- to polysubstituted by halogen, cyano, $C_1$-$C_6$alkyl or $C_1$-$C_6$haloalkyl groups; or
ak) $R_1$ and $R_2$ together with their interconnecting nitrogen atom are pyrazolino, pyrazolidino, pyrrolino, imidazolino, imidazolidino, triazolino, tetrazolino, piperazino, morpholino, thiomorpholino, each of which, independently of each other, may be mono- to polysubstituted by methyl groups, halogen, cyano and nitro; or
al) the fragment

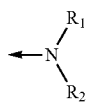

can be

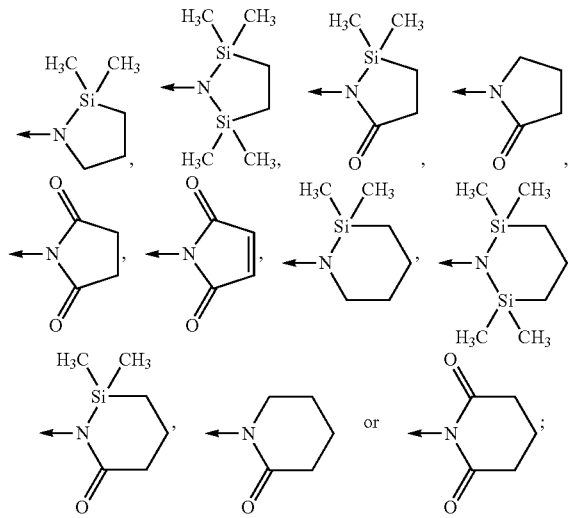

wherein each of the meanings of said fragment can be mono- to polysubstituted by substituents independently selected from the group consisting of halogen, cyano, $C_1$-$C_6$alkyl, $C_1$-$C_6$haloalkyl and $C_1$-$C_6$alkoxy;

ba) $R_3$, $R_4$ and $R_7$, independently from each other, are ba1) hydrogen, halogen, cyano, nitro, mercapto, hydroxy, azido, —$SF_5$, —$NR_{64}R_{65}$, wherein $R_{64}$ and $R_{65}$, independently of each other, are hydrogen, $C_1$-$C_6$alkyl, $C_1$-$C_6$haloalkyl, $C_3$-$C_6$alkenyl, $C_3$-$C_6$haloalkenyl, $C_3$-$C_6$alkynyl, $C_3$-$C_8$cycloalkyl, $C_3$-$C_8$halocycloalkyl, phenyl or benzyl, where phenyl, benzyl for their part may be mono- to polysubstituted on the phenyl ring by substituents independently selected form the group consisting of halogen, cyano, hydroxy, $C_1$-$C_6$alkyl, $C_1$-$C_6$haloalkyl and $C_1$-$C_6$alkoxy, or $R_{64}$ and $R_{65}$ together with their interconnecting nitrogen atom are aziridino, azetidino, pyrazolino, pyrazolidino, pyrrolino, pyrrolidino, imidazolino, imidazolidino, triazolino, tetrazolino, piperazino, piperidino, morpholino, thiomorpholino, each of which, in turn, may be mono- or polysubstituted by substituents selected from the group consisting of methyl, halogen, cyano and nitro; and substituents at nitrogen atoms in the ring systems being other than halogen; or $R_3$, $R_4$ and $R_7$, independently from each other, are —C(=S)$NH_2$, —N=C=O, —N=C=S, amino, $(R_{51})(R_{52})(R_{53})$Si—, $(R_{51})(R_{52})(R_{53})$Si—($C_1$-$C_6$alkyl)-, $(R_{51})(R_{52})(R_{53})$Si—($C_2$-$C_6$alkinyl)-, $(OR_{54})(OR_{55})(OR_{56})$Si— or $(OR_{214})(OR_{215})(OR_{216})$Si—($C_1$-$C_6$alkyl)-; wherein $R_{214}$, $R_{215}$ and $R_{216}$ independently of each other, are halogen, cyano, $C_1$-$C_6$alkyl, $C_2$-$C_6$alkenyl, $C_3$-$C_8$cycloalkyl, $C_5$-$C_8$cycloalkenyl, $C_2$-$C_6$alkynyl, benzyl or phenyl; or $R_3$, $R_4$ and $R_7$, independently from each other, are ba2) $C_1$-$C_6$alkylthio, $C_1$-$C_6$alkylsulfinyl, $C_1$-$C_6$alkylsulfonyl, $C_1$-$C_6$haloalkylthio, $C_1$-$C_6$haloalkylsulfinyl, $C_1$-$C_6$haloalkylsulfonyl, aminosulfinyl, aminosulfonyl, $C_1$-$C_6$alkoxy, $C_1$-$C_6$haloalkoxy, $C_3$-$C_6$alkenyloxy, $C_3$-$C_6$haloalkenyloxy, $C_3$-$C_6$alkinyloxy, ($C_1$-$C_6$alkyl)aminosulfonyl, di($C_1$-$C_6$alkyl)aminosulfonyl, $C_1$-$C_6$alkoxy, $C_2$-$C_6$alkenyloxy, $C_2$-$C_6$alkynyloxy, $C_1$-$C_6$alkyl-S(=O)($R_{14}$)=N—, ($R_{14}$)S(=O)(=N—$R_{13}$)—, ($R_{14}$)($R_{15}$)S(=O)=N—, —S—$C_3$-$C_6$-alkenyl, —S—$C_3$-$C_6$-alkynyl, —S—$C_3$-$C_8$-cycloalkyl, S-benzyl, or —S—$C_3$-$C_6$-alkenyl, —S—$C_3$-$C_6$-alkynyl, —S—$C_3$-$C_8$-cycloalkyl or S-benzyl; all of which can be mono- to polysubstituted by substituents selected from the group consisting of halogen, cyano, $C_1$-$C_6$-alkyl, $C_1$-$C_6$-haloalkyl, $C_1$-$C_6$-alkoxy; or $R_3$, $R_4$ and $R_7$, independently from each other, are ba3) $C_1$-$C_6$alkyl, $C_2$-$C_6$alkenyl or $C_2$-$C_6$alkynyl, or $C_1$-$C_6$alkyl, $C_2$-$C_6$alkenyl or $C_2$-$C_6$alkynyl mono- to polysubstituted by substituents independently selected from the group consisting of halogen, hydroxy, mercapto, cyano, nitro, $C_1$-$C_6$alkyl, $C_1$-$C_6$haloalkyl, $C_1$-$C_6$alkoxy, $C_1$-$C_6$hydroxyalkyl, tri(alkyl)silyl, $C_1$-$C_6$haloalkoxy, $C_1$-$C_6$alkylthio, $C_1$-$C_6$haloalkylthio, $C_1$-$C_6$alkylsulfinyl, $C_1$-$C_6$haloalkylsulfinyl, $C_1$-$C_6$alkylsulfonyl and $C_1$-$C_6$haloalkylsulfonyl; or $R_3$, $R_4$ and $R_7$, independently from each other, are ba4) formyl, $C_2$-$C_7$alkoxycarbonyl, $C_2$-$C_7$haloalkoxycarbonyl, $C_3$-$C_7$alkenyloxycarbonyl, $C_3$-$C_7$haloalkenyloxycarbonyl, $C_2$-$C_7$alkylcarbonyl, carboxy, —C(=O)—Cl, —C(=O)—F, $C_2$-$C_7$haloalkylcarbonyl, $C_3$-$C_7$alkenylcarbonyl or $C_3$-$C_7$haloalkenylcarbonyl; or $R_3$, $R_4$ and $R_7$, independently from each other, are ba5) phenyl, phenoxy, benzyl or benzyloxy, or phenoxy, benzyl or benzyloxy mono- to polysubstituted by substituents independently selected from the group consisting of halogen, cyano, nitro, hydroxy, mercapto, azido, amino, —$SF_5$, $C_1$-$C_6$alkyl, $C_1$-$C_6$haloalkyl, $C_1$-$C_6$alkoxy, $C_1$-$C_6$haloalkoxy, $C_1$-$C_6$alkylthio, $C_1$-$C_6$alkylsulfinyl and $C_1$-$C_6$alkylsulfonyl; or bb) $R_3$, $R_4$ and $R_7$, independently of each other, are the groups A-, A-O— or A-($C_1$-$C_6$alkyl)-, wherein the group A is as defined above under ah);

d) R6 is hydrogen, fluoro, bromo, chloro, cyano or CHO; and $R_{100}$ is SH—, nitro, halogen, imidazolyl, triazolyl, $C_1$-$C_6$alkylthio, $C_1$-$C_6$alkylsulfenyl or $C_1$-$C_6$alkysulfonyl.

13. A method of controlling or preventing infestation of useful plants by phytopathogenic microorganisms, wherein a compound of formula I according to claim 1 or a composition, comprising this compound as active ingredient, is applied to the plants, to parts thereof or the locus thereof.

14. A composition for controlling and protecting against phytopathogenic microorganisms, comprising a compound of formula I according to claim 1 and an inert carrier.

* * * * *